United States Patent
Colley et al.

(10) Patent No.: US 11,640,859 B2
(45) Date of Patent: *May 2, 2023

(54) DATA BASED CANCER RESEARCH AND TREATMENT SYSTEMS AND METHODS

(71) Applicant: Tempus Labs, Chicago, IL (US)

(72) Inventors: Shane Colley, Chicago, IL (US); Isaiah Simpson, Chicago, IL (US); Brian Reuter, Chicago, IL (US); Robert Tell, Chicago, IL (US); Hailey Lefkofsky, Chicago, IL (US); Hunter Lane, Chicago, IL (US); Kevin White, Chicago, IL (US); Nike Beaubier, Chicago, IL (US); Stephen Bush, Chicago, IL (US); Aly Khan, Chicago, IL (US); Denise Lau, Chicago, IL (US); Kaanan Shah, Chicago, IL (US); Eric Lefkofsky, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 99 days.

This patent is subject to a terminal disclaimer.

(21) Appl. No.: 16/771,451

(22) PCT Filed: Oct. 17, 2019

(86) PCT No.: PCT/US2019/056713
§ 371 (c)(1),
(2) Date: Jun. 10, 2020

(87) PCT Pub. No.: WO2020/081795
PCT Pub. Date: Apr. 23, 2020

(65) Prior Publication Data
US 2021/0233664 A1   Jul. 29, 2021

Related U.S. Application Data

(60) Provisional application No. 62/902,950, filed on Sep. 19, 2019, provisional application No. 62/746,997, filed on Oct. 17, 2018.

(51) Int. Cl.
*G16H 50/70* (2018.01)
*G16H 10/60* (2018.01)
(Continued)

(52) U.S. Cl.
CPC ............. *G16H 50/70* (2018.01); *G16B 50/30* (2019.02); *G16H 10/60* (2018.01); *G16H 20/00* (2018.01); *G16H 50/20* (2018.01)

(58) Field of Classification Search
CPC .. G16H 20/00–10; G16H 50/70; G16H 10/60; G16B 50/30
See application file for complete search history.

(56) References Cited

U.S. PATENT DOCUMENTS

| 6,804,656 B1 | 10/2004 | Rosenfeld |
| 9,031,926 B2 | 5/2015 | Milward |

(Continued)

FOREIGN PATENT DOCUMENTS

WO   2020023420 A2   1/2020

OTHER PUBLICATIONS

Jeremy Ronk, Structured, semi structured and unstructured data, Sep. 1, 2014, Wordpress (Year: 2014).*

(Continued)

*Primary Examiner* — Shahid Merchant
*Assistant Examiner* — Karen A Hranek
(74) *Attorney, Agent, or Firm* — Quarles & Brady LLP

(57) ABSTRACT

A method and system for conducting genomic sequencing, the method comprising storing a set of user application programs wherein each of the programs requires an application specific subset of data, for each of a plurality of patients that have cancerous cells and that receive cancer treatment, obtaining clinical records data in original forms including cancer state information, treatment types and treatment efficacy information, storing the clinical records (Continued)

data in a semi-structured first database, for each patient, using a genomic sequencer to generate genomic sequencing data for the patient's cancerous cells and normal cells, storing the sequencing data in the first database, shaping at least a subset of the first database data to generate system structured data including clinical record data and sequencing data wherein the system structured data is optimized for searching, storing the system structured data in a second database, for each user application program, selecting the application specific subset of data from the second database and storing the application specific subset of data in a structure optimized for application program interfacing in a third database.

83 Claims, 82 Drawing Sheets

(51) Int. Cl.
  *G16H 50/20* (2018.01)
  *G16B 50/30* (2019.01)
  *G16H 20/00* (2018.01)

(56) References Cited

U.S. PATENT DOCUMENTS

| | | | |
|---|---|---|---|
| 9,208,217 B2 | 12/2015 | Milward | |
| 9,424,532 B1 | 8/2016 | Abedini | |
| 2001/0051353 A1* | 12/2001 | Kornblith | G01N 33/5011 435/803 |
| 2002/0049782 A1* | 4/2002 | Herzenberg | G16H 70/00 715/234 |
| 2002/0173702 A1 | 11/2002 | Lebel | |
| 2003/0046114 A1* | 3/2003 | Davies | G16H 50/20 705/3 |
| 2003/0143572 A1* | 7/2003 | Lu | G16B 50/00 435/91.2 |
| 2004/0122790 A1 | 6/2004 | Walker | |
| 2005/0125256 A1* | 6/2005 | Schoenberg | G06Q 40/08 705/2 |
| 2007/0005621 A1 | 1/2007 | Lesh | |
| 2007/0143149 A1* | 6/2007 | Buttner | G16H 10/60 705/3 |
| 2008/0162393 A1 | 6/2008 | Iliff | |
| 2008/0195600 A1 | 8/2008 | Deakter | |
| 2009/0319244 A1 | 12/2009 | West | |
| 2010/0029498 A1 | 2/2010 | Gnirke | |
| 2011/0255790 A1 | 10/2011 | Duggan | |
| 2011/0288877 A1 | 11/2011 | Ofek | |
| 2012/0004893 A1* | 1/2012 | Vaidyanathan | G06K 9/62 703/11 |
| 2012/0110016 A1 | 5/2012 | Phillips | |
| 2012/0123184 A1 | 5/2012 | Otto | |
| 2012/0265544 A1 | 10/2012 | Hwang | |
| 2012/0310899 A1* | 12/2012 | Wasserman | G06F 16/252 707/E17.127 |
| 2013/0096947 A1 | 4/2013 | Shah | |
| 2013/0246049 A1 | 9/2013 | Mirhaji | |
| 2014/0122117 A1 | 5/2014 | Masarie | |
| 2014/0244625 A1 | 8/2014 | Seghezzi | |
| 2014/0249761 A1 | 9/2014 | Carroll | |
| 2014/0278461 A1 | 9/2014 | Artz | |
| 2014/0280353 A1 | 9/2014 | Delany | |
| 2014/0330583 A1* | 11/2014 | Madhavan | G16B 50/20 705/3 |
| 2014/0365242 A1 | 12/2014 | Neff | |
| 2015/0006558 A1 | 1/2015 | Leighton | |
| 2015/0106125 A1 | 4/2015 | Farooq | |
| 2015/0178386 A1 | 6/2015 | Oberkampf | |
| 2015/0213194 A1 | 7/2015 | Wolf | |
| 2015/0324527 A1 | 11/2015 | Siegel | |
| 2015/0331909 A1 | 11/2015 | Sundquist | |
| 2016/0019666 A1 | 1/2016 | Amarasingham | |
| 2017/0046425 A1 | 2/2017 | Tonkin | |
| 2017/0109502 A1 | 4/2017 | Labkoff | |
| 2017/0177597 A1 | 6/2017 | Asimenos | |
| 2017/0177822 A1 | 6/2017 | Fogel | |
| 2017/0199965 A1 | 7/2017 | Dekel | |
| 2017/0237805 A1 | 8/2017 | Worley | |
| 2018/0046764 A1 | 2/2018 | Katwala | |
| 2018/0060523 A1 | 3/2018 | Farh | |
| 2018/0068083 A1 | 3/2018 | Cohen | |
| 2018/0085015 A1 | 3/2018 | Crowder | |
| 2018/0101584 A1 | 4/2018 | Pattnaik et al. | |
| 2018/0121618 A1 | 5/2018 | Smith | |
| 2018/0144003 A1 | 5/2018 | Formoso | |
| 2018/0311224 A1 | 11/2018 | Hedley | |
| 2018/0373844 A1 | 12/2018 | Ferrandez-Escamez | |
| 2019/0006048 A1* | 1/2019 | Gupta | G16H 20/10 |
| 2019/0050530 A1 | 2/2019 | De La Vega | |
| 2019/0057774 A1 | 2/2019 | Velez | |
| 2019/0080044 A1* | 3/2019 | Shini | C12Q 1/6881 |
| 2019/0108912 A1 | 4/2019 | Spurlock, III | |
| 2019/0206524 A1 | 7/2019 | Baldwin | |
| 2019/0214145 A1* | 7/2019 | Kurek | A61K 31/366 |
| 2020/0005461 A1 | 1/2020 | Tip | |
| 2020/0118644 A1 | 4/2020 | Khan | |
| 2020/0176098 A1 | 6/2020 | Lucas | |
| 2020/0219619 A1 | 7/2020 | Feczko | |

OTHER PUBLICATIONS

El-Sappagh et al., A proposed model for data warehouse ETL processes, May 8, 2011, Journal of King Saud University—Computer and Information Sciences 23 (Year: 2011).*
Rokach L., Maimon O., Decision Trees, 2005, Data Mining and Knowledge Discovery Handbook, pp. 165-192 (Year: 2005).
International Searching Authority. International Search Report and Written Opinion for application PCT/US2020/047704. dated Nov. 20, 2020.
Dnanexus. Working with UK Biobank: A Research Guide. Accessed online on Dec. 31, 2020. Available at https://web.archive.org/save/https://dna-nexus-prod-s3-assets-51tcpaqcp0pd.s3.amazonaws.com/images/files/DNAnexus_WhitePaper_Working-with-UKB-Data_2.pdf.
Caris Life Sciences. Code: Comprehensive Oncology Data Explorer. Slideshow May 2017. Accessed on Dec. 16, 2020 at https://www.karmanos.org/Uploads/Public/Documents/Karmanos/CODE%20slides_5.2017.pptx%20.
International Searching Authority. International Search Report and Written Opinion for application PCT/US2021/017517. dated Apr. 29, 2021. 11 pages.
The ASCO Post. 2018 ASCO: Impact Trial Matches Treatment to Genetic Changes in the Tumor to Improve Survival Across Multiple Cancer Types—The ASCO Post. Jun. 6, 2018 (2018). Available at: http://www.ascopost.com/News/58897.
Tomlins, S. A. et al. Recurrent fusion of TMPRSS2 and ETS transcription factor genes in prostate cancer. Science 310, 644-648 (2005).
Tsou, Ching-Huei et al. "Watson for Patient Record Analytics (aka Watson Emra)," IBM Research, Aug. 2017, 5 pages. Retrieved from Internet. URL: https://researcher.watson.ibm.com/researcher/view_group.php?id=7664.
Unger, J. M., et al. Systematic Review and Meta-Analysis of the Magnitude of Structural, Clinical, and Physician and Patient Barriers to Cancer Clinical Trial Participation. J. Natl. Inst. 111, 245-255 (2019).
Wang, Z. et al. Significance of the TMPRSS2:ERG gene fusion in prostate cancer. Mol. Med. Rep. 16, 5450-5458 (2017).
Wheler, J. J. et al. Cancer Therapy Directed by Comprehensive Genomic Profiling: A Single Center Study. Cancer Res. 76, 3690-3701 (2016).
Wilson, T. R., et al. Neuregulin-1—Mediated Autocrine Signaling Underlies Sensitivity to HER2 Kinase Inhibitors in a Subset of Human Cancers. Cancer Cell 20, 158-172 (2011).

(56) References Cited

OTHER PUBLICATIONS

Wu, Yonghui et al. "A Study of Neural Word Embeddings for Named Entity Recognition in Clinical Text," AMIA Annual Symp. Proc. 2015; Published online Nov. 5, 2015, pp. 1326-1333.

Yan, M. et al. HER2 expression status in diverse cancers: review of results from 37,992 patients. Cancer Metastasis Rev. 34, 157-64 (2015).

Yang, L. et al. NRG1-dependent activation of HER3 induces primary resistance to trastuzumab in HER2-overexpressing breast cancer cells. Int. J. Oncol. 51, 1553-1562 (2017).

Yonesaka, K. et al. Activation of ERBB2 Signaling Causes Resistance to the EGFR-Directed Therapeutic Antibody Cetuximab. Sci. Transl. Med. 3, 99ra86-99ra86 (2011).

Yong, W P, et al. "The role of pharmacogenetics in cancer therapeutics." British journal of clinical pharmacology 62.1 (2006): 35-46.

Yun, S. et al. Clinical significance of overexpression of NRG1 and its receptors, HER3 and HER4, in gastric cancer patients. Gastric Cancer 21, 225-236 (2018).

Zehir, A. et al. Mutational landscape of metastatic cancer revealed from prospective clinical sequencing of 10,000 patients. Nat. Med. 23, 703-713 (2017).

Zeng, et al., "Extracting principal diagnosis, co-morbidity and smoking status for asthma research: evaluation of a natural language processing system", BMC Medical Informatics and Decision Making 2006, 6:30, retrieved from the internet at: https://bmcmedinformdecismak.biomedcentral.com/articles/101186/1472-6947-6-30 on Dec. 3, 2019, 9 pages.

Zhang, Yuan et al. "Aspect-augmented Adversarial Networks for Domain Adaptation" sentiarXiv:1701.00188v2 [cs. CL], Sep. 25, 2017, 14 pages.

Bertsimas, D., et al. "Personalized diabetes management using electronic medical records." Diabetes care 40.2 (2017): 210-217.

Coutinho, A. D., et al. "Real-world treatment patterns and outcomes of patients with small cell lung cancer progressing after 2 lines of therapy." Lung Cancer 127 (2019): 53-58.

Dempster, A.P. et al. (1977). "Maximum Likelihood from Incomplete Data via the EM Algorithm". Journal of the Royal Statistical Society, Series B. 39 (1): 1-38.

Flaig, T. W., et al. "Treatment evolution for metastatic castration-resistant prostate cancer with recent introduction of novel agents: retrospective analysis of real-world data." Cancer Medicine 5.2 (2016): 182.

Gangul, R. Line of Therapy Analytics: A key to commercial drug success. Feb. 15, 2017. Available online https://www.saama.com/blog/line-therapy-analytics-key-commercial-drug-success/.

Malangone-Monaco, E., et al. "Prescribing patterns of oral antineoplastic therapies observed in the treatment of patients with advanced prostate cancer between 2012 and 2014: results of an oncology EMR analysis." Clinical therapeutics 38.8 (2016): 1817-1824.

Optum. Determining Lines of Therapy (LOT) in Oncology in Claims Databases. 2017. Available online at https://cdn-aem.optum.com/content/dam/optum3/optum/en/resources/white-papers/wf520768_guidelines-for-determining-lines-of-therapy.pdf.

Rajkumar, S. V., et al. "Guidelines for determination of the No. of prior lines of therapy in multiple myeloma." Blood, The Journal of the American Society of Hematology 126.7 (2015): 921-922.

Tsang, J-P. Deploying Machine Learning for Commercial Analytics. PMSA.net. Version accessed Dec. 15, 2018. Available online at https://web.archive.org/web/20181215152550/http://www.pmsa.net/jpmsa-vol06-article09.

"Algorithm Implementation/Strings/Levenshtein distance," Wikibooks, last edited on Jan. 5, 2019, 39 pages. Retrieved from Internet. URL: https://en.wikibooks.org/wiki/Algorithm_Implementation/Strings/Levenshtein_distance#Python.

"Amazon Textract—Easily extract text and data from virtually any document," Amazon, Nov. 28, 2018, 6 pages. Retrieved from Internet. URL: https://aws.amazon.com/textract/.

"CliNER," Text Machine Lab 2014, Nov. 10, 2017, 2 pages. Retrieved from Internet. URL: http://text-machine.cs.uml.edu/cliner/.

"Clinithink CLiX CNLP (Harness unstructured data to drive value across the healthcare continuum)," Clinithink Limited, 2015, 1 page. Retrieved from Internet. URL: http://clinithink.com/wp-content/uploads//2015/01/Clinithink-CLiX-CNLP-Sell-Sheet-US.pdf.

"Evernote Scannable on the App Store," Jun. 18, 2018, 3 pages. Retrieved from Internet. URL: https://itunes apple.com/us/app/evernote-scannable/id883338188?mt=8.

"I2E: The world's leading Text Mining platform," 2019 Linguamatics, Aug. 14, 2018, 5 pages. Retrieved from Internet. URL: https://www.linguamatics.com/products-services/about-i2e.

"PHP: levenshtein—Manual," latest comment dated in 2014, 32 pages. Retrieved from Internet. URL: http://www.php.net/levenshtein.

"Talk:Algorithm Implementation/Strings/Levenshtein distance," Wikibooks, last edited on Nov. 2, 2016, 2 pages. Retrieved from Internet. URL: https://en.wikibooks.org/wiki/Talk:Algorithm_Implementation/Strings/Levenshtein_distance#Bug_in_vectorized_(5th)_version.

"Why cTAKES? See the animation below for a sampling of cTAKES capabilities," The Apache Software Foundation, Apr. 25, 2017, 1 page. Retrieved from Internet. URL: http://ctakes.apache.org/whycTAKES.html.

AACR Project GENIE Consortium. AACR Project GENIE: Powering Precision Medicine through an International Consortium. Cancer Discov. 7, 818-831 (2017).

Alexandrov, L. B. et al. Signatures of mutational processes in human cancer. Nature 500, 415-421 (2013).

Allen, J. et al. Barriers to Patient Enrollment in Therapeutic Clinical Trials for Cancer: A Landscape Report. (2018).

Aronson, Alan "MetaMap—A Tool For Recognizing UMLS Concepts in Text," Jan. 11, 2019, 2 pages. Retrieved from Internet. URL: https://metamap.nlm.nih.gov/.

Ayers, M. et al. IFN-?-related mRNA profile predicts clinical response to PD-1 blockade. J. Clin. Invest. 127, 2930-2940 (2017).

Balatero, David (dbalatero/levenshtein-ffi) "Fast string edit distance computation, using the Damerau-Levenshtein algorithm," GitHub, Inc., latest comment dated on Aug. 10, 2014, 2 pages. Retrieved from Internet. URL: https://github.com/dbalatero/levenshtein-ffi.

Beaubier, N. et al. Clinical Validation of the Tempus xT Next-Generation Sequencing Targeted Oncology Assay. Oncotarget 10, 2384-2396 (2019).

Chae, Y. K. et al. Association of tumor mutational burden with DNA repair mutations and response to anti-PD-1/PD-L1 therapy in non-small cell lung cancer. Clin. Lung Cancer (2018). doi:10.1016/J.CLLC.2018.09.008.

Chatterjee, P. et al. The TMPRSS2-ERG Gene Fusion Blocks XRCC4-Mediated Nonhomologous End-Joining Repair and Radiosensitizes Prostate Cancer Cells to PARP Inhibition. Mol. Cancer Ther. 14, 1896-1906 (2015).

Chen, Huizhong et al. "Robust Text Detection in Natural Images With Edge-Enhanced Maximally Stable Extremal Regions," 2011 18th IEEE International Conference on Image Processing, Sep. 11-14, 2011, 4 pages.

Choi, Edward et al. "Coarse-to-Fine Question Answering for Long Documents," Proceedings of the 55th Annual Meeting of the Association for Computational Linguistics, Vancouver, Canada, Jul. 30-Aug. 4, 2017, pp. 209-220.

Choi, Edward et al. "Doctor AI: Predicting Clinical Events via Recurrent Neural Networks," Proceedings of Machine Learning for Healthcare 2016, JMLR W&C Track vol. 56, 2016, pp. 1-18.

Collobert, Ronan et al. "Natural Language Processing (Almost) from Scratch," Journal of Machine Learning Research 12, (2011) pp. 2493-2537.

Conneau, Alexis et al. "Very Deep Convolutional Networks for Text Classification," arXiv: 1606.01781 [cs.CL], Jan. 27, 2017, 10 pages.

Conway, J. R., et al. UpSetR: an R package for the visualization of intersecting sets and their properties. Bioinformatics 33, 2938-2940 (2017).

Cristescu, R. et al. Pan-tumor genomic biomarkers for PD-1 checkpoint blockade—based immunotherapy. Science 362, eaar3593 (2018).

(56) References Cited

OTHER PUBLICATIONS

Darvin, P., et al. Immune checkpoint inhibitors: recent progress and potential biomarkers. Exp. Mol. Med. 50, 165 (2018).
Das, Rajarshi et al. "Chains of Reasoning over Entities, Relations, and Text using Recurrent Neural Networks," Proceedings of the 15th Conference of the European Chapter of the Association for Computational Linguistics: vol. 1, Valencia, Spain, Apr. 3-7, 2017, pp. 132-141.
De Bruijn, Berry et al. "Machine-learned solutions for three stages of clinical information extraction: the state of the art at i2b2 2010," 18 J. Am. Med. Inform. Assoc. 2011, May 12, 2011, pp. 557-562.
Desrichard, A., et al. Cancer Neoantigens and Applications for Immunotherapy. (2016). doi:10.1158/1078-0432. CCR-14-3175.
Dhir, M. et al. Impact of genomic profiling on the treatment and outcomes of patients with advanced gastrointestinal malignancies. Cancer Med. 6, 195-206 (2017).
Dienstmann, R. et al. Standardized decision support in next generation sequencing reports of somatic cancer variants. Mol. Oncol. 8, 859-873 (2014).
Dienstmann, R., et al. "Database of genomic biomarkers for cancer drugs and clinical targetability in solid tumors." Cancer discovery 5.2 (2015): 118-123.
Dobin, A. et al. STAR: ultrafast universal RNA-seq aligner. Bioinformatics 29, 15-21 (2013).
Dozat, Timothy et al. "Deep Biaffine Attention for Neural Dependency Parsing," Published as a conference paper at ICLR2017, arXiv:1611.01734 [cs.CL], Mar. 10, 2017, pp. 1-8.
Faust, G. G. et al. SAMBLASTER: fast duplicate marking and structural variant read extraction. Bioinformatics 30, 2503-2505 (2014).
Fernandes, G. et al. Next-generation Sequencing-based genomic profiling: Fostering innovation in cancer care? Clinics 72, 588-594 (2017).
Finan, C. et al. The druggable genome and support for target identification and validation in drug development. Sci. Transl. Med. 9, eaag1166 (2017).
Forbes, S. A. et al. COSMIC: somatic cancer genetics at high-resolution. Nucleic Acids Res. 45, D777-D783 (2017).
Genthial, Guillaum "Sequence Tagging with Tensorflow (bi-LSTM + CRF with character embeddings for NER and POS)," Guillaume Genthial blog, Apr. 5, 2017, 23 pages.
Goldman, M. et al. The UCSC Xena platform for public and private cancer genomics data visualization and interpretation. bioRxiv 326470 (2019). doi:10.1101/326470.
Gong, J. et al. Value-based genomics. Oncotarget 9, 15792-15815 (2018).
Goodman, A. M. et al. Tumor Mutational Burden as an Independent Predictor of Response to Immunotherapy in Diverse Cancers. MoL Cancer Ther. 16, 2598-2608 (2017).
Griffith, M. et al. CIViC is a community knowledgebase for expert crowdsourcing the clinical interpretation of variants in cancer. Nat. Genet. 49, 170-174 (2017).
Han, M.-E. et al. Overexpression of NRG1 promotes progression of gastric cancer by regulating the self-renewal of cancer stem cells. J. Gastroenterol. 50, 645-656 (2015).
Hartmaier, R. J. et al. High-Throughput Genomic Profiling of Adult Solid Tumors Reveals Novel Insights into Cancer Pathogenesis. Cancer Res. 77, 2464-2475 (2017).
He, Dafang et al. "Multi-scale Multi-task FCN for Semantic p. Segmentation and Table Detection," IEEE, 2017 14th IAPR International Conference on Document Analysis and Recognition, Nov. 9-15, 2017, pp. 254-261.
He, Luheng et al. "Deep Semantic Role Labeling: WhatWorks and What's Next" Proceedings of the 55th Annual Meeting of the Association for Computational Linguistics, Vancouver, Canada, Jul. 30-Aug. 4, 2017, pp. 473-483.
Hegde, G. V. et al. Blocking NRG1 and Other Ligand-Mediated Her4 Signaling Enhances the Magnitude and Duration of the Chemotherapeutic Response of Non-Small Cell Lung Cancer. Sci. Transl. Med. 5, 171ra18-171ra18 (2013).
Institute of Medicine of the National Academies. Clinical Trials in Cancer. Chapter 6 in Transforming Clinical Research in the United States: Challenges and Opportunities: Workshop Summary (ed. Institute of Medicine (US) Forum on Drug Discovery, Development, and T.) (National Academies Press, 2010).
International Searching Authority, International Search Report and Written Opinion for application PCT/US2019/056713 dated Feb. 27, 2020.
International Searching Authority, International Search Report and Written Opinion for application PCT/US2019/064329. dated Apr. 1, 2020.
Kavasidis, I. et al. "A Saliency-based Convolutional Neural Network for Table and Chart Detection in Digitized Documents," Submitted to IEEE Transactions on Multimedia, Apr. 17, 2018, pp. 1-13.
Kim, Youngjun et al. "A Study of Concept Extraction Across Different Types of Clinical Notes," AMIA Annu Symp Proc. 2015; Nov. 5, 2015, pp. 737-746.
Lafferty, John et al. "Conditional Random Fields: Probabilistic Models for Segmenting and Labeling Sequence Data," Proceedings of the 18th International Conference on Machine Learning 2001 (ICML 2001), Jun. 28, 2001, pp. 282-289.
Lample, Guillaume et al. "Neural Architectures for Named Entity Recognition," Association for Computational Linguistics, Proceedings of NAACL-HLT 2016, San Diego, California, Jun. 12-17, 2016, pp. 260-270.
Lang, Francois-Michel et al. "Increasing UMLS Coverage and Reducing Ambiguity via Automated Creation of Synonymous Terms: First Steps toward Filling UMLS Synonymy Gaps," Semantic Scholar, 2017, pp. 1-26.
Laserson, Jonathan et al. "TextRay: Mining Clinical Reports to Gain a Broad Understanding of Chest X-rays," arXiv:1806.02121 [cs.CV], Jun. 6, 2018, 13 pages.
Lau, D., et al. RNA Sequencing of the Tumor Microenvironment in Precision Cancer Immunotherapy. Trends in Cancer 5, 149-156 (2019).
Lawrence, M. S. et al. Mutational heterogeneity in cancer and the search for new cancer-associated genes. Nature 499, 214-218 (2013).
Layer, R. M., et al. LUMPY: a probabilistic framework for structural variant discovery. Genome Biol. 15, R84 (2014).
Le, D. T. et al. Mismatch repair deficiency predicts response of solid tumors to PD-1 blockade. Science 357, 409-413 (2017).
Lee, Kenton et al. "End-to-end Neural Coreference Resolution," arXiv:1707.07045 [cs.CL], Dec. 15, 2017, 10 pages.
Lei, Tao et al. "Rationalizing Neural Predictions," arXiv:1606.04155 [cs.CL], Nov. 2, 2016, 11 pages.
Lek, M. et al. Analysis of protein-coding genetic variation in 60,706 humans. Nature 536, 285-291 (2016).
Li, H. et al. Fast and accurate short read alignment with Burrows-Wheeler transform. Bioinformatics 25, 1754-1760 (2009).
Li, M. M. et al. Standards and Guidelines for the Interpretation and Reporting of Sequence Variants in Cancer. J. Mol. Diagnostics 19, 4-23 (2017).
Liao, Y., et al. featurecounts: an efficient general purpose program for assigning sequence reads to genomic features. Bioinformatics 30, 923-930 (2014).
Ling, Yuan et al. "Learning to Diagnose: Assimilating Clinical Narratives using Deep Reinforcement Learning," Proceedings of the The 8th International Joint Conference on Natural Language Processing, Taipei, Taiwan, Nov. 27-Dec. 1, 2017, pp. 895-905.
Lipton, Zachary et al. "Learning to Diagnose with LSTM Recurrent Neural Networks," ICLR 2016, arXiv:1511.03677 [cs.LG], pp. 1-18.
Lonsdale, J. et al. The Genotype-Tissue Expression (GTEx) project. Nat. Genet. 45, 580-585 (2013).
Luraghi, P. et al. A Molecularly Annotated Model of Patient-Derived Colon Cancer Stem-Like Cells to Assess Genetic and Nongenetic Mechanisms of Resistance to Anti-EGFR Therapy Clin. Cancer Res 24, 807-820 (2018).
Ma, Xuezhe et al. "End-to-end Sequence Labeling via Bi-directional LSTM-CNNs-CRF," arXiv:1603.01354v5 [cs.LG], May 29, 2016, 12 pages.

(56) References Cited

OTHER PUBLICATIONS

Mackenzie, Andrei (andrei-m/levenshtein.js) "Levenshtein distance between two given strings implemented in JavaScript and usable as a Node.js module," GitHub, Inc., latest comment dated on Feb. 2, 2018, 9 pages. Retrieved from Internet. URL: https://gist.github.com/andrei-m/982927.
Madhavan, S. et al. ClinGen Cancer Somatic Working Group—standardizing and democratizing access to cancer molecular diagnostic data to drive translational research. Pac. Symp. Biocomput. 23, 247-258 (2018).
Maxwell, K. N. et al. BRCA locus-specific loss of heterozygosity in germline BRCA1 and BRCA2 carriers. Nat. Commun. 8, 319 (2017).
Mendell, J. et al. Clinical Translation and Validation of a Predictive Biomarker for Patritumab, an Anti-human Epidermal Growth Factor Receptor 3 (HER3) Monoclonal Antibody, in Patients With Advanced Non-small Cell Lung Cancer. EBioMedicine 2, 264-271 (2015).
Mihalcea, Rada et al. "Part IV Graph-Based Natural Language Processing" excerpted from a book "Graphbased Natural Language Processing and Information Retrieval," Cambridge University Press, First published 2011 (Reprinted 2012), 63 pages.
Miller, A. et al. High somatic mutation and neoantigen burden are correlated with decreased progression-free survival in multiple myeloma. Blood Cancer J. 7, e612 (2017).
Mysore, Sheshera S. "Segmentation of Non-text Objects with Connected Operators" Msheshera, May 21, 2017, 2 pages. Retrieved from Internet URL: http://msheshera.github.io/non-text-segment-connected-operators.html.
Narasimhan, Karthik et al. "Improving Information Extraction by Acquiring External Evidence with Reinforcement Learning," arXiv: 1603.07954v3 [cs.CL], Sep. 27, 2016, 12 pages.
Neelakantan, Arvind et al. "Learning Dictionaries for Named Entity Recognition using Minimal Supervision," Proceedings of the 14th Conference of the European Chapter of the Association for Computational Linguistics, Gothenburg, Sweden, Apr. 26-30, 2014, pp. 452-461.
Newman, A. M. et al. Robust enumeration of cell subsets from tissue expression profiles. Nat. Methods 12,453-7 (2015).
Newton, Y. et al. TumorMap: Exploring the Molecular Similarities of Cancer Samples in an Interactive Portal. Cancer Res. 77, e111-e114 (2017).
Peng, L. et al. Large-scale RNA-Seq Transcriptome Analysis of 4043 Cancers and 548 Normal Tissue Controls across 12 TCGA Cancer Types. Sci. Rep. 5, 13413 (2015).
Peters, Matthew. E. et al. "Semi-supervised sequence tagging with bidirectional language models," arXiv:1705.00108v1 [cs.CL], Apr. 29, 2017, 10 pages.
Prakash, Aaditya et al. "Condensed Memory Networks for Clinical Diagnostic Inferencing," arXiv:1612.01848v2 [cs.CL], Jan. 3, 2017, 8 pages.
Radovich, M. et al. Clinical benefit of a precision medicine based approach for guiding treatment of refractory cancers. Oncotarget 7, 56491-56500 (2016).
Reiman, D. et al. Integrating RNA expression and visual features for immune infiltrate prediction. Biocomputing 2019, 284-295 (2018).
Richards, S. et al. Standards and guidelines for the interpretation of sequence variants: a joint consensus recommendation of the American College of Medical Genetics and Genomics and the Association for Molecular Pathology. Genet. Med. 17, 405-24 (2015).
Robinson, D. R. et al. Integrative clinical genomics of metastatic cancer. Nature 548, 297-303 (2017).
Rooney, M. S. et al. Molecular and Genetic Properties of Tumors Associated with Local Immune Cytolytic Activity. Cell 160, 48-61 (2015).
Rosenthal, R., et al. deconstructSigs: delineating mutational processes in single tumors distinguishes DNA repair deficiencies and patterns of carcinoma evolution. Genome Biol. 17, (2016).
Roufas, C. et al. The Expression and Prognostic Impact of Immune Cytolytic Activity-Related Markers in Human Malignancies: A Comprehensive Meta-analysis. Front. Oncol. 8, 27 (2018).
Sager, Naomi et al. "Natural Language Processing and the Representation of Clinical Data," Journal of the American Medical Informatics Association, vol. 1, No. 2, Mar./Apr. 1994, pp. 142-160.
Sambyal, Nitigya et al. "Automatic Text Extraction and Character Segmentation Using Maximally Stable Extremal Regions," arXiv:1608.03374 [cs.CV], Aug. 11, 2016, 6 pages.
Savova, et al., "Mayo clinical Text Analysis and Knowledge Extraction System (cTAKES): architecture, component evaluation and applications", J Am Med Inform Assoc 2010; 17: 507-513., retrieved from the internet at: https://academic.oup.com/jamia/article/17/5/507/830823, on Dec. 3, 2019, 7 pages.
Sheng, Q. et al. An Activated ErbB3/NRG1 Autocrine Loop Supports In Vivo Proliferation in Ovarian Cancer Cells. Cancer Cell 17, 298-310 (2010).
Solomon, B., et al. ALK Gene Rearrangements: A New Therapeutic Target in a Molecularly Defined Subset of Non-small Cell Lung Cancer. J. Thorac. Oncol. 4, 1450-1454 (2009).
Szolek, A. et al. OptiType: precision HLA typing from next-generation sequencing data. Bioinformatics 30, 3310-3316 (2014).
Teer, J. K. et al. Evaluating somatic tumor mutation detection without matched normal samples. Hum. Genomics 11, 22 (2017).
Partial Supplementary European Search Report issued by the European Patent Office in application EP 19873536.7 dated Jun. 28, 2022.
Haarbrandt et al., "HiGHmed An Open Platform Approach to Enhance Care and Research Across Institutional Boundaries," 57 Methods of Information in Medicine S 01, pp. e66-e81 (Jul. 1, 2018).
Dean et al., "Engineering Scalable, Secure, Multi-Tenant Cloud for Heathcare Data," 2017 IEEE World Congress on Services, IEEE, pp. 21-29 (Jun. 25, 2017).

* cited by examiner

Diagnosis

ICD-10 [          ]

Site
[Pancreatic ▼]

Date of diagnosis
[MM ▼] [DD ▼] [2016 ▼]

Date of recurrence
[MM ▼] [DD ▼] [YYYY ▼]

∨ Tumor Charecterization
Histology
[Adenocarcinoma ▼]

Date of charecterization
[MM ▼] [DD ▼] [2016 ▼]

---

Patient Progress Note 2016

Dwayne Holder – DOB: 08/08/1971

Progress Notes
DTP Hematology/Oncology Follow-up Office Visit

Diagnosis: Pancreatic adenocarcinoma, now metastatic with liver mets
Current therapy: C4D15 on ABI-0007-ST-001 study.
Gem/Abraxane/Nivolumab
Prior therapy: Whipple procedure Oncologic Hx:
- diagnosed with T3N1 pancreatic adenocarcinoma in 2016.
- He initially presented with constipation and went to ER with cecal volvulus which re parium study. CI showed malrotation of the colon and his cecum. Abnormal spot wa pancreas at this time and he was referred for further evaluation. EUS with a 3 cm le in the pancreastic head which was positive for adenocarcinoma. Imaging of the abd prior to surgery demonstrated a pancreatic lesion in the head of the pancreas meas defined hypotensity in the right hepatic lobe that was enlarged and suspicious for m Presented at tumor board and it was unclera if it truly was a metastatic foci.
- Underwent whipple procedure on with T3N1Mx disease, and positive margins at th

Fig. 9

APPROVED THERAPIES

 Erlotinib

| GENE | VARIANT | INDICATION | EVIDENCE | ASSOCIATION | DRUG DETAILS |
|---|---|---|---|---|---|
| KRAS | Exon 2 | Pancreatic | PMID20921471 | Neutral | Exon 2 mutations have been associated with reduces response rates or resistance to EGFR inhibitors in non-small cell lung and colorectal cancer. The NICCN guidelines for colorectal cancer contain recommendations that the targeted therapies cetuximab and panitumumab should only be used in the context of wild type KRAS. |

 Palbociclib
off-label

| GENE | VARIANT | INDICATION | EVIDENCE | ASSOCIATION | DRUG DETAILS |
|---|---|---|---|---|---|
| COKN2A | Loss Of Function | ovarian cancer | PMID:21278246 | Response | Palbociclib is a drug for the treatment of ER-positive and HER2-negative breast cancer developed by Pfizer. It is a selective inhibitor of the cyclin-dependent kinases CDK4 and CDK6 |

| PERTINENT GENES | |
|---|---|
| Gene | |
| TP53 | ⊖ no significant alterations found |
| SMAD4 | ⊖ no significant alterations found |
| KRAS | ✓ p.G12V |

| RELEVANT FINDINGS | | |
|---|---|---|
| - SOMATIC | | THERAPIES |
| KRAS | ○ P.G12V | Gemcitabine+Erlotnib<br>Gemcitabine+Trametinib<br>Trametinib<br>+6 more |
| CDKN2A | ○ P.A78fs | CDK4/6 inhibitors<br>Alvocidib<br>Palbociclib<br>+7 more |

Fig. 18a

- GERMLINE

BRCA2    )( p.S611*

TYMS1    )( p.Y3095*

PHARMACOGENETICS

| GENE | DRUG | ALTERATION | EVIDENCE | EFFECT |
|---|---|---|---|---|
| TPMT | Gemcitabine+ Erlotinib | Germline Positional | Consensus PMD 23652803 | Adverse Event |

PROGNOSTIC INDICATORS

| GENE | DRUG | ALTERATION | EVIDENCE | EFFECT |
|---|---|---|---|---|
| BRCA2 | Gemcitabine+ Erlotinib | Germline Positional | Consensus PMD 22274685 | Better Outcome |

OTHER VARIANTS

| | |
|---|---|
| )( Germline: Uncertain significance | 5 |
| )( Germline: Benign or likely benign | 3 |
| o Somatic: Uncertain significance | 2 |
| o Somatic: Benign or likely benign | 3 |
| [] Fusion | 5 |
| = Copy Number Variation | 1 |
| ≎ RNA Expression | 2 |

Fig. 18b

| Exemplary Oncology Panel - 1711 Genes |||||||||| 
|---|---|---|---|---|---|---|---|---|---|
| No. | Symbol | No. | Symbol | No. | Symbol | No. | Symbol | No. | Symbol |
| 1 | AATK | 39 | ALK | 77 | ATAD2 | 115 | BCLAF1 | 153 | BTK |
| 2 | ABCA1 | 40 | ALKBH6 | 78 | ATAD2B | 116 | BCOR | 154 | BTRC |
| 3 | ABCB1 | 41 | ALOX12B | 79 | ATF1 | 117 | BCORL1 | 155 | BUB1 |
| 4 | ABCB11 | 42 | ALOX5 | 80 | ATM | 118 | BCR | 156 | BUB1B |
| 5 | ABCB4 | 43 | AMER1 | 81 | ATR | 119 | BDNF | 157 | BUB3 |
| 6 | ABCC1 | 44 | APC | 82 | ATRX | 120 | BID | 158 | CACNA1C |
| 7 | ABCC2 | 45 | APEX1 | 83 | AURKA | 121 | BIRC2 | 159 | CACNA1S |
| 8 | ABCG1 | 46 | APH1A | 84 | AURKB | 122 | BIRC3 | 160 | CACNB2 |
| 9 | ABCG2 | 47 | APOA1 | 85 | AURKC | 123 | BIRC5 | 161 | CADM2 |
| 10 | ABI1 | 48 | APOB | 86 | AXIN1 | 124 | BIRC6 | 162 | CALR |
| 11 | ABL1 | 49 | AR | 87 | AXIN2 | 125 | BLK | 163 | CAMTA1 |
| 12 | ABL2 | 50 | ARAF | 88 | AXL | 126 | BLM | 164 | CAPRIN2 |
| 13 | ACE | 51 | AREG | 89 | B2M | 127 | BLNK | 165 | CARD10 |
| 14 | ACSL6 | 52 | ARFRP1 | 90 | BABAM1 | 128 | BMI1 | 166 | CARD11 |
| 15 | ACTA2 | 53 | ARHGAP10 | 91 | BACH1 | 129 | BMPR1A | 167 | CARD6 |
| 16 | ACTC1 | 54 | ARHGAP26 | 92 | BACH2 | 130 | BMPR1B | 168 | CARD8 |
| 17 | ACVR1 | 55 | ARHGAP35 | 93 | BAG4 | 131 | BMX | 169 | CARM1 |
| 18 | ACVR1B | 56 | ARID1A | 94 | BAP1 | 132 | BPTF | 170 | CASC11 |
| 19 | ACVR2A | 57 | ARID1B | 95 | BARD1 | 133 | BRAF | 171 | CASP8 |
| 20 | ACVR2B | 58 | ARID2 | 96 | BAX | 134 | BRCA1 | 172 | CBFA2T2 |
| 21 | ADAM17 | 59 | ARID5B | 97 | BAZ1A | 135 | BRCA2 | 173 | CBFA2T3 |
| 22 | ADAMTS20 | 60 | ARNT | 98 | BAZ1B | 136 | BRD1 | 174 | CBFB |
| 23 | ADGRA2 | 61 | ARNT2 | 99 | BAZ2A | 137 | BRD2 | 175 | CBL |
| 24 | ADGRB3 | 62 | ARPC1A | 100 | BAZ2B | 138 | BRD3 | 176 | CBLB |
| 25 | ADGRL2 | 63 | ARPC1B | 101 | BBC3 | 139 | BRD4 | 177 | CBLC |
| 26 | ADGRL3 | 64 | ARTN | 102 | BCAR3 | 140 | BRD7 | 178 | CBX1 |
| 27 | ADRB1 | 65 | ARX | 103 | BCL10 | 141 | BRD8 | 179 | CBX2 |
| 28 | ADRB2 | 66 | ASCL1 | 104 | BCL11A | 142 | BRD9 | 180 | CBX3 |
| 29 | AFF1 | 67 | ASCL2 | 105 | BCL11B | 143 | BRDT | 181 | CBX4 |
| 30 | AFF2 | 68 | ASCL3 | 106 | BCL2 | 144 | BRIP1 | 182 | CBX5 |
| 31 | AFF3 | 69 | ASCL4 | 107 | BCL2A1 | 145 | BRPF1 | 183 | CBX6 |
| 32 | AHR | 70 | ASCL5 | 108 | BCL2L1 | 146 | BRPF3 | 184 | CBX7 |
| 33 | AIP | 71 | ASH1L | 109 | BCL2L11 | 147 | BRWD1 | 185 | CBX8 |
| 34 | AJUBA | 72 | ASH2L | 110 | BCL2L2 | 148 | BRWD3 | 186 | CCDC6 |
| 35 | AKAP9 | 73 | ASPSCR1 | 111 | BCL3 | 149 | BTC | 187 | CCNB3 |
| 36 | AKT1 | 74 | ASXL1 | 112 | BCL6 | 150 | BTG1 | 188 | CCND1 |
| 37 | AKT2 | 75 | ASXL2 | 113 | BCL7A | 151 | BTG2 | 189 | CCND2 |
| 38 | AKT3 | 76 | ASXL3 | 114 | BCL9 | 152 | BTG3 | 190 | CCND3 |

Fig. 22a

| | Exemplary Oncology Panel - 1711 Genes | | | | | | | | |
|---|---|---|---|---|---|---|---|---|---|
| No. | Symbol | No. | Symbol | No. | Symbol | No. | Symbol | No. | Symbol |
| 38 | AKT3 | 76 | ASXL3 | 114 | BCL9 | 152 | BTG3 | 190 | CCND3 |
| 191 | CCNE1 | 229 | CDK14 | 267 | CHD4 | 305 | CSF2RA | 343 | DAXX |
| 192 | CCNE2 | 230 | CDK15 | 268 | CHD5 | 306 | CSF2RB | 344 | DBH |
| 193 | CCNL1 | 231 | CDK16 | 269 | CHD6 | 307 | CSF3R | 345 | DCC |
| 194 | CD1D | 232 | CDK17 | 270 | CHD7 | 308 | CSK | 346 | DCUN1D1 |
| 195 | CD22 | 233 | CDK18 | 271 | CHD9 | 309 | CSNK1D | 347 | DCUN1D2 |
| 196 | CD274 | 234 | CDK19 | 272 | CHEK1 | 310 | CSNK1E | 348 | DDB2 |
| 197 | CD276 | 235 | CDK2 | 273 | CHEK2 | 311 | CTCF | 349 | DDIT3 |
| 198 | CD28 | 236 | CDK20 | 274 | CHIC1 | 312 | CTCFL | 350 | DDR1 |
| 199 | CD40 | 237 | CDK3 | 275 | CHIC2 | 313 | CTLA4 | 351 | DDR2 |
| 200 | CD40LG | 238 | CDK4 | 276 | CHUK | 314 | CTNNA1 | 352 | DDX3X |
| 201 | CD44 | 239 | CDK5 | 277 | CIC | 315 | CTNNA2 | 353 | DDX5 |
| 202 | CD70 | 240 | CDK6 | 278 | CIITA | 316 | CTNNA3 | 354 | DDX6 |
| 203 | CD79A | 241 | CDK7 | 279 | CKS1B | 317 | CTNNB1 | 355 | DEK |
| 204 | CD79B | 242 | CDK8 | 280 | CKS2 | 318 | CTNND1 | 356 | DHFR |
| 205 | CD80 | 243 | CDK9 | 281 | CLIP1 | 319 | CTSD | 357 | DHH |
| 206 | CD86 | 244 | CDKN1A | 282 | CMPK1 | 320 | CTSL | 358 | DIAPH1 |
| 207 | CDC14A | 245 | CDKN1B | 283 | CNKSR1 | 321 | CTSS | 359 | DIAPH2 |
| 208 | CDC20 | 246 | CDKN1C | 284 | CNOT3 | 322 | CUL3 | 360 | DIAPH3 |
| 209 | CDC25A | 247 | CDKN2A | 285 | CNTFR | 323 | CUL4A | 361 | DICER1 |
| 210 | CDC25B | 248 | CDKN2B | 286 | COL3A1 | 324 | CUL4B | 362 | DIRAS3 |
| 211 | CDC25C | 249 | CDKN2C | 287 | COMT | 325 | CUX1 | 363 | DIS3 |
| 212 | CDC42 | 250 | CDKN3 | 288 | COPS3 | 326 | CYLD | 364 | DKC1 |
| 213 | CDC6 | 251 | CDX1 | 289 | CRBN | 327 | CYP17A1 | 365 | DMXL1 |
| 214 | CDC73 | 252 | CDX2 | 290 | CREB1 | 328 | CYP1A2 | 366 | DNM2 |
| 215 | CDH1 | 253 | CEBPA | 291 | CREB3L1 | 329 | CYP21A2 | 367 | DNMT1 |
| 216 | CDH10 | 254 | CEBPB | 292 | CREB3L2 | 330 | CYP2A6 | 368 | DNMT3A |
| 217 | CDH11 | 255 | CEBPD | 293 | CREB3L4 | 331 | CYP2B6 | 369 | DNMT3B |
| 218 | CDH2 | 256 | CEBPE | 294 | CREBBP | 332 | CYP2C19 | 370 | DNMT3L |
| 219 | CDH20 | 257 | CEBPG | 295 | CREM | 333 | CYP2C8 | 371 | DOCK2 |
| 220 | CDH3 | 258 | CEBPZ | 296 | CRHR1 | 334 | CYP2C9 | 372 | DOT1L |
| 221 | CDH5 | 259 | CECR2 | 297 | CRK | 335 | CYP2D6 | 373 | DPYD |
| 222 | CDH7 | 260 | CENPE | 298 | CRKL | 336 | CYP2J2 | 374 | DRD1 |
| 223 | CDK1 | 261 | CES1 | 299 | CRLF2 | 337 | CYP2R1 | 375 | DRD2 |
| 224 | CDK10 | 262 | CES2 | 300 | CRTC1 | 338 | CYP3A4 | 376 | DSC2 |
| 225 | CDK11A | 263 | CHD1 | 301 | CRTC2 | 339 | CYP3A5 | 377 | DSG2 |
| 226 | CDK11B | 264 | CHD1L | 302 | CRTC3 | 340 | CYP4F2 | 378 | DSP |
| 227 | CDK12 | 265 | CHD2 | 303 | CSF1 | 341 | DACH1 | 379 | DUSP22 |
| 228 | CDK13 | 266 | CHD3 | 304 | CSF1R | 342 | DACH2 | 380 | DVL1 |

Fig. 22b

| Exemplary Oncology Panel - 1711 Genes | | | | | | | | | |
|---|---|---|---|---|---|---|---|---|---|
| No. | Symbol | No. | Symbol | No. | Symbol | No. | Symbol | No. | Symbol |
| 191 | CCNE1 | 229 | CDK14 | 267 | CHD4 | 305 | CSF2RA | 343 | DAXX |
| 192 | CCNE2 | 230 | CDK15 | 268 | CHD5 | 306 | CSF2RB | 344 | DBH |
| 193 | CCNL1 | 231 | CDK16 | 269 | CHD6 | 307 | CSF3R | 345 | DCC |
| 194 | CD1D | 232 | CDK17 | 270 | CHD7 | 308 | CSK | 346 | DCUN1D1 |
| 195 | CD22 | 233 | CDK18 | 271 | CHD9 | 309 | CSNK1D | 347 | DCUN1D2 |
| 196 | CD274 | 234 | CDK19 | 272 | CHEK1 | 310 | CSNK1E | 348 | DDB2 |
| 197 | CD276 | 235 | CDK2 | 273 | CHEK2 | 311 | CTCF | 349 | DDIT3 |
| 198 | CD28 | 236 | CDK20 | 274 | CHIC1 | 312 | CTCFL | 350 | DDR1 |
| 199 | CD40 | 237 | CDK3 | 275 | CHIC2 | 313 | CTLA4 | 351 | DDR2 |
| 200 | CD40LG | 238 | CDK4 | 276 | CHUK | 314 | CTNNA1 | 352 | DDX3X |
| 201 | CD44 | 239 | CDK5 | 277 | CIC | 315 | CTNNA2 | 353 | DDX5 |
| 202 | CD70 | 240 | CDK6 | 278 | CIITA | 316 | CTNNA3 | 354 | DDX6 |
| 203 | CD79A | 241 | CDK7 | 279 | CKS1B | 317 | CTNNB1 | 355 | DEK |
| 204 | CD79B | 242 | CDK8 | 280 | CKS2 | 318 | CTNND1 | 356 | DHFR |
| 205 | CD80 | 243 | CDK9 | 281 | CLIP1 | 319 | CTSD | 357 | DHH |
| 206 | CD86 | 244 | CDKN1A | 282 | CMPK1 | 320 | CTSL | 358 | DIAPH1 |
| 207 | CDC14A | 245 | CDKN1B | 283 | CNKSR1 | 321 | CTSS | 359 | DIAPH2 |
| 208 | CDC20 | 246 | CDKN1C | 284 | CNOT3 | 322 | CUL3 | 360 | DIAPH3 |
| 209 | CDC25A | 247 | CDKN2A | 285 | CNTFR | 323 | CUL4A | 361 | DICER1 |
| 210 | CDC25B | 248 | CDKN2B | 286 | COL3A1 | 324 | CUL4B | 362 | DIRAS3 |
| 211 | CDC25C | 249 | CDKN2C | 287 | COMT | 325 | CUX1 | 363 | DIS3 |
| 212 | CDC42 | 250 | CDKN3 | 288 | COPS3 | 326 | CYLD | 364 | DKC1 |
| 213 | CDC6 | 251 | CDX1 | 289 | CRBN | 327 | CYP17A1 | 365 | DMXL1 |
| 214 | CDC73 | 252 | CDX2 | 290 | CREB1 | 328 | CYP1A2 | 366 | DNM2 |
| 215 | CDH1 | 253 | CEBPA | 291 | CREB3L1 | 329 | CYP21A2 | 367 | DNMT1 |
| 216 | CDH10 | 254 | CEBPB | 292 | CREB3L2 | 330 | CYP2A6 | 368 | DNMT3A |
| 217 | CDH11 | 255 | CEBPD | 293 | CREB3L4 | 331 | CYP2B6 | 369 | DNMT3B |
| 218 | CDH2 | 256 | CEBPE | 294 | CREBBP | 332 | CYP2C19 | 370 | DNMT3L |
| 219 | CDH20 | 257 | CEBPG | 295 | CREM | 333 | CYP2C8 | 371 | DOCK2 |
| 220 | CDH3 | 258 | CEBPZ | 296 | CRHR1 | 334 | CYP2C9 | 372 | DOT1L |
| 221 | CDH5 | 259 | CECR2 | 297 | CRK | 335 | CYP2D6 | 373 | DPYD |
| 222 | CDH7 | 260 | CENPE | 298 | CRKL | 336 | CYP2J2 | 374 | DRD1 |
| 223 | CDK1 | 261 | CES1 | 299 | CRLF2 | 337 | CYP2R1 | 375 | DRD2 |
| 224 | CDK10 | 262 | CES2 | 300 | CRTC1 | 338 | CYP3A4 | 376 | DSC2 |
| 225 | CDK11A | 263 | CHD1 | 301 | CRTC2 | 339 | CYP3A5 | 377 | DSG2 |
| 226 | CDK11B | 264 | CHD1L | 302 | CRTC3 | 340 | CYP4F2 | 378 | DSP |
| 227 | CDK12 | 265 | CHD2 | 303 | CSF1 | 341 | DACH1 | 379 | DUSP22 |
| 228 | CDK13 | 266 | CHD3 | 304 | CSF1R | 342 | DACH2 | 380 | DVL1 |

Fig. 22c

Exemplary Oncology Panel - 1711 Genes

| No. | Symbol | No. | Symbol | No. | Symbol | No. | Symbol | No. | Symbol |
|---|---|---|---|---|---|---|---|---|---|
| 381 | DVL2 | 419 | EPHA5 | 457 | EXT1 | 495 | FGF14 | 533 | FOSL2 |
| 382 | DVL3 | 420 | EPHA6 | 458 | EXT2 | 496 | FGF16 | 534 | FOXA1 |
| 383 | DYRK2 | 421 | EPHA7 | 459 | EXTL1 | 497 | FGF17 | 535 | FOXA2 |
| 384 | E2F1 | 422 | EPHA8 | 460 | EZH1 | 498 | FGF18 | 536 | FOXA3 |
| 385 | E2F3 | 423 | EPHB1 | 461 | EZH2 | 499 | FGF19 | 537 | FOXG1 |
| 386 | E2F5 | 424 | EPHB2 | 462 | FADD | 500 | FGF2 | 538 | FOXL1 |
| 387 | E2F6 | 425 | EPHB3 | 463 | FAM175A | 501 | FGF20 | 539 | FOXL2 |
| 388 | E2F7 | 426 | EPHB4 | 464 | FAM46C | 502 | FGF21 | 540 | FOXM1 |
| 389 | EBF1 | 427 | EPHB6 | 465 | FANCA | 503 | FGF22 | 541 | FOXN3 |
| 390 | ECT2L | 428 | EPOR | 466 | FANCB | 504 | FGF23 | 542 | FOXO1 |
| 391 | EED | 429 | ERBB2 | 467 | FANCC | 505 | FGF3 | 543 | FOXO3 |
| 392 | EGF | 430 | ERBB3 | 468 | FANCD2 | 506 | FGF4 | 544 | FOXO4 |
| 393 | EGFR | 431 | ERBB4 | 469 | FANCE | 507 | FGF5 | 545 | FOXP1 |
| 394 | EGR1 | 432 | ERCC1 | 470 | FANCF | 508 | FGF6 | 546 | FOXP2 |
| 395 | EGR2 | 433 | ERCC2 | 471 | FANCG | 509 | FGF7 | 547 | FOXP3 |
| 396 | EHF | 434 | ERCC3 | 472 | FANCI | 510 | FGF8 | 548 | FOXP4 |
| 397 | EHMT1 | 435 | ERCC4 | 473 | FANCL | 511 | FGF9 | 549 | FOXQ1 |
| 398 | EHMT2 | 436 | ERCC5 | 474 | FANCM | 512 | FGFR1 | 550 | FRK |
| 399 | EIF1AX | 437 | EREG | 475 | FAS | 513 | FGFR2 | 551 | FRS2 |
| 400 | ELANE | 438 | ERF | 476 | FASLG | 514 | FGFR3 | 552 | FRS3 |
| 401 | ELF1 | 439 | ERG | 477 | FAT1 | 515 | FGFR4 | 553 | FSHR |
| 402 | ELF2 | 440 | ESCO1 | 478 | FAT2 | 516 | FGR | 554 | FUBP1 |
| 403 | ELF3 | 441 | ESCO2 | 479 | FAT3 | 517 | FH | 555 | FUS |
| 404 | ELF4 | 442 | ESPL1 | 480 | FAT4 | 518 | FHIT | 556 | FYN |
| 405 | ELF5 | 443 | ESR1 | 481 | FBN1 | 519 | FIGF | 557 | FZR1 |
| 406 | ELK1 | 444 | ESR2 | 482 | FBXO11 | 520 | FKBP10 | 558 | G6PC3 |
| 407 | ELK3 | 445 | ESRRA | 483 | FBXO8 | 521 | FKBP5 | 559 | G6PD |
| 408 | ELK4 | 446 | ETS1 | 484 | FBXW11 | 522 | FKBP9 | 560 | GAB1 |
| 409 | ELP3 | 447 | ETS2 | 485 | FBXW7 | 523 | FLCN | 561 | GAB2 |
| 410 | EML4 | 448 | ETV1 | 486 | FEN1 | 524 | FLI1 | 562 | GABPA |
| 411 | EMSY | 449 | ETV2 | 487 | FER | 525 | FLT1 | 563 | GALNT12 |
| 412 | EP300 | 450 | ETV3 | 488 | FES | 526 | FLT3 | 564 | GATA1 |
| 413 | EPCAM | 451 | ETV3L | 489 | FEV | 527 | FLT3LG | 565 | GATA2 |
| 414 | EPGN | 452 | ETV4 | 490 | FGF1 | 528 | FLT4 | 566 | GATA3 |
| 415 | EPHA1 | 453 | ETV5 | 491 | FGF10 | 529 | FOLH1 | 567 | GATA5 |
| 416 | EPHA2 | 454 | ETV6 | 492 | FGF11 | 530 | FOS | 568 | GATA6 |
| 417 | EPHA3 | 455 | ETV7 | 493 | FGF12 | 531 | FOSB | 569 | GDNF |
| 418 | EPHA4 | 456 | EWSR1 | 494 | FGF13 | 532 | FOSL1 | 570 | GFI1 |

Fig. 22d

Exemplary Oncology Panel - 1711 Genes

| No. | Symbol | No. | Symbol | No. | Symbol | No. | Symbol | No. | Symbol |
|---|---|---|---|---|---|---|---|---|---|
| 571 | GFI1B | 609 | HBEGF | 647 | HOXA13 | 685 | IKBKAP | 723 | ING1 |
| 572 | GFRA4 | 610 | HCK | 648 | HOXA3 | 686 | IKBKB | 724 | ING4 |
| 573 | GGCX | 611 | HDAC1 | 649 | HOXA9 | 687 | IKBKE | 725 | INHBA |
| 574 | GHR | 612 | HDAC10 | 650 | HOXB13 | 688 | IKZF1 | 726 | INPP4B |
| 575 | GID4 | 613 | HDAC11 | 651 | HOXB3 | 689 | IKZF2 | 727 | INSR |
| 576 | GLA | 614 | HDAC2 | 652 | HOXC10 | 690 | IKZF3 | 728 | INSRR |
| 577 | GLCCI1 | 615 | HDAC3 | 653 | HOXC11 | 691 | IL10RA | 729 | INTS12 |
| 578 | GLI1 | 616 | HDAC4 | 654 | HOXC13 | 692 | IL10RB | 730 | IQGAP1 |
| 579 | GLI2 | 617 | HDAC5 | 655 | HOXD10 | 693 | IL11RA | 731 | IQGAP2 |
| 580 | GLI3 | 618 | HDAC6 | 656 | HOXD11 | 694 | IL12RB1 | 732 | IQGAP3 |
| 581 | GLIS1 | 619 | HDAC7 | 657 | HOXD13 | 695 | IL12RB2 | 733 | IRAK1 |
| 582 | GLIS2 | 620 | HDAC8 | 658 | HOXD3 | 696 | IL13RA1 | 734 | IRF4 |
| 583 | GLIS3 | 621 | HDAC9 | 659 | HOXD4 | 697 | IL15RA | 735 | IRF5 |
| 584 | GNA11 | 622 | HDGF | 660 | HR | 698 | IL17RA | 736 | IRF6 |
| 585 | GNA13 | 623 | HELLS | 661 | HRAS | 699 | IL17RB | 737 | IRS1 |
| 586 | GNAQ | 624 | HES1 | 662 | HSD11B2 | 700 | IL17RC | 738 | IRS2 |
| 587 | GNAS | 625 | HES2 | 663 | HSD3B1 | 701 | IL18R1 | 739 | IRS4 |
| 588 | GNRHR | 626 | HES4 | 664 | HSP90AA1 | 702 | IL18RAP | 740 | ITK |
| 589 | GOT1 | 627 | HEY1 | 665 | HSP90AB1 | 703 | IL1R1 | 741 | ITPKB |
| 590 | GPC3 | 628 | HEY2 | 666 | HSPBAP1 | 704 | IL1R2 | 742 | JADE1 |
| 591 | GPC5 | 629 | HGF | 667 | HTR1A | 705 | IL1RAP | 743 | JAK1 |
| 592 | GPS2 | 630 | HIF1A | 668 | HTR2A | 706 | IL20RA | 744 | JAK2 |
| 593 | GRB10 | 631 | HIF1AN | 669 | ICK | 707 | IL20RB | 745 | JAK3 |
| 594 | GRB2 | 632 | HIST1H1E | 670 | ICOS | 708 | IL21R | 746 | JARID2 |
| 595 | GRB7 | 633 | HIST1H3B | 671 | ICOSLG | 709 | IL22RA1 | 747 | JAZF1 |
| 596 | GREM1 | 634 | HIST1H4E | 672 | ID1 | 710 | IL22RA2 | 748 | JMJD1C |
| 597 | GRIN2A | 635 | HLA-A | 673 | ID2 | 711 | IL23R | 749 | JMJD4 |
| 598 | GRK4 | 636 | HLA-B | 674 | ID3 | 712 | IL2RA | 750 | JMJD6 |
| 599 | GRK5 | 637 | HLF | 675 | ID4 | 713 | IL2RB | 751 | JMJD7 |
| 600 | GRM3 | 638 | HLTF | 676 | IDH1 | 714 | IL2RG | 752 | JMJD8 |
| 601 | GRM8 | 639 | HMGA1 | 677 | IDH2 | 715 | IL3 | 753 | JUN |
| 602 | GSK3A | 640 | HMGA2 | 678 | IFNLR1 | 716 | IL3RA | 754 | JUNB |
| 603 | GSK3B | 641 | HMGCR | 679 | IGF1 | 717 | IL4R | 755 | JUND |
| 604 | GSTT1 | 642 | HNF1A | 680 | IGF1R | 718 | IL5RA | 756 | JUP |
| 605 | GTPBP4 | 643 | HNF1B | 681 | IGF2 | 719 | IL6R | 757 | KAT2A |
| 606 | GUCY1A2 | 644 | HNRNPA3 | 682 | IGF2R | 720 | IL6ST | 758 | KAT2B |
| 607 | H3F3A | 645 | HOXA10 | 683 | IHH | 721 | IL7R | 759 | KAT5 |
| 608 | HAX1 | 646 | HOXA11 | 684 | IKBIP | 722 | IL9R | 760 | KAT6A |

Fig. 22e

| Exemplary Oncology Panel - 1711 Genes ||||||||||
|---|---|---|---|---|---|---|---|---|---|
| No. | Symbol | No. | Symbol | No. | Symbol | No. | Symbol | No. | Symbol |
| 761 | KAT6B | 799 | KMT2B | 837 | MAGED1 | 875 | MAPK1 | 913 | MIPOL1 |
| 762 | KAT7 | 800 | KMT2C | 838 | MAGI2 | 876 | MAPK10 | 914 | MITF |
| 763 | KAT8 | 801 | KMT2D | 839 | MAK | 877 | MAPK11 | 915 | MKL1 |
| 764 | KCNH2 | 802 | KMT2E | 840 | MALT1 | 878 | MAPK12 | 916 | MKL2 |
| 765 | KCNJ5 | 803 | KRAS | 841 | MAML1 | 879 | MAPK13 | 917 | MLF1 |
| 766 | KCNQ1 | 804 | LATS1 | 842 | MAML2 | 880 | MAPK14 | 918 | MLH1 |
| 767 | KDM1A | 805 | LATS2 | 843 | MAML3 | 881 | MAPK15 | 919 | MLH3 |
| 768 | KDM1B | 806 | LCK | 844 | MAMLD1 | 882 | MAPK3 | 920 | MLLT1 |
| 769 | KDM2A | 807 | LDB1 | 845 | MAOA | 883 | MAPK4 | 921 | MLLT10 |
| 770 | KDM2B | 808 | LDLR | 846 | MAP2K1 | 884 | MAPK6 | 922 | MLLT11 |
| 771 | KDM3A | 809 | LEF1 | 847 | MAP2K2 | 885 | MAPK7 | 923 | MLLT3 |
| 772 | KDM3B | 810 | LEPR | 848 | MAP2K3 | 886 | MAPK8 | 924 | MLLT6 |
| 773 | KDM4A | 811 | LGR4 | 849 | MAP2K4 | 887 | MAPK9 | 925 | MLST8 |
| 774 | KDM4B | 812 | LGR5 | 850 | MAP2K5 | 888 | MAST1 | 926 | MN1 |
| 775 | KDM4C | 813 | LGR6 | 851 | MAP2K6 | 889 | MAST2 | 927 | MNX1 |
| 776 | KDM4D | 814 | LHCGR | 852 | MAP2K7 | 890 | MATK | 928 | MOB1A |
| 777 | KDM5A | 815 | LIFR | 853 | MAP3K1 | 891 | MAU2 | 929 | MOB1B |
| 778 | KDM5B | 816 | LMNA | 854 | MAP3K10 | 892 | MAX | 930 | MOS |
| 779 | KDM5C | 817 | LMO1 | 855 | MAP3K11 | 893 | MBD1 | 931 | MPG |
| 780 | KDM5D | 818 | LMO2 | 856 | MAP3K12 | 894 | MBD3 | 932 | MPL |
| 781 | KDM6A | 819 | LMO7 | 857 | MAP3K13 | 895 | MC1R | 933 | MRE11A |
| 782 | KDM6B | 820 | LMTK2 | 858 | MAP3K14 | 896 | MCL1 | 934 | MSH2 |
| 783 | KDM7A | 821 | LMTK3 | 859 | MAP3K15 | 897 | MCPH1 | 935 | MSH3 |
| 784 | KDM8 | 822 | LPP | 860 | MAP3K19 | 898 | MDM2 | 936 | MSH4 |
| 785 | KDR | 823 | LRP1B | 861 | MAP3K2 | 899 | MDM4 | 937 | MSH6 |
| 786 | KDSR | 824 | LRP5 | 862 | MAP3K3 | 900 | MDS2 | 938 | MSI2 |
| 787 | KEAP1 | 825 | LRP6 | 863 | MAP3K4 | 901 | MECOM | 939 | MST1 |
| 788 | KEL | 826 | LRRK2 | 864 | MAP3K5 | 902 | MED12 | 940 | MST1R |
| 789 | KHSRP | 827 | LSM1 | 865 | MAP3K6 | 903 | MED12L | 941 | MTAP |
| 790 | KIF1B | 828 | LTK | 866 | MAP3K7 | 904 | MED29 | 942 | MTCP1 |
| 791 | KIT | 829 | LYL1 | 867 | MAP3K8 | 905 | MEF2B | 943 | MTDH |
| 792 | KITLG | 830 | LYN | 868 | MAP3K9 | 906 | MEN1 | 944 | MTOR |
| 793 | KLF12 | 831 | LZTR1 | 869 | MAP4 | 907 | MERTK | 945 | MUSK |
| 794 | KLF4 | 832 | MAD1L1 | 870 | MAP4K1 | 908 | MET | 946 | MUTYH |
| 795 | KLF5 | 833 | MAD2L1 | 871 | MAP4K2 | 909 | MGA | 947 | MXD1 |
| 796 | KLF6 | 834 | MAD2L2 | 872 | MAP4K3 | 910 | MGMT | 948 | MYB |
| 797 | KLF8 | 835 | MAF | 873 | MAP4K4 | 911 | MID1 | 949 | MYBL1 |
| 798 | KMT2A | 836 | MAFB | 874 | MAP4K5 | 912 | MINK1 | 950 | MYBL2 |

Fig. 22f

| Exemplary Oncology Panel - 1711 Genes |||||||||||
|---|---|---|---|---|---|---|---|---|---|
| No. | Symbol | No. | Symbol | No. | Symbol | No. | Symbol | No. | Symbol |
| 951 | MYBPC3 | 989 | NF2 | 1027 | NPM1 | 1065 | PAK2 | 1103 | PDPK1 |
| 952 | MYC | 990 | NFATC1 | 1028 | NPPB | 1066 | PAK3 | 1104 | PDS5A |
| 953 | MYCL | 991 | NFATC2 | 1029 | NPR1 | 1067 | PAK4 | 1105 | PDS5B |
| 954 | MYCN | 992 | NFATC3 | 1030 | NQO1 | 1068 | PAK6 | 1106 | PEAR1 |
| 955 | MYD88 | 993 | NFATC4 | 1031 | NR0B1 | 1069 | PAK7 | 1107 | PEG3 |
| 956 | MYH11 | 994 | NFE2L2 | 1032 | NR3C1 | 1070 | PALB2 | 1108 | PERP |
| 957 | MYH7 | 995 | NFIA | 1033 | NR3C2 | 1071 | PALLD | 1109 | PGF |
| 958 | MYL2 | 996 | NFIB | 1034 | NR4A1 | 1072 | PARK2 | 1110 | PGR |
| 959 | MYL3 | 997 | NFIC | 1035 | NR4A2 | 1073 | PARP1 | 1111 | PHB |
| 960 | MYLK | 998 | NFIX | 1036 | NR4A3 | 1074 | PARP2 | 1112 | PHF1 |
| 961 | MYOD1 | 999 | NFKB1 | 1037 | NRAS | 1075 | PARP4 | 1113 | PHF2 |
| 962 | NA | 1000 | NFKB2 | 1038 | NRG1 | 1076 | PATZ1 | 1114 | PHF6 |
| 963 | NAB1 | 1001 | NFKBIA | 1039 | NRG2 | 1077 | PAX1 | 1115 | PHF8 |
| 964 | NAB2 | 1002 | NFKBIB | 1040 | NRG3 | 1078 | PAX2 | 1116 | PHIP |
| 965 | NAT2 | 1003 | NFKBID | 1041 | NRG4 | 1079 | PAX3 | 1117 | PHLPP1 |
| 966 | NBN | 1004 | NFKBIE | 1042 | NRIP1 | 1080 | PAX4 | 1118 | PHLPP2 |
| 967 | NCK1 | 1005 | NFKBIZ | 1043 | NRTN | 1081 | PAX5 | 1119 | PHOX2A |
| 968 | NCK2 | 1006 | NGF | 1044 | NSD1 | 1082 | PAX6 | 1120 | PHOX2B |
| 969 | NCOA1 | 1007 | NHP2 | 1045 | NT5C2 | 1083 | PAX7 | 1121 | PICALM |
| 970 | NCOA2 | 1008 | NIPBL | 1046 | NTF3 | 1084 | PAX8 | 1122 | PIK3C2A |
| 971 | NCOA3 | 1009 | NKX2-1 | 1047 | NTF4 | 1085 | PAX9 | 1123 | PIK3C2B |
| 972 | NCOA4 | 1010 | NKX2-2 | 1048 | NTRK1 | 1086 | PAXIP1 | 1124 | PIK3C2G |
| 973 | NCOR1 | 1011 | NKX2-3 | 1049 | NTRK2 | 1087 | PBRM1 | 1125 | PIK3C3 |
| 974 | NCOR2 | 1012 | NKX2-4 | 1050 | NTRK3 | 1088 | PBX1 | 1126 | PIK3CA |
| 975 | NCSTN | 1013 | NKX2-5 | 1051 | NUMB | 1089 | PBX2 | 1127 | PIK3CB |
| 976 | NDRG1 | 1014 | NKX2-6 | 1052 | NUMBL | 1090 | PBX3 | 1128 | PIK3CD |
| 977 | NEK1 | 1015 | NKX2-8 | 1053 | NUP214 | 1091 | PBX4 | 1129 | PIK3CG |
| 978 | NEK10 | 1016 | NKX3-1 | 1054 | NUP93 | 1092 | PCBP1 | 1130 | PIK3R1 |
| 979 | NEK11 | 1017 | NKX3-2 | 1055 | NUP98 | 1093 | PCSK9 | 1131 | PIK3R2 |
| 980 | NEK2 | 1018 | NLRP1 | 1056 | NUTM1 | 1094 | PDCD1 | 1132 | PIK3R3 |
| 981 | NEK3 | 1019 | NOD2 | 1057 | NUTM2A | 1095 | PDCD1LG2 | 1133 | PIK3R4 |
| 982 | NEK4 | 1020 | NONO | 1058 | NUTM2B | 1096 | PDGFA | 1134 | PIM1 |
| 983 | NEK5 | 1021 | NOP10 | 1059 | NUTM2F | 1097 | PDGFB | 1135 | PIM2 |
| 984 | NEK6 | 1022 | NOTCH1 | 1060 | NUTM2G | 1098 | PDGFC | 1136 | PIM3 |
| 985 | NEK7 | 1023 | NOTCH2 | 1061 | ODC1 | 1099 | PDGFD | 1137 | PKHD1 |
| 986 | NEK8 | 1024 | NOTCH2NL | 1062 | OLIG2 | 1100 | PDGFRA | 1138 | PKP2 |
| 987 | NEK9 | 1025 | NOTCH3 | 1063 | OSMR | 1101 | PDGFRB | 1139 | PLA2G2A |
| 988 | NF1 | 1026 | NOTCH4 | 1064 | PAK1 | 1102 | PDK1 | 1140 | PLAG1 |

Fig. 22g

| Exemplary Oncology Panel - 1711 Genes |||||||||| 
|---|---|---|---|---|---|---|---|---|---|
| No. | Symbol | No. | Symbol | No. | Symbol | No. | Symbol | No. | Symbol |
| 1141 | PLAGL1 | 1179 | PRDM12 | 1217 | PSEN2 | 1255 | RAD51 | 1293 | RIT1 |
| 1142 | PLAGL2 | 1180 | PRDM13 | 1218 | PSENEN | 1256 | RAD51AP1 | 1294 | RNF213 |
| 1143 | PLCG1 | 1181 | PRDM14 | 1219 | PSIP1 | 1257 | RAD51B | 1295 | RNF40 |
| 1144 | PLCG2 | 1182 | PRDM15 | 1220 | PSPN | 1258 | RAD51C | 1296 | RNF43 |
| 1145 | PLK1 | 1183 | PRDM16 | 1221 | PTCH1 | 1259 | RAD51D | 1297 | ROBO2 |
| 1146 | PLK2 | 1184 | PRDM2 | 1222 | PTCH2 | 1260 | RAD52 | 1298 | ROCK1 |
| 1147 | PLK3 | 1185 | PRDM4 | 1223 | PTEN | 1261 | RAD54B | 1299 | ROCK2 |
| 1148 | PLK4 | 1186 | PRDM5 | 1224 | PTGIS | 1262 | RAD54L | 1300 | ROR1 |
| 1149 | PMAIP1 | 1187 | PRDM6 | 1225 | PTGS1 | 1263 | RAF1 | 1301 | ROR2 |
| 1150 | PML | 1188 | PRDM7 | 1226 | PTGS2 | 1264 | RAP1GDS1 | 1302 | ROS1 |
| 1151 | PMS1 | 1189 | PRDM8 | 1227 | PTK2 | 1265 | RARA | 1303 | RPA1 |
| 1152 | PMS2 | 1190 | PRDM9 | 1228 | PTK2B | 1266 | RARB | 1304 | RPL5 |
| 1153 | PNRC1 | 1191 | PREX2 | 1229 | PTK6 | 1267 | RARG | 1305 | RPN1 |
| 1154 | POLD1 | 1192 | PRF1 | 1230 | PTK7 | 1268 | RASA1 | 1306 | RPS6KB1 |
| 1155 | POLE | 1193 | PRKACA | 1231 | PTPN11 | 1269 | RB1 | 1307 | RPS6KB2 |
| 1156 | POR | 1194 | PRKACB | 1232 | PTPN2 | 1270 | RBM10 | 1308 | RPTOR |
| 1157 | POT1 | 1195 | PRKAG2 | 1233 | PTPN21 | 1271 | RBM14 | 1309 | RRM1 |
| 1158 | POU2AF1 | 1196 | PRKAR1A | 1234 | PTPN6 | 1272 | RBM15 | 1310 | RSPO2 |
| 1159 | POU2F2 | 1197 | PRKAR1B | 1235 | PTPRB | 1273 | RBMX | 1311 | RSPO3 |
| 1160 | POU5F1 | 1198 | PRKCI | 1236 | PTPRC | 1274 | RBMXL1 | 1312 | RUNX1 |
| 1161 | POU5F1B | 1199 | PRKD1 | 1237 | PTPRD | 1275 | RBMXL2 | 1313 | RUNX1T1 |
| 1162 | POU5F2 | 1200 | PRKDC | 1238 | PTPRF | 1276 | RBPJ | 1314 | RUNX2 |
| 1163 | POU6F1 | 1201 | PRLR | 1239 | PTPRG | 1277 | REC8 | 1315 | RUNX3 |
| 1164 | POU6F2 | 1202 | PRMT1 | 1240 | PTPRJ | 1278 | RECQL4 | 1316 | RUVBL1 |
| 1165 | PPARA | 1203 | PRMT2 | 1241 | PTPRK | 1279 | REL | 1317 | RXRA |
| 1166 | PPARD | 1204 | PRMT3 | 1242 | PTPRM | 1280 | RELA | 1318 | RYK |
| 1167 | PPARG | 1205 | PRMT5 | 1243 | PTPRQ | 1281 | RELB | 1319 | RYR1 |
| 1168 | PPFIA1 | 1206 | PRMT6 | 1244 | PTPRR | 1282 | RET | 1320 | RYR2 |
| 1169 | PPM1D | 1207 | PRMT7 | 1245 | PTPRT | 1283 | RHEB | 1321 | SAMD9 |
| 1170 | PPP1R1C | 1208 | PRMT8 | 1246 | PTTG1 | 1284 | RHOA | 1322 | SAV1 |
| 1171 | PPP2R1A | 1209 | PRPF40B | 1247 | PVT1 | 1285 | RHOB | 1323 | SBDS |
| 1172 | PPP2R1B | 1210 | PRPF6 | 1248 | RAB23 | 1286 | RHOH | 1324 | SCN5A |
| 1173 | PPP2R2B | 1211 | PRRX1 | 1249 | RAB25 | 1287 | RHOT1 | 1325 | SDHA |
| 1174 | PPP6C | 1212 | PRRX2 | 1250 | RABEP1 | 1288 | RICTOR | 1326 | SDHAF2 |
| 1175 | PRCC | 1213 | PRSS1 | 1251 | RAC1 | 1289 | RIPK1 | 1327 | SDHB |
| 1176 | PRDM1 | 1214 | PRSS3 | 1252 | RAC2 | 1290 | RIPK2 | 1328 | SDHC |
| 1177 | PRDM10 | 1215 | PRSS8 | 1253 | RAD21 | 1291 | RIPK3 | 1329 | SDHD |
| 1178 | PRDM11 | 1216 | PSEN1 | 1254 | RAD50 | 1292 | RIPK4 | 1330 | SET |

Fig. 22h

| Exemplary Oncology Panel - 1711 Genes ||||||||||
|---|---|---|---|---|---|---|---|---|---|
| No. | Symbol | No. | Symbol | No. | Symbol | No. | Symbol | No. | Symbol |
| 1331 | SETBP1 | 1369 | SLC19A1 | 1407 | SMC4 | 1445 | SPRY2 | 1483 | SUV420H2 |
| 1332 | SETD1A | 1370 | SLC22A1 | 1408 | SMC5 | 1446 | SPRY3 | 1484 | SUZ12 |
| 1333 | SETD1B | 1371 | SLC22A2 | 1409 | SMC6 | 1447 | SRC | 1485 | SYK |
| 1334 | SETD2 | 1372 | SLC22A3 | 1410 | SMCHD1 | 1448 | SRGAP3 | 1486 | SYNE1 |
| 1335 | SETD3 | 1373 | SLC22A6 | 1411 | SMO | 1449 | SRMS | 1487 | TAF1 |
| 1336 | SETD4 | 1374 | SLC26A3 | 1412 | SMURF1 | 1450 | SRSF2 | 1488 | TAF15 |
| 1337 | SETD5 | 1375 | SLC47A1 | 1413 | SMURF2 | 1451 | SS18 | 1489 | TAF1L |
| 1338 | SETD6 | 1376 | SLC47A2 | 1414 | SMYD1 | 1452 | SS18L1 | 1490 | TAL1 |
| 1339 | SETD7 | 1377 | SLC6A3 | 1415 | SMYD2 | 1453 | SSTR1 | 1491 | TAL2 |
| 1340 | SETD8 | 1378 | SLC6A4 | 1416 | SMYD3 | 1454 | SSTR2 | 1492 | TAOK1 |
| 1341 | SETD9 | 1379 | SLCO1A2 | 1417 | SMYD4 | 1455 | SSTR3 | 1493 | TAOK2 |
| 1342 | SETDB1 | 1380 | SLCO1B1 | 1418 | SMYD5 | 1456 | SSTR4 | 1494 | TAOK3 |
| 1343 | SETDB2 | 1381 | SLCO1B3 | 1419 | SOCS1 | 1457 | SSTR5 | 1495 | TBC1D12 |
| 1344 | SETMAR | 1382 | SLCO2B1 | 1420 | SOS1 | 1458 | SSX1 | 1496 | TBL1X |
| 1345 | SF1 | 1383 | SLIT2 | 1421 | SOS2 | 1459 | SSX2 | 1497 | TBL1XR1 |
| 1346 | SF3A1 | 1384 | SLX4 | 1422 | SOX1 | 1460 | SSX3 | 1498 | TBP |
| 1347 | SF3B1 | 1385 | SMAD1 | 1423 | SOX10 | 1461 | SSX4 | 1499 | TBX18 |
| 1348 | SFPQ | 1386 | SMAD2 | 1424 | SOX17 | 1462 | STAG1 | 1500 | TBX2 |
| 1349 | SFRP1 | 1387 | SMAD3 | 1425 | SOX2 | 1463 | STAG2 | 1501 | TBX22 |
| 1350 | SGK1 | 1388 | SMAD4 | 1426 | SOX21 | 1464 | STARD3 | 1502 | TBX3 |
| 1351 | SGOL1 | 1389 | SMAD5 | 1427 | SOX3 | 1465 | STAT1 | 1503 | TBXAS1 |
| 1352 | SGOL2 | 1390 | SMAD6 | 1428 | SOX8 | 1466 | STAT2 | 1504 | TCEB1 |
| 1353 | SH2B3 | 1391 | SMAD7 | 1429 | SOX9 | 1467 | STAT3 | 1505 | TCF12 |
| 1354 | SH2D1A | 1392 | SMAD9 | 1430 | SP100 | 1468 | STAT4 | 1506 | TCF3 |
| 1355 | SH3GL1 | 1393 | SMARCA1 | 1431 | SP110 | 1469 | STAT5A | 1507 | TCF4 |
| 1356 | SHB | 1394 | SMARCA2 | 1432 | SP140 | 1470 | STAT5B | 1508 | TCF7 |
| 1357 | SHC1 | 1395 | SMARCA4 | 1433 | SP140L | 1471 | STAT6 | 1509 | TCF7L1 |
| 1358 | SHC2 | 1396 | SMARCA5 | 1434 | SP3 | 1472 | STK11 | 1510 | TCF7L2 |
| 1359 | SHC3 | 1397 | SMARCB1 | 1435 | SPDEF | 1473 | STK19 | 1511 | TCL1A |
| 1360 | SHC4 | 1398 | SMARCC1 | 1436 | SPEN | 1474 | STK3 | 1512 | TCL1B |
| 1361 | SHFM1 | 1399 | SMARCD1 | 1437 | SPI1 | 1475 | STK36 | 1513 | TEAD1 |
| 1362 | SHH | 1400 | SMARCD2 | 1438 | SPIB | 1476 | STK4 | 1514 | TEAD2 |
| 1363 | SHOC2 | 1401 | SMARCD3 | 1439 | SPIC | 1477 | STYK1 | 1515 | TEAD3 |
| 1364 | SKI | 1402 | SMARCE1 | 1440 | SPOP | 1478 | SUFU | 1516 | TEAD4 |
| 1365 | SKIL | 1403 | SMC1A | 1441 | SPOPL | 1479 | SULT1A1 | 1517 | TEC |
| 1366 | SKOR1 | 1404 | SMC1B | 1442 | SPRED1 | 1480 | SUV39H1 | 1518 | TEF |
| 1367 | SKP2 | 1405 | SMC2 | 1443 | SPRED2 | 1481 | SUV39H2 | 1519 | TEK |
| 1368 | SLC15A2 | 1406 | SMC3 | 1444 | SPRED3 | 1482 | SUV420H1 | 1520 | TENM2 |

Fig. 22i

| Exemplary Oncology Panel - 1711 Genes ||||||||||
|---|---|---|---|---|---|---|---|---|---|
| No. | Symbol | No. | Symbol | No. | Symbol | No. | Symbol | No. | Symbol |
| 1521 | TERC | 1559 | TNFRSF14 | 1597 | TSHZ3 | 1635 | WAS | 1673 | XRCC2 |
| 1522 | TERF1 | 1560 | TNFRSF17 | 1598 | TWIST1 | 1636 | WASL | 1674 | YAP1 |
| 1523 | TERT | 1561 | TNK1 | 1599 | TWIST2 | 1637 | WHSC1 | 1675 | YEATS4 |
| 1524 | TET1 | 1562 | TNK2 | 1600 | TXK | 1638 | WHSC1L1 | 1676 | YES1 |
| 1525 | TET2 | 1563 | TNKS | 1601 | TYK2 | 1639 | WIF1 | 1677 | YWHAB |
| 1526 | TET3 | 1564 | TNKS2 | 1602 | TYRO3 | 1640 | WISP1 | 1678 | YWHAE |
| 1527 | TFE3 | 1565 | TNNI3 | 1603 | U2AF1 | 1641 | WNK1 | 1679 | YWHAH |
| 1528 | TFEB | 1566 | TNNT2 | 1604 | U2AF2 | 1642 | WNK2 | 1680 | YWHAQ |
| 1529 | TFEC | 1567 | TOP1 | 1605 | UBE2D1 | 1643 | WNK3 | 1681 | YWHAZ |
| 1530 | TFG | 1568 | TOP2A | 1606 | UBE2D2 | 1644 | WNK4 | 1682 | YY1 |
| 1531 | TGFA | 1569 | TOP2B | 1607 | UBE2D3 | 1645 | WNT1 | 1683 | ZAP70 |
| 1532 | TGFB1 | 1570 | TP53 | 1608 | UBE2D4 | 1646 | WNT10A | 1684 | ZBTB16 |
| 1533 | TGFB2 | 1571 | TP53BP1 | 1609 | UBE4A | 1647 | WNT10B | 1685 | ZBTB20 |
| 1534 | TGFBR1 | 1572 | TP63 | 1610 | UBR5 | 1648 | WNT11 | 1686 | ZBTB33 |
| 1535 | TGFBR2 | 1573 | TPM1 | 1611 | UGT1A1 | 1649 | WNT16 | 1687 | ZBTB5 |
| 1536 | THPO | 1574 | TPMT | 1612 | UGT1A4 | 1650 | WNT2 | 1688 | ZBTB7B |
| 1537 | TIE1 | 1575 | TPTE | 1613 | UHRF1 | 1651 | WNT2B | 1689 | ZC3H12A |
| 1538 | TINF2 | 1576 | TPTE2 | 1614 | UHRF2 | 1652 | WNT3 | 1690 | ZC3H12D |
| 1539 | TLK1 | 1577 | TRAF1 | 1615 | USB1 | 1653 | WNT3A | 1691 | ZC3H7B |
| 1540 | TLK2 | 1578 | TRAF2 | 1616 | USP9X | 1654 | WNT4 | 1692 | ZCCHC7 |
| 1541 | TLR1 | 1579 | TRAF3 | 1617 | USP9Y | 1655 | WNT5A | 1693 | ZEB2 |
| 1542 | TLR10 | 1580 | TRAF3IP1 | 1618 | UTY | 1656 | WNT5B | 1694 | ZFHX3 |
| 1543 | TLR2 | 1581 | TRAF3IP2 | 1619 | VAV1 | 1657 | WNT6 | 1695 | ZMYM3 |
| 1544 | TLR4 | 1582 | TRAF3IP3 | 1620 | VAV2 | 1658 | WNT7A | 1696 | ZMYND11 |
| 1545 | TLR5 | 1583 | TRAF6 | 1621 | VAV3 | 1659 | WNT7B | 1697 | ZMYND8 |
| 1546 | TLR6 | 1584 | TRAF7 | 1622 | VDR | 1660 | WNT8A | 1698 | ZNF217 |
| 1547 | TLR7 | 1585 | TRIB1 | 1623 | VEGFA | 1661 | WNT8B | 1699 | ZNF384 |
| 1548 | TLR8 | 1586 | TRIB2 | 1624 | VEGFB | 1662 | WNT9A | 1700 | ZNF423 |
| 1549 | TLR9 | 1587 | TRIB3 | 1625 | VEGFC | 1663 | WNT9B | 1701 | ZNF444 |
| 1550 | TLX1 | 1588 | TRIM24 | 1626 | VGLL1 | 1664 | WRN | 1702 | ZNF471 |
| 1551 | TLX2 | 1589 | TRIM28 | 1627 | VGLL2 | 1665 | WT1 | 1703 | ZNF521 |
| 1552 | TLX3 | 1590 | TRIM33 | 1628 | VGLL3 | 1666 | WWTR1 | 1704 | ZNF607 |
| 1553 | TMC6 | 1591 | TRIM66 | 1629 | VGLL4 | 1667 | XBP1 | 1705 | ZNF639 |
| 1554 | TMC8 | 1592 | TRIO | 1630 | VHL | 1668 | XIAP | 1706 | ZNF668 |
| 1555 | TMEM127 | 1593 | TRRAP | 1631 | VHLL | 1669 | XIRP2 | 1707 | ZNF703 |
| 1556 | TMEM43 | 1594 | TSC1 | 1632 | VKORC1 | 1670 | XPA | 1708 | ZNF704 |
| 1557 | TMPRSS2 | 1595 | TSC2 | 1633 | VTCN1 | 1671 | XPC | 1709 | ZNF750 |
| 1558 | TNFAIP3 | 1596 | TSHR | 1634 | WAPL | 1672 | XPO1 | 1710 | ZNRF3 |
| | | | | | | | | 1711 | ZRSR2 |

Fig. 22j

| \multicolumn{8}{c}{Exemplary Clinically Actionable Tier 1 - 130 Genes} |
|---|---|---|---|---|---|---|---|
| No. | Symbol | No. | Symbol | No. | Symbol | No. | Symbol |
| 1 | ABCB1 | 39 | ERBB3 | 77 | MDM2 | 114 | ROS1 |
| 2 | ABL1 | 40 | ERBB4 | 78 | MET | 115 | RUNX1 |
| 3 | AKT1 | 41 | ERCC1 | 79 | MGMT | 116 | SGK1 |
| 4 | AKT2 | 42 | ERCC2 | 80 | MITF | 117 | SMAD4 |
| 5 | ALK | 43 | EREG | 81 | MLH1 | 118 | SMARCA4 |
| 6 | AR | 44 | ESR1 | 82 | MTOR | 119 | SMARCB1 |
| 7 | ARAF | 45 | ETS2 | 83 | MYD88 | 120 | SMO |
| 8 | AREG | 46 | FANCA | 84 | NF1 | 121 | STK11 |
| 9 | ATM | 47 | FANCC | 85 | NF2 | 122 | TOP1 |
| 10 | ATRX | 48 | FBXW7 | 86 | NOTCH1 | 123 | TOP2A |
| 11 | AURKA | 49 | FGF3 | 87 | NPM1 | 124 | TP53 |
| 12 | B2M | 50 | FGFR1 | 88 | NRAS | 125 | TSC1 |
| 13 | BCL2L11 | 51 | FGFR2 | 89 | NRG1 | 126 | TSC2 |
| 14 | BIRC5 | 52 | FGFR3 | 90 | NTRK1 | 127 | UGT1A1 |
| 15 | BRAF | 53 | FLCN | 91 | NTRK3 | 128 | VEGFA |
| 16 | BRCA1 | 54 | FLT3 | 92 | PALB2 | 129 | VHL |
| 17 | BRCA2 | 55 | FOXP3 | 93 | PDGFRA | 130 | WT1 |
| 18 | BRD4 | 56 | GNA11 | 94 | PDGFRB | | |
| 19 | BTK | 57 | GNAQ | 95 | PGR | | |
| 20 | CCND1 | 58 | HDAC2 | 96 | PIK3CA | | |
| 21 | CD274 | 59 | HGF | 97 | PIK3CB | | |
| 22 | CDK4 | 60 | HIF1A | 98 | PIK3R1 | | |
| 23 | CDK6 | 61 | HRAS | 99 | PLCG2 | | |
| 24 | CDKN1A | 62 | IDH1 | 100 | PML | | |
| 25 | CDKN1B | 63 | IDH2 | 101 | PMS2 | | |
| 26 | CDKN2A | 64 | IGF1R | 102 | POLE | | |
| 27 | CEBPA | 65 | IGF2 | 103 | PTCH1 | | |
| 28 | CHEK2 | 66 | JAK1 | 104 | PTEN | | |
| 29 | CSF3R | 67 | JAK2 | 105 | PTGS2 | | |
| 30 | CTLA4 | 68 | JUN | 106 | RAC1 | | |
| 31 | CTNNB1 | 69 | KDR | 107 | RAD50 | | |
| 32 | DDR2 | 70 | KIT | 108 | RAD51C | | |
| 33 | DNMT1 | 71 | KMT2A | 109 | RAF1 | | |
| 34 | DNMT3A | 72 | KRAS | 110 | RB1 | | |
| 35 | DPYD | 73 | LRP1B | 111 | RET | | |
| 36 | EGFR | 74 | MAP2K1 | 112 | RICTOR | | |
| 37 | EPHB4 | 75 | MAP2K2 | 113 | RNF43 | | |

Fig. 23

| 41 Clinically Actionable RNA Based Gene Rearrangements | | | |
|---|---|---|---|
| No. | Symbol | No. | Symbol |
| 1 | ABL1 | 22 | NRG1 |
| 2 | ALK | 23 | NTRK1 |
| 3 | BCL11A | 24 | NTRK2 |
| 4 | BCL2 | 25 | NTRK3 |
| 5 | BCR | 26 | PDGFRA |
| 6 | BRAF | 27 | PDGFRB |
| 7 | BRD4 | 28 | PML |
| 8 | CBFB | 29 | RET |
| 9 | CCDC6 | 30 | ROS1 |
| 10 | CCND1 | 31 | TFE3 |
| 11 | CTLA4 | 32 | JAK2 |
| 12 | EGFR | 33 | CRLF2 |
| 13 | ESR1 | 34 | RAF1 |
| 14 | ETV6 | 35 | NOTCH2 |
| 15 | FGFR1 | 36 | AKT3 |
| 16 | FGFR2 | 37 | ERBB4 |
| 17 | FGFR3 | 38 | NOTCH1 |
| 18 | FLT3 | 39 | PTC1 |
| 19 | KMT2A | 40 | TMPRSS2 |
| 20 | MET | 41 | RARA |
| 21 | NR4A3 | | |

Fig. 24

Exemplary Variant Data

| id | 1 | chr_pos_ref_alt | chrom | pos | ref | alt | sample_type | variant_caller | variant_type | coverage | base_fraction | mutation effect | gene | mutation name | filtered | filters_applied |
|---|---|---|---|---|---|---|---|---|---|---|---|---|---|---|---|---|
| 2049 | 17SEQ3_5_T_S_R_xO | 1_1275563_G_C | 1 | 12755 63 | G | C | somatic | somat freebayes | SNP | 325 | 9.2 | splice_region_variant&intron_variant | DVL1 | c.770-6>C | 0 | |
| 2050 | 17SEQ3_5_T_S_R_xO | 1_1650797_ATTT_GT | 1 | 16507 97 | ATTT | GTTT C | somatic | somat freebayes | MNP | 431 | 19 | missense_variant | CDK1 1B | p.EKC107E KR | 0 | |
| 2051 | 17SEQ3_5_T_S_R_xO | 1_10435441 | 1 | 10435 441 | TTTG | T | somatic | somat freebayes | INDEL | 274 | 6.2 | intron_variant | KIF1 B | c.5270+28_5270+30del GTT | 0 | |
| 2052 | 17SEQ3_5_T_S_R_xO | 1_14105094 | 1 | 14105 094 | AGA | A | somatic | somat freebayes | INDEL | 371 | 3.2 | disruptive_inframe_deletion | PRD M2 | p.E273del | 1 | var_reads |
| 2053 | 17SEQ3_5_T_S_R_xO | 1_23107918_G_A | 1 | 23107 918 | G | A | somatic | somat freebayes | SNP | 501 | 2 | synonymous_variant | EPHB 2 | p.T22T | 1 | var_reads,v ar_support |
| 2054 | 17SEQ3_5_T_S_R_xO | 1_25234555_A_G | 1 | 25234 555 | A | G | somatic | somat freebayes | SNP | 686 | 10 | intron_variant | RUN X3 | c.587-647T>C | 0 | |
| 2055 | 17SEQ3_5_T_S_R_xO | 1_25234574_C_T | 1 | 25234 574 | C | T | somatic | somat freebayes | SNP | 735 | 8.2 | intron_variant | RUN X3 | c.587-666G>A | 0 | |
| 2056 | 17SEQ3_5_T_S_R_xO | 1_27022833_T_G | 1 | 27022 833 | TTTG | G | somatic | somat freebayes | SNP | 126 | 8.7 | 5_prime_UTR_variant | ARID 1A | c.-62T>G | 0 | |
| 2057 | 17SEQ3_5_T_S_R_xO | 1_44072576_C_T | 1 | 44072 576 | C | C | somatic | somat freebayes | SNP | 632 | 1.4 | missense_variant | PTPR M | p.T1265M | 0 | |
| 2058 | 17SEQ3_5_T_S_R_xO | 1_46494558_C_T | 1 | 46494 558 | CT | C | somatic | somat freebayes | INDEL | 421 | 2.4 | frameshift_variant | MAS T2 | p.F726fs | 1 | var_reads,v ar_support |

FIG. 25

Exemplary CNV Data

| ID | Run ID | Chromosome | Start | End | Gene | MeanT | MeanN | Amp | Copy Number |
|---|---|---|---|---|---|---|---|---|---|
| 1 | 142803-201819-2b235d9b | 1 | 63183 | 63353 | | 17.68 | 119.37 | Loss | 1 |
| 2 | 142803-201819-2b235d9b | 1 | 63431 | 63601 | | 17.68 | 230.63 | Loss | 1 |
| 3 | 142803-201819-2b235d9b | 1 | 63612 | 63782 | | 18.42 | 243.16 | Loss | 1 |
| 4 | 142803-201819-2b235d9b | 1 | 69426 | 69596 | | 1.47 | 0 | Loss | 1 |
| 5 | 142803-201819-2b235d9b | 1 | 91451 | 91621 | | 0 | 0.74 | Loss | 1 |
| 6 | 142803-201819-2b235d9b | 1 | 931276 | 931446 | | 284.42 | 1234.21 | Loss | 1 |
| 7 | 142803-201819-2b235d9b | 1 | 932001 | 932171 | | 37.58 | 92.84 | Loss | 1 |
| 8 | 142803-201819-2b235d9b | 1 | 934428 | 934822 | HES4 | 85.49 | 268.59 | Loss | 1 |
| 9 | 142803-201819-2b235d9b | 1 | 934889 | 935010 | HES4 | 242.7 | 979.08 | Loss | 1 |
| 10 | 142803-201819-2b235d9b | 1 | 935061 | 935382 | HES4 | 153.78 | 543.52 | Loss | 1 |

Fig. 26

| Heme Related - xT Gene Panel | | | |
|---|---|---|---|
| No. | Symbol | No. | Symbol |
| 1 | ARHGAP26 | 35 | MAP3K7 |
| 2 | BCL10 | 36 | MAPK1 |
| 3 | BCL11B | 37 | MIB1 |
| 4 | BCL7A | 38 | MKI67 |
| 5 | BCR | 39 | NCOR2 |
| 6 | BIRC3 | 40 | NT5C2 |
| 7 | CBLB | 41 | NUP98 |
| 8 | CBLC | 42 | P2RY8 |
| 9 | CD22 | 43 | PCBP1 |
| 10 | CD70 | 44 | PHF6 |
| 11 | CIITA | 45 | PIM1 |
| 12 | CKS1B | 46 | POT1 |
| 13 | CSF3R | 47 | RAD21 |
| 14 | CUX1 | 48 | RHOA |
| 15 | CXCR4 | 49 | SETBP1 |
| 16 | DDX3X | 50 | SGK1 |
| 17 | DNM2 | 51 | SMARCA1 |
| 18 | EBF1 | 52 | SMC1A |
| 19 | ECT2L | 53 | SMC3 |
| 20 | EPOR | 54 | SRSF2 |
| 21 | ETV6 | 55 | STAT5A |
| 22 | FBXO11 | 56 | STAT5B |
| 23 | FHIT | 57 | STAT6 |
| 24 | FOXO1 | 58 | SUZ12 |
| 25 | FOXO3 | 59 | TBL1XR1 |
| 26 | HDAC1 | 60 | TCF3 |
| 27 | HDAC4 | 61 | TCL1A |
| 28 | HIST1H1E | 62 | TNFRSF17 |
| 29 | HIST1H3B | 63 | TP63 |
| 30 | KMT2B | 64 | TRAF3 |
| 31 | LEF1 | 65 | TUSC3 |
| 32 | MAF | 66 | WHSC1 |
| 33 | MAFB | 67 | ZRSR2 |
| 34 | MALT1 | | |

Fig. 27a

| \multicolumn{12}{c}{Heme and Solid Tumor Related - xT Gene Panel} |
|---|---|---|---|---|---|---|---|---|---|---|---|
| No. | Symbol | No. | Symbol | No. | Symbol | No. | Symbol | No. | Symbol | No. | Symbol |
| 1 | ABCB1 | 39 | CBL | 77 | ERBB2 | 115 | GATA1 | 153 | MAP2K2 | 191 | PDCD1 |
| 2 | ABCC3 | 40 | CCND1 | 78 | ERBB3 | 116 | GATA2 | 154 | MAP2K4 | 192 | PDCD1LG2 |
| 3 | ABL1 | 41 | CCND2 | 79 | ERBB4 | 117 | GATA3 | 155 | MAP3K1 | 193 | PDGFRA |
| 4 | AKT1 | 42 | CCND3 | 80 | ERG | 118 | GNA11 | 156 | MCL1 | 194 | PDGFRB |
| 5 | AKT2 | 43 | CCNE1 | 81 | ESR1 | 119 | GNA13 | 157 | MDM2 | 195 | PDK1 |
| 6 | AKT3 | 44 | CD274 | 82 | ETS1 | 120 | GNAQ | 158 | MDM4 | 196 | PIK3CA |
| 7 | ALK | 45 | CD79A | 83 | ETV1 | 121 | GNAS | 159 | MED12 | 197 | PIK3CG |
| 8 | AMER1 | 46 | CD79B | 84 | ETV4 | 122 | GRIN2A | 160 | MEF2B | 198 | PIK3R1 |
| 9 | APC | 47 | CDC73 | 85 | ETV5 | 123 | HGF | 161 | MEN1 | 199 | PIK3R2 |
| 10 | AR | 48 | CDH1 | 86 | EWSR1 | 124 | HNF1A | 162 | MET | 200 | PLCG2 |
| 11 | ARAF | 49 | CDK12 | 87 | EZH2 | 125 | HRAS | 163 | MITF | 201 | PPP2R1A |
| 12 | ARID1A | 50 | CDK4 | 88 | FAM46C | 126 | HSP90AA1 | 164 | MLH1 | 202 | PRDM1 |
| 13 | ARID2 | 51 | CDK6 | 89 | FANCA | 127 | IDH1 | 165 | MPL | 203 | PRKAR1A |
| 14 | ASXL1 | 52 | CDK8 | 90 | FANCC | 128 | IDH2 | 166 | MRE11A | 204 | PTCH1 |
| 15 | ATM | 53 | CDKN1B | 91 | FANCD2 | 129 | IKBKE | 167 | MSH2 | 205 | PTEN |
| 16 | ATR | 54 | CDKN2A | 92 | FANCE | 130 | IKZF1 | 168 | MSH3 | 206 | PTPN11 |
| 17 | ATRX | 55 | CDKN2B | 93 | FANCF | 131 | IL7R | 169 | MSH6 | 207 | RAD50 |
| 18 | AURKA | 56 | CDKN2C | 94 | FANCG | 132 | INPP4B | 170 | MTOR | 208 | RAD51 |
| 19 | AURKB | 57 | CEBPA | 95 | FANCL | 133 | IRF1 | 171 | MUTYH | 209 | RAF1 |
| 20 | AXIN1 | 58 | CHD2 | 96 | FAS | 134 | IRF4 | 172 | MYC | 210 | RARA |
| 21 | AXL | 59 | CHEK1 | 97 | FBXW7 | 135 | IRS2 | 173 | MYCL | 211 | RB1 |
| 22 | B2M | 60 | CHEK2 | 98 | FGF10 | 136 | JAK1 | 174 | MYCN | 212 | RET |
| 23 | BAP1 | 61 | CIC | 99 | FGF14 | 137 | JAK2 | 175 | MYD88 | 213 | RICTOR |
| 24 | BARD1 | 62 | CREBBP | 100 | FGF23 | 138 | JAK3 | 176 | NF1 | 214 | RNF43 |
| 25 | BCL2 | 63 | CRKL | 101 | FGF3 | 139 | JUN | 177 | NF2 | 215 | ROS1 |
| 26 | BCL6 | 64 | CRLF2 | 102 | FGF4 | 140 | KAT6A | 178 | NFE2L2 | 216 | RPTOR |
| 27 | BCOR | 65 | CSF1R | 103 | FGF6 | 141 | KDM5A | 179 | NFKBIA | 217 | RUNX1 |
| 28 | BCORL1 | 66 | CTCF | 104 | FGFR1 | 142 | KDM5C | 180 | NKX2-1 | 218 | SDHA |
| 29 | BLM | 67 | CTNNA1 | 105 | FGFR2 | 143 | KDM6A | 181 | NOTCH1 | 219 | SDHB |
| 30 | BRAF | 68 | CTNNB1 | 106 | FGFR3 | 144 | KDR | 182 | NOTCH2 | 220 | SDHC |
| 31 | BRCA1 | 69 | DAXX | 107 | FGFR4 | 145 | KEAP1 | 183 | NPM1 | 221 | SDHD |
| 32 | BRCA2 | 70 | DDR2 | 108 | FLCN | 146 | KIT | 184 | NRAS | 222 | SETD2 |
| 33 | BRD4 | 71 | DNMT3A | 109 | FLT1 | 147 | KLHL6 | 185 | NTRK1 | 223 | SF3B1 |
| 34 | BRIP1 | 72 | DOT1L | 110 | FLT3 | 148 | KMT2A | 186 | NTRK2 | 224 | SMAD2 |
| 35 | BTK | 73 | EGFR | 111 | FLT4 | 149 | KMT2C | 187 | NTRK3 | 225 | SMAD4 |
| 36 | CALR | 74 | EP300 | 112 | FOXL2 | 150 | KRAS | 188 | PALB2 | 226 | SMARCA4 |
| 37 | CARD11 | 75 | EPHA7 | 113 | FOXP1 | 151 | LRP1B | 189 | PAX5 | 227 | SMARCB1 |
| 38 | CBFB | 76 | EPHB1 | 114 | FRS2 | 152 | MAP2K1 | 190 | PBRM1 | 228 | SMO |

Fig. 27b1

| Heme and Solid Tumor Related - xT Gene Panel ||
|---|---|
| No. | Symbol |
| 229 | SOCS1 |
| 230 | SOX10 |
| 231 | SOX2 |
| 232 | SPEN |
| 233 | SPOP |
| 234 | SRC |
| 235 | STAG2 |
| 236 | STAT3 |
| 237 | STAT4 |
| 238 | STK11 |
| 239 | SUFU |
| 240 | TAF1 |
| 241 | TET2 |
| 242 | TGFBR2 |
| 243 | TMPRSS2 |
| 244 | TNFAIP3 |
| 245 | TNFRSF14 |
| 246 | TOP1 |
| 247 | TP53 |
| 248 | TSC1 |
| 249 | TSC2 |
| 250 | TSHR |
| 252 | U2AF1 |
| 253 | VHL |
| 254 | WT1 |
| 255 | XPO1 |

Fig. 27b2

| Solid Tumor Related - xT Gene Panel | | | | | | | | | |
|---|---|---|---|---|---|---|---|---|---|
| No. | Symbol | No. | Symbol | No. | Symbol | No. | Symbol | No. | Symbol |
| 1 | ABL2 | 39 | CYP1B1 | 77 | FGF8 | 115 | HLA-DQB1 | 153 | MAD2L2 |
| 2 | ACTA2 | 40 | CYP2D6 | 78 | FGF9 | 116 | HLA-DQB2 | 154 | MAX |
| 3 | ACVR1B | 41 | CYP3A5 | 79 | FH | 117 | HLA-DRA | 155 | MC1R |
| 4 | AJUBA | 42 | DDB2 | 80 | FLG | 118 | HLA-DRB1 | 156 | MGMT |
| 5 | APOB | 43 | DICER1 | 81 | FNTB | 119 | HLA-DRB5 | 157 | MLH3 |
| 6 | ARHGAP35 | 44 | DIRC2 | 82 | FOXA1 | 120 | HLA-DRB6 | 158 | MLLT3 |
| 7 | ARID1B | 45 | DIS3 | 83 | FOXQ1 | 121 | HLA-E | 159 | MS4A1 |
| 8 | ARID5B | 46 | DIS3L2 | 84 | FUBP1 | 122 | HLA-F | 160 | MTAP |
| 9 | ASNS | 47 | DKC1 | 85 | G6PD | 123 | HLA-G | 161 | MTHFR |
| 10 | ATIC | 48 | DPYD | 86 | GALNT12 | 124 | HNF1B | 162 | MTRR |
| 11 | ATP7B | 49 | DYNC2H1 | 87 | GATA4 | 125 | HOXB13 | 163 | MYB |
| 12 | AXIN2 | 50 | EGF | 88 | GATA6 | 126 | HSPH1 | 164 | MYH11 |
| 13 | BCL2L1 | 51 | EGLN1 | 89 | GEN1 | 127 | IDO1 | 165 | NBN |
| 14 | BCL2L11 | 52 | ELF3 | 90 | GLI1 | 128 | IFIT1 | 166 | NCOR1 |
| 15 | BCLAF1 | 53 | ENG | 91 | GPC3 | 129 | IFIT2 | 167 | NHP2 |
| 16 | BMPR1A | 54 | EPCAM | 92 | GPS2 | 130 | IFIT3 | 168 | NOP10 |
| 17 | BTG1 | 55 | EPHA2 | 93 | GREM1 | 131 | IFNAR1 | 169 | NOTCH3 |
| 18 | BUB1B | 56 | EPHB2 | 94 | GRM3 | 132 | IFNAR2 | 170 | NQO1 |
| 19 | C10orf54 | 57 | ERCC1 | 95 | GSTP1 | 133 | IFNGR1 | 171 | NRG1 |
| 20 | C11orf30 | 58 | ERCC2 | 96 | H19 | 134 | IFNGR2 | 172 | NSD1 |
| 21 | C11orf65 | 59 | ERCC3 | 97 | H3F3A | 135 | IFNL3 | 173 | NTHL1 |
| 22 | C3orf70 | 60 | ERCC4 | 98 | HAS3 | 136 | IL10RA | 174 | NUDT15 |
| 23 | C8orf34 | 61 | ERCC5 | 99 | HAVCR2 | 137 | IL15 | 175 | PAK1 |
| 24 | CASP8 | 62 | ERCC8 | 100 | HDAC2 | 138 | IL2RA | 176 | PALLD |
| 25 | CASR | 63 | ERRFI1 | 101 | HIF1A | 139 | IL6R | 177 | PARK2 |
| 26 | CBR3 | 64 | ETS2 | 102 | HIST1H4E | 140 | ING1 | 178 | PAX3 |
| 27 | CCDC6 | 65 | FAM175A | 103 | HLA-A | 141 | IRF2 | 179 | PAX7 |
| 28 | CD19 | 66 | FANCB | 104 | HLA-B | 142 | ITPKB | 180 | PAX8 |
| 29 | CD40 | 67 | FANCI | 105 | HLA-C | 143 | KEL | 181 | PDPK1 |
| 30 | CDKN1A | 68 | FANCM | 106 | HLA-DMA | 144 | KIF1B | 182 | PHOX2B |
| 31 | CDKN1C | 69 | FAT1 | 107 | HLA-DMB | 145 | KLLN | 183 | PIAS4 |
| 32 | CEP57 | 70 | FCGR2A | 108 | HLA-DOA | 146 | KMT2D | 184 | PIK3C2B |
| 33 | CFTR | 71 | FCGR3A | 109 | HLA-DOB | 147 | LAG3 | 185 | PIK3CB |
| 34 | CHD4 | 72 | FDPS | 110 | HLA-DPA1 | 148 | LDLR | 186 | PIK3CD |
| 35 | CTC1 | 73 | FGF1 | 111 | HLA-DPB1 | 149 | LMNA | 187 | PML |
| 36 | CTLA4 | 74 | FGF2 | 112 | HLA-DPB2 | 150 | LMO1 | 188 | PMS1 |
| 37 | CTRC | 75 | FGF5 | 113 | HLA-DQA1 | 151 | LYN | 189 | PMS2 |
| 38 | CYLD | 76 | FGF7 | 114 | HLA-DQA2 | 152 | LZTR1 | 190 | POLD1 |

Fig. 27c1

| Solid Tumor Related - xT Gene Panel | | | | | | | | | |
|---|---|---|---|---|---|---|---|---|---|
| No. | Symbol | No. | Symbol | No. | Symbol | No. | Symbol | No. | Symbol |
| 191 | POLE | 209 | RAD51D | 227 | SEMA3C | 245 | TCF7L2 | 262 | XPC |
| 192 | POLH | 210 | RAD54L | 228 | SH2B3 | 246 | TIGIT | 263 | XRCC1 |
| 193 | POU2F2 | 211 | RANBP2 | 229 | SLC26A3 | 247 | TMEM127 | 264 | XRCC2 |
| 194 | PPP1R15A | 212 | RASA1 | 230 | SLC47A2 | 248 | TMEM173 | 265 | XRCC3 |
| 195 | PPP2R2A | 213 | RBM10 | 231 | SLIT2 | 249 | TNF | 266 | YEATS4 |
| 196 | PPP6C | 214 | RECQL4 | 232 | SLX4 | 250 | TNFRSF9 | 267 | ZFHX3 |
| 197 | PRCC | 215 | RINT1 | 233 | SMAD3 | 251 | TOP2A | 268 | ZNF217 |
| 198 | PREX2 | 216 | RIT1 | 234 | SMARCE1 | 252 | TPM1 | 269 | ZNF471 |
| 199 | PRSS1 | 217 | RNF139 | 235 | SOD2 | 253 | TPMT | 270 | ZNF620 |
| 200 | PRSS2 | 218 | RPL5 | 236 | SOX9 | 254 | TYMS | 271 | ZNF750 |
| 201 | PTCH2 | 219 | RPS15 | 237 | SPINK1 | 255 | UBE2T | 272 | ZNRF3 |
| 202 | PTPN13 | 220 | RPS6KB1 | 238 | SPRED1 | 256 | UGT1A1 | | |
| 203 | PTPN22 | 221 | RSF1 | 239 | SYK | 257 | UGT1A9 | | |
| 204 | PTPRD | 222 | RUNX1T1 | 240 | TANC1 | 258 | UMPS | | |
| 205 | QKI | 223 | RXRA | 241 | TAP1 | 259 | VEGFA | | |
| 206 | RAC1 | 224 | SCG5 | 242 | TAP2 | 260 | WEE1 | | |
| 207 | RAD51B | 225 | SDHAF2 | 243 | TBC1D12 | 261 | WRN | | |
| 208 | RAD51C | 226 | SEC23B | 244 | TBX3 | 262 | XPA | | |

Fig. 27c2

| | | | | | |
|---|---|---|---|---|---|
| ABCB1 | BCL6 | CDK8 | DIS3L2 | FANCC | G6PD |
| ABCC3 | BCL7A | CDKN1A | DKC1 | FANCD2 | GABRA6 |
| ABL1 | BCLAF1 | CDKN1B | DNM2 | FANCE | GALNT12 |
| ABL2 | BCOR | CDKN1C | DNMT3A | FANCF | GATA1 |
| ABRAXAS1 | BCORL1 | CDKN2A** | DOT1L | FANCG | GATA2** |
| ACTA2 | BCR | CDKN2B | DPYD | FANCI | GATA3 |
| ACVR1(ALK2) | BIRC3 | CDKN2C | DYNC2H1 | FANCL | GATA4 |
| ACVR1B | BLM | CEBPA** | EBF1 | FANCM | GATA6 |
| AGO1 | BMPR1A** | CEP57 | ECT2L | FAS | GEN1 |
| AJUBA | BRAF | CFTR | EGF | FAT1 | GLI1 |
| AKT1 | BRCA1** | CHD2 | EGFR** | FBXO11 | GLI2 |
| AKT2 | BRCA2** | CHD4 | EGLN1 | FBXW7 | GNA11 |
| AKT3 | BRD4 | CHD7 | EIF1AX | FCGR2A | GNA13 |
| ALK | BRIP1** | CHEK1 | ELF3 | FCGR3A | GNAQ |
| AMER1 | BTG1 | CHEK2** | ELOC(TCEB1) | FDPS | GNAS |
| APC** | BTK | CIC | EMSY | FGF1 | GPC3 |
| APLNR | BUB1B | CIITA | ENG | FGF10 | GPS2 |
| APOB | C11orf65 | CKS1B | EP300 | FGF14 | GREM1 |
| AR | C3orf70 | CREBBP | EPCAM** | FGF2 | GRIN2A |
| ARAF | C8orf34 | CRKL | EPHA2 | FGF23 | GRM3 |
| ARHGAP26 | CALR | CRLF2 | EPHA7 | FGF3 | GSTP1 |
| ARHGAP35 | CARD11 | CSF1R | EPHB1 | FGF4 | H19 |
| ARID1A | CARM1 | CSF3R | EPHB2 | FGF5 | H3F3A |
| ARID1B | CASP8 | CTC1 | EPOR | FGF6 | HAS3 |
| ARID2 | CASR | CTCF | ERBB2(HER2) | FGF7 | HAVCR2 |
| ARID5B | CBFB | CTLA4 | ERBB3 | FGF8 | HDAC1 |
| ASNS | CBL | CTNNA1 | ERBB4 | FGF9 | HDAC2 |
| ASPSCR1 | CBLB | CTNNB1 | ERCC1 | FGFR1 | HDAC4 |
| ASXL1 | CBLC | CTRC | ERCC2 | FGFR2 | HGF |
| ATIC | CBR3 | CUL1 | ERCC3 | FGFR3 | HIF1A |
| ATM** | CCDC6 | CUL3 | ERCC4 | FGFR4 | HIST1H1E |
| ATP7B | CCND1 | CUL4A | ERCC5 | FH** | HIST1H3B |
| ATR | CCND2 | CUL4B | ERCC6 | FHIT | HIST1H4E |
| ATRX | CCND3 | CUX1 | ERG | FLCN** | HLA-A |
| AURKA | CCNE1 | CXCR4 | ERRFI1 | FLT1 | HLA-B |
| AURKB | CD19 | CYLD | ESR1 | FLT3 | HLA-C |
| AXIN1 | CD22 | CYP1B1 | ETS1 | FLT4 | HLA-DMA |
| AXIN2** | CD274(PD-L1) | CYP2D6 | ETS2 | FNTB | HLA-DMB |
| AXL | CD40 | CYP3A5 | ETV1 | FOXA1 | HLA-DOA |
| B2M | CD70 | CYSLTR2 | ETV4 | FOXL2 | HLA-DOB |
| BAP1 | CD79A | DAXX | ETV5 | FOXO1 | HLA-DPA1 |
| BARD1 | CD79B | DDB2 | ETV6 | FOXO3 | HLA-DPB1 |
| BCL10 | CDC73 | DDR2 | EWSR1 | FOXP1 | HLA-DPB2 |
| BCL11B | CDH1** | DDX3X | EZH2 | FOXQ1 | HLA-DQA1 |
| BCL2 | CDK12 | DICER1 | FAM46C | FRS2 | HLA-DQA2 |
| BCL2L1 | CDK4 | DIRC2 | FANCA | FUBP1 | HLA-DQB1 |
| BCL2L11 | CDK6 | DIS3 | FANCB | FUS | HLA-DQB2 |

FIG. 27c3a

| | | | | | | | |
|---|---|---|---|---|---|---|---|
| HLA-DRA | KDM5A | MET | NT5C2 | POU2F2 | RNF43 | SPOP | TNFRSF9 |
| HLA-DRB1 | KDM5C | MGMT | NTHL1 | PPARA | ROS1 | SPRED1 | TOP1 |
| HLA-DRB5 | KDM5D | MIB1 | NTRK1 | PPARD | RPL5 | SRC | TOP2A |
| HLA-DRB6 | KDM6A | MITF | NTRK2 | PPARG | RPS15 | SRSF2 | TP53** |
| HLA-E | KDR | MKI67 | NTRK3 | PPM1D | RPS6KB1 | STAG2 | TP63 |
| HLA-F | KEAP1 | MLH1** | NUDT15 | PPP1R15A | RPTOR | STAT3 | TPM1 |
| HLA-G | KEL | MLH3 | NUP98 | PPP2R1A | RRM1 | STAT4 | TPMT |
| HNF1A | KIF1B | MLLT3 | OLIG2 | PPP2R2A | RSF1 | STAT5A | TRAF3 |
| HNF1B | KIT | MN1 | P2RY8 | PPP6C | RUNX1** | STAT5B | TRAF7 |
| HOXA11 | KLF4 | MPL | PAK1 | PRCC | RUNX1T1 | STAT6 | TSC1** |
| HOXB13 | KLHL6 | MRE11A | PALB2** | PRDM1 | RXRA | STK11** | TSC2** |
| HRAS | KLLN | MS4A1 | PALLD | PREX2 | SCG5 | SUFU | TSHR |
| HSD11B2 | KMT2A | MSH2** | PAX3 | PRKAR1A | SDHA | SUZ12 | TUSC3 |
| HSD3B1 | KMT2B | MSH3** | PAX5 | PRKDC | SDHAF2** | SYK | TYMS |
| HAD3B2 | KMT2C | MSH6** | PAX7 | PRKN | SDHB** | SYNE1 | U2AF1 |
| HSP90AA1 | KMT2D | MTAP | PAX8 | PRSS1 | SDHC** | TAF1 | UBE2T |
| HSPH1 | KRAS | MTHFD2 | PBRM1 | PTCH1 | SDHD** | TANC1 | UGT1A1 |
| IDH1 | L2HGDH | MTHFR | PCBP1 | PTCH2 | SEC23B | TAP1 | UGT1A9 |
| IDH2 | LAG3 | MTOR | PDCD1 | PTEN** | SEMA3C | TAP2 | UMPS |
| IDO1 | LATS1 | MTRR | PDCD1LG2 | PTPN11 | SETBP1 | TARBP2 | VEGFA |
| IFIT1 | LCK | MUTYH** | PDGFRA | PTPN13 | SETD2 | TBC1D12 | VEGFB |
| IFIT2 | LDLR | MYB | PDGFRB | PTPN22 | SF3B1 | TBL1XR1 | VHL** |
| IFIT3 | LEF1 | MYC | PDK1 | PTPRD | SGK1 | TBX3 | VSIR |
| IFNAR1 | LMNA | MYCL | PHF6 | PTPRT | SH2B3 | TCF3 | WEE1 |
| IFNAR2 | LMO1 | MYCN | PHGDH | QKI | SHH | TCF7L2 | WNK1 |
| IFNGR1 | LRP1B | MYD88 | PHLPP1 | RAC1 | SLC26A3 | TCL1A | WNK2 |
| IFNGR2 | LYN | MYH11 | PHLPP2 | RAD21 | SLC47A2 | TERT* | WRN |
| IFNL3 | LZTR1 | NBN** | PHOX2B | RAD50 | SLC9A3R1 | TET2 | WT1** |
| IKBKE | MAD2L2 | NCOR1 | PIAS4 | RAD51 | SLIT2 | TFE3 | XPA |
| IKZF1 | MAF | NCOR2 | PIK3C2B | RAD51B | SLX4 | TFEB | XPC |
| IL10RA | MAFB | NF1 | PIK3CA | RAD51C** | SMAD2 | TFEC | XPO1 |
| IL15 | MAGI2 | NF2** | PIK3CB | RAD51D** | SMAD3 | TGFBR1 | XRCC1 |
| IL2RA | MALT1 | NFE2L2 | PIK3CD | RAD54L | SMAD4** | TGFBR2 | XRCC2 |
| IL6R | MAP2K1 | NFKBIA | PIK3CG | RAF1 | SMARCA1 | TIGIT | XRCC3 |
| IL7R | MAP2K2 | NHP2 | PIK3R1 | RANBP2 | SMARCA4 | TMEM127 | YEATS4 |
| ING1 | MAP2K4 | NKX2-1 | PIK3R2 | RARA | SMARCB1 | TMEM173 | ZFHX3 |
| INPP4B | MAP3K1 | NOP10 | PIM1 | RASA1 | SMARCE1 | TMPRSS2 | ZMYM3 |
| IRF1 | MAP3K7 | NOTCH1 | PLCG1 | RB1** | SMC1A | TNF | ZNF217 |
| IRF2 | MAPK1 | NOTCH2 | PLCG2 | RBM10 | SMC3 | TNFAIP3 | ZNF471 |
| IRF4 | MAX | NOTCH3 | PML | RECQL4 | SMO | TNFRSF14 | ZNF620 |
| IRS2 | MC1R | NOTCH4 | PMS1 | RET** | SOCS1 | TNFRSF17 | ZNF750 |
| ITPKB | MCL1 | NPM1 | PMS2** | RHEB | SOD2 | | ZNRF3 |
| JAK1 | MDM2 | NQO1 | POLD1** | RHOA | SOX10 | | ZRSR2 |
| JAK2 | MDM4 | NRAS | POLE** | RICTOR | SOX2 | FIG. 27c3b | |
| JAK3 | MED12 | NRG1 | POLH | RINT1 | SOX9 | | |
| JUN | MEF2B | NSD1 | POLQ | RIT1 | SPEN | | |
| KAT6A | MEN1** | NSD2 | POT1 | RNF139 | SPINK1 | | |

| Gene Rearrangement By DNA Sequencing - xT Gene Panel | | | |
|---|---|---|---|
| No. | Symbol | No. | Symbol |
| 1 | ABL1 | 12 | NRG1 |
| 2 | ALK | 13 | NTRK1 |
| 3 | BCR | 14 | NTRK3 |
| 4 | BRAF | 15 | PAX8 |
| 5 | EGFR | 16 | PDGFRA |
| 6 | ETV6 | 17 | PML |
| 7 | EWSR1 | 18 | RARA |
| 8 | FGFR2 | 19 | RET |
| 9 | FGFR3 | 20 | ROS1 |
| 10 | MYB | 21 | TMPRSS2 |
| 11 | MYC | | |

Fig. 27d

| No. | Symbol | No. | Symbol | No. | Symbol | No. | Symbol | No. | Symbol |
|---|---|---|---|---|---|---|---|---|---|
| \multicolumn{10}{|c|}{Additional Exemplary Gene Panel} |

| No. | Symbol | No. | Symbol | No. | Symbol | No. | Symbol | No. | Symbol |
|---|---|---|---|---|---|---|---|---|---|
| 1 | ABL1 | 39 | (EMSY) | 77 | CUL3 | 115 | FGF6 | 153 | ID3 |
| 2 | ACVR1B | 40 | CALR | 78 | CUL4A | 116 | FGFR1 | 154 | IDH1 |
| 3 | AKT1 | 41 | CARD11 | 79 | CXCR4 | 117 | FGFR2 | 155 | IDH2 |
| 4 | AKT2 | 42 | CASP8 | 80 | CYP17A1 | 118 | FGFR3 | 156 | IGF1R |
| 5 | AKT3 | 43 | CBFB | 81 | DAXX | 119 | FGFR4 | 157 | IKBKE |
| 6 | ALK | 44 | CBL | 82 | DDR1 | 120 | FH | 158 | IKZF1 |
| 7 | ALOX12B | 45 | CCND1 | 83 | DDR2 | 121 | FLCN | 159 | INPP4B |
| 8 | AMER1 | 46 | CCND2 | 84 | DIS3 | 122 | FLT1 | 160 | IRF2 |
| 9 | APC | 47 | CCND3 | 85 | DNMT3A | 123 | FLT3 | 161 | IRF4 |
| 10 | AR | 48 | CCNE1 | 86 | DOT1L | 124 | FOXL2 | 162 | IRS2 |
| 11 | ARAF | 49 | CD22 | 87 | EED | 125 | FUBP1 | 163 | JAK1 |
| 12 | ARFRP1 | 50 | CD274 | 88 | EGFR | 126 | GABRA6 | 164 | JAK2 |
| 13 | ARID1A | 51 | (PD-L1) | 89 | EP300 | 127 | GATA3 | 165 | JAK3 |
| 14 | ASXL1 | 52 | CD70 | 90 | EPHA3 | 128 | GATA4 | 166 | JUN |
| 15 | ATM | 53 | CD79A | 91 | EPHB1 | 129 | GATA6 | 167 | KDM5A |
| 16 | ATR | 54 | CD79B | 92 | EPHB4 | 130 | GID4 | 168 | KDM5C |
| 17 | ATRX | 55 | CDC73 | 93 | ERBB2 | 131 | GNA11 | 169 | KDM6A |
| 18 | AURKA | 56 | CDH1 | 94 | ERBB3 | 132 | GNA13 | 170 | KDR |
| 19 | AURKB | 57 | CDK12 | 95 | ERBB4 | 133 | GNAQ | 171 | KEAP1 |
| 20 | AXIN1 | 58 | CDK4 | 96 | ERCC4 | 134 | GNAS | 172 | KEL |
| 21 | AXL | 59 | CDK6 | 97 | ERG | 135 | GRM3 | 173 | KIT |
| 22 | BAP1 | 60 | CDK8 | 98 | ERRFI1 | 136 | GSK3B | 174 | KLHL6 |
| 23 | BARD1 | 61 | CDKN1A | 99 | ESR1 | 137 | H3F3A | 175 | KMT2A |
| 24 | BCL2 | 62 | CDKN1B | 100 | EZH2 | 138 | HDAC1 | 176 | KMT2D |
| 25 | BCL2L1 | 63 | CDKN2A | 101 | FAM46C | 139 | HGF | 177 | KRAS |
| 26 | BCL2L2 | 64 | CDKN2B | 102 | FANCA | 140 | HNF1A | 178 | LTK |
| 27 | BCL6 | 65 | CDKN2C | 103 | FANCC | 141 | HRAS | 179 | LYN |
| 28 | BCOR | 66 | CEBPA | 104 | FANCG | 142 | HSD3B1 | 180 | MAF |
| 29 | BCORL1 | 67 | CHEK1 | 105 | FANCL | 143 | FGF6 | 181 | MAP2K1 |
| 30 | BRAF | 68 | CHEK2 | 106 | FAS | 144 | FGFR1 | 182 | MAP2K2 |
| 31 | BRCA1 | 69 | CIC | 107 | FBXW7 | 145 | FGFR2 | 183 | MAP2K4 |
| 32 | BRCA2 | 70 | CREBBP | 108 | FGF10 | 146 | FGFR3 | 184 | MAP3K1 |
| 33 | BRD4 | 71 | CRKL | 109 | FGF12 | 147 | FGFR4 | 185 | MAP3K13 |
| 34 | BRIP1 | 72 | CSF1R | 110 | FGF14 | 148 | FH | 186 | MAPK1 |
| 35 | BTG1 | 73 | CSF3R | 111 | FGF19 | 149 | FLCN | 187 | MCL1 |
| 36 | BTG2 | 74 | CTCF | 112 | FGF23 | 150 | FLT1 | 188 | MDM2 |
| 37 | BTK | 75 | CTNNA1 | 113 | FGF3 | 151 | FLT3 | 189 | MDM4 |
| 38 | C11orf30 | 76 | CTNNB1 | 114 | FGF4 | 152 | FOXL2 | 190 | MED12 |

Fig. 28a

| \multicolumn{10}{c}{Additional Exemplary Gene Panel} |
|---|---|---|---|---|---|---|---|---|---|
| No. | Symbol | No. | Symbol | No. | Symbol | No. | Symbol | No. | Symbol |
| 191 | MSH3 | 216 | P2RY8 | 241 | PRDM1 | 266 | RPTOR | 291 | TBX3 |
| 192 | MSH6 | 217 | PALB2 | 242 | PRKAR1A | 267 | SDHA | 292 | TEK |
| 193 | MST1R | 218 | PARK2 | 243 | PRKCI | 268 | SDHB | 293 | TET2 |
| 194 | MTAP | 219 | PARP1 | 244 | PTCH1 | 269 | SDHC | 294 | TGFBR2 |
| 195 | MTOR | 220 | PARP2 | 245 | PTEN | 270 | SDHD | 295 | TIPARP |
| 196 | MUTYH | 221 | PARP3 | 246 | PTPN11 | 271 | SETD2 | 296 | TNFAIP3 |
| 197 | MYC | 222 | PAX5 | 247 | PTPRO | 272 | SF3B1 | 297 | TNFRSF14 |
| 198 | MYCL | 223 | PBRM1 | 248 | QKI | 273 | SGK1 | 298 | TP53 |
| 199 | MYCN | 224 | PDCD1 | 249 | RAC1 | 274 | SMAD2 | 299 | TSC1 |
| 200 | MYD88 | 225 | PDCD1LG2 | 250 | RAD21 | 275 | SMAD4 | 300 | TSC2 |
| 201 | NBN | 226 | PDGFRA | 251 | RAD51 | 276 | SMARCA4 | 301 | TYRO3 |
| 202 | NF1 | 227 | PDGFRB | 252 | RAD51B | 277 | SMARCB1 | 302 | U2AF1 |
| 203 | NF2 | 228 | PDK1 | 253 | RAD51C | 278 | SMO | 303 | VEGFA |
| 204 | NFE2L2 | 229 | PIK3C2B | 254 | RAD51D | 279 | SNCAIP | 304 | VHL |
| 205 | NFKBIA | 230 | PIK3C2G | 255 | RAD52 | 280 | SOCS1 | 305 | WHSC1 |
| 206 | NKX2-1 | 231 | PIK3CA | 256 | RAD54L | 281 | SOX2 | 306 | WHSC1L1 |
| 207 | NOTCH1 | 232 | PIK3CB | 257 | RAF1 | 282 | SOX9 | 307 | WT1 |
| 208 | NOTCH2 | 233 | PIK3R1 | 258 | RARA | 283 | SPEN | 308 | XPO1 |
| 209 | NOTCH3 | 234 | PIM1 | 259 | RB1 | 284 | SPOP | 309 | XRCC2 |
| 210 | NPM1 | 235 | PMS2 | 260 | RBM10 | 285 | SRC | 310 | ZNF217 |
| 211 | NRAS | 236 | POLD1 | 261 | REL | 286 | STAG2 | 311 | ZNF703 |
| 212 | NT5C2 | 237 | POLE | 262 | RET | 287 | STAT3 | | |
| 213 | NTRK1 | 238 | PPARG | 263 | RICTOR | 288 | STK11 | | |
| 214 | NTRK2 | 239 | PPP2R1A | 264 | RNF43 | 289 | SUFU | | |
| 215 | NTRK3 | 240 | PPP2R2A | 265 | ROS1 | 290 | SYK | | |

Fig. 28b

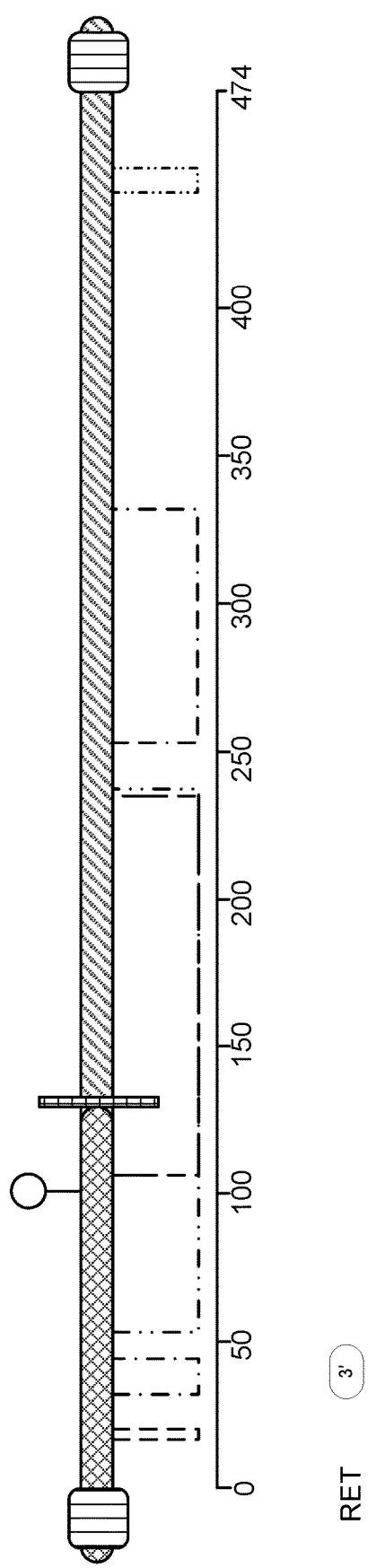
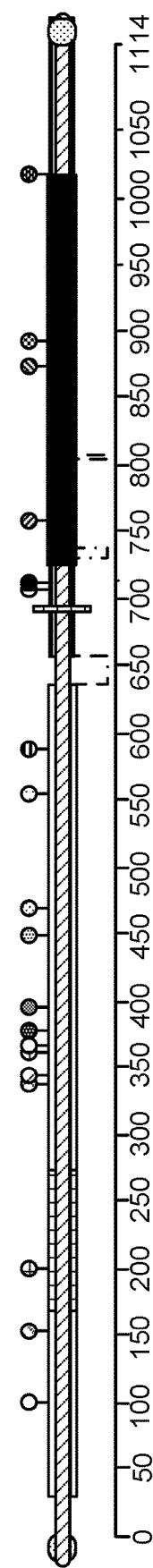
Fig. 34

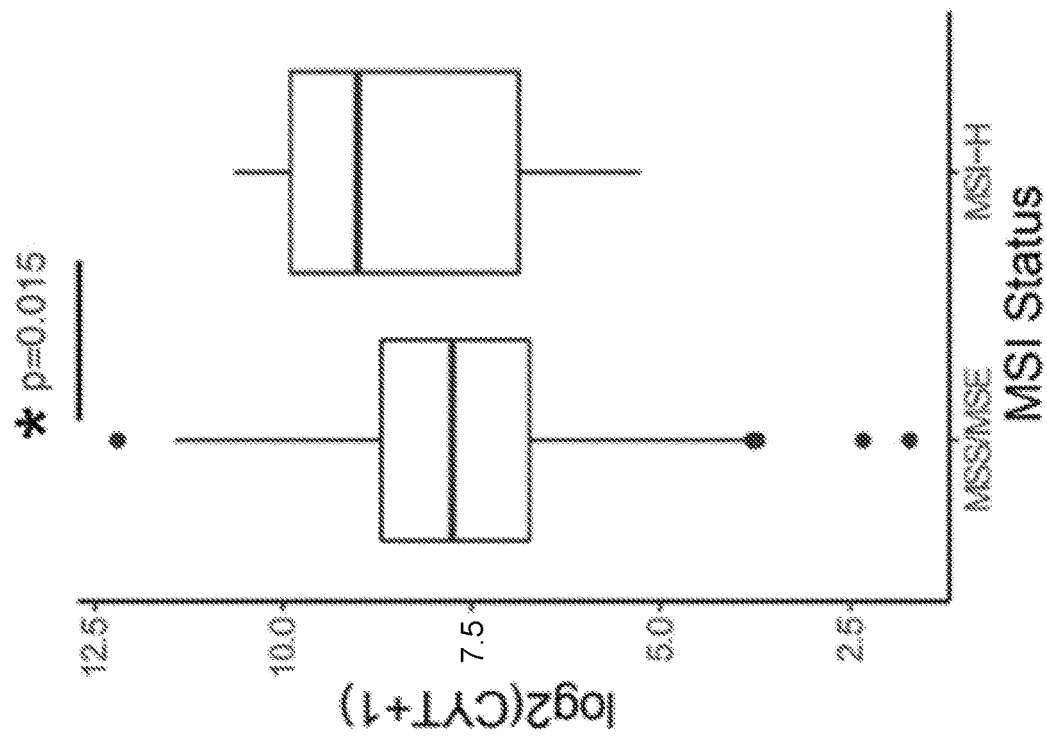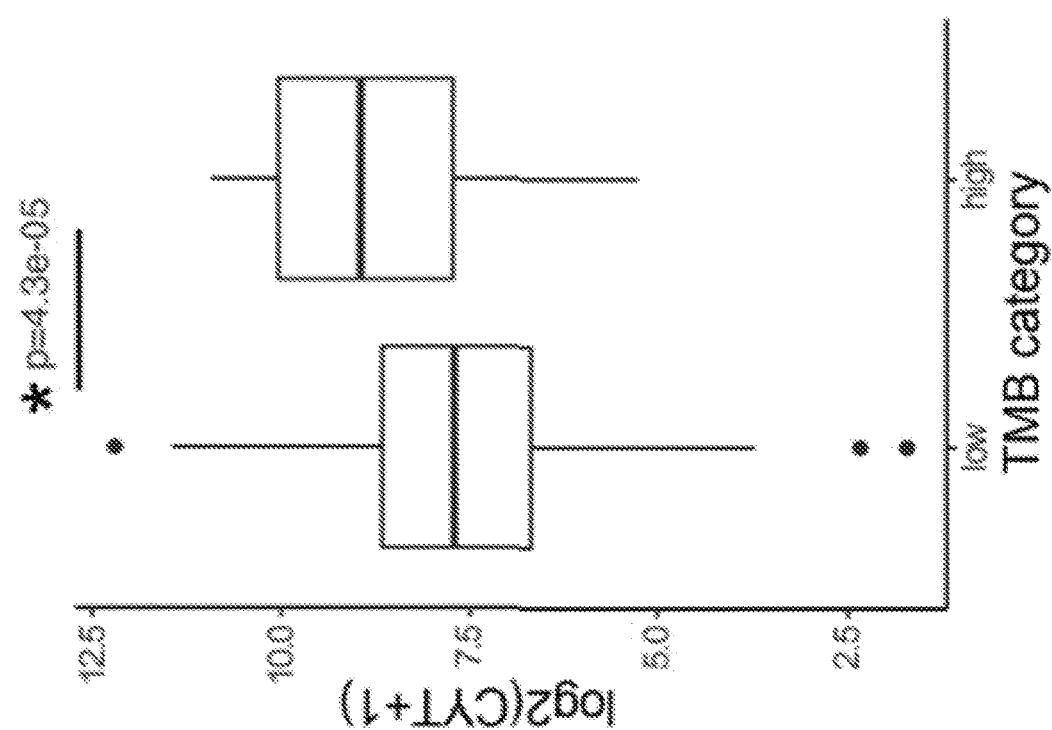
Fig. 39

DATA BASED CANCER RESEARCH AND TREATMENT SYSTEMS AND METHODS

CROSS-REFERENCE TO RELATED APPLICATIONS

This application is a U.S. national stage application, filed pursuant to 35 U.S.C. § 371, of international application No. PCT/US2019/056713, which was filed on Oct. 17, 2019, and is titled "Data Based Cancer Research and Treatment Systems and Methods," which claims priority to U.S. provisional patent application No. 62/746,997 which was filed on Oct. 17, 2018, titled "Data Based Cancer Research and Treatment Systems and Methods," both of which are incorporated herein in their entirety by reference. This application also claims the benefit of priority to U.S. provisional patent application No. 62/902,950, which was filed on Sep. 19, 2019, and is titled "System and Method for Expanding Clinical Options for Cancer Patients Using Integrated Genomic Profiling".

STATEMENT REGARDING FEDERALLY SPONSORED RESEARCH OR DEVELOPMENT

Not applicable.

BACKGROUND OF THE DISCLOSURE

The present invention relates to systems and methods for obtaining and employing data related to physical and genomic patient characteristics as well as diagnosis, treatments and treatment efficacy to provide a suite of tools to healthcare providers, researchers and other interested parties enabling those entities to develop new cancer state-treatment-results insights and/or improve overall patient healthcare and treatment plans for specific patients.

The present disclosure is described in the context of a system related to cancer research, diagnosis, treatment and results analysis. Nevertheless, it should be appreciated that the present disclosure is intended to teach concepts, features and aspects that will be useful in many different health related contexts and therefore the specification should not be considered limited to a cancer related systems unless specifically indicated for some system aspect.

Hereafter, unless indicated otherwise, the following terms and phrases will be used in this disclosure as described. The term "provider" will be used to refer to an entity that operates the overall system disclosed herein and, in most cases, will include a company or other entity that runs servers and maintains databases and that employs people with many different skill sets required to construct, maintain and adapt the disclosed system to accommodate new data types, new medical and treatment insights, and other needs. Exemplary provider employees may include researchers, data abstractors, physicians, pathologists, radiologists, data scientists, and many other persons with specialized skill sets.

The term "physician" will be used to refer generally to any health care provider including but not limited to a primary care physician, a medical specialist, a physician, a nurse, a medical assistant, etc., The term "researcher" will be used to refer generally to any person that performs research including but not limited to a pathologist, a radiologist, a physician, a data scientist, or some other health care provider. One person may operate both a physician and a researcher while others may simply operate in one of those capacities.

The phrase "system specialist" will be used generally to refer to any provider employee that operates within the disclosed systems to collect, develop, analyze or otherwise process system data, tissue samples or other information types (e.g., medical images) to generate any intermediate system work product or final work product where intermediate work product includes any data set, conclusions, tissue or other samples, grown tissues or samples, or other information for consumption by one or more other system specialists and where final work product includes data, conclusions or other information that is placed in a final or conclusory report for a system client or that operates within the system to perform research, to adapt the system to changing needs, data types or client requirements. For instance, the phrase "abstractor specialist" will be used to refer to a person that consumes data available in clinical records provided by a physician to generate normalized and structured data for use by other system specialists, the phrase "programming specialist" will be used to refer to a person that generates or modifies application program code to accommodate new data types and or clinical insights, etc.

The phrase "system user" will be used generally to refer to any person that uses the disclosed system to access or manipulate system data for any purpose and therefore will generally include physicians and researchers that work for the provider or that partner with the provider to perform services for patients or for other partner research institutions as well as system specialists that work for the provider.

The phrase "cancer state" will be used to refer to a cancer patient's overall condition including diagnosed cancer, location of cancer, cancer stage, other cancer characteristics (e.g., tumor characteristics), other user conditions (e.g., age, gender, weight, race, habits (e.g., smoking, drinking, diet)), other pertinent medical conditions (e.g., high blood pressure, dry skin, other diseases, etc.), medications, allergies, other pertinent medical history, current side effects of cancer treatments and other medications, etc.

The term "consume" will be used to refer to any type of consideration, use, modification, or other activity related to any type of system data, tissue samples, etc., whether or not that consumption is exhaustive (e.g., used only once, as in the case of a tissue sample that cannot be reproduced) or inexhaustible so that the data, sample, etc., persists for consumption by multiple entities (e.g., used multiple times as in the case of a simple data value).

The term "consumer" will be used to refer to any system entity that consumes any system data, samples, or other information in any way including each of specialists, physicians, researchers, clients that consume any system work product, and software application programs or operational code that automatically consume data, samples, information or other system work product independent of any initiating human activity.

The phrase "treatment planning process" will be used to refer to an overall process that includes one or more sub-processes that process clinical and other patient data and samples (e.g., tumor tissue) to generate intermediate data deliverables and eventually final work product in the form of one or more final reports provided to system clients. These processes typically include varying levels of exploration of treatment options for a patient's specific cancer state but are typically related to treatment of a specific patient as opposed to more general exploration for the purpose of more general research activities. Thus, treatment planning may include data generation and processes used to generate that data, consideration of different treatment options and effects of those options on patient illness, etc., resulting in ultimate prescriptive plans for addressing specific patient ailments.

Medical treatment prescriptions or plans are typically based on an understanding of how treatments affect illness (e.g., treatment results) including how well specific treatments eradicate illness, duration of specific treatments, duration of healing processes associated with specific treatments and typical treatment specific side effects. Ideally treatments result in complete elimination of an illness in a short period with minimal or no adverse side effects. In some cases cost is also a consideration when selecting specific medical treatments for specific ailments.

Knowledge about treatment results is often based on analysis of empirical data developed over decades or even longer time periods during which physicians and/or researchers have recorded treatment results for many different patients and reviewed those results to identify generally successful ailment specific treatments. Researchers and physicians give medicine to patients or treat an ailment in some other fashion, observe results and, if the results are good, the researchers and physicians use the treatments again to treat similar ailments. If treatment results are bad, a researcher foregoes prescribing the associated treatment for a next encountered similar ailment and instead tries some other treatment, hopefully based on prior treatment efficacy data. Treatment results are sometimes published in medical journals and/or periodicals so that many physicians can benefit from a treating physician's insights and treatment results.

In many cases treatment results for specific illnesses vary for different patients. In particular, in the case of cancer treatments and results, different patients often respond differently to identical or similar treatments. Recognizing that different patients experience different results given effectively the same treatments in some cases, researchers and physicians often develop additional guidelines around how to optimize ailment treatments based on specific patient cancer state. For instance, while a first treatment may be best for a young relatively healthy woman suffering colon cancer, a second treatment associated with fewer adverse side effects may be optimal for an older relatively frail man with a similar colon same cancer diagnosis. In many cases patient conditions related to cancer state may be gleaned from clinical medical records, via a medical examination and/or via a patient interview, and may be used to develop a personalized treatment plan for a patient's specific cancer state. The idea here is to collect data on as many factors as possible that have any cause-effect relationship with treatment results and use those factors to design optimal personalized treatment plans.

In treatment of at least some cancer states, treatment and results data is simply inconclusive. To this end, in treatment of some cancer states, seemingly indistinguishable patients with similar conditions often react differently to similar treatment plans so that there is no cause and effect between patient conditions and disparate treatment results. For instance, two women may be the same age, indistinguishably physically fit and diagnosed with the same exact cancer state (e.g., cancer type, stage, tumor characteristics, etc.). Here, the first woman may respond to a cancer treatment plan well and may recover from her disease completely in 8 months with minimal side effects while the second woman, administered the same treatment plan, may suffer several severe adverse side effects and may never fully recover from her diagnosed cancer. Disparate treatment results for seemingly similar cancer states exacerbate efforts to develop treatment and results data sets and prescriptive activities. In these cases, unfortunately, there are cancer state factors that have cause and effect relationships to specific treatment results that are simply currently unknown and therefore those factors cannot be used to optimize specific patient treatments at this time.

Genomic sequencing has been explored to some extent as another cancer state factor (e.g., another patient condition) that can affect cancer treatment efficacy. To this end, at least some studies have shown that genetic features (e.g., DNA related patient factors (e.g., DNA and DNA alterations) and/or DNA related cancerous material factors (e.g., DNA of a tumor)) as well as RNA and other genetic sequencing data can have cause and effect relationships with at least some cancer treatment results for at least some patients. For instance, in one chemotherapy study using SULT1A1, a gene known to have many polymorphisms that contribute to a reduction of enzyme activity in the metabolic pathways that process drugs to fight breast cancer, patients with a SULT1A1 mutation did not respond optimally to tamoxifen, a widely used treatment for breast cancer. In some cases these patients were simply resistant to the drug and in others a wrong dosage was likely lethal. Side effects ranged in severity depending on varying abilities to metabolize tamoxifen. Raftogianis R, Zalatoris J. Walther S. *The role of pharmacogenetics in cancer therapy, prevention and risk.* Medical Science Division. 1999: 243-247. Other cases where genetic features of a patient and/or a tumor affect treatment efficacy are well known.

While corollaries between genomic features and treatment efficacy have been shown in a small number of cases, it is believed that there are likely many more genomic features and treatment results cause and effect relationships that have yet to be discovered. Despite this belief, genetic testing in cancer cases is the rare exception, not the norm, for several reasons. One problem with genetic testing is that testing is expensive and has been cost prohibitive in many cases.

Another problem with genetic testing for treatment planning is that, as indicated above, cause and effect relationships have only been shown in a small number of cases and therefore, in most cancer cases, if genetic testing is performed, there is no linkage between resulting genetic factors and treatment efficacy. In other words, in most cases how genetic test results can be used to prescribe better treatment plans for patients is unknown so the extra expense associated with genetic testing in specific cases cannot be justified. Thus, while promising, genetic testing as part of first-line cancer treatment planning has been minimal or sporadic at best.

While the lack of genetic and treatment efficacy data makes it difficult to justify genetic testing for most cancer patients, perhaps the greater problem is that the dearth of genomic data in most cancer cases impedes processes required to develop cause and effect insights between genetics and treatment efficacy in the first place. Thus, without massive amounts of genetic data, there is no way to correlate genetic factors with treatment efficacy to develop justification for the expense associated with genetic testing in future cancer cases.

Yet one other problem posed by lack of genomic data is that if a researcher develops a genomic based treatment efficacy hypothesis based on a small genomic data set in a lab, the data needed to evaluate and clinically assess the hypothesis simply does not exist and it often takes months or even years to generate the data needed to properly evaluate the hypothesis. Here, if the hypothesis is wrong, the researcher may develop a different hypothesis which, again, may not be properly evaluated without developing a whole new set of genomic data for multiple patients over another several year period.

For some cancer states treatments and associated results are fully developed and understood and are generally consistent and acceptable (e.g., high cure rate, no long term effects, minimal or at least understood side effects, etc.). In other cases, however, treatment results cause and effect data associated with other cancer states is underdeveloped and/or inaccessible for several reasons. First, there are more than 250 known cancer types and each type may be in one of first through four stages where, in each stage, the cancer may have many different characteristics so that the number of possible "cancer varieties" is relatively large which makes the sheer volume of knowledge required to fully comprehend all treatment results unwieldy and effectively inaccessible.

Second, there are many factors that affect treatment efficacy including many different types of patient conditions where different conditions render some treatments more efficacious for one patient than other treatments or for one patient as opposed to other patients. Clearly capturing specific patient conditions or cancer state factors that do or may have a cause and effect relationship to treatment results is not easy and some causal conditions may not be appreciated and memorialized at all.

Third, for most cancer states, there are several different treatment options where each general option can be customized for a specific cancer state and patient condition set. The plethora of treatment and customization options in many cases makes it difficult to accurately capture treatment and results data in a normalized fashion as there are no clear standardized guidelines for how to capture that type of information.

Fourth, in most cases patient treatments and results are not published for general consumption and therefore are simply not accessible to be combined with other treatment and results data to provide a more fulsome overall data set. In this regard, many physicians see treatment results that are within an expected range of efficacy and conclude that those results cannot add to the overall cancer treatment knowledge base and therefore those results are never published. The problem here is that the expected range of efficacy can be large (e.g., 20% of patients fully heal and recover, 40% live for an extended duration, 40% live for an intermediate duration and 20% do not appreciably respond to a treatment plan) so that all treatment results are within an "expected" efficacy range and treatment result nuances are simply lost.

Fifth, currently there is no easy way to build on and supplement many existing illness-treatment-results databases so that as more data is generated, the new data and associated results cannot be added to existing databases as evidence of treatment efficacy or to challenge efficacy. Thus, for example, if a researcher publishes a study in a medical journal, there is no easy way for other physicians or researchers to supplement the data captured in the study. Without data supplementation over time, treatment and results corollaries cannot be tested and confirmed or challenged.

Sixth, the knowledge base around cancer treatments is always growing with different clinical trials in different stages around the world so that if a physician's knowledge is current today, her knowledge will be dated within months if not weeks. Thousands of oncological articles are published each year and many are verbose and/or intellectually arduous to consume (e.g., the articles are difficult to read and internalize), especially by extremely busy physicians that have limited time to absorb new materials and information. Distilling publications down to those that are pertinent to a specific physician's practice takes time and is an inexact endeavor in many cases.

Seventh, in most cases there is no clear incentive for physicians to memorialize a complete set of treatment and results data and, in fact, the time required to memorialize such data can operate as an impediment to collecting that data in a useful and complete form. To this end, prescribing and treating physicians are busy diagnosing and treating patients based on what they currently understand and painstakingly capturing a complete set of cancer state, treatment and results data without instantaneously reaping some benefit for patients being treated in return (e.g. a new insight, a better prescriptive treatment tool, etc.) is often perceived as a "waste" of time. In addition, because time is often of the essence in cancer treatment planning and plan implementation (e.g., starting treatment as soon as possible can increase efficacy in many cases), most physicians opt to take more time attending to their patients instead of generating perfect and fulsome treatments and results data sets.

Eighth, the field of next generation sequencing ("NGS") for cancer genomics is new and NGS faces significant challenges in managing related sequencing, bioinformatics, variant calling, analysis, and reporting data. Next generation sequencing involves using specialized equipment such as a next generation gene sequencer, which is an automated instrument that determines the order of nucleotides in DNA and RNA. The instrument reports the sequences as a string of letters, called a read, which the analyst compares to one or more reference genomes of the same genes, which is like a library of normal and variant gene sequences associated with certain conditions. With no settled NGS standards, different NGS providers have different approaches for sequencing cancer patient genomics and, based on their sequencing approaches, generate different types and quantities of genomics data to share with physicians, researchers, and patients. Different genomic datasets exacerbate the task of discerning and, in some cases, render it impossible to discern, meaningful genetics-treatment efficacy insights as required data is not in a normalized form, was never captured or simply was never generated.

In addition to problems associated with collecting and memorializing treatment and results data sets, there are problems with digesting or consuming recorded data to generate useful conclusions. For instance, recorded cancer state, treatment and results data is often incomplete. In most cases physicians are not researchers and they do not follow clearly defined research techniques that enforce tracking of all aspects of cancer states, treatments and results and therefore data that is recorded is often missing key information such as, for instance, specific patient conditions that may be of current or future interest, reasons why a specific treatment was selected and other treatments were rejected, specific results, etc. In many cases where cause and effect relationships exist between cancer state factors and treatment results, if a physician fails to identify and record a causal factor, the results cannot be tied to existing cause and effect data sets and therefore simply cannot be consumed and added the overall cancer knowledge data set in a meaningful way.

Another impediment to digesting collected data is that physicians often capture cancer state, treatment and results data in forms that make it difficult if not impossible to process the collected information so that the data can be normalized and used with other data from similar patient treatments to identify more nuanced insights and to draw more robust conclusions. For instance, many physicians prefer to use pen and paper to track patient care and/or use personal shorthand or abbreviations for different cancer state descriptions, patient conditions, treatments, results and even conclusions. Using software to glean accurate information from hand written notes is difficult at best and the task is exacerbated when hand written records include personal abbreviations and shorthand representations of information that software simply cannot identify with the physician's intended meaning.

One positive development in the area of cancer treatment planning has been establishment of cancer committees or boards at cancer treating institutions where committee members routinely consider treatment planning for specific patient cancer states as a committee. To this end, it has been recognized that the task of prescribing optimized treatment plans for diagnosed cancer states is exacerbated by the fact that many physicians do not specialize in more than one or a small handful of cancer treatment options (e.g., radiation therapy, chemotherapy, surgery, etc.). For this reason, many physicians are not aware of many treatment options for specific ailment-patient condition combinations, related treatment efficacy and/or how to implement those treatment options. In the case of cancer boards, the idea is that different board members bring different treatment experiences, expertise and perspectives to bear so that each patient can benefit from the combined knowledge of all board members and so that each board member's awareness of treatment options continually expands.

While treatment boards are useful and facilitate at least some sharing of experiences among physicians and other healthcare providers, unfortunately treatment committees only consider small snapshots of treatment options and associated results based on personal knowledge of board members. In many cases boards are forced to extrapolate from "most similar" cancer states they are aware of to craft patient treatment plans instead of relying on a more fulsome collection of cancer state-treatment-results data, insights and conclusions. In many cases the combined knowledge of board members may not include one or several important perspectives or represent important experience bases so that a final treatment plan simply cannot be optimized.

To be useful cancer state, treatment and efficacy data and conclusions based thereon have to be rendered accessible to physicians, researchers and other interested parties. In the case of cancer treatments where cancer states, treatments, results and conclusions are extremely complicated and nuanced, physician and researcher interfaces have to present massive amounts of information and show many data corollaries and relationships. When massive amounts of information are presented via an interface, interfaces often become extremely complex and intimidating which can result in misunderstanding and underutilization. What is needed are well designed interfaces that make complex data sets simple to understand and digest. For instance, in the case of cancer states, treatments and results, it would be useful to provide interfaces that enable physicians to consider de-identified patient data for many patients where the data is specifically arranged to trigger important treatment and results insights. It would also be useful if interfaces had interactive aspects so that the physicians could use filters to access different treatment and results data sets, again, to trigger different insights, to explore anomalies in data sets, and to better think out treatment plans for their own specific patients.

In some cases specific cancers are extremely uncommon so that when they do occur, there is little if any data related to treatments previously administered and associated results. With no proven best or even somewhat efficacious treatment option to choose from, in many of these cases physicians turn to clinical trials.

Cancer research is progressing all the time at many hospitals and research institutions where clinical trials are always being performed to test new medications and treatment plans, each trial associated with one or a small subset of specific cancer states (e.g., cancer type, state, tumor location and tumor characteristics). A cancer patient without other effective treatment options can opt to participate in a clinical trial if the patient's cancer state meets trial requirements and if the trial is not yet fully subscribed (e.g., there is often a limit to the number of patients that can participate in a trial).

At any time there are several thousand clinical trials progressing around the world and identifying trial options for specific patients can be a daunting endeavor. Matching patient cancer state to a subset of ongoing trials is complicated and time consuming. Pairing down matching trials to a best match given location, patient and physician requirements and other factors exacerbates the task of considering trial participation. In addition, considering whether or not to recommend a clinical trial to a specific patient given the possibility of trial treatment efficacy where the treatments are by their very nature experimental, especially in light of specific patient conditions, is a daunting activity that most physicians do not take lightly. It would be advantageous to have a tool that could help physicians identify clinical trial options for specific patients with specific cancer states and to access information associated with trial options.

As described above, optimized cancer treatment deliberation and planning involves consideration of many different cancer state factors, treatment options and treatment results as well as activities performed by many different types of service providers including, for instance, physicians, radiologists, pathologists, lab technicians, etc. One cancer treatment consideration most physicians agree affects treatment efficacy is treatment timing where earlier treatment is almost always better. For this reason, there is always a tension between treatment planning speed and thoroughness where one or the other of speed and thoroughness suffers.

One other problem with current cancer treatment planning processes is that it is difficult to integrate new pertinent treatment factors, treatment efficacy data and insights into existing planning databases. In this regard, known treatment planning databases and application programs have been developed based on a predefined set of factors and insights and changing those databases and applications often requires a substantial effort on the part of a software engineer to accommodate and integrate the new factors or insights in a meaningful way where those factors and insights are properly considered along with other known factors and insights. In some cases the substantial effort required to integrate new factors and insights simply means that the new factors or insights will not be captured in the database or used to affect planning. In other cases the effort means that the new factors or insights are only added to the system at some delayed time after a software engineer has applied the required and substantial reprogramming effort. In still other cases, the required effort means that physicians that want to apply new insights and factors may attempt to do so based on their own experiences and understandings instead of in a more scripted and rules based manner. Unfortunately, rendering a new insight actionable in the case of cancer treatment is a literal matter of life and death and therefore any delay or inaccurate application can have the worst effect on current patient prognosis.

One other problem with existing cancer treatment efficacy databases and systems is that they are simply incapable of optimally supporting different types of system users. To this end, data access, views and interfaces needed for optimal use are often dependent upon what a system user is using the system for. For instance, physicians often want treatment options, results and efficacy data distilled down to simple correlations while a cancer researcher often requires much more detailed data access required to develop new hypothesis related to cancer state, treatment and efficacy relationships. In known systems, data access, views and interfaces are often developed with one consuming client in mind such as, for instance, physicians, pathologists, radiologists, a cancer treatment researcher, etc., and are therefore optimized for that specific system user type which means that the system is not optimized for other user types and cannot be easily changed to accommodate needs of those other user types.

With the advent of NGS it has become possible to accurately detect genetic alterations in relevant cancer genes in a single comprehensive assay with high sensitivity and specificity. However, the routine use of NGS testing in a clinical context faces several challenges. First, many tissue samples include minimal high quality DNA and RNA required for meaningful testing. In this regard, nearly all clinical specimens comprise formalin fixed paraffin embedded tissue (FFPET), which, in many cases, has been shown to include degraded DNA and RNA. Exacerbating matters, many samples available for testing contain limited amounts of tissue, which in turn limits the amount of nucleic acid attainable from the tissue. For this reason, accurate profiling in clinical specimens requires an extremely sensitive assay capable of detecting gene alterations in specimens with a low tumor percentage. Second, millions of bases within the tumor genome are assayed. For this reason, rigorous statistical and analytical approaches for validation are required in order to demonstrate the accuracy of NGS technology for use in clinical settings and in developing cause and effect efficacy insights.

Thus, what is needed is a system that is capable of efficiently capturing all treatment relevant data including cancer state factors, treatment decisions, treatment efficacy and exploratory factors (e.g., factors that may have a causal relationship to treatment efficacy) and structuring that data to optimally drive different system activities including memorialization of data and treatment decisions, database analytics and user applications and interfaces. In addition, the system should be highly and rapidly adaptable so that it can be modified to absorb new data types and new treatment and research insights as well as to enable development of new user applications and interfaces optimized to specific user activities.

BRIEF SUMMARY OF THE DISCLOSURE

It has been recognized that an architecture where system processes are compartmentalized into loosely coupled and distinct micro-services that consume defined subsets of system data to generate new data products for consumption by other micro-services as well as other system resources enables maximum system adaptability so that new data types as well as treatment and research insights can be rapidly accommodated. To this end, because micro-services operate independently of other system resources to perform defined processes where the only development constraints are related to system data consumed and data products generated, small autonomous teams of scientists and software engineers can develop new micro-services with minimal system constraints thereby enabling expedited service development.

The system enables rapid changes to existing micro-services as well as development of new micro-services to meet any data handling and analytical needs. For instance, in a case where a new record type is to be ingested into an existing system, a new record ingestion micro-service can be rapidly developed for new record intake purposes resulting in addition of the new record in a raw data form to a system database as well as a system alert notifying other system resources that the new record is available for consumption. Here, the intra-micro-service process is independent of all other system processes and therefore can be developed as efficiently and rapidly as possible to achieve the service specific goal. As an alternative, an existing record ingestion micro-service may be modified independent of other system processes to accommodate some aspect of the new record type. The micro-service architecture enables many service development teams to work independently to simultaneously develop many different micro-services so that many aspects of the overall system can be rapidly adapted and improved at the same time.

According to another aspect of the present disclosure, in at least some disclosed embodiments system data may be represented in several differently structured databases that are optimally designed for different purposes. To this end, it has been recognized that system data is used for many different purposes such as memorialization of original records or documents, for data progression memorialization and auditing, for internal system resource consumption to generate interim data products, for driving research and analytics, and for supporting user application programs and related interfaces, among others. It has also been recognized that a data structure that is optimal for one purpose often is sub-optimal for other purposes. For instance, data structured to optimize for database searching by a data scientist may have a completely different structure than data optimized to drive a physician's application program and associated user interface. As another instance, data optimized for database searching by a data scientist usually has a different structure than raw data represented in an original clinical medical record that is stored to memorialize the original record.

By storing system data in purpose specific data structures, a diverse array of system functionality is optimally enabled. Advantages include simpler and more rapid application and micro-service development, faster analytics and other system processes and more rapid user application program operations.

Particularly useful systems disclosed herein include three separate databases including a "data lake" database, a "data vault" database and a "data marts" database. The data lake database includes, among other data, original raw data as well as interim micro-service data products and is used primarily to memorialize original raw data and data progression for auditing purposes and to enable data recreation that is tied to prior points in time. The data vault database includes data structured optimally to support database access and manipulation and typically includes routinely accessed original data as well as derived data. The data marts database includes data structured to support specific user application programs and user interfaces including original as well as derived data.

In some cases the disclosed inventions include a method for conducting genomic sequencing, the method comprising the steps of storing a set of user application programs wherein each of the programs requires an application specific subset of data to perform application processes and generate user output, for each of a plurality of patients that have cancerous cells and that receive cancer treatment, (a) obtaining clinical records data in original forms where the clinical records data includes cancer state information, treatment types and treatment efficacy information; (b) storing the clinical records data in a semi-structured first database, (c) for each patient, using a next generation genomic sequencer to generate genomic sequencing data for the patient's cancerous cells and normal cells, d) storing the sequencing data in the first database, (e) shaping at least a subset of the first database data to generate system structured data including clinical record data and sequencing data wherein the system structured data is optimized for searching, (f) storing the system structured data in a second database, (g) for each user application program, (i) selecting the application specific subset of data from the second database and (ii) storing the application specific subset of data in a structure optimized for application program interfacing in a third database.

In at least some cases the method includes the step of storing a plurality of micro-service programs where each micro-service program includes a data consume definition, a data product to generate definition and a data shaping process that converts consumed data to a data product, the step of shaping including running a sequence of micro-service programs on data in the first database to retrieve data, shape the retrieved data into data products and publish the data products back to the second database as structured data.

In at least some cases the method includes storing a new data alert in an alert list in response to a new clinical record or a new micro-service data product being stored in the second database. In at least some cases the method includes each micro-service program monitoring the alert list and determining if stored data is to be consumed by that micro-service program independent of all other micro-service programs. In at least some embodiments at least a subset of the micro-service programs operate sequentially to condition data.

In at least some embodiments at least a subset of the micro-service programs specify the same data to consume definition. In at least some embodiments the step of shaping includes at least one manual step to be performed by a system user and wherein the system adds a data shaping activity to a user's work queue in response to at least one of the alerts being added to the alert list. In at least some embodiments the first database includes both unstructured original clinical data records and semi-structured data generated by the micro-service programs.

In at least some embodiments each micro-service program operates automatically and independently when data that meets the data to consume definition is stored to the first database. In at least some embodiments the application programs include operational programs and wherein at least a subset of the operational programs comprise a physician suite of programs useable to consider cancer state treatment options. In at least some embodiments at least a subset of the operational programs comprise a suite of data shaping programs usable by a system user to shape data stored in the first database. In at least some embodiments the data shaping programs are for use by a radiologist.

In at least some embodiments the data shaping programs are for use by a pathologist. In at least some cases the method includes a set of visualization tools and associated interfaces useable by a system user to analyze the second database data. In at least some embodiments the third database includes a subset of the second database data. In at least some embodiments the third database includes data derived from the second database data. In at least some cases the method includes the steps of presenting a user interface to a system user that includes data that indicates how genomic sequencing data affects different treatment efficacies.

In at least some embodiments each cancer state includes a plurality of factors, the method further including the steps of using a processor to automatically perform the steps of analyzing patient genomic sequencing data that is associated with patients having at least a common subset of cancer state factors to identify treatments of genomically similar patients that experience treatment efficacies above a threshold level. In at least some embodiments each cancer state includes a plurality of factors, the method further including the steps of using a processor to automatically identify, for specific cancer types, highly efficacious cancer treatments and, for each highly efficacious cancer treatment, identify at least one genomic sequencing data subset that is different for patients that experienced treatment efficacy above a first threshold level when compared to patients that experienced treatment efficacy below a second threshold level.

In other embodiments the invention includes a method for conducting genomic sequencing, the method comprising the steps of, for each of a plurality of patients that have cancerous cells and that receive cancer treatment, (a) obtaining clinical records data in original forms where the clinical records data includes cancer state information, treatment types and treatment efficacy information, (b) storing the clinical records data in a semi-structured first database, (c) obtaining a tumor specimen from the patient, (d) growing the tumor specimen into a plurality of tissue organoids, (e) treating each tissue organoids with an organoid specific treatment, (f) collecting and storing organoid treatment efficacy information in the first database, (g) using a processor to examining the first database data including organoid treatment efficacy and clinical record data to identify at least one optimal treatment for a specific cancer patient.

In at least some cases the method includes the steps of storing a set of user application programs wherein each of the programs requires an application specific subset of data to perform application processes and generate user output, shaping at least a subset of the first database data to generate system structured data including clinical record data and organoid treatment efficacy data wherein the system structured data is optimized for searching, storing the system structured data in a second database, for each user application program, selecting the application specific subset of data from at least one of the first and second databases and storing the application specific subset of data in a structure optimized for application program interfacing in a third database. In at least some cases the method includes the steps of using a genomic sequencer to generate genomic sequencing data for each of the patients and the patient's cancerous cells and storing the sequencing data in the first database, the step of examining the first database data including examining each of the organoid treatment efficacy data, the genomic sequencing data and the clinical record data to identify at least one optimal treatment for a specific cancer patient.

In at least some embodiments the sequencing data includes DNA sequencing data. In at least some embodiments the sequencing data include RNA sequencing data. In at least some embodiments the sequencing data includes only DNA sequencing data. In at least some embodiments the sequencing data includes only RNA sequencing data. In at least some embodiments the sequencing is conducted using the xT gene panel. In at least some embodiments the sequencing is conducted using a plurality of genes from the xT gene panel. In at least some embodiments the sequencing is conducted using at least one gene from the xF gene panel. In at least some embodiments the sequencing is conducted using the xE gene panel. In at least some embodiments the sequencing is conducted using at least one gene from the xE gene panel.

In at least some embodiments sequencing is done on the KRAS gene. In at least some embodiments sequencing is done on the PIK3CA gene. In at least some embodiments sequencing is done on the CDKN2A gene. In at least some embodiments sequencing is done on the PTEN gene. In at least some embodiments sequencing is done on the ARID1A gene. In at least some embodiments sequencing is done on the APC gene. In at least some embodiments sequencing is done on the ERBB2 gene. In at least some embodiments sequencing is done on the EGFR gene. In at least some embodiments sequencing is done on the IDH1 gene. In at least some embodiments sequencing is done on the CDKN2B gene. In at least some embodiments the sequencing includes MAP kinase cascade. In at least some embodiments the sequencing includes EGFR. In at least some embodiments the sequencing includes BRA. In at least some embodiments the sequencing includes NRAS.

In at least some embodiments the sequencing is performed on a particular cancer type. In at least some embodiments at least one of the micro-services is a variant annotation service. In at least some embodiments the application programs include operational programs and wherein at least one of the operational programs is a variant annotation program. In at least some embodiments the application programs include operational programs and wherein at least one of the operational programs is a clinical data structuring application for converting unstructured raw clinical medical records into structured records. In at least some embodiments the data vault database includes a database of molecular sequencing data. In at least some embodiments the molecular sequencing data includes DNA data.

In at least some embodiments the molecular sequencing data includes RNA data. In at least some embodiments the molecular sequencing data includes normalized RNA data. In at least some embodiments the molecular sequencing data includes tumor-normal sequencing data. In at least some embodiments the molecular sequencing data includes variant calls. In at least some embodiments the molecular sequencing data includes variants of unknown significance. In at least some embodiments the molecular sequencing data includes germline variants. In at least some embodiments the molecular sequencing data includes MSI information.

In at least some embodiments the molecular sequencing data includes TMB information. In at least some cases the method includes the step of determining an MSI value for the cancerous cells. In at least some cases the method includes determining a TMB value for the cancerous cells. In at least some cases the method includes identifying a TMB value greater than 9 mutations/Mb. In at least some cases the method includes detecting a genomic alteration that results in a chimeric protein product. In at least some cases the method includes detecting a genomic alteration that drives EML4-ALK. In at least some cases the method includes the step of determining neoantigen load. In at least some cases the method includes the step of identifying a cytolytic index. In at least some cases the method includes distinguishing a population of immune cells (dependent: TMG-high/TMB-low).

In at least some cases the method includes the step of determining CD274 expression. In at least some cases the method includes reporting an overexpression of MYC. In at least some cases the method includes detecting a fusion event. In at least some embodiments the fusion event is a TMPRSS-ERG fusion. In at least some cases the method includes the step of detecting a PD-L1 in a lung cancer patient. In at least some cases the method includes indicating a PARP inhibitor. In at least some embodiments the PARP inhibitor is for BRCA1. In at least some embodiments the PARP inhibitor is for BRCA2. In at least some cases the method includes the steps of recommending an immunotherapy. In at least some embodiments the recommended immunotherapy is one of CAR-T therapy, antibody therapy, cytokine therapy, adoptive t-cell therapy, anti-CD47 therapy, anti-GD2 therapy, immune checkpoint inhibitor and neoantigen therapy.

In at least some embodiments the cancer cells are from a tumor tissue and the non-cancer cells are blood cells. In at least some embodiments the cancerous cells are cell free DNA from blood. In at least some embodiments the cancer cells are from fresh tissue. In at least some embodiments the cancer cells are from a FFPE slide. In at least some embodiments the cancer cells are from frozen tissue. In at least some embodiments the cancer cells are from biopsied tissue. In at least some embodiments sequencing is done on the TP53 gene.

To the accomplishment of the foregoing and related ends, the invention, then, comprises the features hereinafter fully described. The following description and the annexed drawings set forth in detail certain illustrative aspects of the invention. However, these aspects are indicative of but a few of the various ways in which the principles of the invention can be employed. Other aspects, advantages and novel features of the invention will become apparent from the following detailed description of the invention when considered in conjunction with the drawings.

BRIEF DESCRIPTION OF THE SEVERAL VIEWS OF THE DRAWINGS

FIG. 9 is a schematic view of an abstractor's display screen used to generate a structured data record from data in an unstructured or semi-structured record;

FIG. 18a is an exemplary top portion of a screenshot of a user interface for reporting and exploring approved therapies while FIG. 18b shows the lower portion of the FIG. 18a screenshot;

FIGS. 22a through 22j include an exemplary 1711 gene panel listing that may be interrogated during genomic sequencing in at least some embodiments of the present disclosure;

FIG. 23 includes a clinically actionable 130 gene panel listing that may be interrogated during genomic sequencing in at least some embodiments of the present disclosure;

FIG. 24 includes a clinically actionable 41 RNA based gene rearrangements listing that may be interrogated during genomic sequencing in at least some embodiments of the present disclosure;

FIG. 25 includes a table that lists exemplary variant data that is consistent with at least some aspects of the present disclosure;

FIG. 26 includes exemplary CVA data that is consistent with at least some implementations and aspects of the present disclosure;

FIGS. 27a through 27d includes additional gene panel tables that may be interrogated in at least some embodiments of the present disclosure;

FIGS. 28a and 28b include yet one other gene panel table that may be interrogated;

FIG. 34 is a schematic illustrating data related to one rearrangement detected via RNA sequencing related to the exemplary xT panel;

FIG. 39 includes two schematics illustrating two gene expression scores for low and high TMB and MSI populations generated using techniques that are consistent with at least some aspects of the present disclosure related to the exemplary xT panel;

Figure 1:
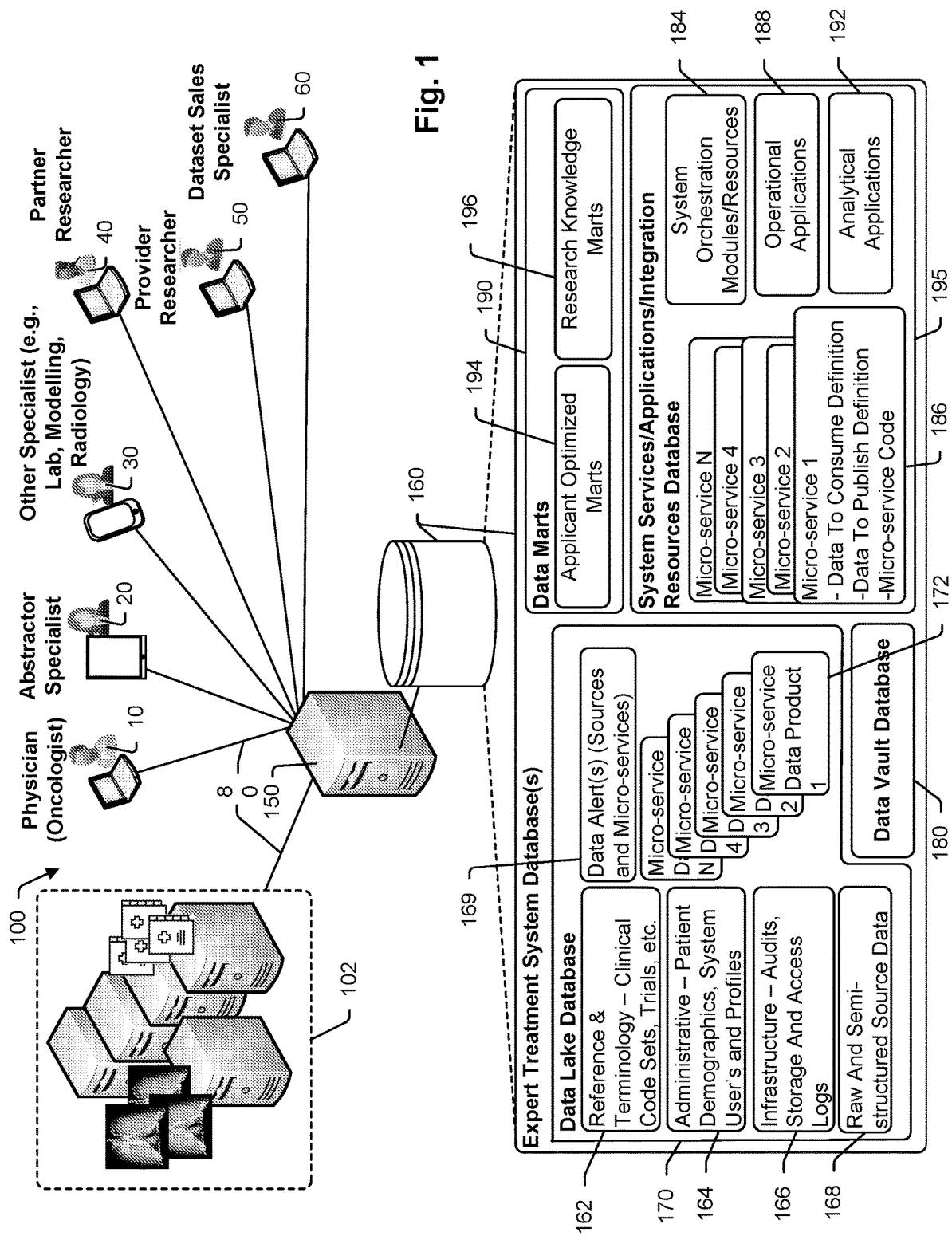
FIG. 1 is a schematic diagram illustrating a computer and communication system that is consistent with at least some aspects of the present disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE DISCLOSURE

The various aspects of the subject invention are now described with reference to the annexed drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

The phrase "Allelic Fraction" or "AF" will be used to refer to the percentage of reads supporting a candidate variant divided by a total number of reads covering a candidate locus.

The phrase "base pair" or "bp" will be used to refer to a unit consisting of two nucleobases bound to each other by hydrogen bonds. The size of an organism's genome is measured in base pairs because DNA is typically double stranded.

The phrase "Single Nucleotide Polymorphism" or "SNP" will be used to refer to a variation within a DNA sequence with respect to a known reference at a level of a single base pair of DNA.

The phrase "insertions and deletions" or "indels" will be used to refer to a variant resulting from the gain or loss of DNA base pairs within an analyzed region.

The phrase "Multiple Nucleotide Polymorphism" or "MNP" will be used to refer to a variation within a DNA sequence with respect to a known reference at a level of two or more base pairs of DNA, but not varying with respect to total count of base pairs. For example an AA to CC would be an MNP, but an AA to C would be a different form of variation (e.g., an indel).

The phrase "Copy Number Variation" or "CNV" will be used to refer to the process by which large structural changes in a genome associated with tumor aneuploidy and other dysregulated repair systems are detected. These processes are used to detect large scale insertions or deletions of entire genomic regions. CNV is defined as structural insertions or deletions greater than a certain base pair ("bp") in size, such as 500 bp.

The phrase "Germline Variants" will be used to refer to genetic variants inherited from maternal and paternal DNA. Germline variants may be determined through a matched tumor-normal calling pipeline.

The phrase "Somatic Variants" will be used to refer to variants arising as a result of dysregulated cellular processes associated with neoplastic cells. Somatic variants may be detected via subtraction from a matched normal sample.

The phrase "Gene Fusion" will be used to refer to the product of large scale chromosomal aberrations resulting in the creation of a chimeric protein. These expressed products can be non-functional, or they can be highly over or under active. This can cause deleterious effects in cancer such as hyper-proliferative or anti-apoptotic phenotypes.

The phrase "RNA Fusion Assay" will be used to refer to a fusion assay which uses RNA as the analytical substrate. These assays may analyze for expressed RNA transcripts with junctional breakpoints that do not map to canonical regions within a reference range.

The term "Microsatellites" refers to short, repeated sequences of DNA.

The phrase "Microsatellite instability" or "MSI" refers to a change that occurs in the DNA of certain cells (such as tumor cells) in which the number of repeats of microsatellites is different than the number of repeats that was in the DNA when it was inherited. The cause of microsatellite instability may be a defect in the ability to repair mistakes made when DNA is copied in the cell.

"Microsatellite Instability-High" or "MSI-H" tumors are those tumors where the number of repeats of microsatellites in the cancer cell is significantly different than the number of repeats that are in the DNA of a benign cell. This phenotype may result from defective DNA mismatch repair. In MSI PCR testing, tumors where 2 or more of the 5 microsatellite markers on the Bethesda panel are unstable are considered MSI-H.

"Microsatellite Stable" or "MSS" tumors are tumors that have no functional defects in DNA mismatch repair and have no significant differences in microsatellite regions between tumor and normal tissue.

"Microsatellite Equivocal" or "MSE" tumors are tumors with an intermediate phenotype that cannot be clearly classified as MSI-H or MSS based on the statistical cutoffs used to define those two categories.

The phrase "Limit of Detection" or "LOD" refers to the minimal quantity of variant present that an assay can reliably detect. All measures of precision and recall are with respect to the assay LOD.

The phrase "BAM File" means a (B)inary file containing (A)lignment (M)aps that include genomic data aligned to a reference genome.

The phrase "Sensitivity of called variants" refers to a number of correctly called variants divided by a total number of loci that are positive for variation within a sample.

The phrase "specificity of called variants" refers to a number of true negative sites called as negative by an assay divided by a total number of true negative sites within a sample. Specificity can be expressed as (True negatives)/(True negatives+false positives).

The phrase "Positive Predictive Value" or "PPV" means the likelihood that a variant is properly called given that a variant has been called by an assay. PPV can be expressed as (number of true positives)/(number of false positives+number of true positives).

The disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

Unless indicated otherwise, while the disclosed system is used for many different purposes (e.g., data collection, data analysis, treatment, research, etc.), in the interest of simplicity and consistency, the overall disclosed system will be referred to hereinafter as "the disclosed system".

I. System Overview

Referring now to the figures that accompany this written description and more specifically referring to FIG. 1, the present disclosure will be described in the context of an exemplary system 100 where data is received at a system server 150 from many different data sources 102, is stored in a database 160, is manipulated in many different ways by internal system micro-service programs to condition or "shape" the data to generate new interim data or to structure data in different structured formats for consumption by user application programs and to then drive the user application programs to provide user interfaces via any of several different types of user interface devices. While a single server 150 and a single database 160 are shown in FIG. 1 in the interest of simplifying this explanation, it should be appreciated that in most cases, the system 100 will include a plurality of distributed servers and databases that are linked via local and/or wide area networks and/or the Internet or some other type of communication infrastructure. An exemplary simplified communication network is labelled 80 in FIG. 1. Network connections can be any type including hard wired, wireless, etc., and may operate pursuant to any suitable communication protocols.

The disclosed system 10 enables many different system clients to securely link to server 150 using various types of computing devices to access system application program interfaces optimized to facilitate specific activities performed by those clients. For instance, in FIG. 1 a physician 10 is shown using a laptop computer (not labelled) to link to server 150, an abstractor specialist 20 is shown using a tablet type computing device to link, another specialist 30 is shown using a smartphone device to link to server 150, etc. Other types of personal computing devices are contemplated including virtual and augmented reality headsets, projectors, wearable devices (e.g., a smart watch, etc.). FIG. 1 shows other exemplary system users linked to server 150 including a partner researcher 40, a provider researcher 50 and a data sales specialist 60, all of which are shown using laptop computers.

In at least some embodiments when a physician uses system 100, a physician's user interface(s) is optimally designed to support typical physician activities that the system supports including activities geared toward patient treatment planning. Similarly, when a researcher like a pathologist or a radiologist uses system 100, interfaces optimally designed to support activities performed by those system clients are provided.

System specialists (e.g. employees of the provider that controls/maintains overall system 100) also use interface computing devices to link to server 150 to perform various processes and functions. In FIG. 1 exemplary system specialists include abstractor 20, the dataset sales specialist 60 and a "general" specialist 30 referred to as a "lab, modeling, radiology" specialist to indicate that the system accommodates many different additional specialist types. Different specialists will use system 100 to perform many different functions where each specialist requires specific skill sets needed to perform those functions. For instance, abstractor specialists are trained to ingest clinical records from sources 102 and convert that data to normalized and system optimized structured data sets. A lab specialist is trained to acquire and process non-tumorous patient and/or tumor tissue samples, grow organoids, generate one or both of DNA and RNA genomic data for one or each of non-tumorous and tumorous tissue, treat organoids and generate results. Other specialists are trained to assess treatment efficacy, perform data research to identify new insights of various types and/or to modify the existing system to adapt to new insights, new data types, etc. The system interfaces and tool sets available to provider specialists are optimized for specific needs and tasks performed by those specialists.

Referring yet again to FIG. 1, system database 160 includes several different sub-databases including, in at least some embodiments, a data lake database 170 (hereinafter "the lake database"), a data vault database 180, a data marts database 190 and a system services/applications and integration resource database 195. While database 195 is shown to includes several different types of information as well as system programs, in other cases one or each of the sets of information or programs in database 195 may be stored in a different one of the databases 170, 180 or 190. In general, data lake database 170 is used to store several different data types including system reference data 162, system administration data 164, infrastructure data 166, raw source data 168 and micro-service data products 172 (e.g., data generated by micro-services).

Reference data 162 includes references and terminology used within data received from source devices 102 when available such as, for instance, clinical code sets, specialized terms and phrases, etc. In addition, reference data 162 includes reference information related to clinical trials including detailed trial descriptions, qualifications, requirements, caveats, current phases, interim results, conclusions, insights, hypothesis, etc.

In at least some cases reference data 162 includes gene descriptions, variant descriptions, etc. Variant descriptions may be incorporated in whole or in part from known sources, such as the Catalogue of Somatic Mutations in Cancer (COSMIC) (Wellcome Sanger Institute, operated by Genome Research Limited, London, England, available at https://cancer.sanger.ac.uk/cosmic). In some cases, reference data 162 may structure and format data to support clinical workflows, for instance in the areas of variant assessment and therapies selection. The reference data 162 may also provide a set of assertions about genes in cancer and evidence-based precision therapy options. Inputs to reference data 162 may include NCCN, FDA, PubMed, conference abstracts, journal articles, etc. Information in the reference data 162 may be annotated by gene; mutation type (somatic, germline, copy number variant, fusion, expression, epigenetic, somatic genome wide, etc.); disease; evidence type (therapeutic, prognostic, diagnostic, associated, etc.); and other notes.

Referring still to FIG. 1, reference data 162 may further comprise gene curation information. A sequencing panel often has a predetermined number of gene profiles that are sequenced as part of the panel. For instance, one type of sequencing panel in the market (i.e., xT, Tempus Labs, Inc, Chicago, Ill.) makes use of 595 gene profiles (see tables in FIG. 27 series of figures) while another makes use of 1711 gene profiles (see tables in FIG. 22 series of figures). Reference data 162 may store a centralized gene knowledge base and comprise variant prioritization and filtering information that may be utilized for Gain Of Function (GOF), Loss Of Function (LOF), CNV, and fusions. For purposes of precision care, evidence may be annotated based on mutation type and disease; therapeutic evidence may include drug(s) and effect (response, resistance, etc.); prognostic effect may include outcome (favorable, unfavorable, etc.). Therapeutic evidence and prognostic evidence may include evidence source level (preclinical, case study, clinical research, guidelines, etc.). Preclinical information may be from mouse models, PDX, cell lines, etc. Case study information may be from groups of one or more patients. Clinical research may be information from a larger study or results from clinical trials. Guideline information may come from NCCN, WHO, etc.

The administrative data 164 includes patient demographic data as well as system user information including user identifications, user verification information (e.g., usernames, passwords, etc.), constraints on system features usable by specific system users, constraints on data access by users including limitations to specific patient data, data types, data uses, time and other data access limits, etc.

In at least some cases system 100 is designed to memorialize entire life cycles of every dataset or element collected or generated by system 100 so that a system user can recreate any dataset corresponding to any point in time by replicating system processes up to that point in time. Here, the idea is that a researcher or other system user can use this data re-creation capability to verify data and conclusions based thereon, to manipulate interim data products as part of an exploration process designed to test other hypothesis based on system data, etc. To this end, infrastructure data 166 includes complete data storage, access, audit and manipulation logs that can be used to recreate any system data previously generated. In addition, infrastructure data 166 is usable to trace user access and storage for access auditing purposes.

Referring still to FIG. 1, lake database 170 also includes raw unmodified data 168 from sources 102. For instance, original clinical medical records from physicians are stored in their original format as are any medical images and radiology reports, pathology reports, organoid documentation, and any other data type related to patient treatment, treatment efficacy, etc. In addition the raw original data, metadata related thereto is also identified and stored at 168. Exemplary metadata includes source identity, data type, date and time data received, any data formatting information available, etc. The metadata listed here is not exhaustive and other metadata types may also be obtained and stored. Raw sequencing data, such as BAM files, may be stored in lake database 170. Unless indicated otherwise hereafter, the data stored in lake database 170 will be referred to generally as "lake data".

It has been recognized that a fulsome database suitable for cancer research and treatment planning must account for a massive number of complex factors. It has also been recognized that the unstructured or semi-structured lake data is unsuitable for performing many data search processes, analytics and other calculations and data manipulations that are required to support the overall system. In this regard, searching or otherwise manipulating a massive database data set that includes data having many disparate data formats or structures can slow down or even halt system applications. For this reason the disclosed system converts much of the lake data to a system data structure optimized for database manipulation (e.g., for searching, analyzing, calculating, etc.). For example, genomic data may be converted to JSON or Apache Parquet format, however, others are contemplated. The optimized structured data is referred to herein as the "data vault database" 180.

Thus, in FIG. 1, data vault database 180 includes data that has been normalized and optimally structured for storage and database manipulation. For instance, raw original clinical medical records stored at 168 in lake database 170 may be processed to normalize data formats and placed in specific structured data fields optimized for data searching and other data manipulation processes. For instance, raw original clinical medical records, such as progress notes, pathology reports, etc. may be processed into specific structured data fields. Structured data fields may be focused in certain clinical areas, such as demographics, diagnosis, treatment and outcomes, and genetic testing/labs. For instance, structured diagnosis information may include primary diagnosis; tissue of origin; date of diagnosis; date of recurrence; date of biochemical recurrence; date of CRPC, alternative grade; gleason score; gleason score primary; gleason score secondary; gleason score overall; lymphovascular invasion; perineural invasion; venous invasion. Structured diagnosis information may also include tumor characterization, which may be described with a set of structured data, including the type of characterization; date of characterization; diagnosis; standard grade; AJCC values such as AJCC status, AJCC status T, AJCC status N, AJCC Status M, AJCC status stage, and FIGO status stage. Structured diagnosis information may also include tumor size, which may be described with a set of structured size data, including tumor size (greatest dimension), tumor size measure, and tumor size units. Structured diagnosis information may also include structured metastases information. Each metastasis may be described with a set of structured data, including location, date of identification, tumor size, diagnosis, grade, and AJCC values. Structured diagnosis information may also include additional diagnoses. Additional diagnoses may be described with a set of structured data, including tissue of origin, date of diagnosis, date of recurrence, date of biochemical recurrence, date of CRPC, tumor characterizations, and metastases.

Figure 2:
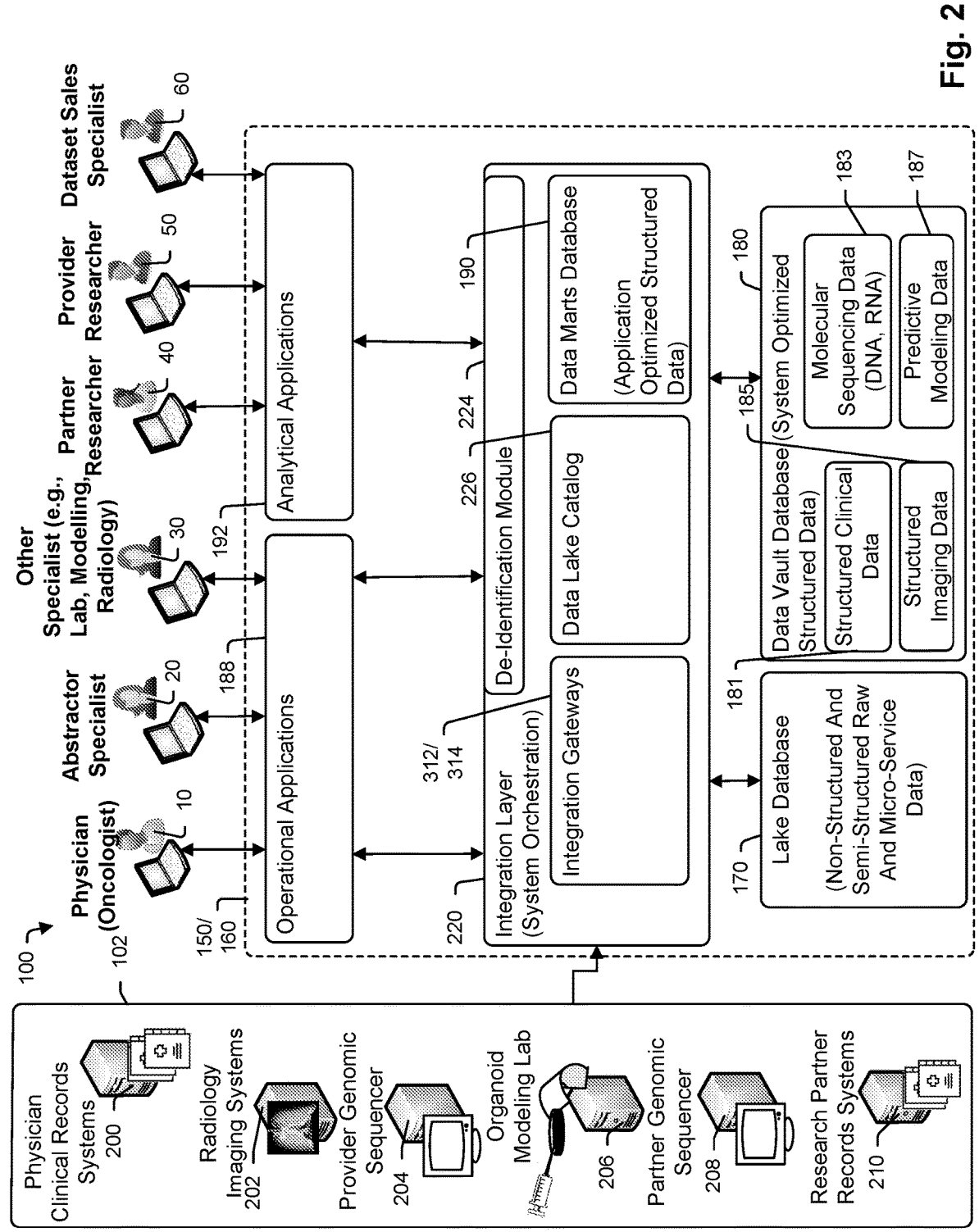
FIG. 2 is a schematic diagram illustrating another view of the FIG. 1 system where functional components that are implemented by the FIG. 1 components are shown in some detail.

As another instance, 2 dimensional slice type images through a patient's tumor may be used to generate a normalized 3 dimensional radiological tumor model having specific attributes of interest and those attributes may be gleaned and stored along with the 3D tumor model in the structured data vault for access by other system resources. In FIG. 2, the data vault database 180 is shown including a structured clinical database 181 for storage of structured clinical data, a molecular sequencing database 183 for storage of molecular sequencing data, a structure imaging database 185 for storage of imaging data, and a predictive modeling database 187 for storage of organoid and other modeling data. Additional databases for specific lines of data may also be added to the data vault database 180. RNA sequencing data in the molecular sequencing data may be normalized, for instance using the methods disclosed in U.S. Provisional Patent App. No. 62/735,349, METHODS OF NORMALIZING AND CORRECTING RNA EXPRESSION DATA, incorporated by reference herein in its entirety. Unless indicated otherwise hereafter, the phrase "canonical data" will be used to refer to the data vault data in its system optimized structured form.

It has further been recognized that certain data manipulations, calculations, aggregates, etc., are routinely consumed by application programs and other system consumers on a recurring albeit often random basis. By shaping at least subsets of normalized system data, smaller sub-databases including application and research specific data sets can be generated and published for consumption by many different applications and research entities which ultimately speeds up the data access and manipulation processes.

Thus, in FIG. 1, data marts database 190 includes data that is specifically structured to support user application programs 194 and/or specific research activities 196. Here, it is contemplated that different user application programs may require different data models (e.g., different data structures) and therefore data marts 190 will typically include many different application or research specific structured data sets. For instance, a first data mart data set may include data arranged consistent with a first data structure model optimized to support a physician's user interfaces, a second data mart data set may include data arranged consistent with a second data structure model optimized to support a radiologist specialist, a third data mart data set may include data arranged consistent with a third data structure model optimized to support a partner researcher, and so on. A single user type may have multiple data mart data sets structured to support different workflows on the same or different raw data.

Similarly, in the case of specific research activities, specific data sets and formats are optimal for specific research activities and the data marts provide a vehicle by which optimized data sets are optimally structured to ensure speedy access and manipulation during research activities. Unless indicated otherwise hereafter, the phrase "mart data" will be used to generally refer to data stored in the data marts 190.

In most cases mart data is mined out of the data vault 180 and is restructured pursuant to application and research data models to generate the mart data for application and research support. In some embodiments system orchestration modules or software programs that are described hereafter will be provided for orchestrating data mining in the system databases as well as restructuring data per different system models when required.

Referring still to FIG. 1, the system services/applications/integration resources database 195 includes various programs and services run by system server 150 to perform and/or guide system functions. To this end, exemplary database 195 includes system orchestration modules/resources 184, a set of first through N micro-services collectively identified by numeral 186, operational user application programs 188 and analytical user application programs 192.

Orchestration modules/resources 184 include overall scheduling programs that define workflows and overall system flow. For instance, one orchestration program may specify that once a new unstructured or semi-structured clinical medical record is stored in lake database 170, several additional processes occur, some in series and some in parallel, to shape and structure new data and data derived from the new data to instantiate new sets of canonical data and mart data in databases 180 and 190. Here, the orchestration program would manage all sub-processes and data handoffs required to orchestrate the overall system processes. One type of orchestration program that could be utilized is a programmatic workflow application, which uses programming to author, schedule and monitor "workflows". A "workflow" is a series of tasks automatically executed in whole or in part by one or more micro-services. In one embodiment, the workflow may be implemented as a series of directed acyclic graphs (DAGs) of tasks or micro-services.

Micro-services 186 are system services that generate interim system data products to be consumed by other system consumers (e.g., applications, other micro-services, etc.). In FIG. 1, first through Nth micro-service data products corresponding to micro-services 186 are shown stored in lake database 170 at 172. When a micro-service data product is published to lake database 170, a data alert or event is added to a data alerts list 169 to announce availability of the newly published data for consumption by other micro-services, application programs, etc. Micro-services are independent and autonomous in that, once a service obtains data required to initiate the service, the service operates independent of other system resources to generate output data products.

In many cases micro-services are completely automated software programs that consume system data and generate interim data products without requiring any user input. For instance, an exemplary fully automated micro-service may include an optical character recognition (OCR) program that accesses an original clinical record in the raw source data 168 and performs an OCR process on that data to generate an OCR tagged clinical record which is stored in lake database 170 as a data product 172. As another instance, another fully automated micro-service may glean data subsets from an OCR tagged clinical record and populate structured record fields automatically with the gleaned data as a first attempt to convert unstructured or semi-structured raw data to a system optimized structure.

In other cases a micro-service requires at least some system user activities including, for instance, data abstraction and structuring services or lab activities, to generate interim data products 172. For instance, in the case of clinical medical record ingestion, in many cases an original clinical record will be unstructured or semi-structured and structuring will require an abstractor specialist 20 (see again FIG. 1) to at least verify data in structured data record fields and in many cases to manually add data to those fields to generate a completely instantiated instance of the structured record as a data product 172. As another instance, in the case of genetic sequencing, a lab technician is required to obtain and load sample tumor or other tissue into a sequencing machine as part of a sequencing process. In cases where a service requires at least some user activities, the service will typically be divided into separate micro-services where a user application operates on a micro-service data product to queue user activities in a user work queue or the like and a separate micro-service responds to the user activity being completed to continue an overall process. While this disclosure describes a small set of micro-services, a working system 100 will typically employ a massive number (e.g., hundreds or even many thousands) of micro-services to drive all of the system capabilities contemplated. It is possible that in the life cycle of analysis for a patient that hundreds or thousands of executions of micro-services will be performed.

In an embodiment, a micro-service creates a data product that may be accessed by an application, where the application provides a worklist and user interface that allows a user to act upon the data product. One example set of micro-services is the set of micro-services for genomic variant characterization and classification. An exemplary micro-service set for genomic variant characterization includes but is not limited to the following set: (1) Variant characterization (a data package containing characterized variant calls for a case, which may include overall classification, reference criteria and other singles used to determine classification, exclusion rules, other flags, etc.); (2) Therapy match (including therapies matched to a variant characterization's list of SNV, indel, CNV, etc. variants via therapy templates); (3) Report (a machine-readable version of the data delivered to a physician for a case); (4) Variants reference sets (a set of unique variants analyzed across all cases); (5) Unique indel regions reference sets (gene-specific regions where pathogenic inframe indels and/or frameshift variants are known to occur); (6) DNA reports; (7) RNA reports; (8) Tumor Mutation Burden (TMB) calculations, etc. Once genomic variant characterization and classification has been completed, other applications and micro-services provide tools for variant scientists or other clinicians or even other micro-services to act upon the data results.

Referring still to FIG. 1, each micro-service includes a service specification including definitions of data that the specified service is to consume, micro-service code defining the service to be performed by the specific micro-service and a definition of the data that is to be published to the lake as an interim data product 172. In each case, the service to be performed includes monitoring the data alerts list 169 or published data on the system communication network for data to be consumed (e.g., monitor for data that fits subscriptions associated with the microservice) by the service and, once the service generates a data product, publishing that data product to the data lake and placing an alert in alerts list 169 or publishing that data. In operation, when a micro-service is to consume a published data product, the service obtains the data product, consumes the product as part of performing the service, publishes new data product(s) to lake database 170 and then places a new data alert in list 169 to announce to other system consumers that the new data is ready for consumption.

Another system for asynchronous communication between micro-services is a publish-subscribe message passing ("pub/sub") system which uses the alerts list 169. In this system type, alerts list 169 may be implemented in the form of a message bus. One example of a message bus that may be utilized is Amazon Simple Notifications Service (SNS). In this system type, micro-services publish messages about their activities on message bus topics that they define. Other micro-services subscribe to these messages as needed to take action in response to activities that occur in other micro-services.

In at least some embodiments, micro-services are not required to directly subscribe to SNS topics. Rather, they set up message queues via a queue service, and subscribe their queues to the SNS Topics that they are interested in. The micro-services then pull messages from their queues at any time for processing, without worrying about missing messages. One example of a queue service is the Amazon Simple Queue Service (SQS) although others are contemplated.

Granularity of SNS topics may be defined on a message subject basis (for instance, 1 topic per message subject), on a domain object basis (for instance, one topic per domain object basis), and/or on a per micro-service basis (for instance, one topic per micro-service basis). Message content may include only essential information for the message in order to prioritize small message size. In at least some cases message content is architectured to avoid inclusion of patient health information or other information for which authorization is required to access.

Different alerts may be employed throughout the system. For instance, alerts may be utilized in connection with the registration of a patient. One example of an alert is "services-patients.created", which is triggered by creation of a new patient in the system. Alerts may be utilized in connection with the analysis of variant call files. One example is "variant-analysis_staging", which is triggered upon the completion of a new variant calling result. Another example is "variant-analysis_staging.ready", which is triggered upon completed ingestion of all input files for a variant calling result. Another example is "case_staging.ready", which is triggered when information in the system is ready for manual user review. Many other alerts are contemplated.

Both orchestration workflows and micro-service alerts may be employed in the system, either alone or in combination. In an example, an event-based micro-service architecture may be utilized to implement a complex workflow orchestration. Orchestrations may be integrated into the system so that they are tailored for specific needs of users. For instance, a provider or another partner who requires the ability to provide structured data into the lake may utilize a partner-specific orchestration to land structured data in the lake, pre-process files, map data, and load data into the data fault. As another example, a provider or other partner who requires the ability to provide unstructured data into the lake may utilize a partner-specific orchestration for pre-processing and providing unstructured data to the data lake. As another example, an orchestration may, upon publishing of data that is qualified for a particular use case (such as for research, or third-party delivery), transform the data and load it into a columnar data store technology. As another example, a "data vault to clinical mart" orchestration may take stable points in time of the data published to data vault by other orchestrations; transform the data into a mart model, and transform the mart data through a de-identification pipeline. As another example, a "commercial partner egress file gateway" may utilize a cohort of patients whose data is defined for delivery, sourcing the data from de-identified data marts and the data lake (including molecular sequencing data) and publish the same to a third-party partner.

Referring still to FIG. 1, operational and analytical applications 188 and 192, respectively, are application programs that provide functionality to various system user types as well as interfaces optimized for use by those system users. Operational applications 188 include application programs that are primarily required to enable cancer state treatment planning processes for specific patients. For instance, operational applications include application programs used by a cancer treating physician to assess treatment options and efficacy for a specific patient. As another instance, operational applications also include application programs used by an abstractor specialist to convert unstructured raw clinical medical records or semi-structured records to system optimized structured records. As another instance, operational applications may also include application programs used by bioinformatics scientists or molecular pathologists to annotate variants. As another instance, operational applications also include application programs used by clinicians to determine whether a patient is a good match for a clinical trial. As yet one other instance, operational applications may include application programs used by physicians to finalize patient reports.

Analytical applications 192, in contrast, include application programs that are provided primarily for research purposes and use by either provider client researchers or provider specialist researchers. For instance, analytical applications 192 include programs that enable a researcher to generate and analyze data sets or derived data sets corresponding to a researcher specified subset of de-identified (e.g., not associated with a specific patient) cancer state characteristics. Here, analysis may include various data views and manipulation tools which are optimized for the types of data presented. Some applications may have features of both analytical applications 192 and operational applications 188.

II. System Database Architecture And General Data Flow

Referring now to FIG. 2, a second representation of disclosed system 100 shows many of the components shown in FIG. 1 in an operational arrangement. The FIG. 2 system includes system data sources 102 and operational system components including an integration layer 220 in addition to the lake database 170, data vault database 180, operational applications 188 and analytical applications 192 that are described above. Exemplary data sources 102 include physician clinical records systems 200, radiology imaging systems 202, provider genomic sequencers 204, organoid modeling labs 206, partner genomic sequencers 208 and research partner records systems 210. The source data types are only exemplary and are not intended to be limiting. In fact, it is contemplated that many other data source types generating other clinically relevant data types will be added to the system over time as other sources and data types of interest are identified and integrated into the overall system.

Referring again to FIG. 2, integration layer 220 includes integration gateways 312/314, a data lake catalog 226 and the data marts database 190 described above with respect to FIG. 1. The integration gateways receive data files and messages from sources 102, glean metadata from those files and messages and route those files and messages on to other system components including data lake database 170 and catalog 226 as well as various system applications. New files are stored in lake database 170 and metadata useful for searching and otherwise accessing the lake data is stored in catalog 226. Again, non-structured and semi-structured raw and micro-service data is stored in lake database 170 and system optimized structured data is stored in vault database 180 while application optimized structured data is stored in data marts database 190.

Referring again to FIG. 2, system users 10, 20, 30 40, 50 and 60 access system data and functionality via the operational and/or analytical applications 188 and 192, respectively. In some instances, in order to protect patient confidentiality, the system user cannot have access to patient medical records that are tied to specific and identified patients. For this reason, integration layer 220 may include a de-identification module which accesses system data, scrubs that data to remove any specific patient identification information and then serves up the de-identified data to the application platform. In other examples, the data vault database may have its structure duplicated, such that a de-identified copy of the data in the data vault database 180 is retained separately from the non de-identified copy of the data in the data vault database. Data in the de-identified copy may be stripped of its identifiers, including patient names; geographic subdivisions smaller than a state, including street address, city, county, precinct, ZIP code, and their equivalent geocodes, except for the initial three digits of the ZIP code if, according to the current publicly available data from the Bureau of the Census: (1) The geographic unit formed by combining all ZIP codes with the same three initial digits contains more than 20,000 people; and (2) The initial three digits of a ZIP code for all such geographic units containing 20,000 or fewer people is changed to 000; elements of dates (except year) for dates that are directly related to an individual, including birth date, admission date, discharge date, death date, and all ages over 89 and all elements of dates (including year) indicative of such age, except that such ages and elements may be aggregated into a single category of age 90 or older; Telephone numbers; Vehicle identifiers and serial numbers, including license plate numbers; Fax numbers; Device identifiers and serial numbers; Email addresses; Web Universal Resource Locators (URLs); Social security numbers; Internet Protocol (IP) addresses; Medical record numbers; Biometric identifiers, including finger and voice prints; Health plan beneficiary numbers; Full-face photographs and any comparable images; Account numbers and other unique identifying numbers, characteristics, or codes; and Certificate/license numbers. Because data in the data vault database 180 is structured, much of the information not permitted for inclusion in the de-identified copy is absent by virtue of the fact that a structured location does not exist for inclusion of such information. For instance, the structure of the data vault database for storing the de-identified copy may not include a field for storing a social security number. As another example, data in the data vault database may be segregated by customer. For example, if one physician 10 wishes for his or her patients to have their data segregated from other data in the data lake database 170, their data may be segregated in a single tenant data vault, such as the single tenant data vault arrangement shown in FIG. 3*a*.

Many users employing the operational applications 188 do have physician-patient relationships, or otherwise are permitted to access records in furtherance of treatment, and so have authority to access patent identified medical, healthcare and other personal records. Other users employing the operational applications have authority to access such records as business associates of a health care provider that is a covered entity. Therefore, in at least some cases, operational applications will link directly into the integration layer of the system without passing through de-identification module 224, or will provide access to the non de-identified data in the database 160. Thus, for instance, a physician treating a specific patient clearly requires access to patient specific information and therefore would use an operational application that presents, among other information, patient identifying information.

In some cases, users employing operational applications will want access to at least some de-identified analytical applications and functionality. For instance, in some cases an operational application may enable a physician to compare a specific patient's cancer state to multiple other patient's cancer states, treatments and treatment efficacies. Here, while the physician clearly needs access to her patient's identifying information and state factors, there is no need and no right for the physician to have access to information specifically identifying the other patients that are associated with the data to be compared. Thus, in some cases one operational application will access a set of patient identified data and other sets of patient de-identified data and may consume all of those data sets.

Figure 3:
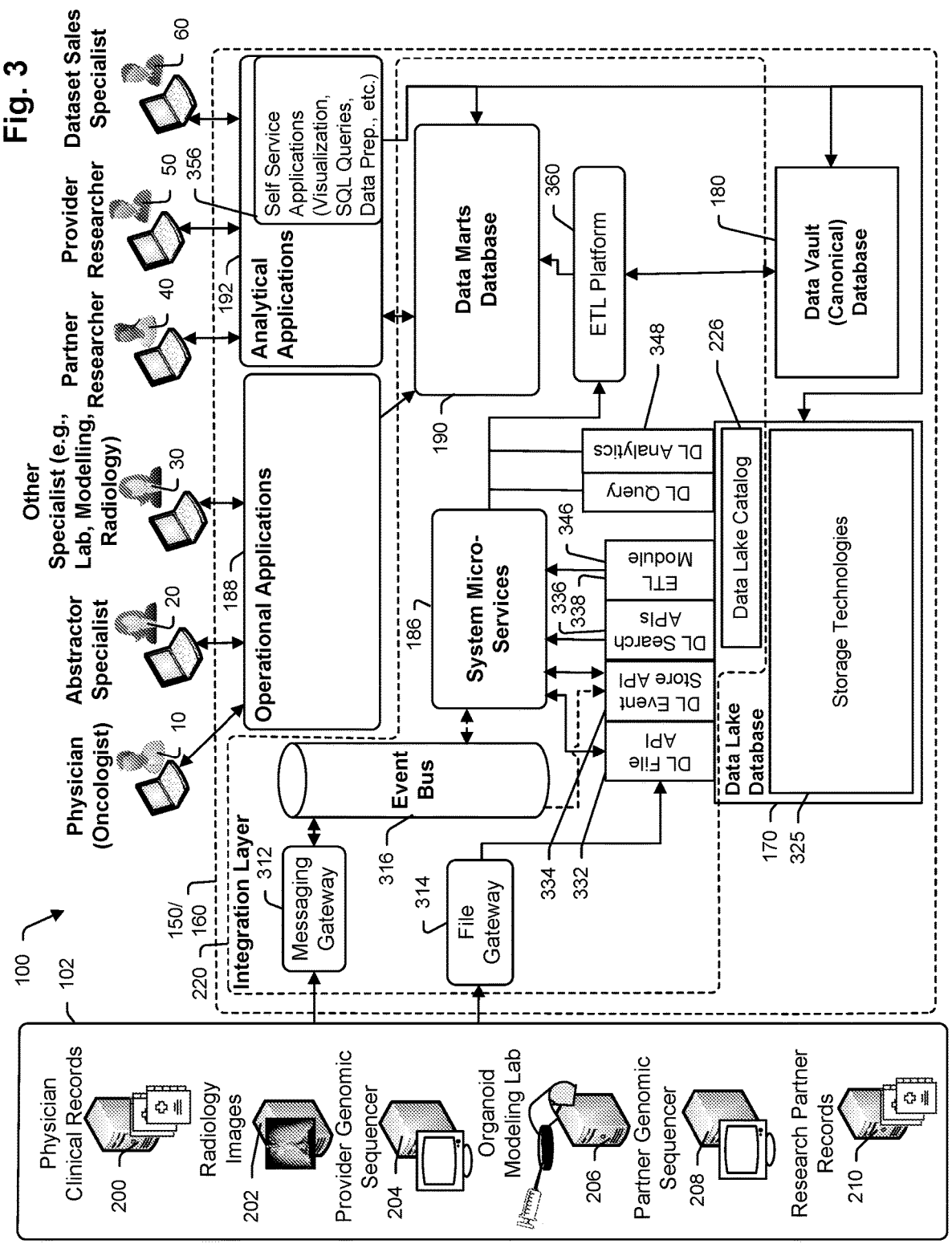
FIG. 3 is a schematic diagram illustrating yet another view of the FIG. 1 system where additional system components are illustrated.

Referring now to FIG. 3, a system representation 100 akin to the one in FIG. 2 is shown, albeit where the FIG. 3 representation is more detailed. In FIG. 3 integration layer 220 includes separate message and file gateways 312 and 314, respectively, an event reporting bus 316, system microservices 186, various data lake APIs 332, 334 and 336, an ETL module 338, data lake query and analytics modules 346 and 348, respectively, an ETL platform 360 as well as data marts database 190.

Referring to FIG. 3, sources 102 are linked via the internet or some other communication network to system 100 via message gateway 312 and file gateway 314. Messages received from data sources 102 at gateway 312 are forwarded on to event bus 326 which routes those messages to other system modules as shown. Messages from other system modules can be routed to the data sources via message gateway 312.

File gateway 314 receives source files and controls the process of adding those files to lake database 170. To this end, the file gateway runs system access security software to glean metadata from any received file and to then determine if the file should be added to the lake database 170 or rejected as, for instance, from an unauthorized source. Once a file is to be added to the lake database, gateway 314 transfers the file to lake database 170 for storage, uses the metadata gleaned from the file to catalog the new file in the lake catalog 226 and posts an alert in the data alert list 169 (see again FIG. 1) announcing that the new data has been published to the lake for consumption.

Referring still to FIG. 3, a subset of micro-services monitoring alert list 169 for data of the type published to lake database 170 access the new data or consume that data when published to the network, perform their data consumption processes, publish new data products to lake database 170 and post new data alerts in list 169 or publish the new data on the network per the publication-subscription architecture described above. In cases where system user activities are required as part of a micro-service, the service schedules those activities to be completed by provider specialists when needed and ingests data generated thereby, eventually publishing new data products to the lake database 170.

The orchestration modules and resources monitor the entire data process and determine when data lake data is to be replicated within the data vault and/or within the data marts in different system or application optimized model formats. Whenever lake data is to be restructured and placed in the data vault or the data marts, ETL platform 360 extracts the data to restructure, transforms the data to the system or application specific data structure required and then loads that data into the respective database 180 or 190. In some cases it is contemplated that ETL platform may only be capable of transforming data from the data lake structure to the data vault structure and from the data vault structure to the application specific data models required in data marts 190.

Referring still to FIG. 3, analytical applications 192 are shown to include, among other applications, "self-service" applications. Here, the phrase "self-service" is used to refer to applications that enable a system user to, in effect, use query tools and data visualization tools, to access and manipulate data sets that are not optimally supported by other user applications. Here, the idea is that, especially in the context of research, system users should not be constrained to specific data sets and analysis and instead should be able to explore different data sets associated with different cancer state factors, different treatments and different treatment efficacies. The self-service tools are designed to allow an authorized system user to develop different data visualizations, unique SQL or other database queries and/or to prepare data in whatever format desired. Hereinafter, unless indicated otherwise, the term "explore" will be used to refer to any self-service activities performed within the disclosed system.

Referring still to FIG. 3, self-service applications 356 enable a system user to explore all system databases in at least some embodiments including the data marts 190, the lake database 170 and the data vault database 180. In other embodiments, because lake database 170 data is either unstructured or only semi-structured, self-service applications may be limited to exploring only the data mart database 190 or the data vault database 180.

III. Data Ingestion, Normalization And Publication

Figure 4:
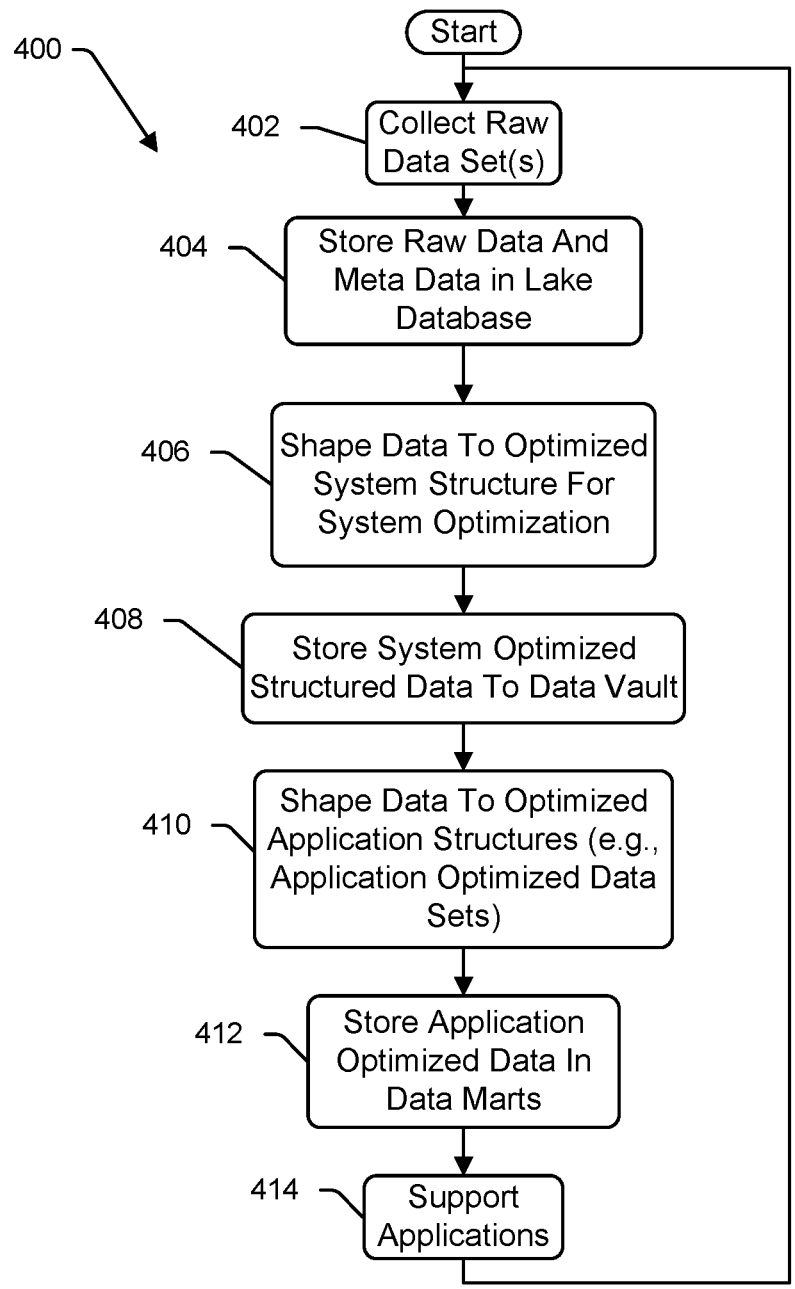
FIG. 4 is a data handling flow chart that is consistent with at least some aspects of the present disclosure.

Referring to FIG. 4, a high level data distribution process 400 is illustrated that is consistent with at least some aspects of the present disclosure. At process block 402, data is collected from various data sources 102 (see again FIGS. 1 through 3) and at block 404, assuming that data is to be ingested into the system 100, the data is stored in lake database 170. Here, data collection is continual over time as more and more data for increasing the system knowledge base is generated regularly by physicians, provider and partner researchers and provider specialists. Specific steps in at least some exemplary data collection processes are described hereafter. The collected original data is stored in the lake database 170 as raw original data (e.g., documents, images, records, files, etc.).

At process block 406, at least a subset of the collected data is "shaped" or otherwise processed to generate structured data that is optimal for database access, searching, processing and manipulation. Here, the data shaping process may take many forms and may include a plurality of data processing steps that ultimately result in optimal system structured data sets. At step 408 the database optimized shaped data is added to similarly structured data already maintained in data vault database 180.

Continuing, at block 410, at least a subset of the data vault data or the lake data is "shaped" or otherwise processed to generate structured data that is optimal to support specific user application programs 188 and 192 (see again FIG. 2). Here, again, the data shaping process may take many forms and may include a plurality of data processing steps that ultimately result in optimal application supporting structured data sets. At step 412 the optimized application structured data is added to similarly structured data already maintained in data marts database 190.

Referring again to FIG. 4, at block 414, system users employ various application programs to access and manipulate system data including the data in any of the lake database 170, data vault database 180 and data marts 190. At block 212, as users use the system, data related to system use is collected after which control passes backup to block 206 where the collected use data is shaped and eventually stored for driving additional applications.

Figure 5:
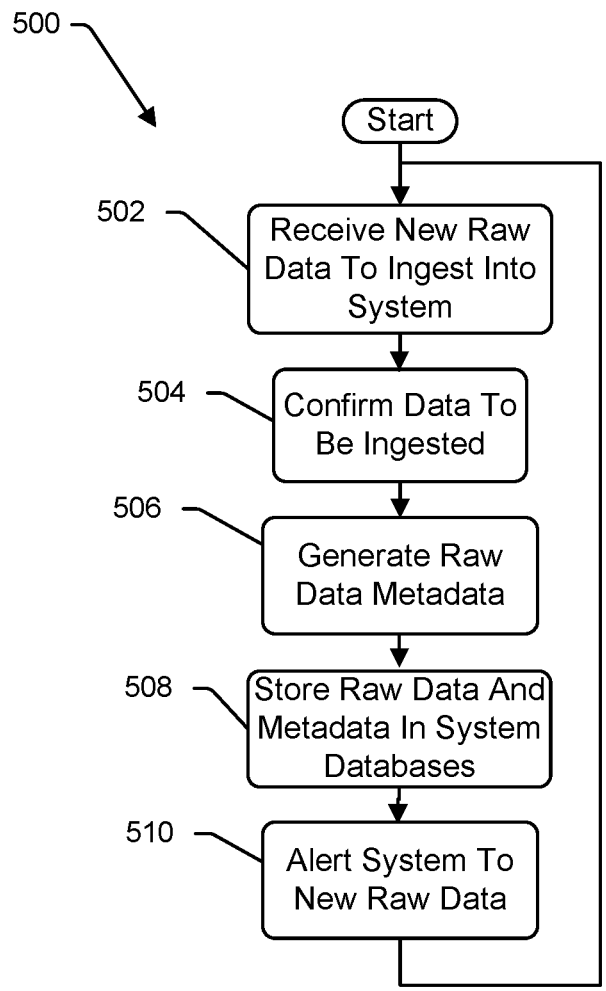
FIG. 5 is a flow chart that shows a process for ingesting raw data into the system and alerting other system components that the raw data is available for consumption.

FIG. 5 includes a flow chart illustrating a process 500 that is consistent with at least some aspects of the present disclosure for ingesting initial raw data into the disclosed system. At process block 502 new raw data is received at the file gateway 314 (see FIG. 2) which, at block 504, determines whether or not the data should be rejected or ingested based on the data source, data format or other transport data used to transmit the received data to the gateway. If the data is to be ingested, gateway 312 gleans metadata from the received data at block 506 which is stored in the data lake catalog 226 (see FIG. 2) while the received data set is stored in data lake 170 at 508. At block 510, an alert is added to the alert list 169 indicting the new data is available to be consumed along with a data type so that other data consumers can recognize when to consume the newly stored data. Control passes back up to block 502 where the process described above continues.

Figure 6:
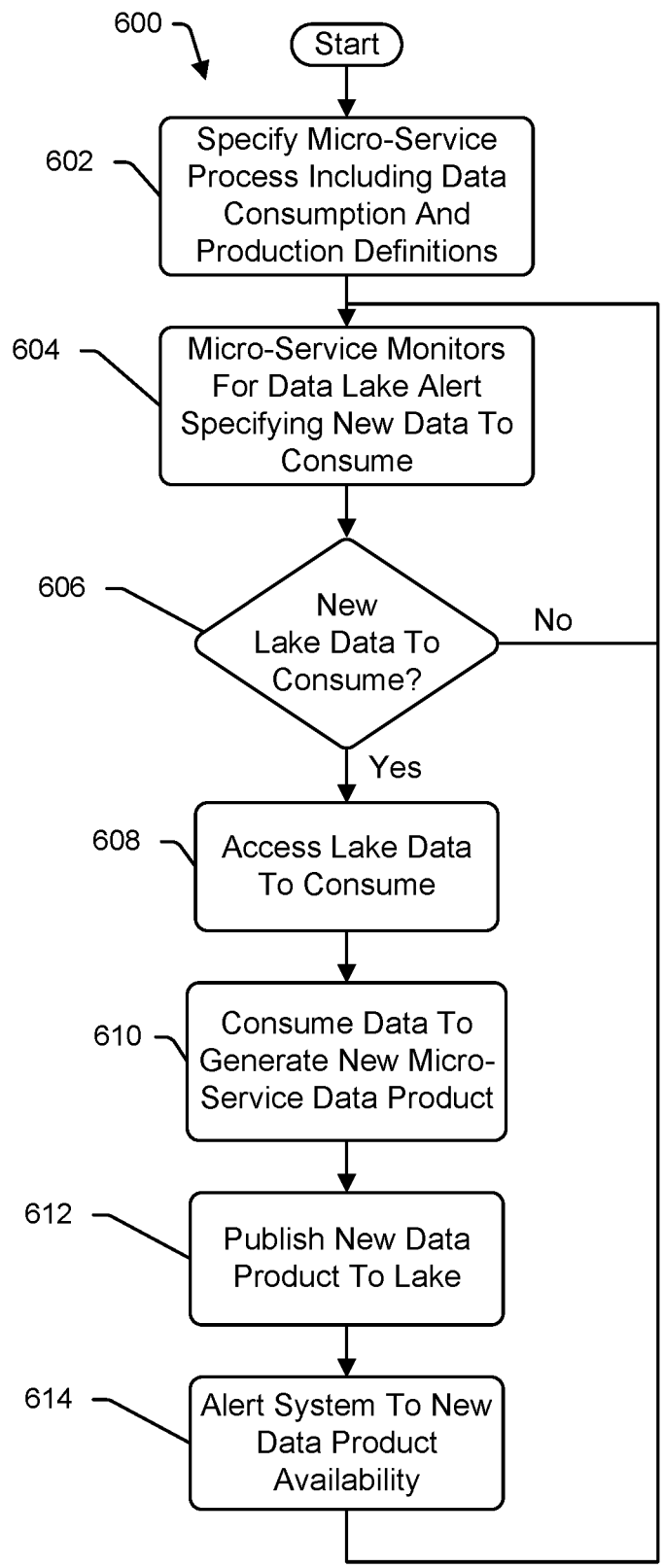
FIG. 6 is a flow chart that shows a micro-service based process for retrieving data from a database, consuming that data to generate new data products and publishing the new data products back to a database while publishing an alert that the new data products are available for consumption.

FIG. 6 is a flow chart illustrating a general process 600 by which system micro-services consume lake data and generate micro-service data products that are published back to the lake database for further consumption by other microservices. At process block 602 a micro-service process is specified that includes data consumption and data product definitions as well as micro-service code for carrying out process steps. At block 604 the micro-service monitors the data lake 170 for alerts specifying new data that meets the data consumption definition for the specific micro-service. At block 606, where new lake data alerts do not specify data that meets the data consumption definition, control passes back up to block 604 where steps 604 and 606 continue to cycle.

Referring still to FIG. 6, once an alert indicates new data that meets the micro-service data consumption definition, control passes to block 608 where the micro-service accesses the lake data to be consumed and that data is consumed at block 610 which generates a new data product. Continuing, at block 612, the new data product is published to data lake database 170 and at 614 another alert is added to the data alert list 169.

Referring still to FIG. 6, process 600 is associated with a single system micro-service. It should be understood that hundreds and in some cases even thousands of microservices will be performed simultaneously and that two or more micro-services may be performed on the same raw data or using prior generated micro-service data product(s) at the same time. In many cases a micro-service will require two or more data sets at the same time and, in those cases, a micro-service will be programmed to monitor for all required data in the data lake and may only be initiated once all required data is indicated in the alerts list 169.

Figure 7:
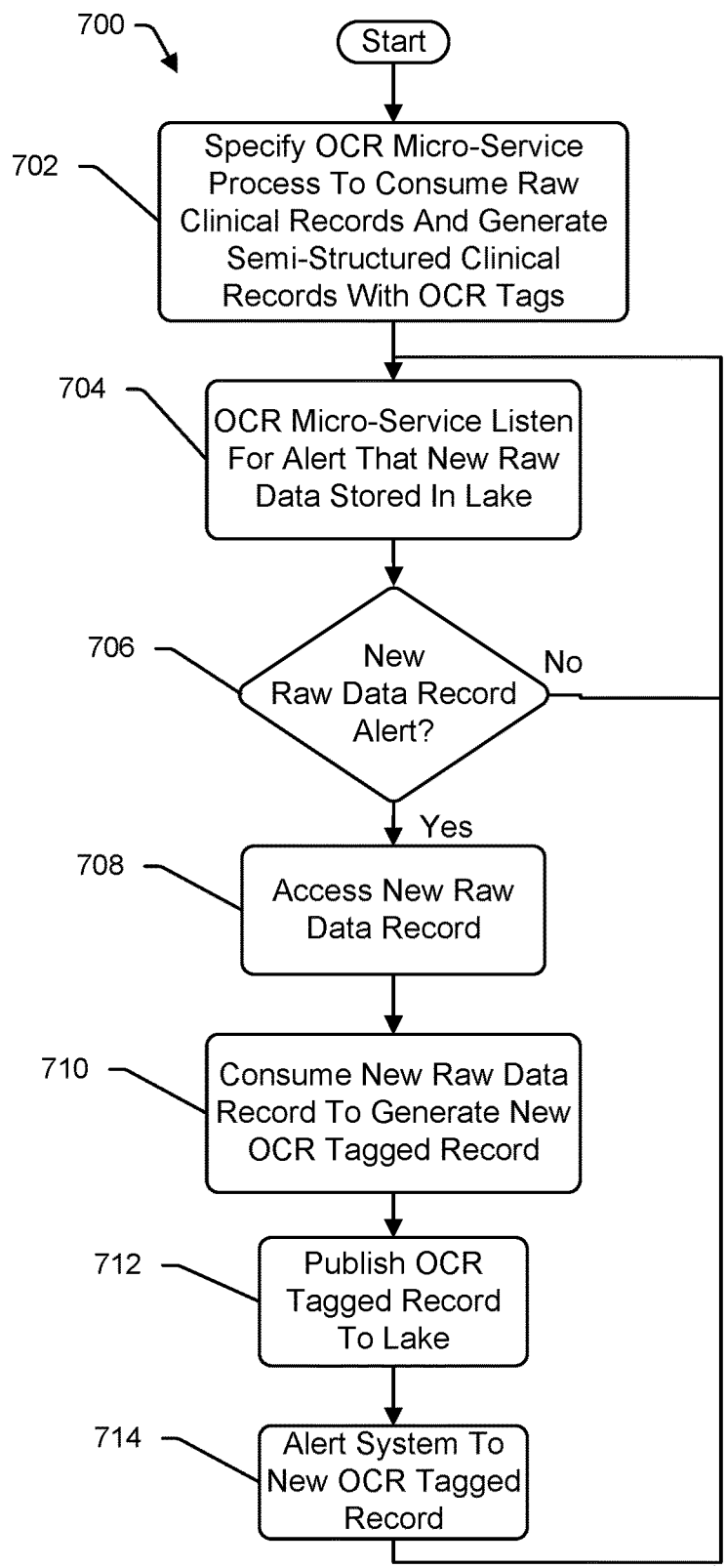
FIG. 7 is a flow chart illustrating a process similar to the FIG. 6 process, albeit where the micro-service is an OCR service.
Figure 8:
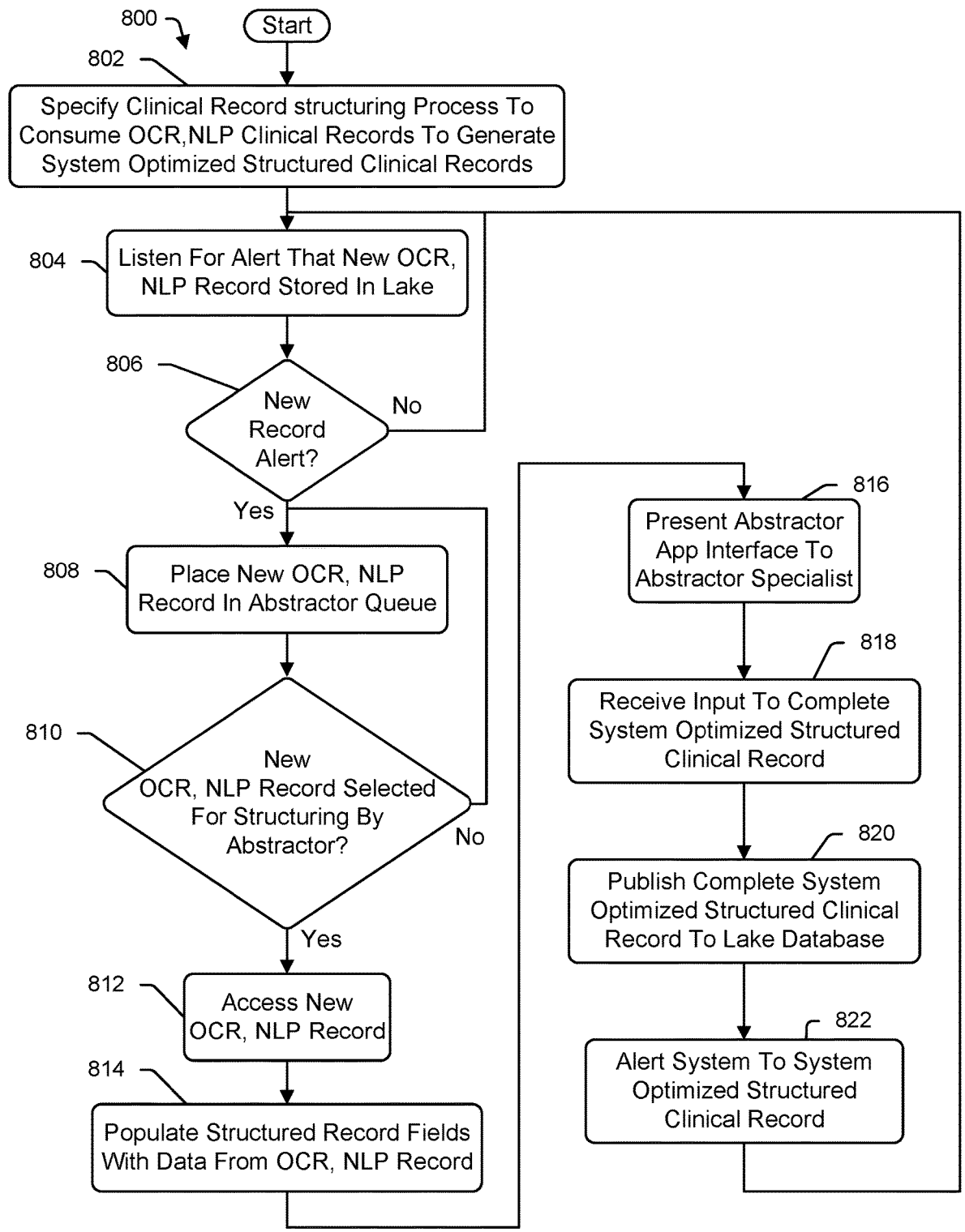
FIG. 8 is a is a flow chart illustrating a process similar to the FIG. 6 process, albeit where the micro-service is a data structuring service.

As described above, some micro-services will be completely automated, so that no user activities are required, while other micro-services will require at least some user activities to perform some service steps. FIG. 7 illustrates a simple fully automated micro-service 700 while FIG. 8 illustrates a micro-service 800 where a user has to perform some activities. In FIG. 7, at process block 702, an OCR micro-service is specified that requires consumption of raw clinical medical records to generate semi-structured clinical medical records with OCR tags appended to document characters. At block 704 the OCR micro-service monitors the system alert list 169 for alerts indicating that new raw clinical records data is stored in the data lake.

At block 706, where there is no new clinical record to be ingested into the system, control passes back up to block 704 and the process 700 cycles through blocks 704 and 706. Once a new clinical record is saved to lake database 170 and an alert related thereto is detected by the OCR micro-service, the micro-service accesses the new raw clinical record from the data lake at 708 and that record is consumed at block 710 to generate a new OCR tagged record. The new OCR tagged record is published back to the lake at 712 and an alert related thereto is added to the data alert list 169 at 714. Once the OCR tagged record is stored in lake database 170, it can be consumed by other micro-services or other system modules or components as required.

The FIG. 8 process 800 is associated with a micro-service for generating a system optimized structured clinical record assuming that an unstructured clinical medical record that has already been tagged with medical terms, phrases and contextual meaning has been generated as a micro-service data product by a prior micro-service. At process block 802, the record structuring micro-service process is defined and includes a data consumption definition that requires OCR, NLP records to be consumed and a data production definition where the system optimized data structure is generated as a micro-service data product. At block 804 the structuring micro-service listens for alerts that new records to consume have been stored in lake database 170. At block 806, where new data to consume has not been stored in the lake database 170, control cycles back through blocks 804 and 806 continually. Once new data to consume has been stored in lake database 170, control passes to block 808 where the micro-service places an alert in an abstractor specialist's work queue identifying the record to consume as requiring specialist activities to complete the micro-service.

Referring still to FIG. 8, at block 810, the system monitors for specialist selection of the queued record for consumption and the system cycles between blocks 808 and 810 until the record is selected. Once the record is selected by the abstractor specialist at 810, control passes to block 812 where the record to be consumed is accessed in database 170. At block 814, the micro-service accesses a structured clinical record file which includes data fields to be populated with data from the accessed clinical record. The micro-service attempts to identify data in the clinical record to populate each field in the structured record at 814 and populates fields with data whenever possible to generate a structured clinical record draft.

Continuing, at block 816 a micro-service presents an abstractor application interface to the abstractor specialist that can be used to verify draft field entries, modify entries or to aid the abstractor specialist in identifying data to populate unfilled structured record fields. To this end, see FIG. 9 that shows an exemplary abstractor interface screenshot 914 that may be viewed by an abstractor specialist which includes an original record in an original record field 900 on the right hand side of the shot and a structured record area 902 on the left hand side of the screenshot. The structured record in area 902 includes a set of fields to be populated with information from the original record or in some other fashion to prepare the structured record for use by system applications. The structured record shown in area 902 only shows a portion of the structured record that fits within area 902 and in most cases the structured record will have hundreds or even thousands of record fields that need to be populated with data. Exemplary structured record fields shown include a site field 904, year fields 905 and a histology field 906.

Referring still to FIG. 9, the original record shown in field 900 has already been subjected to OCR and NLP so that words and phrases have been recognized by a system processor and the text in the document is associated with specific medical words and phrases or other meaning (e.g., dates are recognized as dates, a "Patient's Name" label on an original record is recognized as the phrase "patient's name" and an adjacent field is recognized as a field that likely includes a patient's name, etc.). Again, the processor examines the original record for data that can be used to populate the structured record fields in order to create at least a partially complete draft of the structured record for consideration and completion by the abstractor specialist.

Data in the original record used to populate any field in the structured record is highlighted (see 910, 912) or somehow visually distinguished within the original record to aid the abstractor specialist in located that data in the original record when reviewing data in the structured record fields. The specialist moves through the structured record reviewing data in each field, checking that data against the original record and confirming a match (e.g., via selection of a confirmation icon or the like) or modifying the structured record field data if the automatically populated data is inaccurate (see block 818 in FIG. 8).

In cases where the processor cannot automatically identify data to populate one or more fields in the structured record, the specialist reviews the original record manually to attempt to locate the data required for the field and then enters data if appropriate data is located. Where the micro-service fills in fields that are then to be checked by the specialist, in at least some cases original record data used to populate a next structured record field to be considered by the specialist may be especially highlighted as a further aid to locating the data in the original record. In some cases the micro-service will be able to recognize data in several different formats to be used to fill in a structured record field and will be able to reformat that data to fill in the structured record field with a required form.

Referring again to FIG. 8, at block 820, once the structured clinical record has been completed, the complete system optimized structured clinical record is stored in lake database 170 and then a new data alert is added to alert list 169 at 822 to alert other micro-services and orchestration resources that the complete record is available to be consumed.

In some cases a system micro-service will "learn" from specialist decisions regarding data appropriate for populating different structured data sets. For instance, if a specialist routinely converts an abbreviation in clinical records to a specific medical phrase, in at least some cases the system will automatically learn a new rule related to that persistent conversion and may, in future structured draft records, automatically convert the abbreviation to its expanded form. Many other system learning techniques are contemplated.

In cases where a system micro-service can confirm structured record field information with high confidence, the micro-service may reduce the confirmation burden on the specialist by not highlighting the accurate information in the structured record. For instance, where a patient's date of birth is known, the micro-service may not highlight a patient DOB field in the structured record for confirmation.

Figure 10:
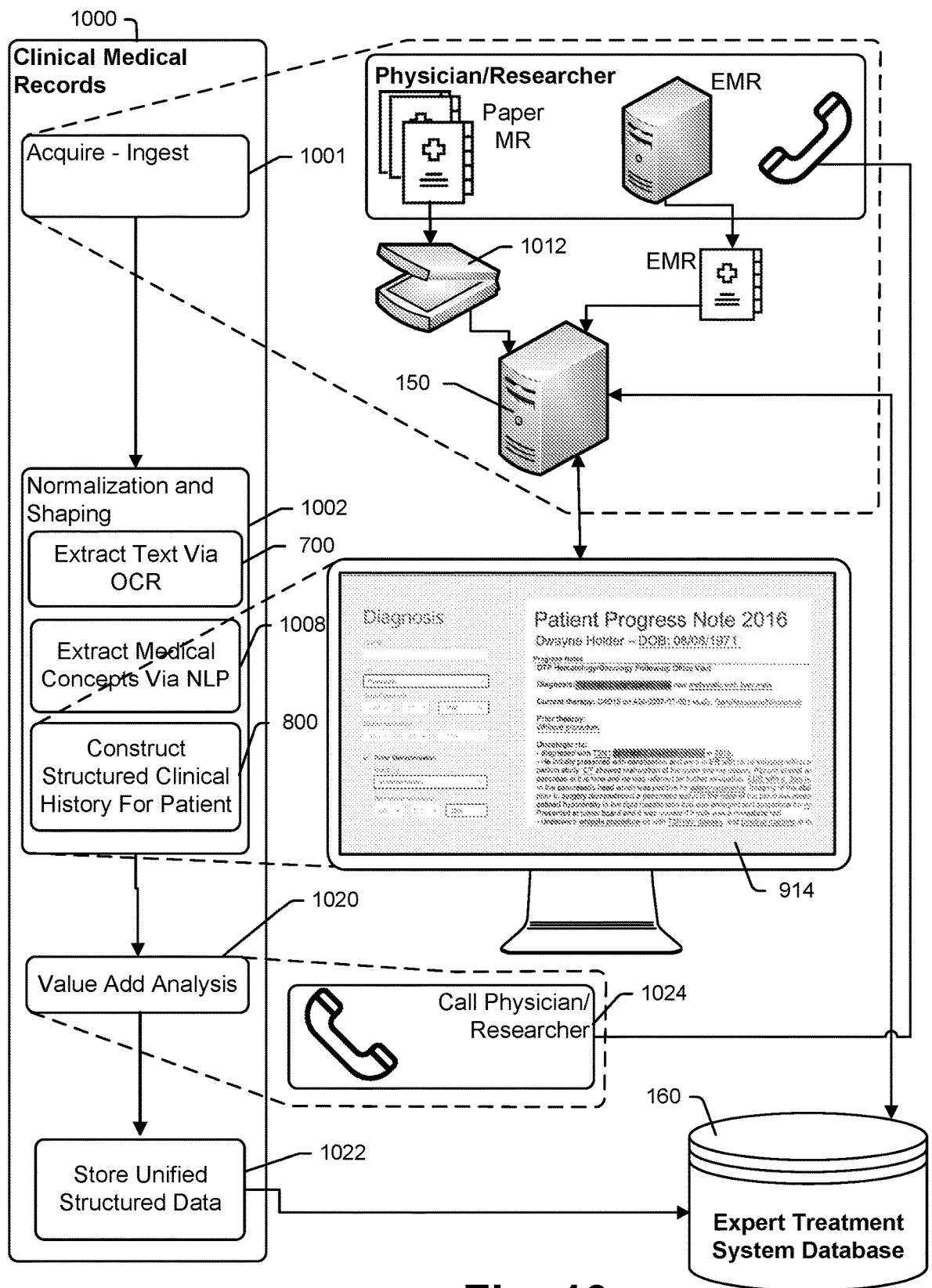
FIG. 10 is a schematic illustrating a multi-micro-service process for ingesting a clinical medical record into the system of FIG. 1.

Referring now to FIG. 10, an exemplary multi-micro-service process 1000 for ingesting a clinical medical record and structuring the record optimally for database activities is illustrated. At step 1001, a medical record is acquired in digital form. Here, where an original record is in paper form, acquiring a digital record may include scanning that record into the system via a scanner 1012 to generate a PDF or other digital representation which is then provided to a system server 150 for storage in database 160. In other cases where the record is already in digital form (e.g., an EMR), the digital record can simply be stored by server 150 in database 160.

A data normalization and shaping process is performed at 1002 that includes accessing an original clinical record from database 160 and presenting that record to a system specialist 40 as shown in FIG. 9. As the original record is accessed or at some other prior time, an OCR micro-service 700 (see again FIG. 7) is used to tag letters in the record. The tagged record is stored in the data lake and an alert is added to the alert list 169. Next, an NLP micro-service 1008 accesses the OCR tagged record and performs an NLP process on the text in that record to generate an NLP processed record which is again stored in the data lake and another alert is added to the alert list 169.

At 800 (see FIG. 8), a draft structured clinical medical record is generated for the patient and is presented to an abstractor specialist via an interface as in FIG. 9 so that the specialist can correct errors.

Referring again to FIG. 10, once the structured record has been filled in to the extent possible based on an original medical record, at block 1020 the specialist may perform some task to attempt to complete record fields that have not been filled. For instance, in a case where a specific structured record field cannot be filled based on information from the original record, the specialist may attempt to track down information related to the field from some other source. For example, in a simple case the specialist may call 1024 a physician that generated the original record to track down missing information. As another example, the specialist may access some other patient record (e.g., an insurance record, a pharmacy record, etc.) that may include additional information useable to populate an empty field. Once the structured record is as complete as possible, that record is stored at 1022 back to the system database 160.

Figure 11:
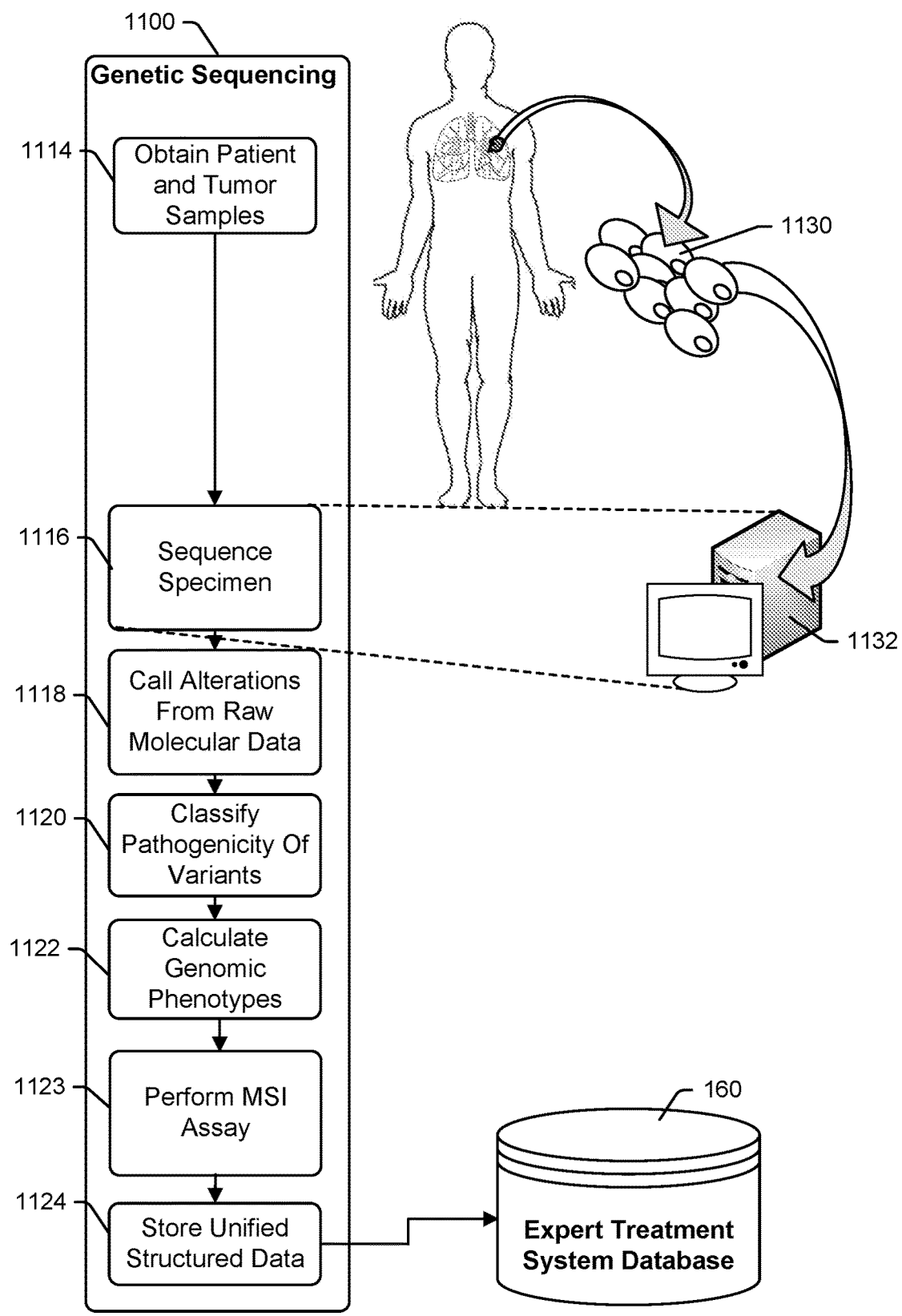
FIG. 11 is a schematic illustrating a multi-micro-service process for generating genomic sequencing and related data that is consistent with at least some aspects of the present disclosure.

Referring now to FIG. 11, an exemplary process 1100 for generating genomic patient and tumor data is illustrated. Robust nucleic acid extraction protocols and sequencing library construction protocols may be applied, and appropriately deep coverage across all targeted regions and appropriately designed analysis algorithms may be utilized. Prior to process 1100, a genomic sequencing order may be received at file gateway 314 and, once ingested, may be stored in lake database 170 for subsequent consumption. Here, when a tumor sample corresponding to the sequencing order is received 1114, the sample is associated with the order and process 1100 continues with the order being assigned to a lab technician's work queue to commence specimen sequencing 1116. At 1116 the specimens are subjected to a genetic sequencing process using sequencing machine 1132 to generate genomic data for both the patient and the tumor specimens. At 1118 alterations from raw molecular data are called and at block 1120 pathogenicity of the variants is classified. At 1122 genomic phenotypes may be calculated. At 1123 an MSI assay may be performed. At 1124 at least a subset of the genomic data and/or an analysis of at least the subset of the genomic data is stored in system database 160.

Referring still to FIG. 11, different approaches may be utilized to implement the genetic sequencing process at 1116. In one example, an oncology assay may be implemented that interrogates all or a subset of cancer-related genes in matched tumor and normal tissue. As used herein, "tumor" tissue or specimen refers to a tumor biopsy or other biospecimen from which the DNA and/or RNA of a cancer tumor may be determined. As used herein, "normal" tissue or specimen refers to a non-tumor biopsy or other biospecimen from which DNA and/or RNA may be determined. As used herein, "matched" refers to the tumor tissue and the normal tissue being correlated at the same position in a DNA and/or RNA sequence, such as a reference sequence. The assay may further provide whole transcriptome RNA sequencing for gene rearrangement detection. The assay may combine tumor and normal DNA sequencing panels with tumor RNA sequencing to detect somatic and germline variants, as well as fusion mRNAs created from chromosomal rearrangements.

The assay may be capable of detecting somatic and germline single nucleotide polymorphisms (SNPs), indels, copy number variants, and gene rearrangements causing chimeric mRNA transcript expression. The assay may identify actionable oncologic variants in a wide array of solid tumor types. The assay may make use of FFPE tumor samples and matched normal blood or saliva samples. The subtraction of variants detected in the normal sample from variants detected in the tumor sample in at least some embodiments provides greater somatic variant calling accuracy. Base substitutions, insertions and deletions (indels), focal gene amplifications and homozygous gene deletions of tumor and germline may be assayed through DNA hybrid capture sequencing. Gene rearrangement events may be assayed through RNA sequencing.

In one example, the assay interrogates one or more of the 1711 cancer-related genes listed in the tables shown in FIG. 22a-22j (referred to herein as the "xE" assay). This targeted gene panel may be divided into a clinically actionable tier, wherein 130 tier 1 genes (see table in FIG. 23) that can influence treatment decisions are assayed with an assigned detection cutoff of 5% variant allele fraction (VAF) i.e. the limit of detection is 5% VAF or lower, and a secondary tier, wherein an additional 1,581 genes (e.g., the difference between the gene set in FIGS. 22a-22j and FIG. 23) are assayed for analytical purposes with an assigned detection cutoff of 10% VAF (limit of detection 10% VAF or lower). The RNA based gene rearrangement detection may also be divided into a primary clinically-actionable tier containing 41 rearrangements (See table in FIG. 24), and a secondary tier that may contain some or all known fusions within the wider literature or novel fusions of putative clinical importance detected by the assay. "Tier 1" genes are genes linked with response or resistance to targeted therapies, resistance to standard of care, or toxicities associated with treatment. The VAF cutoff percentages described herein are exemplary and other cutoff values may be utilized. Reads may be mapped to a human reference genome, such as hg16, hg17, hg18, hg19, etc. (available from the Genome Reference Consortium, at https://www.ncbi.nlm.nih.gov/grc). In another example, the assay may interrogate other gene panels, such as the panels listed in the tables shown in FIGS. 27a, 27b1, 27b2, 27c1 and 27c2 and 27d (herein "the xT panel") or the panel listed in the table shown in FIGS. 28a and 28b.

Figure 11A:
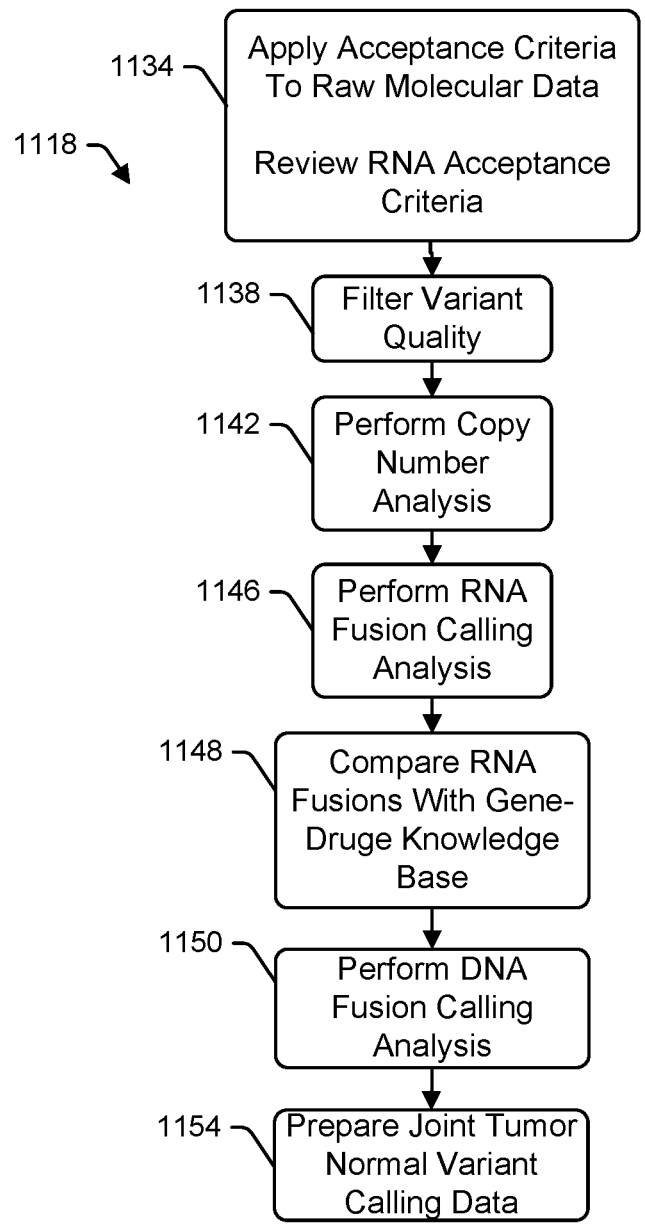
FIG. 11a is a flow chart illustrating an exemplary variant calling process that is consistent with at least some aspects of the present disclosure.

Referring still to FIG. 11, the alterations called in subprocess 1118 may be called through a clinical variant calling process. An exemplary variant calling process is shown in FIG. 11a. At 1134 acceptance criteria are applied to the raw molecular data for clinical variant calling. There may be one or more acceptance criteria, and multiple acceptance criteria may be applied.

One type of acceptance criteria is that a certain percentage of loci assay must exceed a certain coverage. For instance, a first percentage of loci must exceed a certain first coverage and a second percentage of loci must exceed a second coverage. The first percentage of loci may be 60%, 65%, 70%, 75%, 80%, 85%, etc. and the first coverage level may be 150×, 200×, 250×, 300×, etc. The second percentage of loci may be 60%, 65%, 70%, 75%, 80%, 85%, etc. and the second coverage level may be 150×, 200×, 250×, 300×, etc. The first percentage of loci assayed may be lower than the second percentage of loci assayed while the first coverage level may be deeper than the second coverage level.

Another type of acceptance criteria may be that the mean coverage in the tumor sample meets or exceeds a certain coverage threshold, such as 300×, 400×, 500×, 600×, 700×, etc.

Another type of acceptance criteria may be that the total number of reads exceeds a predefined first threshold for the tumor sample and a predefined second threshold for the normal sample. For instance, the total number of reads for the tumor sample must exceed 5 million, 10 million, 15 million, 20 million, 25 million, 30 million, 35 million, 40 million, etc. reads and the total number of reads for the normal sample must exceed 5 million, 10 million, 15 million, 20 million, 25 million, 30 million, 35 million, 40 million, etc. reads. In one example, the threshold for the total number of the reads for the tumor sample may be greater than the total number of reads for the normal sample. For instance, the threshold for the total number of the reads for the tumor sample may be greater than the total number of reads for the normal sample by 5 million, 10 million, 5 million, 10 million, 15 million, 20 million, 25 million, 30 million, 35 million, 40 million, etc. reads.

Another type of acceptance criteria is that reads must maintain an average quality score. The quality score may be an average PHRED quality score, which is a measure of the quality of the identification of the nucleobases generated by automated DNA sequencing. The quality score may be applied to a portion of the raw molecular data. For instance, the quality score may be applied to the forward read. Another type of acceptance criteria is that the percentage of reads that map to the human reference genome. For instance, at least 60%, 65%, 70%, 75%, 80%, 85%, 80%, 95%, etc. of reads must map to the human reference genome.

Still at 1134, RNA acceptance criteria may additionally be reviewed. One type of RNA acceptance criteria is that a threshold level of read pairs will be generated by the sequencer and pass quality trimming in order to continue with fusion analysis. For instance, the threshold level may be 5 million, 10 million, 15 million, 20 million, 25 million, 30 million, 35 million, 40 million, etc. Another type of acceptance criteria is that reads must maintain an average quality score. The quality score may be an average RNA PHRED quality score, which is a measure of the quality of the identification of the nucleobases generated by automated RNA sequencing. The quality score may be applied to a portion of the raw molecular data. For instance, the quality score may be applied to the forward read.

Yet another type of acceptance criteria is that the percentage of reads that map to the human reference genome. For instance, at least 60%, 65%, 70%, 75%, 80%, 85%, 80%, 95%, etc. of reads must map to the human reference genome.

If RNA analysis fails pre or post-analytic quality control, DNA analysis may still be reported. Due to the difficulties of RNA-seq from FFPE, a higher than normal failure rate is expected. Because of this, it may be standard to report the DNA variant calling and copy number analysis section of the assay, no matter the outcome of RNA analysis.

At 1138, the step of variant quality filtering may be performed. Variant quality filtering may be performed for somatic and germline variations. For somatic variant filtering, the variant may have at least a minimum number of reads supporting the variant allele in regions of average genomic complexity. For instance, the minimum number of reads may be 1, 2, 3, 4, 5, 6, 7, etc. A region of the genome may be determined free of variation at a percentage of LLOD (for instance, 5% of LLOD) if it is sequenced to at least a certain read depth. For instance, the read depth may be 100×, 150×, 200×, 250×, 300×, 350×, etc.

The somatic variant may have a minimum threshold for SNPs. For instance, it may have at least 20×, 25×, 30×, 35×, 40×, 45×, 50×, etc. coverage for SNPs. The somatic variant may have a minimum threshold for indels. For instance, at least 50×, 55×, 60×, 65×, 70×, 75×, 80×, 85×, 90×, 95×, 100×, etc. coverage for indels may be required. The variant allele may have at least a certain variant allele fraction for SNPs. For instance, it may have at least 1%, 3%, 5%, 7%, 9%, etc. variant allele fraction for SNPs. The variant allele may have at least a certain variant allele fraction for indels. For instance, it may have a 6%, 8%, 10%, 12%, 14%, etc. variant allele fraction for indels.

The variant allele may have at least a certain read depth coverage of the variant fraction in the tumor compared to the variant fraction in the normal sample. For instance, the variant allele may have 4×, 6×, 8×, 10× etc. the variant fraction in the tumor compared to the variant fraction in the normal sample. Another type of filtering criteria may be that the bases contributing to the variant must have mapping quality greater than a threshold value. For instance, the threshold value may be 20, 25, 30, 35, 40, 45, 50, etc.

Another type of filtering criteria may be that alignments contributing to the variant must have a base quality score greater than a threshold value. For instance, the threshold value may be 10, 15, 20, 25, 30, 35, etc. Variants around homopolymer and multimer regions known to generate artifacts may be filtered in various manners. For instance, strand specific filtering may occur in the direction of the read in order to minimize stranded artifacts. If variants do not exceed the stranded minimum deviation for a specific locus within known artifact generating regions, they may be filtered as artifacts.

Variants may be required to exceed a standard deviation multiple above the median base fraction observed in greater than a predetermined percentage of samples from a process matched germline group in order to ensure the variants are not caused by observed artifact generating processes. For instance, the standard deviation multiple may be 3×, 4×, 5×, 6×, 7×, etc. For instance, the predetermined percentage of samples may be 15%, 20%, 25%, 30%, 35%, etc.

Still at 1138, for germline variant filtering, the germline variant may have a minimum threshold for SNPs. For instance, it may have at least 20×, 25×, 30×, 35×, 40×, 45×, 50×, etc. coverage for SNPs. The germline variant may have a minimum threshold for indels. For instance, at least 50×, 55×, 60×, 65×, 70×, 75×, 80×, 85×, 90×, 95×, 100×, etc. coverage for indels may be required. The germline variant calling may require at least a certain variant allele fraction.

For instance, it may require at least 15%, 20%, 25%, 30%, 35%, 40%, 45% etc. variant allelic fraction.

Another type of filtering criteria may be that the bases contributing to the variant must have mapping quality greater than a threshold value. For instance, the threshold value may be 20, 25, 30, 35, 40, 45, 50, etc. Another type of filtering criteria may be that alignments contributing to the variant must have a base quality score greater than a threshold value. For instance, the threshold value may be 10, 15, 20, 25, 30, 35, etc.

At 1142, copy number analysis may be performed. Copy number alteration may be reported if more than a certain number of copies are detected by the assay, such as 3, 4, 5, 6, 7, 8, 9, 10, etc. Copy number losses may be reported if the ratio of the segments is below a certain threshold. For instance, copy number losses may be reported if the log 2 ratio of the segment is less than −1.0.

At 1146, RNA fusion calling analysis may be conducted. RNA fusions may be compared to information in a gene-drug knowledge database 1148, such as a database described in "Prospective: Database of Genomic Biomarkers for Cancer Drugs and Clinical Targetability in Solid Tumors." Cancer Discovery 5, no. 2 (February 2015): 118-23. doi: 10.1158/2159-8290.CD-14-1118. If the RNA fusion is not present within the gene-drug knowledge database 1148, the RNA fusion may not be presented. RNA fusions may not be called if they display fewer than a threshold of breakpoint spanning reads, such as fewer than 2, 3, 4, 5, 6, 7, 8, 9, 10, etc. breakpoint spanning reads. If an RNA fusion breakpoint is not within the body of two genes (including promotor regions), the fusion may not be called.

At 1150, DNA fusion calling analysis may be performed. At 1154, joint tumor normal variant calling data may be prepared for further downstream processing and analysis. Germline and somatic variant data are loaded to the pipeline database for storage and reporting. For example, for both somatic and germline variations, the data may include information on chromosome, position, reference, alt, sample type, variant caller, variant type, coverage, base fraction, mutation effect, gene, mutation name, and filtering. FIG. 25 shows an exemplary data set in table form that is consistent with at least some embodiments of the above disclosure.

Copy Number Variant (CNV) data may also be loaded to the pipeline database for downstream analysis. For example, the data may include information on chromosome, start position, end position, gene, amplification, copy number, and log 2 ratios. FIG. 26 includes exemplary CNV data.

Following analysis, a workflow processing system may extract and upload the variant data to the bioinformatics database. In one example, the variant data from a normal sample may be compared to the variant data from a tumor sample. If the variant is found in the normal and in the tumor, then it may be determined that the variant is not a cause of the patient's cancer. As a result, the related information for that variant as a cancer-causing variant may not appear on a patient report. Similarly, that variant may not be included in the expert treatment system database 160 with respect to the particular patient. Variant data may include translation information, CNV region findings, single nucleotide variants, single nucleotide variant findings, indel variants, indel variant findings, variant gene findings. Files, such as BAM, FASTQ, and VCF files, may be stored in the expert treatment system database 160.

Referring again to FIG. 11, at 1123, an MSI assay may be performed as a next generation sequencing based test for microsatellite instability. The MSI assay may comprise a panel of microsatellites that are frequently unstable in tumors with mismatch repair deficiencies to determine the frequency of DNA slippage events. Using the assay methods, tumors may be classified into different categories, such as microsatellite instability high (MSI-H), microsatellite stable (MSS), or microsatellite equivocal (MSE). The assay may require FFPE tumor samples with matched normal saliva or blood to determine the MSI status of a tumor. MSI status can provide doctors with clinical insight into therapeutic and clinical trial options for patient care, as well as the need for further genetic testing for conditions such as Lynch Syndrome. The MSI algorithm may be initiated after the raw sequencing data is processed through the bioinformatics pipeline. Upon completion of the MSI algorithm, results may be stored in the expert treatment system database 160. U.S. Prov. Pat. App. No. 62/745,946, filed Oct. 15, 2018, incorporated by reference in its entirety, describes exemplary systems and methods for MSI algorithms.

Referring still to FIG. 11, sub-processes 1116 through 1123 may be substantially or, in some cases even completely automated so that there is little if any lab technician activity required to complete those processes. In other cases each of the sub-processes 1116 through 1123 may include one or more lab technician activities and one or more automated micro-service steps or calculations. Again, in cases where a lab technician performs service steps, the micro-service may present instructions or other interface tools to help guide the technician through the manual service steps. At the end of each manual step some indication that the step has been completed is received by the micro-service. For instance, in some cases a system machine (e.g., the sequencing computer 1132) may provide one or more data products to the micro-service that indicate completion of the step. As another instance, a technician may be queried for specific data related to the stage of the service. As yet one other instance, a technician may simply enter some status indication like, step completed, to indicate that process 1100 should continue.

Figure 11B:
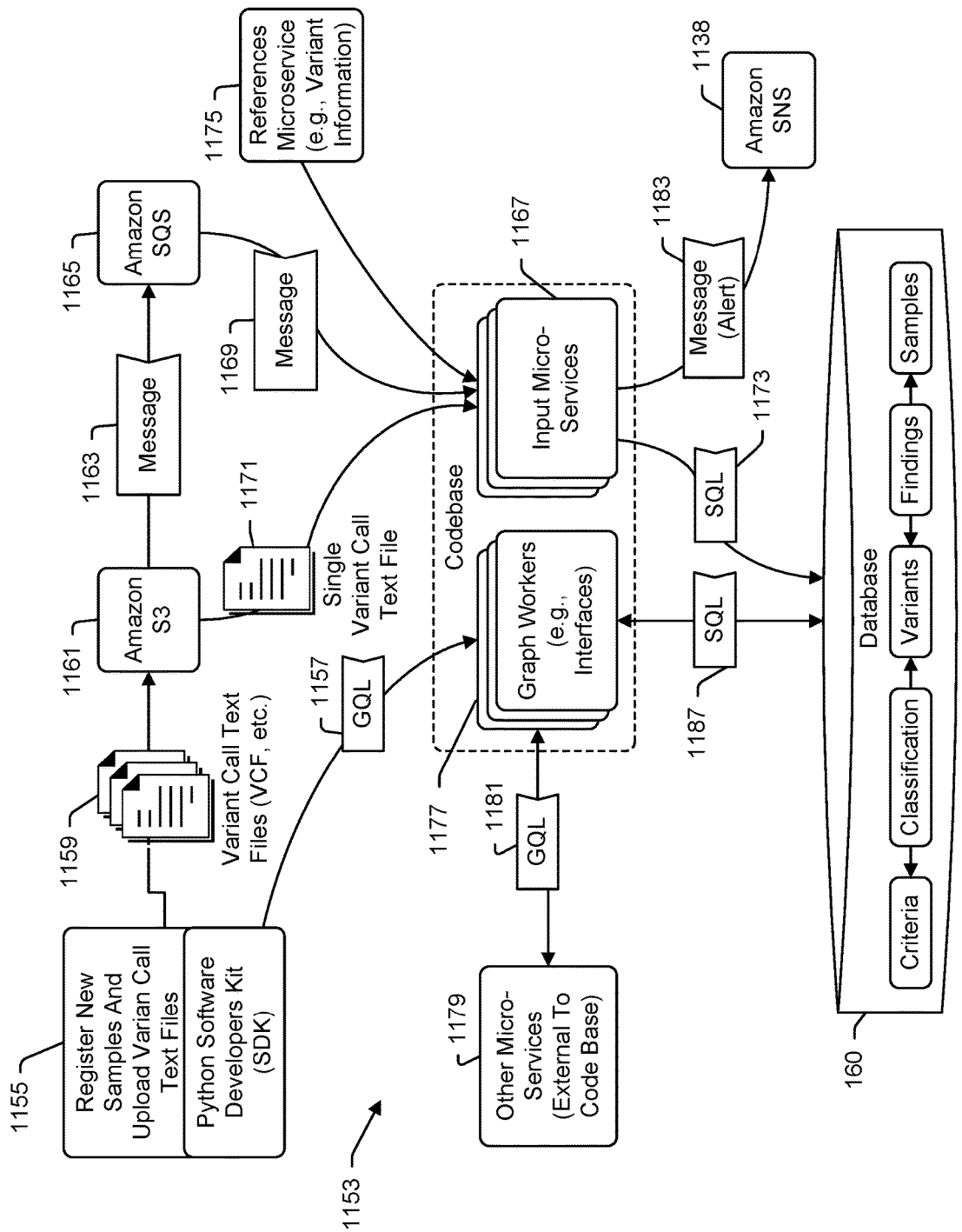
FIG. 11b is a schematic illustrating an exemplary bioinformatics pipeline process that is consistent with at least some embodiments of the present disclosure.
Figure 11C:
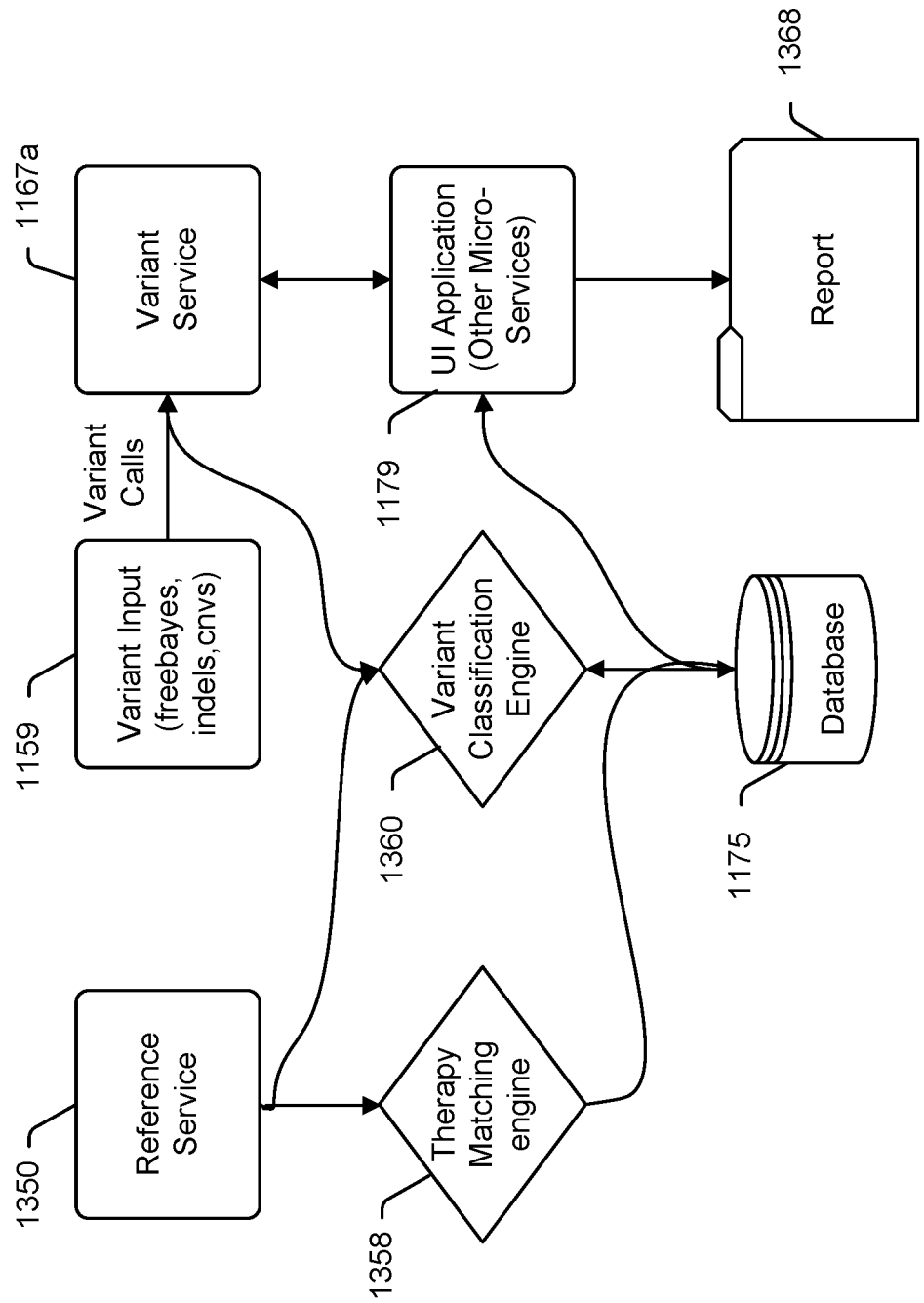
FIG. 11c is a schematic illustrating various system features including a therapy matching engine.

One exemplary workflow 1153 with respect to the bioinformatics pipeline is shown in FIG. 11b. Referring also to FIG. 11c, a client, such as an entity that generates a bioinformatics pipeline, can register new samples 1157 and upload variant call text files 1159 for processing to a cloud service 1161. The cloud service 1161 may initiate an alert by adding a message 1163 to a queue service 1165 (e.g., to an alert list) for each uploaded file. Input micro-services 1167 (1167 in FIG. 11c) receive messages 1169 about each incoming file and process each of those files one at a time (see 1171) as they are received to process and validate each file. The input micro-services 1167 may run as separate node processes and, in at least some cases, generate SQL insertion statements 1173 to add each validated file to the expert treatment system database 160.

Referring still to FIGS. 11b and 11c, the input micro-services 1167 may also run a variant classification engine 1360 on the variant files utilizing a knowledge database of variant information 1175 to calculate many different types of variant criteria, further classification and addition database insertion. The variant micro-service 1167 may publish an alert 1183 when a key event occurs, to which other services 1179 can subscribe in order to react. After a variant call text file is parsed, the variant micro-service may insert variant analysis data into the expert treatment system database 160 including criteria, classifications, variants, findings, and sample information.

Other micro-services 1179 can query 1181 samples, findings, variants, classifications, etc. via an interface 1177 and SQL queries 1187. Authorized users may also be permitted to register samples and post classifications via the other micro-services.

Figure 12:
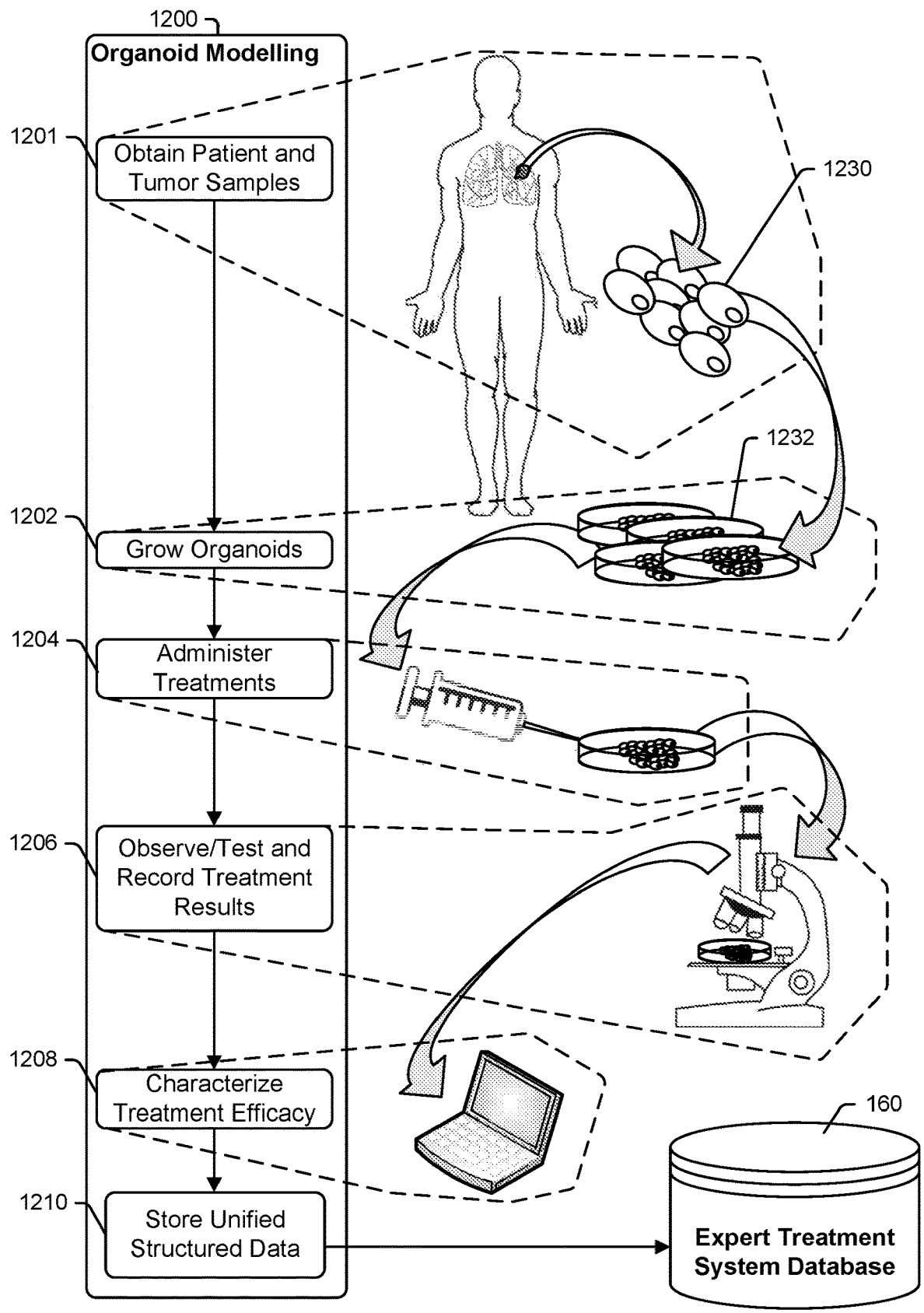
FIG. 12 is a schematic illustrating a multi-micro-service process for generating organoid modelling data that is consistent with at least some aspects of the present disclosure.

Referring to FIG. 12, an organoid modelling process 1200 is illustrated that is consistent with at least some aspects of the present disclosure. At 1201 a tumor specimen 1230 is obtained which is divided into multiple specimens and each specimen is then grown 1202 as a 3D organoid 1232 in a special growth media designed to promote organoid development. At 1204 different cancer treatments are applied to each of the organoids to elicit responses. At 1206 a provider specialist observes the treatment results and at 1208 the results are characterized to assess efficacy of each treatment. At 1210 the results are stored in the system database 160 as part of the unified structured data set for the patient.

Figure 13:
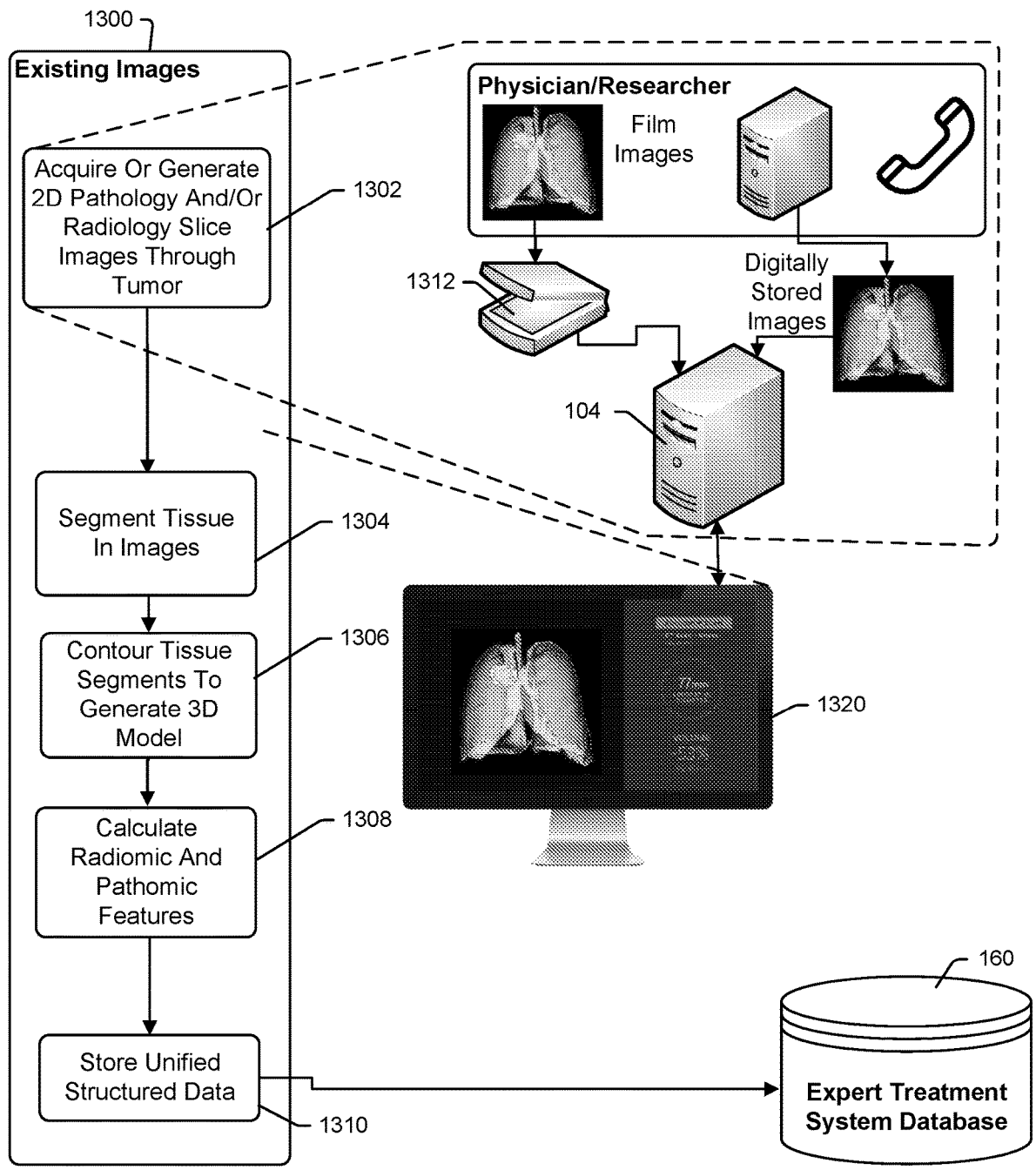
FIG. 13 is a schematic illustrating a multi-micro-service process for generating a 3D model of a patient's tumor as well as identifying a large number of tumor features and characteristics that is consistent with at least some aspects of the present disclosure.

Referring to FIG. 13, a process 1300 for ingesting radiological images into the disclosed system and for identifying treatment relevant tumor features is illustrated. At 1302 a set of 2D medical images including a tumor and surrounding tissue are either generated or acquired from some other source and are stored in system database 160 (e.g., as unaltered images in the lake database). In many cases the 2D images will be in a digital format suitable for processing by a system processor. In other cases the 2D images will be in a format that has to be converted to a data set suitable for system analysis. For instance, in some cases the original images may be on film and may need to be scanned into a digital format prior to creating a 3D tumor model. In some cases original images may not be useable to generate a 3D tumor model and in those cases additional imaging may be required to generate the model.

At 1304 tumor tissue is detected and segmented within each of the 2D images so that tumor tissue and different tissue types are clearly distinguished from surrounding tissues and substances and so that different tumor tissue types are distinguishable within each image. At 1306 the tissue segments within the 2D images are used as a guide for contouring the tissue segments to generate a 3D model of the tumor tissue. At 908 a system processor runs various algorithms to examine the 3D model and identify a set of radiomic (e.g., quantitative features based on data characterization algorithms that are unable to be appreciated via the naked eye) features of the segmented tumor tissue that are clinically and/or biologically meaningful and that can be used to diagnose tumors, assess cancer state, be used in treatment planning and/or for research activities. At 1310 the 3D model and identified features are stored in the system database 160.

While not shown, in some cases a normalization process is performed on the medical images before the 3D model is generated, for example, to ensure a normalization of image intensity distribution, image color, and voxel size for the 3D model. In other cases the normalization process may be performed on a 3D model generated by the disclosed system. In at least some cases the system will support many different segmentation and normalization processes so that 3D models can be generated from many different types of original 2D medical images and from many different imaging modalities (e.g., X-ray, MRI, CT, etc.). U.S. provisional patent application No. 62/693,371 which is titled "3D Radiomic Platform For Managing Biomarker Development" and which was filed on Jul. 2, 2018 teaches a system for ingesting radiological images into the disclosed system and that reference is incorporated herein in its entirety by reference.

Referring again to FIG. 11c, a therapy matching engine 1358 may match therapies based on the information stored in database 160. In one example, the therapy matching engine 1358 matches therapies at the gene level and uses variant-level information to rank the therapies within a case. For each variant in a case, the therapy matching engine 1358 retrieves therapies matching a variant gene from an actionability database 1350. The actionability database 1350 may store a variety of information for different kinds of variants, such as somatic functional, somatic positional, germline functional, germline positional, along with therapies associated with SNVs and indels.

Therapy matching engine 1358 may rank therapies for each gene based on one or more factors. For instance, the therapy matching engine may rank the therapies based on whether the patient disease (such as pancreatic cancer) matches the disease type associated with the therapy evidence, whether the patient variant matches the evidence, and the evidence level for the therapy. For CNVs, the therapy matching engine may automatically determine that the patient variant matches the evidence. For SNVs or indels, the therapy matching engine may evaluate whether the therapy data came from a functional input or a positional input. For positional SNV/indels, if a variant value falls within the range of the variant locus start and variant locus end associated with the evidence, the therapy matching engine may determine that the patient variant matches the evidence. The variant locus start and variant locus end may reflect those locations of the variant in the protein product (an amino acid sequence position).

For functional SNV/indels, if a variant mechanism matches the mechanism associate with the evidence, the therapy matching engine may determine that the patient variant matches the evidence. Therapies may then be ranked by evidence level. The first level may be "consensus" evidence determined by the medical community, such as medical practice guidelines. The next level may be "clinical research" evidence, such as evidence from a clinical trial or other human subject research that a therapy is effective. The next level may be "case study" evidence, such as evidence from a case study published in a medical journal. The next level may be "preclinical" evidence, such as evidence from animal studies or in vitro studies. Ultimately, pdf or other format reports 1368 are generated for consumption.

While a set of data sources and types are described above, it should be appreciated that many other data sets that may be meaningful from a research or treatment planning perspective are contemplated and may be accommodated in the present system to further enhance research and treatment planning capabilities.

Figure 3A:
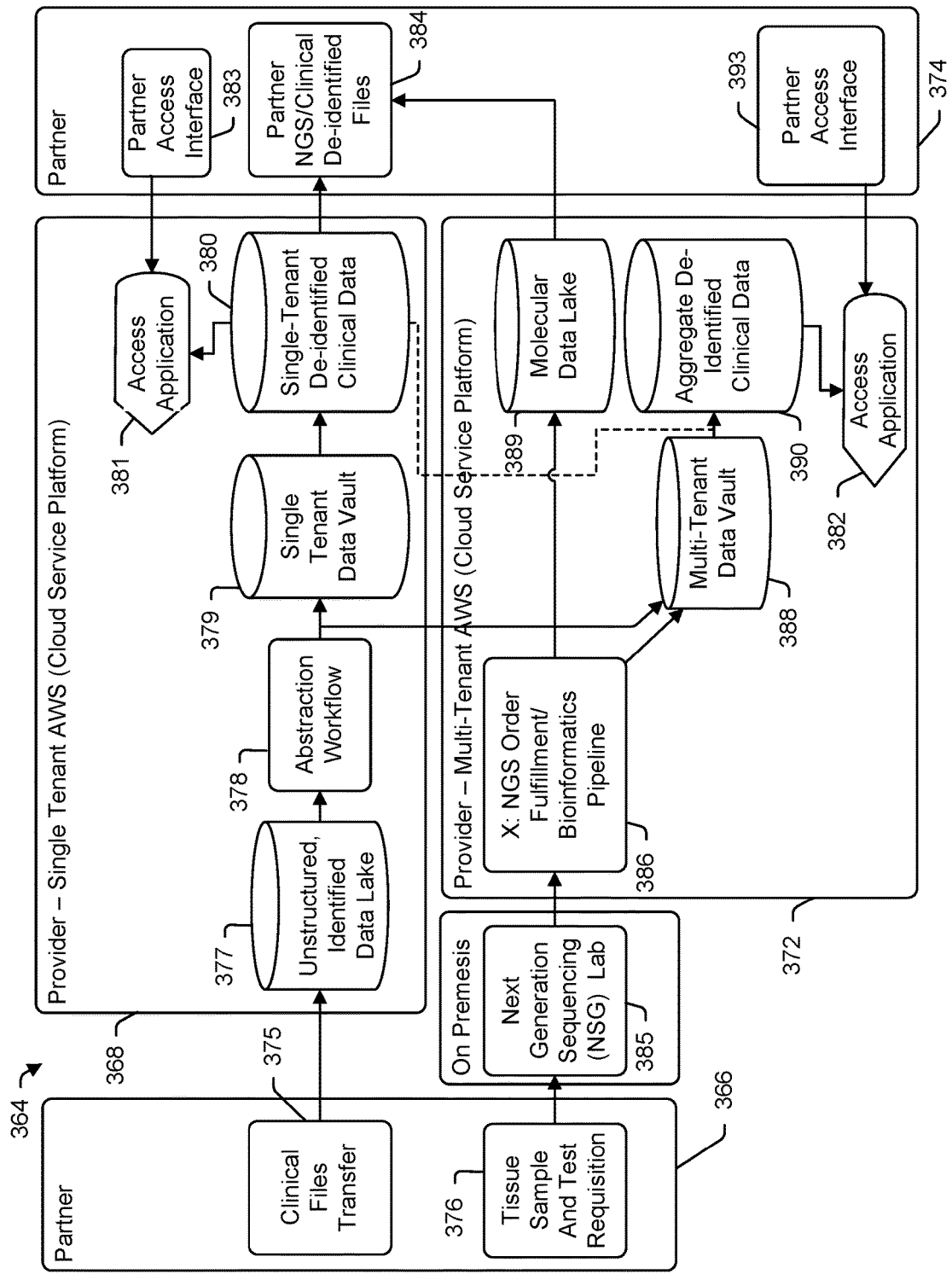
FIG. 3a is a schematic diagram showing a data platform that is consistent with at least some aspects of the present disclosure.

Referring now to FIG. 3a, a schematic is shown that represents an exemplary data platform 364 that is consistent with at least some aspects of the present disclosure. The exemplary platform shows data, information and samples as they exist throughout a system where different system processes and functions are controlled by different entities including an overall system provider that operates both single tenant and multi-tenant cloud service platforms 368 and 372, respectively, partners 366 that provide clinical files as well as tissue samples and related test requisition orders as well as other partners 374 that access processed data and information stored on the service platforms 368 and 372. Partners 366 provide secure clinical files 375 via a file transfer to the single tenant cloud platform 368 and are stored as unstructured and identified files in the lake database. Those files are abstracted and shaped as described above to generate normalized structured clinical data that is stored in a single tenant data vault as well as in a multi-tenant data vault 388. The data from the vault is then de-identified and stored in a de-identified clinical data database which is accessible to authorized partners 374 via system interfaces 383 and applications 381 as described herein.

Referring still to FIG. 3a, partners 366 also provide tissue samples and test requisition orders that drive next generation sequencing lab activity at 385 to generate the bioinformatics pipeline 386 which is stored in both a molecular data lake database 389 and the multi-tenant data vault 388. The data in vault 388 is de-identified and stored in an aggregate de-identified clinical data database 390 where it is accessible to authorized partners via system interfaces 393 and applications 382 as described herein. In addition, the molecular lake data 389 and the de-identified single tenant files 380 are accessible to other authorized partners via other interfaces 384.

IV. User Interfaces

Referring again to FIG. 3, the disclosed system 100 is accessible by many different types of system users that have many different needs and goals including clinical physicians 10 as well as provider specialists like data abstractors 20, lab, modeling and radiology specialists 30, partner researchers 40, provider researchers 50 and dataset sales specialists 60, among others. Because each user type performs different activities aimed at achieving different goals, the application suites 188, 192 and associated user interfaces employed by each user type will typically be at least somewhat if not very different. For instance, a physician's application suite may include 9 separate application programs that are designed to optimally support many oncological treatment consideration and planning processes while an abstractor specialist's application suite may include 5 application programs that are completely separate from the 9 programs in the physician's suite and that are designed to optimally facilitate record abstraction and data structuring processes.

In some cases a system user's program suite will be internally facing meaning that the user is typically a provider employee and that the suite generates data or other information deliverables that are to be consumed within the system 100 itself. For instance, an abstractor application program for structuring data from a raw data set to be consumed by micro-services and other system resources is an example of an internally facing application program. Other system user programs or suites will be externally facing meaning that the user is typically a provider customer and that the suite generates data or other information deliverables that are primarily for use outside the system. For instance, a physician's application program suite that facilitates treatment planning is an example of an externally facing program suite.

Referring now to FIGS. 14 through 21, screenshots of an exemplary physician's user interface that include a series of hyperlinked user interface views that are consistent with at least some aspects of the present disclosure are shown. The screenshots show one natural progression of information consideration wherein each interface is associated with one of the physician's program suite applications 188. While some of the illustrated screenshots are complete, others are only partial and additional screen data would be accessible via either scrolling downward as well known in the graphical arts or by selection of a hyperlink within the presented view that accesses additional information related to the screenshot that includes the selected hyperlink.

Figure 14:
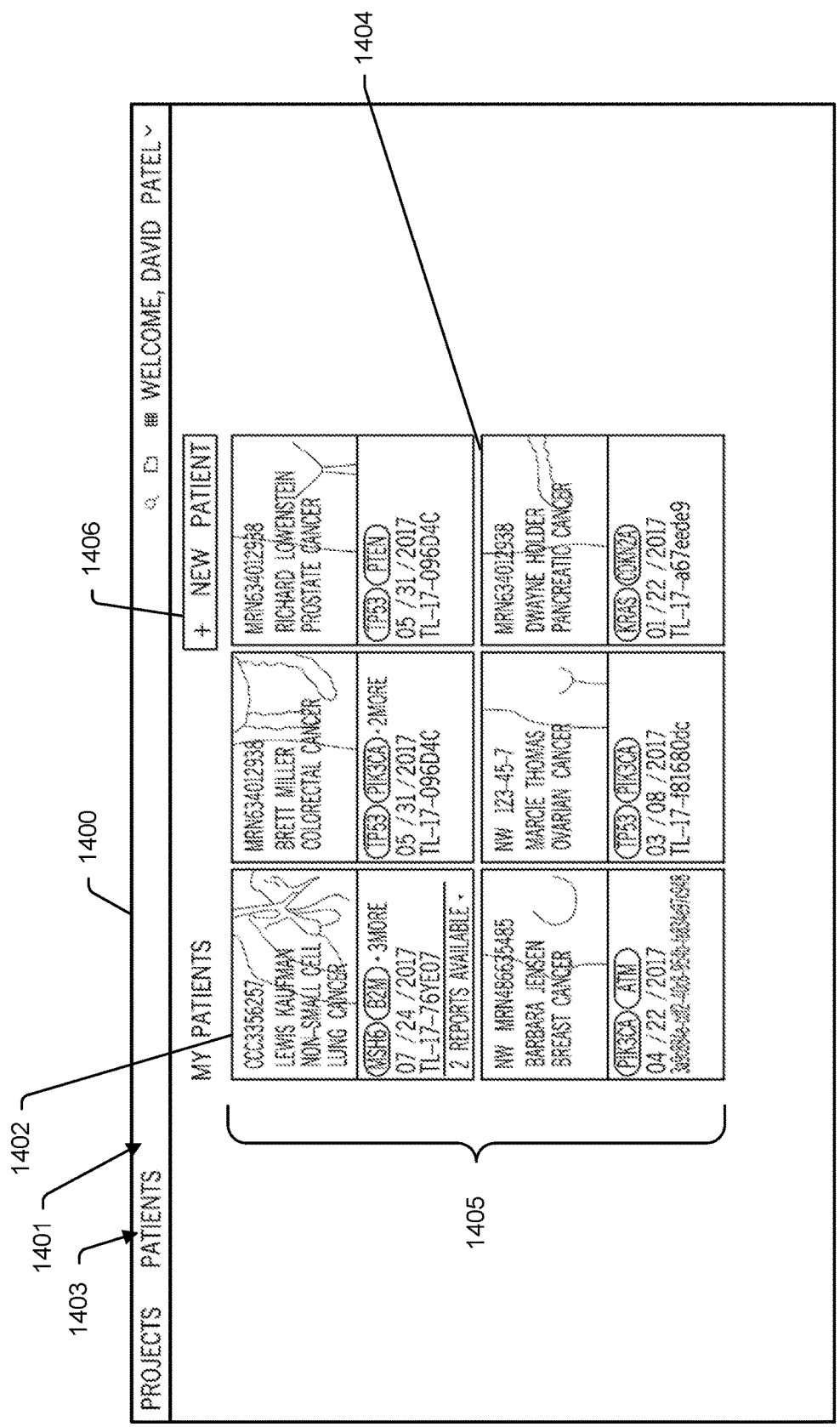
FIG. 14 is a screenshot illustrating a patient list view that may be accessed by a physician using the disclosed system to consider treatment options for a patient.

Referring to FIG. 14, once a physician logs onto system 10 via entry of a username and password or via some other security protocol, the physician is either presented with a patient list screen 1400 or can navigate to that screen. The patient list screen 1400 includes a first navigation bar or ribbon that extends along an upper edge of the view as well as a patient list area 1405 that includes a separate cell or field (two labelled 1402 and 1404) for each of the physician's patients for which the system 100 stores data. Each patient cell (e.g., 1404) includes basic patient information including the patient's name, an identification number and a cancer type and operates as a hyperlink phrase for accessing applications where the system loads data for the patient indicated in the cell. The screen 1400 also includes a "New Patient" icon 1406 that is selectable to add a new patient to the physician's view. The screen 1400 may display all patients of the physician's who have received genomic testing. Each patient cell can represent one or more reports created based on tissue samples. Physicians can also see in-progress patients along with a status indicating an order's progress, such as if the sample has been received. Some physicians may be provided with an additional section displaying reference patients. In these cases, the physician signed into the system 10 is not the patient's ordering physician, but has some other reason to access the patient information, such as because the the ordering physician indicated he or she should receive a copy of the report and be permitted other appropriate access. Certain users of the system 10, such as administrators, may have access to browse all patients within their institution.

Figure 15:
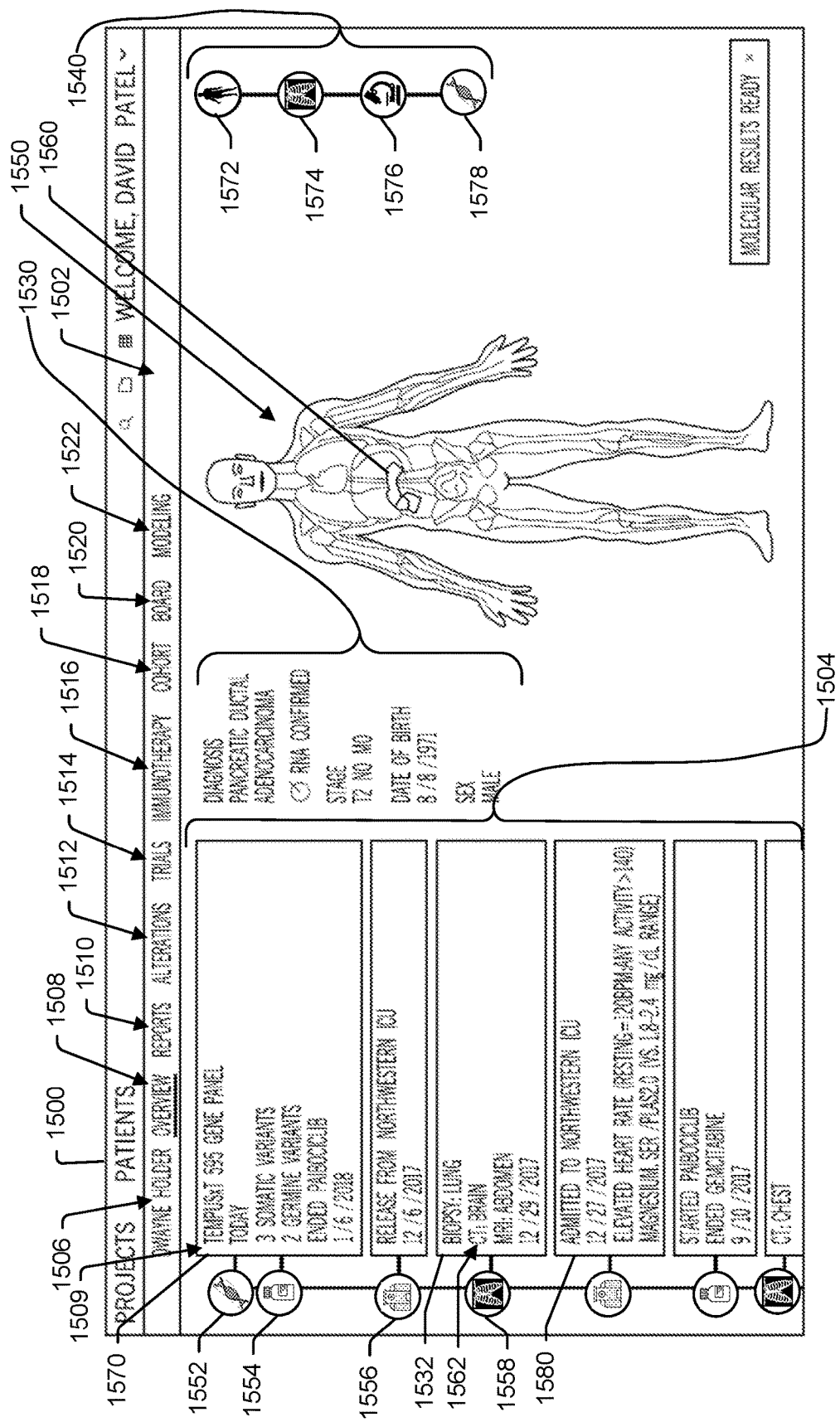
FIG. 15 is a screenshot illustrating an overview view that may be accessed by a physician using the disclosed system to review prior treatment or case activities related to the patient.

Referring again to FIG. 14, upon selecting cell 1404 associated with a patient named Dwayne Holder, the system presents the screenshot 1500 shown in FIG. 15 that includes a second level navigation bar 1502 near the top of the screen 1500 and a workspace 1504 below bar 1502. Navigation bar 1502 persistently identifies the patient 1506 associated with the data currently being viewed by the physician throughout the screenshots illustrated and also includes a separate hyperlink text term for each of several system data views or application programs that can be selected by the physician. In FIG. 15 the view and applications options include an "Overview" option 1508, a "Reports" option 1510, an "Alterations" option 1512, a "Trials" option 1514, an "Immunotherapy" option 1516, a "Cohort" option 1518, a "Board" option 1520 and a "Modelling" option 1522. Many other options will be added to bar 1502 over time as they are developed. A view or application currently accessed by the physician is underlined or otherwise visually distinguished in bar 1502. For instance, in FIG. 15 the overview icon 1508 is shown highlighted to indicate that the information presented in workspace 1504 is associated with the overview data view.

Referring still to FIG. 15, the exemplary overview view includes a patient care timeline 1509 along a left edge of workspace 1504, high level patient cancer state information 1550 in a central portion of workspace 1504 and view selection icons 1540 along a right edge of workspace 1504. Timeline 1509 includes a set of patient care cells 1570, 1580, etc., each of which corresponds to a meaningful care related event associated with treatment of the patient's cancer state. The cells are vertically stacked with earliest cells in time near the bottom of the stack and more recent cells near the top of the stack. Each cell is typically restricted to activities or information associated with a specific date and, in addition to the associated date, may include any subset of several different information types including hospital or clinic admission and release dates, medical imaging descriptors, procedure descriptors, medication start and end dates, treatment procedure start and end descriptors, test descriptors, test or procedure results descriptors and other descriptors. This list is exemplary and not intended to be exhaustive. For instance, cell 1532 that is dated Dec. 29, 2017 indicates that a lung biopsy occurred as well as a brain CT imaging session and an MRI of the patient's abdomen. Information in the timeline 1509 may be loaded from the structured data that results from using the systems and methods described herein, such as those with reference to FIG. 10. Information in the timeline 1509 may also include references to genomic sequencing tests ordered for a patient.

Referring still to FIG. 15, in addition to including the patient care cell stack, the care timeline 1509 includes a vertical activity icon progression 1534 that extends along the left edge of the cell stack. The activity icons in progression 1534 are horizontally aligned with associated textual descriptions of care events in the cell stack. Each activity icon is designed to glanceably indicate an activity type so that a physician can quickly identify activities of specific types within the stacked cells by simply viewing the icons and associated stack event descriptors. For instance, exemplary activity icons include a gene panel publication icon 1552, a medication start/stop icon 1554, a facility admit/release icon 1556 and an imaging session icon 1558. Other icons corresponding to surgery, detected patient medical conditions, and other procedures or important medical events are contemplated.

Referring still to FIG. 15, in at least some cases detailed data related to a care event will be further accessible by selecting one of the activity icons along the left of the cells or events in a cell to hyperlink to the additional information. For instance, the "CT:Brain" text at 1662 may be selectable to link to a CT image viewer to view CT images of the patient's brain that correspond to the event. Other links are contemplated.

Referring again to FIG. 15, general cancer state and patient information at 1550 includes diagnosis, stage, patient date of birth and gender information 1530 as well as an anatomical image that shows a representation of a tumor within a body that is generally consistent with the patient's cancer state. In some cases the tumor representation is just representative of the patient's condition as opposed to directly tied to actual tumor images while in other cases the tumor representation is derived from actual medical images of the patient's tumor.

Referring again to FIG. 15, the patient body image 1550 may be overlaid with structured contours 1560 from the patient's radiology imaging. Represented structures may include primary or metastatic lesions, organs, edema, etc. A physician may click each structured contour to obtain an additional level of detail of information. Clicking the structured contour may isolate it visually for the physician. In the case of a tumor contour, the additional level of detail may include supporting information such as tumor volume, longest 3D diameter, or other features. Certain radiomic features that may be presented to the physician are described in further detail in, for instance, U.S. Provisional Patent Application No. 62/693,371, titled 3D Radiomic Platform for Imaging Biomarker Development, which has been incorporated herein by reference in its entirety.

From this detailed view, the physician may further drill down to an additional, microscopic level of detail. Here, a patient's histopathology results may be displayed. Clinical interpretations are shown, where available from an issued report. The microscopic detail may also display thumbnail images of microscope slides of a patient's specimens.

View selection icons 1540 include a set of icons that allow the physician to select different views of the patient's cancer condition and are progressively more granular. To this end, the exemplary view icons include a body view icon 1572 corresponding to the body view shown in FIG. 15, a medical imaging view icon 1574 for accessing medical X-ray, CT, MRI and other images, a cellular view icon 1576 that shows cellular level images and genomic sequencing data icon 1578 for accessing genomic data views.

Figure 16:
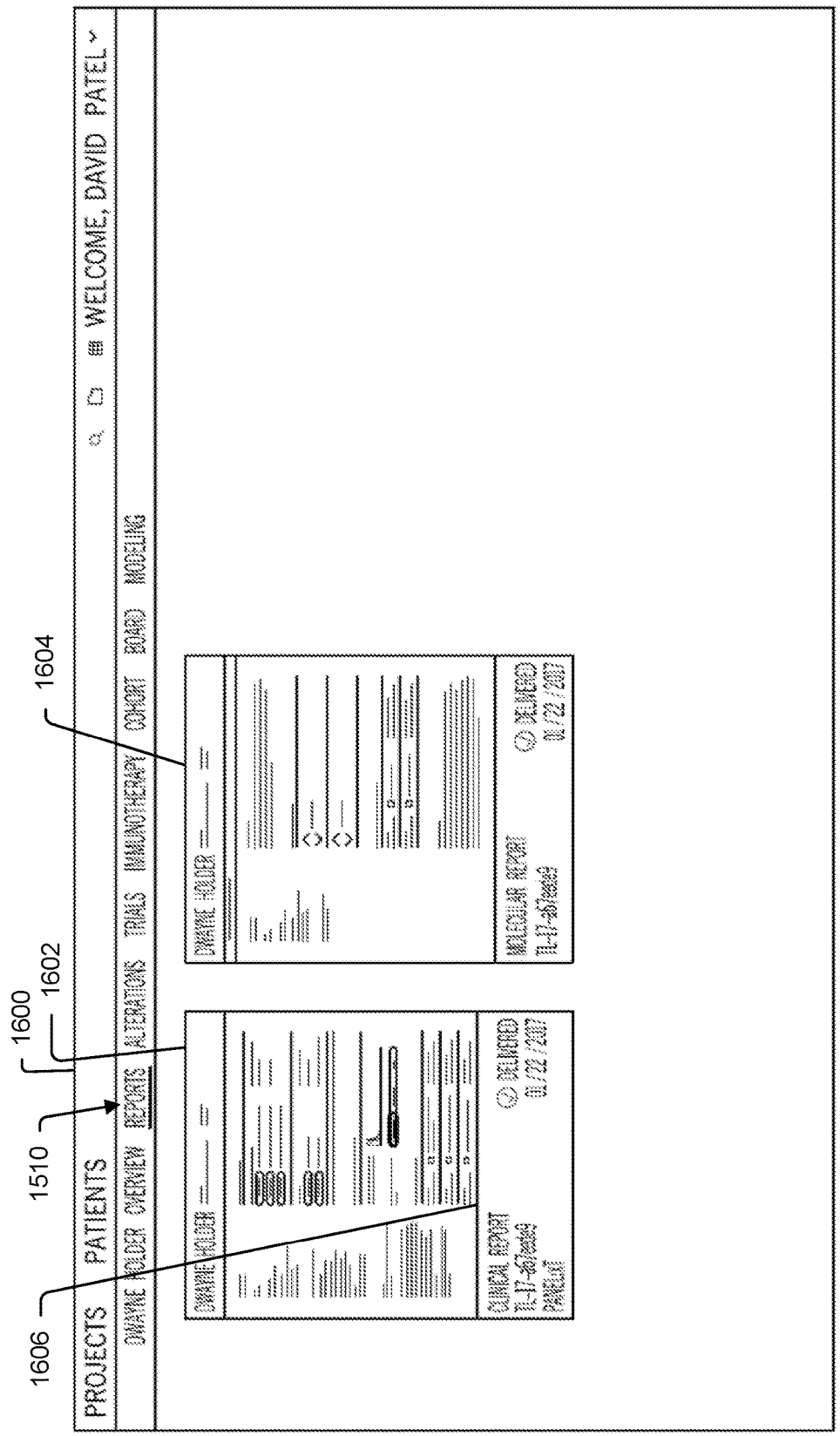
FIG. 16 is a screenshot illustrating screenshot illustrating a reports view that may be used to access patient reports generated by the system 100.

Referring again to FIG. 15, to access specific issued reports associated with the patient the physician selects reports icon 1510 to access a reports screen 1600 shown in FIG. 16. Reports screen 1600 shows the reports icon 1510 highlighted to help orient the physician and includes a report list indicating all reports stored in the system that are associated with the patient. In the exemplary reports view, each report is represented in the list by a reduced size image of the first page of the report and with a general report description field near the bottom of the image. For exemplary report images are shown at 1602 and 1604 and a general report description of the report associated with image 1602 is provided at 1606 indicating report type, date and other characterizing information.

Figure 17:
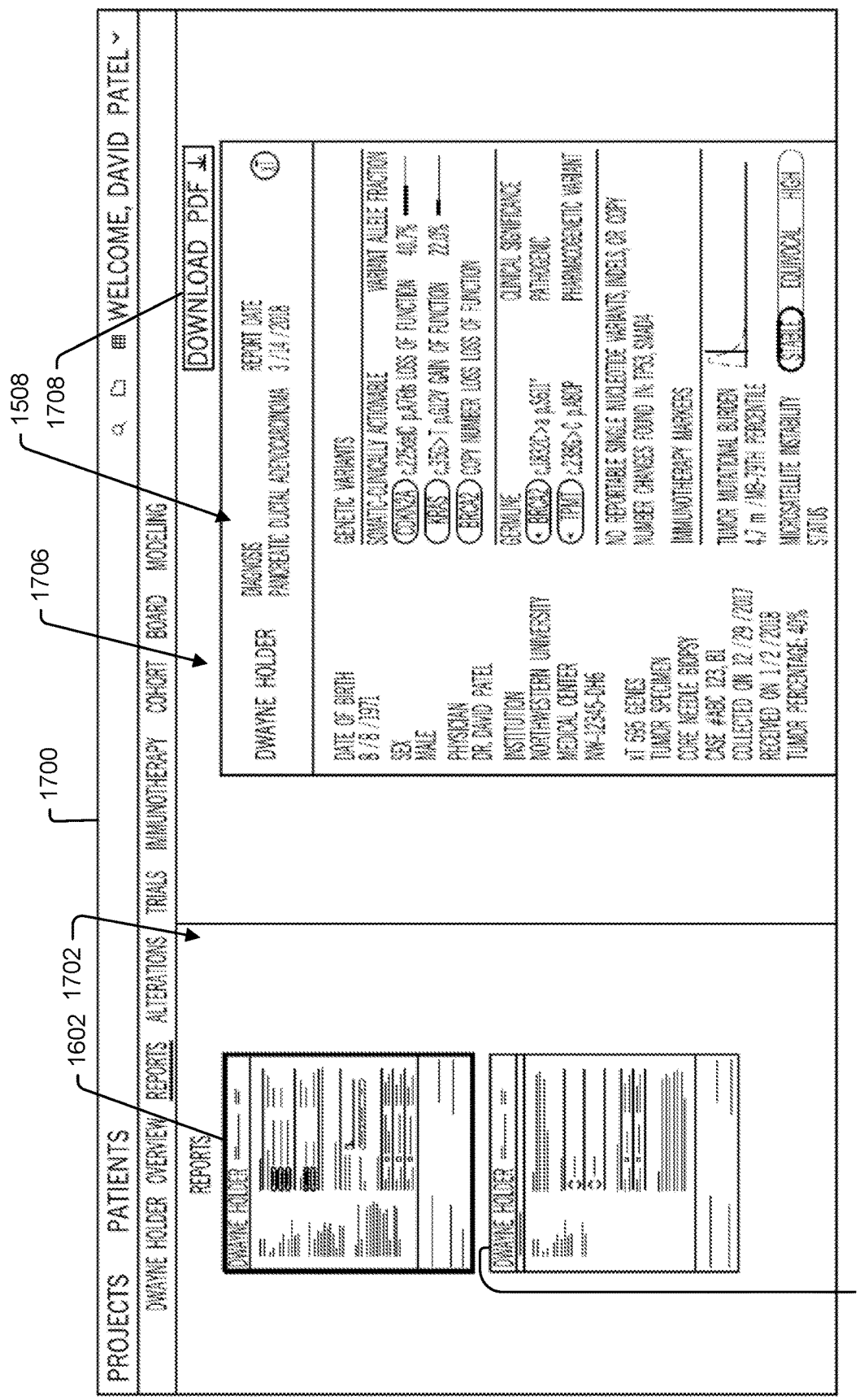
FIG. 17 is a screenshot illustrating a second reports view that shows one report in a larger format.

The physician can select one of the report images to access the full report. For instance, if the physician selects image icon 1602, the screenshot 1700 shown in FIG. 17 is presented that splits the display screen into a report list section 1702 along the left edge of the screen and an enlarged report section 1704 that covers about the right two thirds of the screen where the selected report is presented in a larger format for viewing. The report presents clinically significant information and may take many different forms. Each report is listed again in section 1702 as a reduced size hyper linkable image as shown at 1602 and 1604 where the currently selected report 1602 is highlighted or otherwise visually distinguished. The physician can select a PDF icon 1708 to download a copy of the report to the physician's computer.

A patient may have multiple reports for each specimen or specimen set sequenced. Reports may include DNA sequencing reports, IHC staining reports, RNA expression level reports, organoid growth reports, imaging and/or radiology reports, etc. Each report may contain results of sequencing of the patient's tumor tissue and, where available the normal tissue as well. Normal tissue can be used to identify which alterations, if any, are inherited versus those that the tumor uniquely acquired. Such differentiation often has therapeutic implications.

Figure 17A:
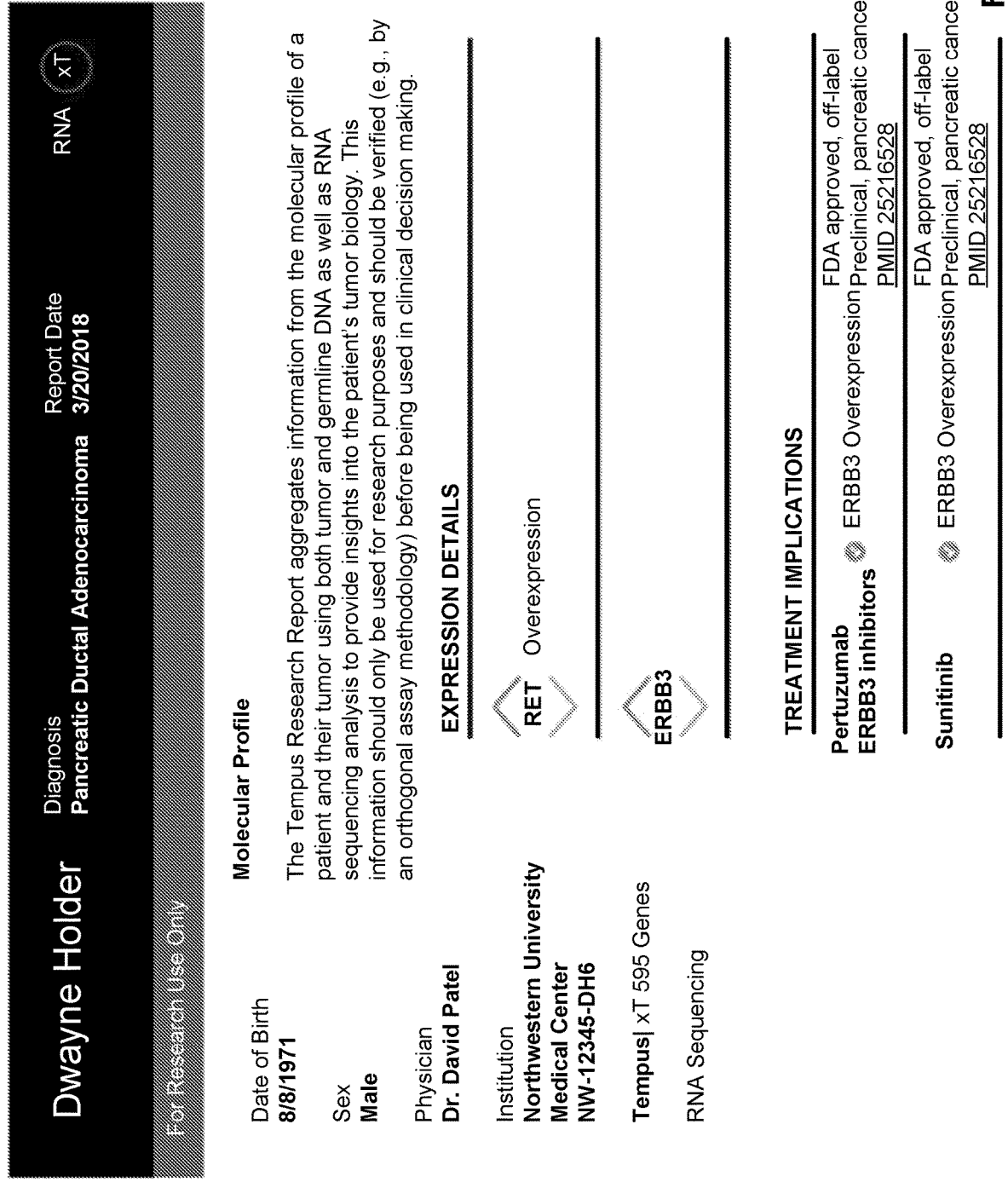
FIG. 17a shows an initial view of an RNA sequence reporting screenshot that is consistent with at least some aspects of the present disclosure.

FIG. 17a shows an exemplary first page of a report screenshot indicating the results of one RNA sequencing process. Profiling of whole RNA transcriptome provides molecular information that is complementary to DNA sequencing and can be clinically important to physicians. For example, RNA sequencing can assist in clinically validated unbiased translocation detection. Overexpression and underexpression of certain genes may be presented to the physician as a result of RNA sequencing. Likewise, treatment implications may be provided to the physician which the physician may take into consideration when determining the best type of treatment for a patient. The physician may decide to verify results, for instance, through an orthogonal assay methodology, before using the results in clinical decision making.

Figure 18:
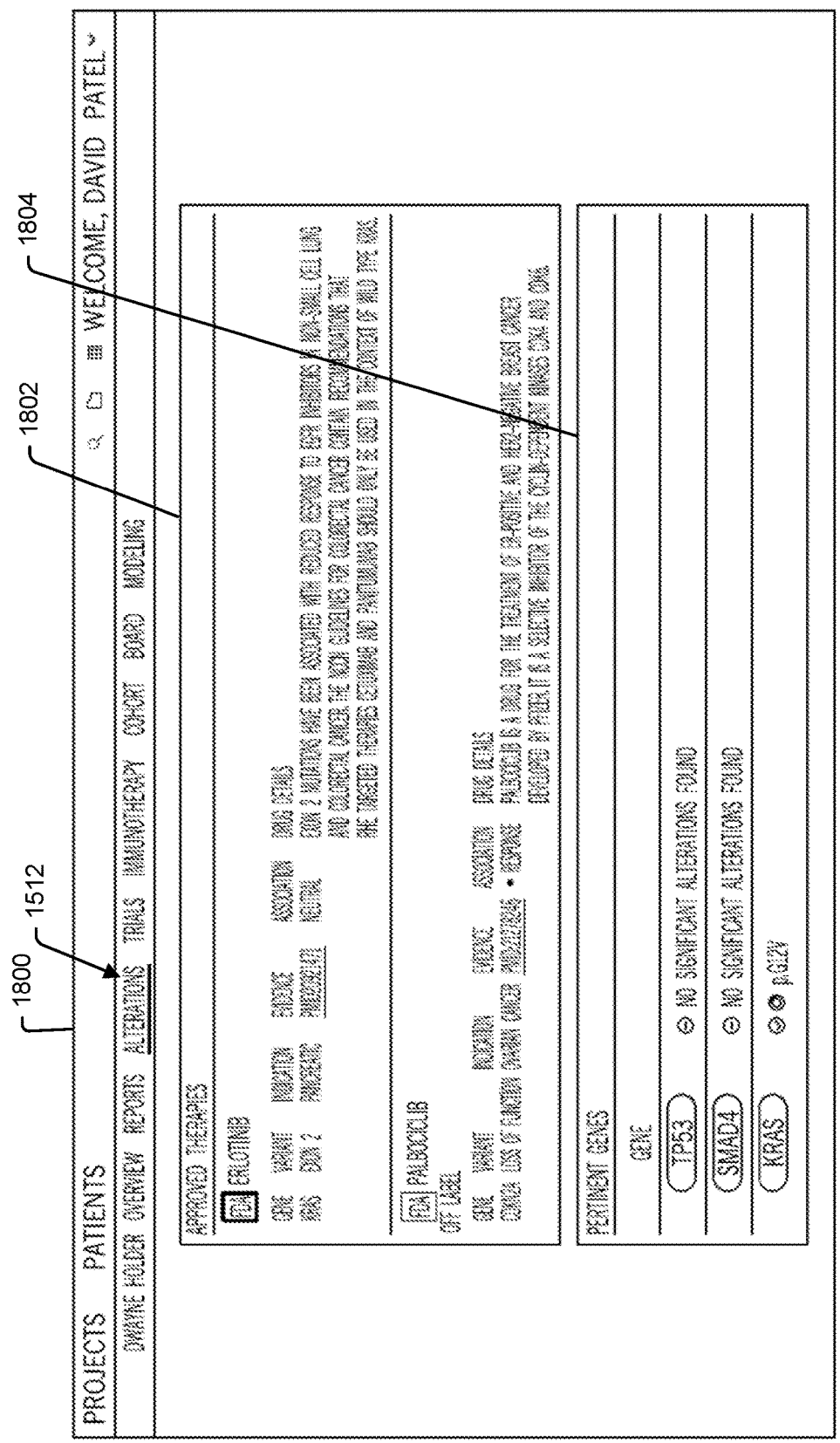
FIG. 18 is a screenshot illustrating an alterations view accessible by a physician to consider molecular tumor alterations.
Figure 19:
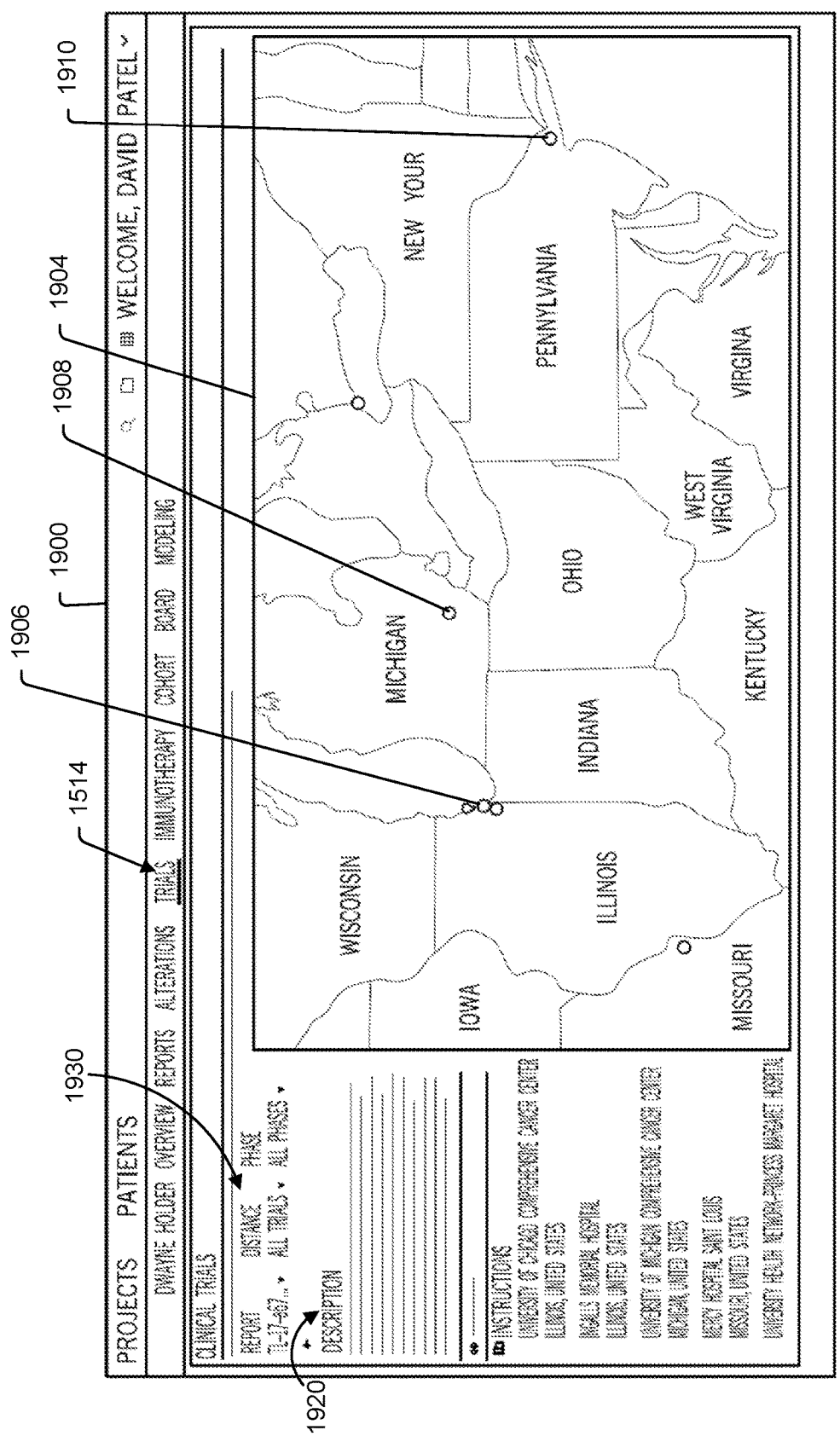
FIG. 19 is a screenshot illustrating a trials view in which a physician views information related to clinical trials on conjunction with considering treatment options for a patient.

To examine information related to a patient's genomic tumor alterations and possible treatment options, the physician selects alterations icon 1512 to access screen 1800 shown in FIG. 18. Screen 1800 includes an approved therapies list 1802 and a pertinent genes list 1804. The therapies list 1802 includes a list of genes for which variants have been identified and for each gene in the list, the associated variant, how the variant is indicated and other information including details regarding considerations corresponding to the associated therapy option. Other screens for considering alterations are contemplated to enable a physician to consider many aspects of treatment efficacy. Additional details may be provided to add context to alterations, such as gene descriptions, explanation of mutation effect, and variant allelic fraction. Alterations may be reported by category, ranging from highly relevant genes to variants of unknown significance.

Selecting an alteration may take the physician to an additional view, shown at FIGS. 18a and 18b (showing different scrolled sections of one view in the two figures), where the physician can delve deeper into the alteration's effect, with supporting data visualizations. Germline alterations associated with diseases may be reported as incidental findings. In FIG. 18a, approved therapies are listed with relevant related information including a gene and variant indicator along with hyperlinks to evidence associated with the therapy and details about each of the therapies.

The physician application suite also provides tools to help the physician identify and consider clinical trials that may be related to treatment options for his patient. To access the trials tools, the physician selects trials icon 1514 to access the screen (not shown) that lists all clinical trials that may be of any interest to the physician given patent cancer state characteristics. For instance, for a patient suffering from pancreatic cancer, the list may indicate 12 different trials occurring within the United States. In some cases the trials may be arranged according to likely most relevant given detailed cancer state factors for the specific patient. The physician can select one of the clinical trials from the list to access a screen 1900 like the one shown in FIG. 19. Screen 1900 includes a map 1904 with markers (three labelled 1906, 1908 and 1910) at map locations corresponding to institutions are participating in the selected trial as well as a general description 1920 of the trial. Screen 1900 also provides a set of filtering tools 1930 in the form of pull down menus the physician can use to narrow down trial options by different factors including distance from the patient's location, trial phase (e.g., not yet initiated, progressing, wrapping up, etc.), and other factors. Here, the idea is that the physician can explore trial options for specific patient cancer states quickly by focusing consideration on the most relevant and convenient trial options for specific patients.

Figure 20:
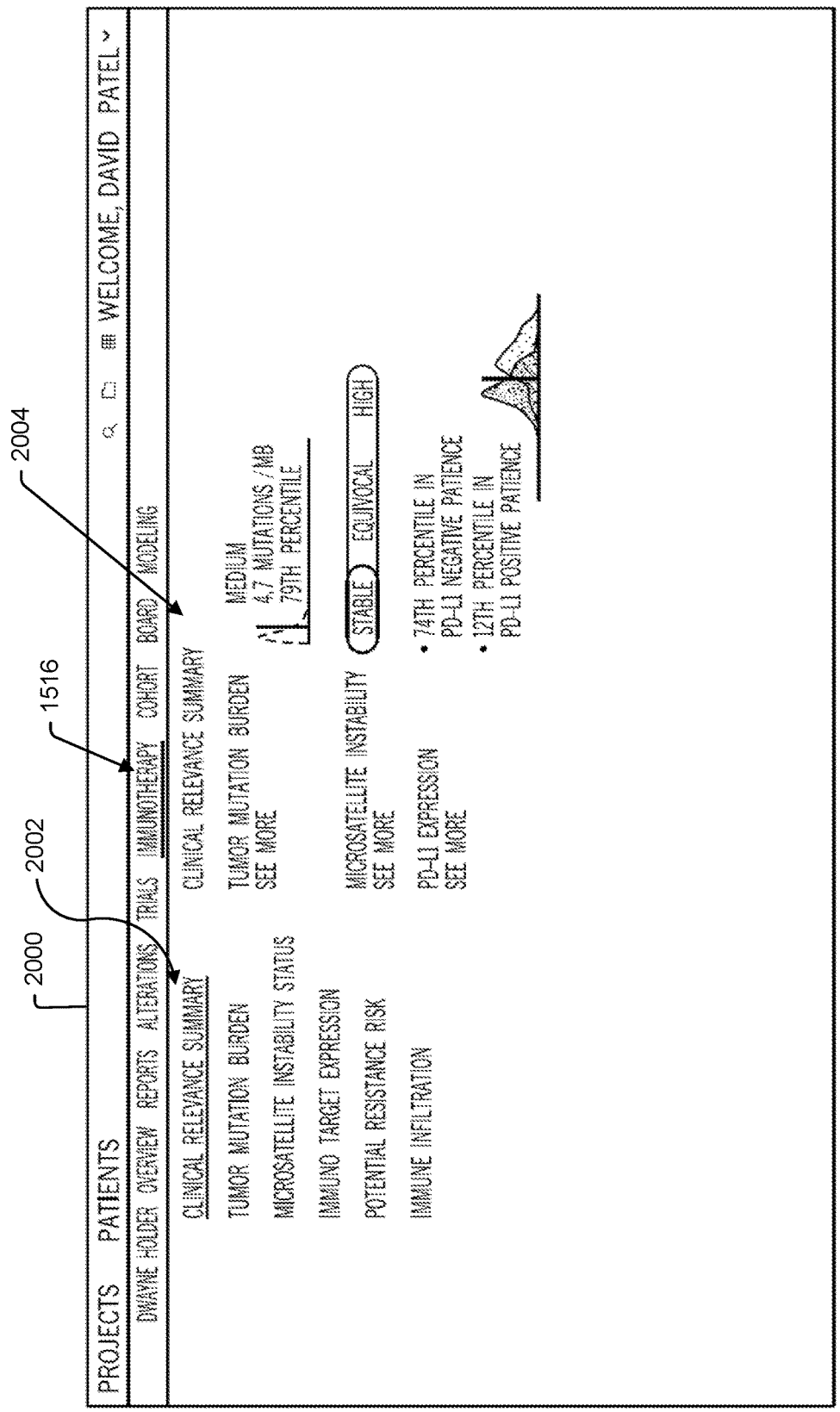
FIG. 20 is a screenshot illustrating an immunotherapy screenshot accessible to a physician for considering immunotherapy efficacy options for treating a patient's cancer state.

The physician application suite provides tools for the physician to consider different immunotherapies that are accessible by selecting immunotherapy icon 1516 from the navigation bar. When icon 1516 is selected, an exemplary immunotherapy screenshot 2000 shown in FIG. 20 is presented. Screenshot 2000 includes a menu of immunotherapy interface options 2002 extending vertically along a left area of the screen and a detailed information area 2004 to the right of the options 2002. In at least some cases the immunotherapy options 2002 will include a summary option, a tumor mutation burden option, a microsatellite instability status option, an immune resistance risk option and an immune infiltration option where each option is selectable to access specific immunotherapy data related to the patient's case. Immunotherapy options 2002 may provide the physician with an indication that an immunotherapy, such as an FDA approved immunotherapy, may be appropriate to prescribe the patient. Examples may include dendritic cell therapies, CAR-T cell therapies, antibody therapies, cytokine therapies, combination immunotherapies, adoptive t-cell therapies, anti-CD47 therapies, anti-GD2 therapies, immune checkpoint inhibitors, oncolytic viruses, polysaccharides, or neoantigens, among others. Area 2004 shows summary information presented when the summary option is selected from the option list 2002. When other list options are selected, related information is used to populate area 2004 with additional related information.

Figure 21:
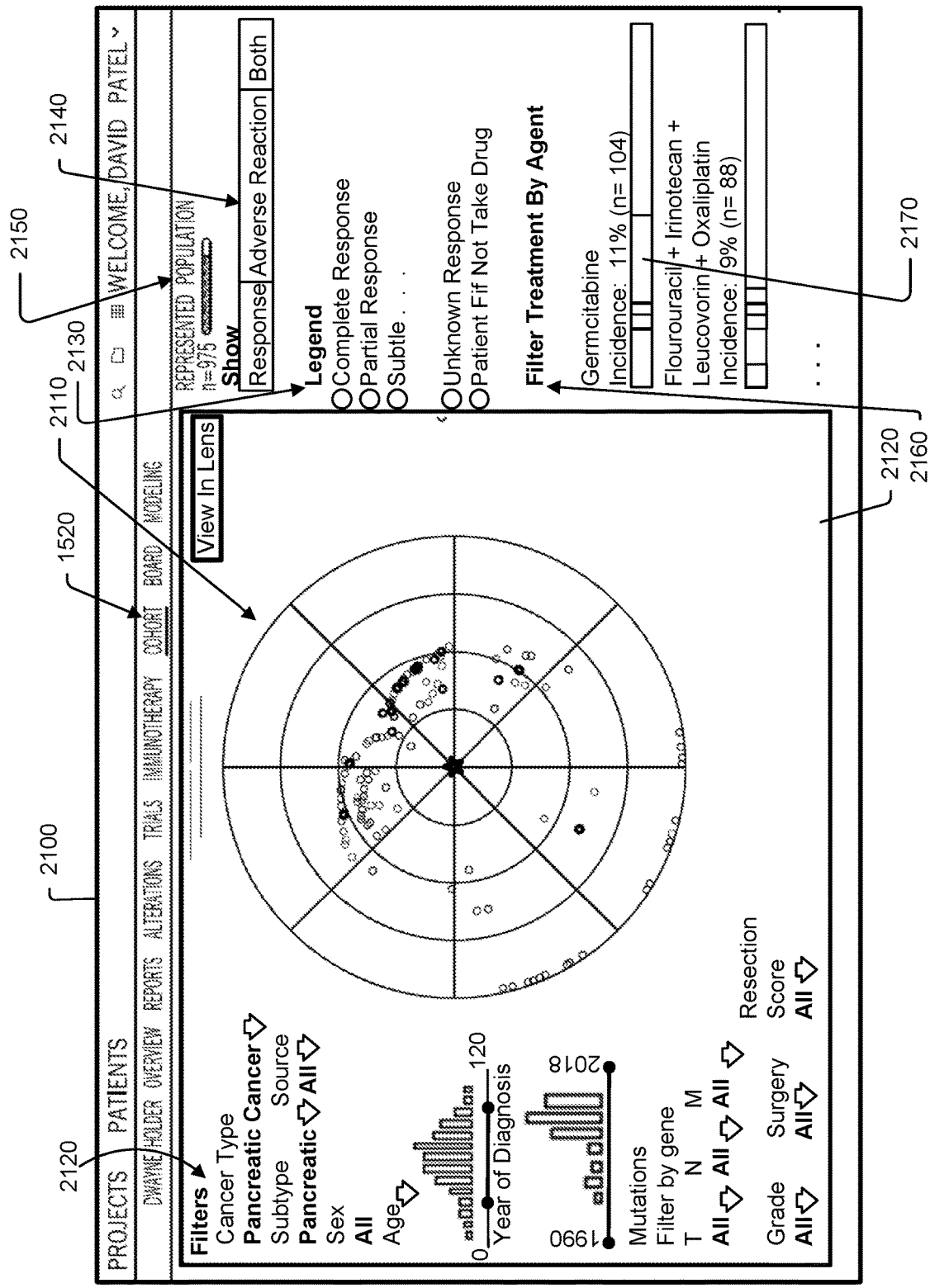
FIG. 21 is a screenshot illustrating an efficacy exploration view where molecular differences between a patient's tumor and other tumors of the same general type are used a primary factor in generating the illustrated graph.

Referring to FIG. 21, the cohort option 1518 can be selected to access an analytical tool that enables the physician to explore prior treatment responses of patients that have the same type of cancer as the patient that the physician is planning treatment for in light of similarities in molecular data between the patients. To this end, once genomic sequencing has been completed for each patient in a set of patients, molecular similarities can be identified between any patients and used as a distance plotting factor on a chart 2110. In FIG. 21, the screen 2100 includes a graph at 2110, filter options at 2120, some view options 2140, graph information at 2150 and additional treatment efficacy bar graphs at 2160.

Referring still to FIG. 21, the illustrated graph presents a tumor associated with the patient for which planning is progressing at a center location as a star and other patient tumors of a similar type (e.g., pancreatic) at different radial distances from the central tumor where molecular similarity is based on distance from the central location so that tumors more similar to the central tumor are near the center and tumors other than the central tumor are located in proximity to one another based on their respective similarity. Angular displacements between the other tumors represented indicate dissimilarity or similarity between any two tumors where a greater angular distance between two tumors indicates greater dissimilarity. Except for the central tumor (e.g., indicated via the star), each of the other tumors is color coded to indicate treatment efficacy. For instance, a green dot may represent a tumor that completely responded to treatment, a yellow dot may indicate a tumor that responded minimally while a red dot indicates a tumor that did not respond. An efficacy legend at 2130 is provided that associates tumor colors with efficacies "e.g., "Complete Response", "Partial Response", etc.). the physician can select different options to show in the graph including response, adverse reaction, or both using icons at 2140.

Referring still to FIG. 21, an initial view 2110 may include all patient tumors that are of the same general type as the central tumor presented on the graph 2110, regardless of other cancer state factors. In FIG. 21, a number "n" is equal to 975 indicating that 975 tumors and associated patients are represented on graph 2110. Filters at 2120 can be used by the physician to select different cancer state filter factors to reduce the n count to include patients that have other factors in common with the patient associated with the central tumor. For instance, patient sex or age or tumor mutations or any factor combination supported by the system may be used to filter n down to a smaller number where multiple factors are common among associated patients.

Referring again to FIG. 21, the efficacy bar graphs 2160 present efficacy data for different treatment types. To this end, screen area 2160 presents a list of medications or combinations thereof that have been used in the past to treat the tumors represented in graph 2110. A separate bar graph is provided for each of the treatment medications or combinations where each bar graph includes different length color coded sub-sections that show efficacy percentages. For instance, for Germcitabine, the bar graph 2170 may include a green section that extends 11% of the length of the total bar graph and a blue section that extends 5% of the length of the total bar graph to indicate that 11% of patients treated with Germcitabine experienced a complete response while 5% experienced only a partial response. Other color coded sections of bar 2170 would indicate other efficacies. The illustrated list only includes two treatment regimens but in most cases the list would be much longer and each list regimen would include its own efficacy bar graph.

IV. Automated Cancer State-Treatment-Efficacy Insights Across Patient Populations Referring again to FIG. 21, the cohort tool shown allows a physician to select different cancer state filters 2120 to be applied to the system database thereby changing the set of patients for which the system presents treatment efficacy data to help the physician explore effects of different factors on efficacy which is intended to lead to new treatment insights like factor-treatment-efficacy relationships. While powerful, this physician driven system is only as good as the physician that operates it and in many cases cancer state-treatment-efficacy relationships simply will not even be considered by a physician if clinically relevant state factors are not selected via the filter tools. While a physician could try every filter combination possible, time restraints would prohibit such an effort. In addition, while a large number of filter options could be added to the filter tools 2120 in FIG. 21, it would be impractical to support all state factors as filter options so that some filter combinations simply could not be considered.

To further the pursuit of new cancer state-treatment-efficacy exploration and research, in at least some embodiments it is contemplated that system processors may be programmed to continually and automatically perform efficacy studies on data sets in an attempt to identify statistically meaningful state factor-treatment-efficacy insights. These insights can be confirmed by researchers or physicians and used thereafter to suggest treatments to physicians for specific cancer states.

V. Exemplary System Techniques And Results

The systems and methods described above may be used with a variety of sequencing panels. One exemplary panel, the 595 gene xT panel referred to above (See again the FIG. 27 series of figures), is focused on actionable mutations. Hereafter we present a description of various techniques and associated results that are consistent with aspects of the present disclosure in the context of an exemplary xT panel.

Techniques and results include the following. SNVs (single nucleotide variants), indels, and CNVs (copy number variants) were detected in all 595 genes. Genomic rearrangements were detected on a 21 gene subset by next generation DNA sequencing, with other genomic rearrangements detected by next generation RNA sequencing (RNA Seq). The panel also indicated MSI (microsatellite instability status) and TMB (tumor mutational burden). DNA tumor coverage was provided at 500× read sequencing depth. Full transcriptome was also provided by RNA sequencing, with unbiased gene rearrangement detection from fusion transcripts and expression changes, sequenced at 50 million reads.

In addition to reporting on somatic variants, when a normal sample is provided, the assay permits reporting of germline incidental findings on a limited set of variants within genes selected based on recommendations from the American College of Medical Genetics (ACMG) and published literature on inherited cancer syndromes.

Mutation Spectrum Analysis For Exemplary 500 Patient xT Group

Subsequent to selection, patients were binned by pre-specified cancer type and filtered for only those variants being classified as therapeutically relevant. The gene set was then filtered for only those genes having greater than 5 variants across the entire group so as to select for recurrently mutated genes. Having collated this set, patients were clustered by mutational similarity across SNPs, indels, amplifications, and homozygous deletions. Subsequently, mutation prevalence data for the MSKCC IMPACT data were extracted from MSKCC Cbioportal (http://www.cbioportal.org/study?id=msk_impact_2017#summary) in order to compare the xT assay variant calls against publicly available variant data for solid tumors. After selecting for only those genes on both panels, variants with a minimum of 2.5% prevalence within their respective group were plotted.

Detection Of Gene Rearrangements From DNA By The xT Assay

Gene rearrangements were detected and analyzed via separate parallel workflows optimized for the detection of structural alterations developed in the JANE workflow language. Following de-multiplexing, tumor FASTQ files were aligned against the human reference genome using BWA (Li et al., 2009). Reads were sorted and duplicates were marked with SAMBlaster (Faust et al., 2014). Utilizing this process, discordant and split reads are further identified and separated. These data were then read into LUMPY (Layer et al., 2014) for structural variant detection. A VCF was generated and then parsed by a fusion VCF parser and the data was pushed to a Bioinformatics database. Structural alterations were then grouped by type, recurrence, and presence within the database and displayed through a quality control application. Known and previously known fusions were highlighted by the application and selected by a variant science team for loading into a patient report.

Detection of Gene Rearrangements from RNA by the xT Assay

Gene rearrangements in RNA were analyzed via a separate workflow that quantitated gene level expression as well as chimeric transcripts via non-canonical exon-exon junctions mapped via split or discordant read pairs. In brief, RNA-sequencing data was aligned to GRCh38 using STAR (Dobin et al., 2009) and expression quantitation per gene was computed via FeatureCounts (Liao et al., 2014). Subsequent to expression quantitation, reads were mapped across exon-exon boundaries to un-annotated splice junctions and evidence was computed for potential chimeric gene products. If sufficient evidence was present for the chimeric transcript, a rearrangement was called as detected.

Gene Expression Data Collection

RNA sequencing data was generated from FFPE tumor samples using an exome-capture based RNA seq protocol. Raw RNA seq reads were aligned using CRISP and gene expression was quantified via the RNA bioinformatics pipeline. One RNA bioinformatics pipeline is now described. Tissues with highest tumor content for each patient may be disrupted by 5 mm beads on a Tissuelyser II (Qiagen). Tumor genomic DNA and total RNA may be purified from the same sample using the AllPrep DNA/RNA/miRNA kit (Qiagen). Matched normal genomic DNA from blood, buccal swab or saliva may be isolated using the DNeasy Blood & Tissue Kit (Qiagen). RNA integrity may be measured on an Agilent 2100 Bioanalyzer using RNA Nano reagents (Agilent Technologies). RNA sequencing may be performed either by poly(A)+transcriptome or exome-capture transcriptome platform. Both poly(A)+ and capture transcriptome libraries may be prepared using 1~2 ug of total RNA. Poly(A)+ RNA may be isolated using Sera-Mag oligo(dT) beads (Thermo Scientific) and fragmented with the Ambion Fragmentation Reagents kit (Ambion, Austin, Tex.). cDNA synthesis, end-repair, A-base addition, and ligation of the Illumina index adapters may be performed according to Illumina's TruSeq RNA protocol (Illumina). Libraries may be size-selected on 3% agarose gel. Recovered fragments may be enriched by PCR using Phusion DNA polymerase (New England Biolabs) and purified using AMPure XP beads (Beckman Coulter). Capture transcriptomes may be prepared as above without the up-front mRNA selection and captured by Agilent SureSelect Human all exon v4 probes following the manufacturer's protocol. Library quality may be measured on an Agilent 2100 Bioanalyzer for product size and concentration. Paired-end libraries may be sequenced by the Illumina HiSeq 2000 or HiSeq 2500 (2×100 nucleotide read length), with sequence coverage to 40-75M paired reads. Reads that passed the chastity filter of Illumina BaseCall software may be used for subsequent analysis. Further details of the pipeline raw read counts may be normalized to correct for GC content and gene length using full quantile normalization and adjusted for sequencing depth via the size factor method (see Robinson, D. R. et al. Integrative clinical genomics of metastatic cancer. Nature 548, 297-303 (2017)). Normalized gene expression data was log, base 10, transformed and used for all subsequent analyses.

Reference Database

Gene expression data generated (as previously described) was combined with publicly available gene expression data for cancer samples and normal tissue samples to create a Reference Database. For this analysis, we specifically include data from The Cancer Genome Atlas (TOGA) Project and Genotype-Tissue Expression (GTEx) project. Raw data from these publically available datasets were downloaded via the GDC or SRA and processed via an RNAseq pipeline (described above). In total 4,865 TOGA samples and 6,541 GTEx samples were processed and included as part of the larger Reference Database for this analysis. After processing, these datasets were corrected to account for batch effect differences between sequencing protocols across institutions (i.e. TCGA & and the Reference Database). For example, TCGA and GTEx both sequenced fresh, frozen tissue using a standard polyA capture based protocol.

Gene Expression Calling

For each patient, the expression of key genes was compared to the Reference Database to determine overexpression or underexpression. 42 genes for over- or underexpression based on the specific cancer type of the sample were evaluated. The list of genes evaluated can vary based on expression calls, cancer type, and time of sample collection. In order to make an expression call, the percentile of expression of the new patient was calculated relative to all cancer samples in the database, all normal samples in the database, matched cancer samples, and matched normal samples. For example, a breast cancer patient's tumor expression was compared to all cancer samples, all normal samples, all breast cancer samples, and all breast normal tissue samples within the Reference Database. Based on these percentiles criteria specific to each gene and cancer type to determine overexpression was identified.

t-Distributed Stochastic Neighbor Embedding (t-SNE) RNA Analysis

The t-SNE plot was generated using the Rtsne package in R [R version 3.4.4 and Rtsne version 0.13] based on principal components analysis of all samples (N=482) across all genes (N=17,869). A perplexity parameter of 30 and theta parameter of 0.3 was used for this analysis.

Cancer Type Prediction

A random forest model was used to generate cancer type predictions. The model was trained on 804 samples and 4,526 TOGA samples across cancer types from the Reference Database. For the purposes of this analysis, hematological malignancies were excluded. Both datasets were sampled equally during the construction of the model to account for differences in the size of the training data. The random forest model was calculated using the Ranger package in R [R version 3.4.4 and ranger 0.9.0]. Model accuracy was calculated within the training dataset using a leave-one-out approach. Based on this data, the overall classification accuracy was 81%.

Tumor Mutational Burden (TMB)

TMB was calculated by determining the dividend of the number of non-synonymous mutations divided by the megabase size of the panel (2.4 MB). All non-silent somatic coding mutations, including missense, indel, and stop loss variants, with coverage greater than 100× and an allelic fraction greater than 5% were included in the number of non-synonymous mutations.

Human Leukocyte Antigen (HLA) Class I Typing

HLA class I typing for each patient was performed using Optitype on DNA sequencing (Szolek 2014). Normal samples were used as the default reference for matched tumor-normal samples. Tumor sample-determined HLA type was used in cases where the normal sample did not meet internal HLA coverage thresholds or the sample was run as tumor-only.

Neoantigen Prediction

Neoantigen prediction was performed on all non-silent mutations identified by the xT pipeline. For each mutation, the binding affinities for all possible 8-11aa peptides containing that mutation were predicted using MHCflurry (Rubinsteyn 2016). For alleles where there was insufficient training data to generate an allele-specific MHCflurry model, binding affinities were predicted for the nearest neighbor HLA allele as assessed by amino acid homology. A mutation was determined to be antigenic if any resulting peptide was predicted to bind to any of the patient's HLA alleles using a 500 nM affinity threshold. RNA support was calculated for each variant using varlens (https://dithub.com/openvax/varlens). Predicted neoantigens were determined to have RNA support if at least one read supporting the variant allele could be detected in the RNA-seq data.

Microsatellite Instability (MSI) Status

The exemplary xT panel includes probes for 43 microsatellites that are frequently unstable in tumors with mismatch repair deficiencies. The MSI classification algorithm uses reads mapping to those regions to classify tumors into three categories: microsatellite instability-high (MSI-H), microsatellite stable (MSS), or microsatellite equivocal (MSE). This assay can be performed with paired tumor-normal samples or tumor-only samples.

MSI testing in paired mode begins with identifying accurately mapped reads to the microsatellite loci. To be a microsatellite locus mapping read, the read must be mapped to the microsatellite locus during the alignment step of the exemplary xT bioinformatics pipeline and also contain the 5 base pairs in both the front and rear flank of the microsatellite, with any number of expected repeating units in between. All the loci with sufficient coverage are tested for instability, as measured by changes in the distribution of the number of repeat units in the tumor reads compared to the normal reads using the Kolmogorov-Smirnov test. If $p<=0.05$, the locus is considered unstable. The proportion of unstable loci is fed into a logistic regression classifier trained on samples from the TOGA colorectal and endometrial groups that have clinically determined MSI statuses.

MSI testing in unpaired mode also begins with identifying accurately mapped reads to the microsatellite loci, using the same requirements as described above. The mean number of repeat units and the variance of the number of repeat units is calculated for each microsatellite locus. A vector containing the mean and variance data for each microsatellite locus is put into a support vector machine classification algorithm trained on samples from the TOGA colorectal and endometrial groups that have clinically determined MSI statuses.

Both algorithms return the probability of the patient being MSI-H, which is then translated into a MSI status of MSS, MSE, or MSI-H.

Cytolytic Index (CYT)

CYT was calculated as the geometric mean of the normalized RNA counts of granzyme A (GZMA) and perforin (PRF1) (Rooney, M. S., Shukla, S. A., Wu, C. J., Getz, G. & Hacohen, N. Molecular and Genetic Properties of Tumors Associated with Local Immune Cytolytic Activity. Cell 160, 48-61 (2015)).

Interferon Gamma Gene Signature Score

Twenty-eight interferon gamma (IFNG) pathway-related genes (Ayers M., J Clin Invest 2017) were used as the basis for an IFNG gene. Hierarchical clustering was performed based on Euclidean distance using the R package ComplexHeatmap (version 1.17.1) and the heatmap was annotated with PD-L1 positive IHC staining, TMB-high, or MSI-high status. IFNG score was calculated using the arithmetic mean of the 28 genes.

Knowledge Database (KDB)

In order to determine therapeutic actionability for sequenced patients, a KDB with structured data regarding drug/gene interactions and precision medicine assertions is maintained. The KDB of therapeutic and prognostic evidence is compiled from a combination of external sources (including but not exclusive to NCCN, CIViC{28138153}, and DGIdb{28356508}) and from constant annotation by provider experts. Clinical actionability entries in the KDB are structured by both the disease in which the evidence applies, and by the level of evidence. Therapeutic actionability entries are binned into Tiers of somatic evidence by patient disease matches as laid out by the ASCO/AMP/CAP working group {27993330}. Briefly, Tier I Level A (IA) evidence are biomarkers that follow consensus guidelines and match disease type. Tier I Level B (IB) evidence are biomarkers that follow clinical research and match disease type. Tier II Level C (IIC) evidence biomarkers follow the off-label use of consensus guidelines and Tier II Level D (IID) evidence biomarkers follow clinical research or case reports. Tier III evidence are variants with no therapies. Patients are then matched to actionability entries by gene, specific variant, patient disease, and level of evidence.

Alteration Classification, Prioritization, and Reporting

Somatic alterations are interpreted based on a collection of internally weighted criteria that are composed of knowledge of known evolutionary models, functional data, clinical data, hotspot regions within genes, internal and external somatic databases, primary literature, and other features of somatic drivers {24768039}{29218886}. The criteria are features of a derived heuristic algorithm that buckets them into one of four categories (Pathogenic/VUS/Benign/Reportable). Pathogenic variants are typically defined as driver events or tumor prognostic signals. Benign variants are defined as those alterations that have evidence indicating a neutral state in the population and are removed from reporting. VUS variants are variants of unknown significance and are seen as passenger events. Reportable variants are those that could be seen as diagnostic, offer therapeutic guidance or are associated with disease but are not key driver events. Gene amplifications, deletions and translocations were reported based on the features of known gene fusions, relevant breakpoints, biological relevance and therapeutic actionability.

For the tumor-only analysis germline variants were computationally identified and removed using by an internal algorithm that takes copy number, tumor purity, and sequencing depth into account. There was further filtering on observed frequency in a population database (positions with AF>1% ExAC non-TOGA group). The algorithm was purposely tuned to be conservative when calling germline variants in therapeutic genes minimizing removal of true somatic pathogenic alterations that occur within the general population. Alterations observed in an internal pool of 50 unmatched normal samples were also removed. The remaining variants were analyzed as somatic at a $VAF>=5\%$ and $Coverage>=90$. Using normal tissue, true germline variants were able to be flagged and somatic analysis contamination was evaluated. The Tumor/Normal variants were also set at the Tumor-only VAF/Coverage thresholds for analysis.

Clinical trial matching occurs through a process of associating a patient's actionable variants and clinical data to a curated database of clinical trials. Clinical trials are verified as open and recruiting patients before report generation.

Germline Pathogenic And Variants of Unknown Significance (VUS)

Alterations identified in the Tumor/Normal match samples are reported as secondary findings for consenting patients. These are a subset of genes recommended by the ACMG (Richards, S. et al. Standards and guidelines for the interpretation of sequence variants: a joint consensus recommendation of the American College of Medical Genetics and Genomics and the Association for Molecular Pathology. Genet. Med. 17, 405-24 (2015)) and genes associated with cancer predisposition or drug resistance.

In an example patient group analysis, a group of 500 cancer patients was selected where each patient had undergone clinical tumor and germline matched sequencing using the panel of genes at FIGS. 27a, 27b, 27c1, 27c2, and 27d (known herein as the "xT" assay). In order to be eligible for inclusion in the group, each case was required to have complete data elements for tumor-normal matched DNA sequencing, RNA sequencing, clinical data, and therapeutic data. Subsequent to filtering for eligibility, a set of patients was randomly sampled via a pseudo-random number generator. Patients were divided among seven broad cancer categories including tumors from brain (50 patients), breast (50 patients), colorectal (51 patients), lung (49 patients), ovarian and endometrial (99 patients), pancreas (50 patients), and prostate (52 patients). Additionally, 48 tumors from a combined set of rare malignancies and 51 tumors of unknown origin were included for analyses for a total of nine broad cancer categories. These patients were collated together as a single group and used for subsequent group analyses.

Figure 29:
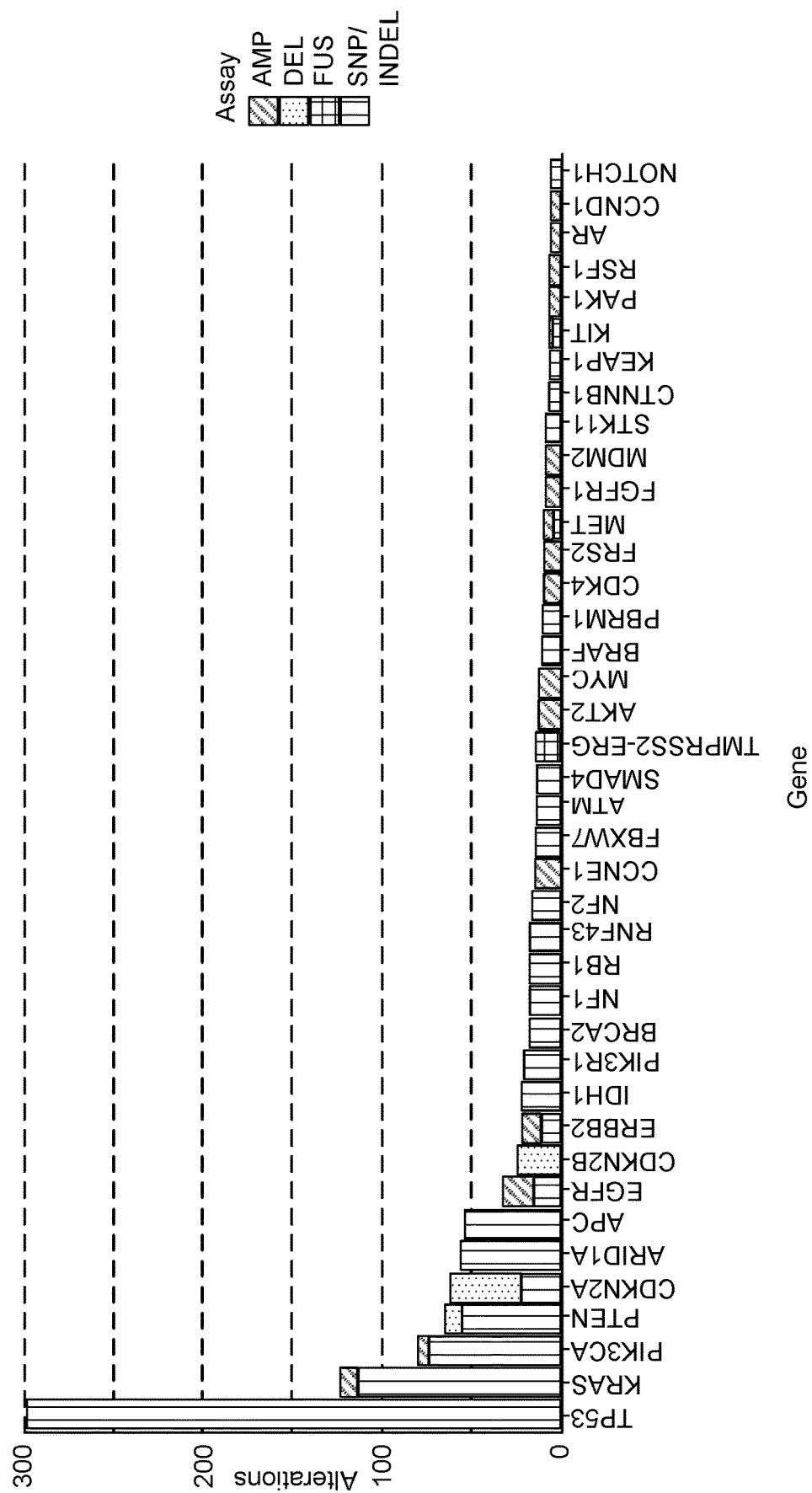
FIG. 29 is a bar chart illustrating data for a 500 patient group that clusters mutation similarities for gene, mutation type, and cancer type derived for an exemplary xT panel using techniques that are consistent with aspects of the present disclosure.

The mutational spectra for the studied group was compared with broad patterns of genomic alterations observed in large-scale studies across major cancer types. First, data from all 500 patients was plotted by gene, mutation type, and cancer type, and then clustered by mutational similarity (FIG. 29). The most commonly mutated genes included well-known driver mutations, including mutations in more than 5% of all cases in the group for TP53, KRAS, PIK3CA, CDKN2A, PTEN, ARID1A, APC, ERBB2, EGFR, IDH1, and CDKN2B. These genes are known hallmarks of cancer and commonly found in solid tumors. Of these genes, CDKN2A, CDKN2B, and PTEN were most commonly found to be homozygously deleted, indicating loss-of-function mutations likely coinciding with loss of heterozygosity. These data demonstrate expected molecular signatures commonly seen in clinical solid tumor samples.

Figure 30:
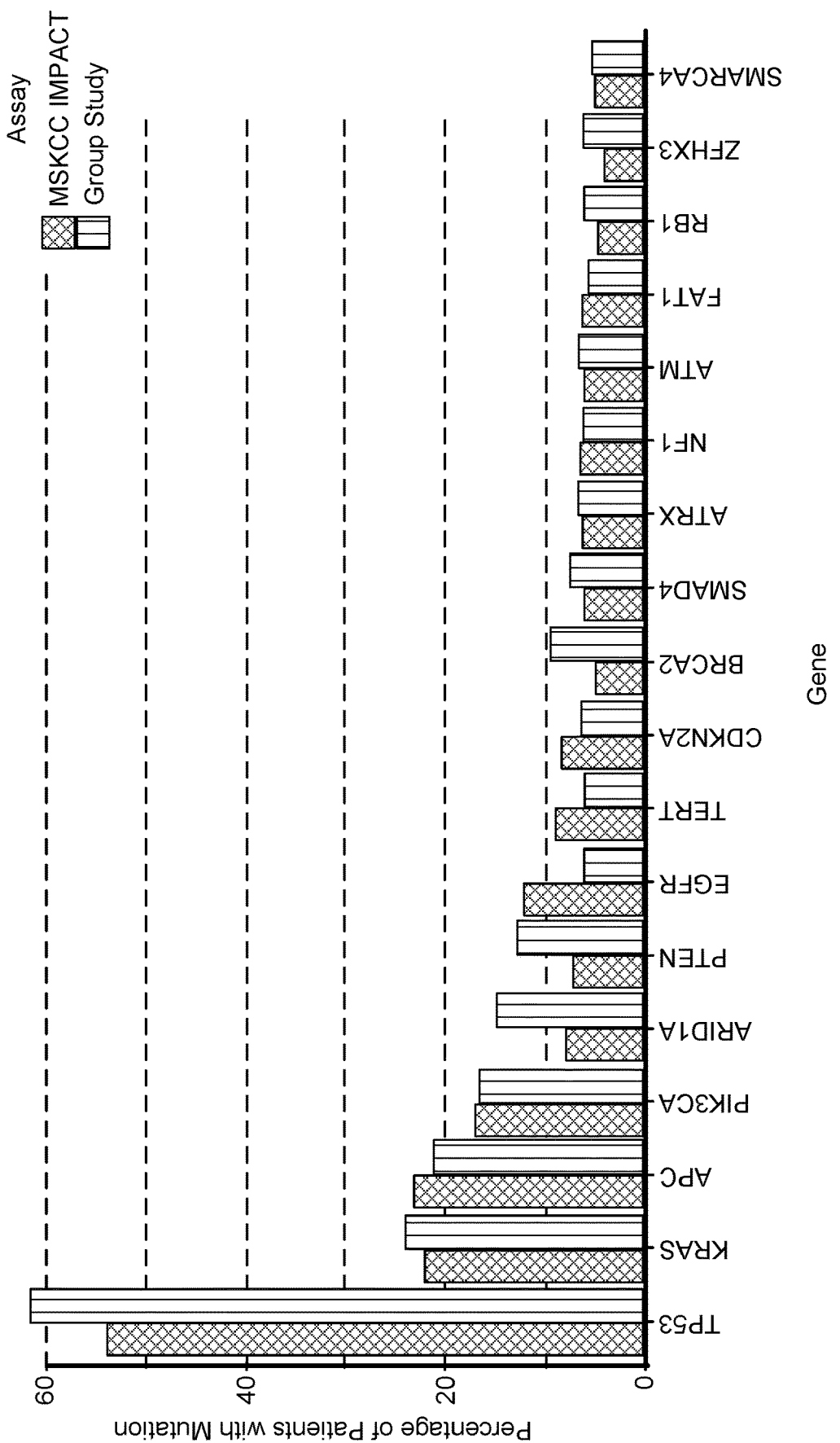
FIG. 30 is a bar chart comparing study results generated for the exemplary xT panel using at least some processes described in this specification with previously published pan-cancer analysis using an IMPACT panel.

Previous pan-cancer mutation analyses have established mutational spectra within and across tumor types, and provide context to which the study group sequencing data may be compared. In FIG. 30, the study group results were compared to a previously published pan-cancer analysis using the Memorial Sloan Kettering Cancer Center (MSKCC) IMPACT panel (Zehir, A. et al. Mutational landscape of metastatic cancer revealed from prospective clinical sequencing of 10,000 patients. Nat. Med. 23, 703-713 (2017)). In both datasets, we observed the same commonly mutated genes, including TP53, KRAS, APC and PIK3CA. These genes were observed at similar relative frequencies compared to the MSKCC group. These results indicate the mutation spectra within the study group is representative of the broader population of tumors that have been sequenced in large-scale studies.

Because both tumor and germline samples were sequenced in the group, the effect of germline sequencing on the accuracy of somatic mutation identification could be examined. Fiftyone cases were randomly selected from the study group with a range of tumor mutational burden profiles. Their variants were re-evaluated using a tumor-only analytical pipeline. After filtering the dataset using a population database and focusing on coding variants from the 51 samples, 2,544 variants were identified that had a false positive rate of 12.5%. By further filtering with an internally developed list of technical artifacts (e.g., artifacts from DNA sequencing process), an internal pool of matched normal samples, and classification criteria, 74% of the false somatic variants (false positive rate of 2.3%) were removed while still retaining all true somatic alterations.

Figure 31:
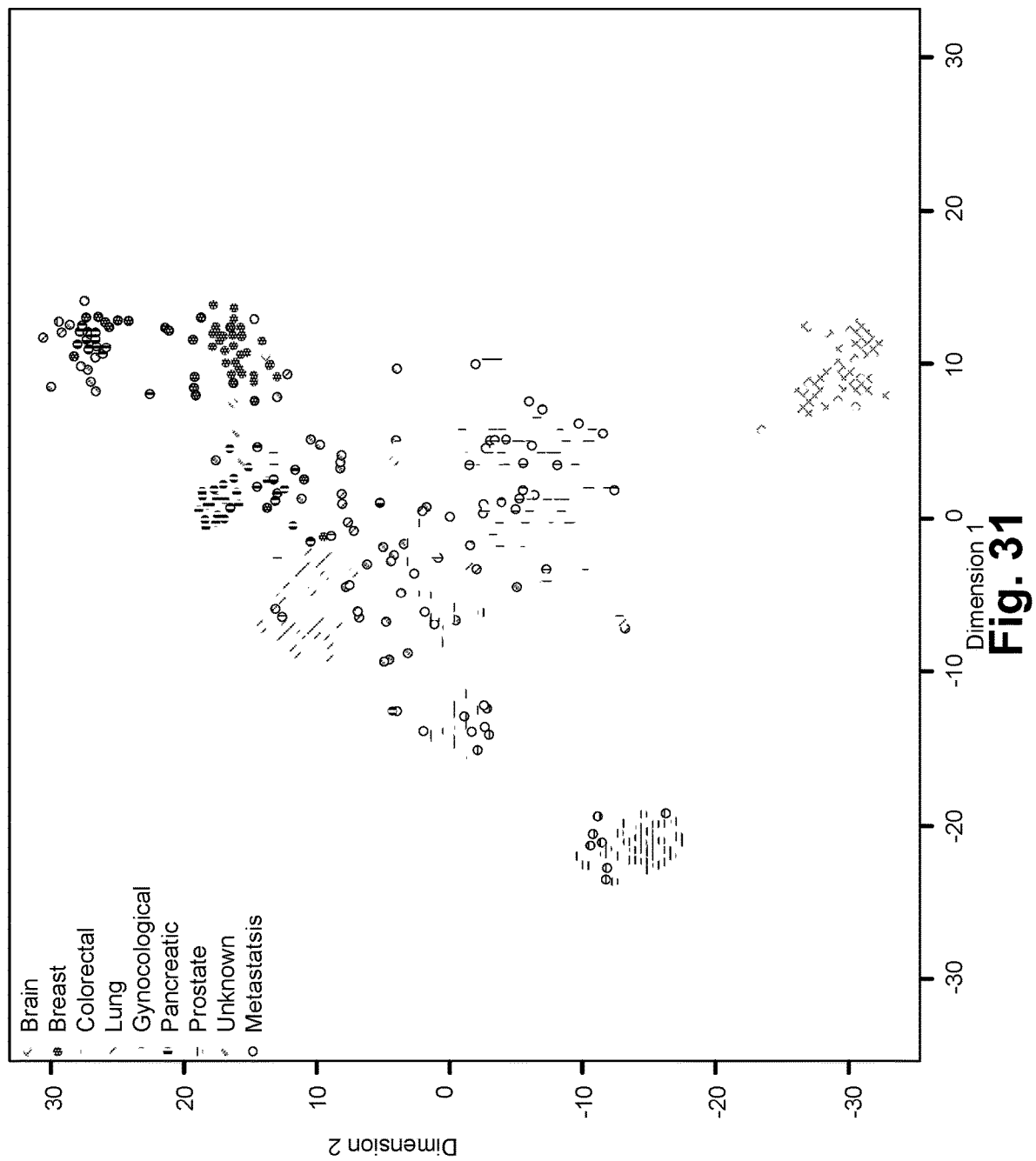
FIG. 31 is a graph illustrating expression profiles for tumor types related to the exemplary xT panel described in the present disclosure.

To further characterize the tumors in the study group, RNA expression profiles for patients in the group were examined. Similar tumor types tend to have similar expression profiles (FIG. 31). On average, samples within a cancer type as determined by pathologic diagnosis showed a higher pairwise correlation within the corresponding TCGA cancer group compared to between TCGA cancer groups (p-values=$10^{-6}$-$10^{-16}$). This clustering of samples by TCGA cancer group is observed in the t-SNE plot shown in FIG. 32. For some tumor types, such as prostate cancer, metastatic samples cluster very closely to non-metastatic tumor samples. However other cancer types, most notably pancreatic cancer and colorectal cancer, form a distinct metastatic tumor cluster that also contains breast tumors and tumors of unknown origin. This effect is likely due to the effect of the background tissue on the expression profile of the tumor sample. For example, metastatic samples from the liver frequently, but not always, cluster together. This effect can also depend on the level of tumor purity within the sample.

Figure 32:
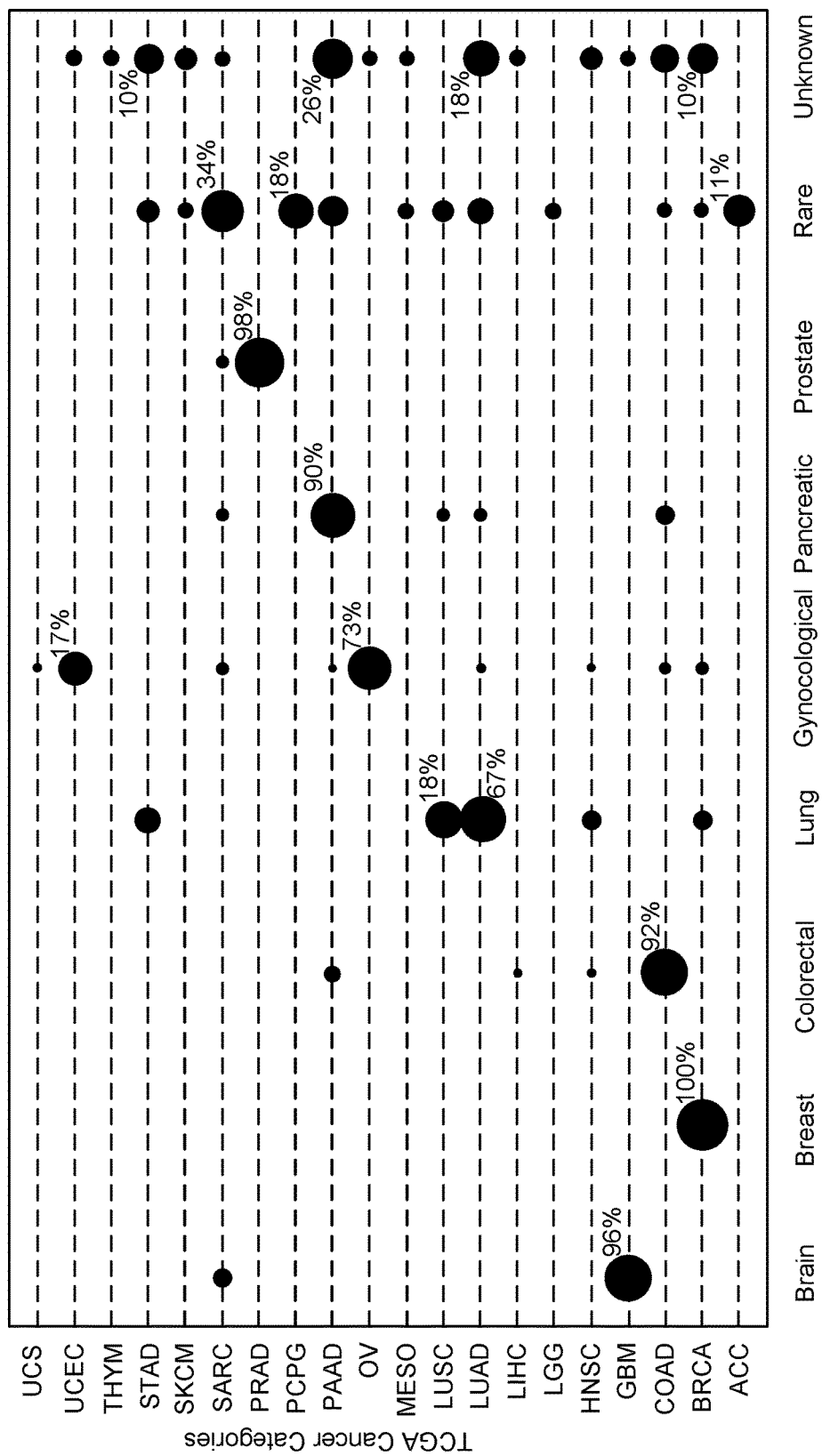
FIG. 32 is a graph illustrating clustering of samples by TCGA cancer group in a t-SNE plot for the exemplary xT panel.

Given the high-dimensionality of the data, we sought to determine whether we could predict cancer types using gene expression data. We developed a random forest cancer type predictor using a combination of publically available TCGA expression data and expression data generated at Tempus Labs. TCGA cancer type predictions compared to the xT group samples are shown in FIG. 32. For example, 100% of breast cancer samples were correctly classified. Interestingly, using this method we are able to accurately classify these tumors even when the samples are biopsied from metastatic sites.

Additionally, it is notable that some of the "misclassified" samples may actually represent biologically and pathologically relevant classifications. For example, of the 50 brain tumors in our dataset, 48 (96%) were classified as gliomas, while 2 were classified as sarcomas.

One of these tumors carries a histopathologic diagnosis of "solitary fibrous tumor, hemangiopericytoma type, WHO grade III", which is indeed a sarcoma. The other was diagnosed as "glioblastoma, WHO grade IV (gliosarcoma), with smooth muscle and epithelial differentiation". The immunohistochemical profile is GFAP negative with desmin and SMA focally positive, supporting the diagnosis of gliosarcoma. It can be argued that the algorithm classified this tumor correctly by grouping it with sarcomas, and in fact, gliosarcomas carry a worse prognosis and have the ability to metastasize, differentiating them clinically from traditional glioblastoma.

Similarly, a case with a histopathologic diagnosis favoring carcinosarcoma was identified by the model as SARC in a patient with a history of prostate cancer presenting with a pelvic mass five years after surgery. The immunohistochemical profile of the tumor showed it was negative for the prostate markers prostatic acid phosphatase (PSAP) and prostatic specific antigen (PSA) and positive for SMA, consistent with sarcoma, which was thought to be secondary to prostate fossa radiation treatment. However, gene rearrangement analysis identified a TMPRSS2-ERG, suggesting that the tumor was in fact recurrent prostate cancer with sarcomatoid features.

The constellation of gene rearrangements and fusions in the study group were also examined. These types of genomic alterations can result in proteins that drive malignancies, such as EML4-ALK, which results in constitutive activation of ALK through removal of the transmembrane domain.

Figure 33:
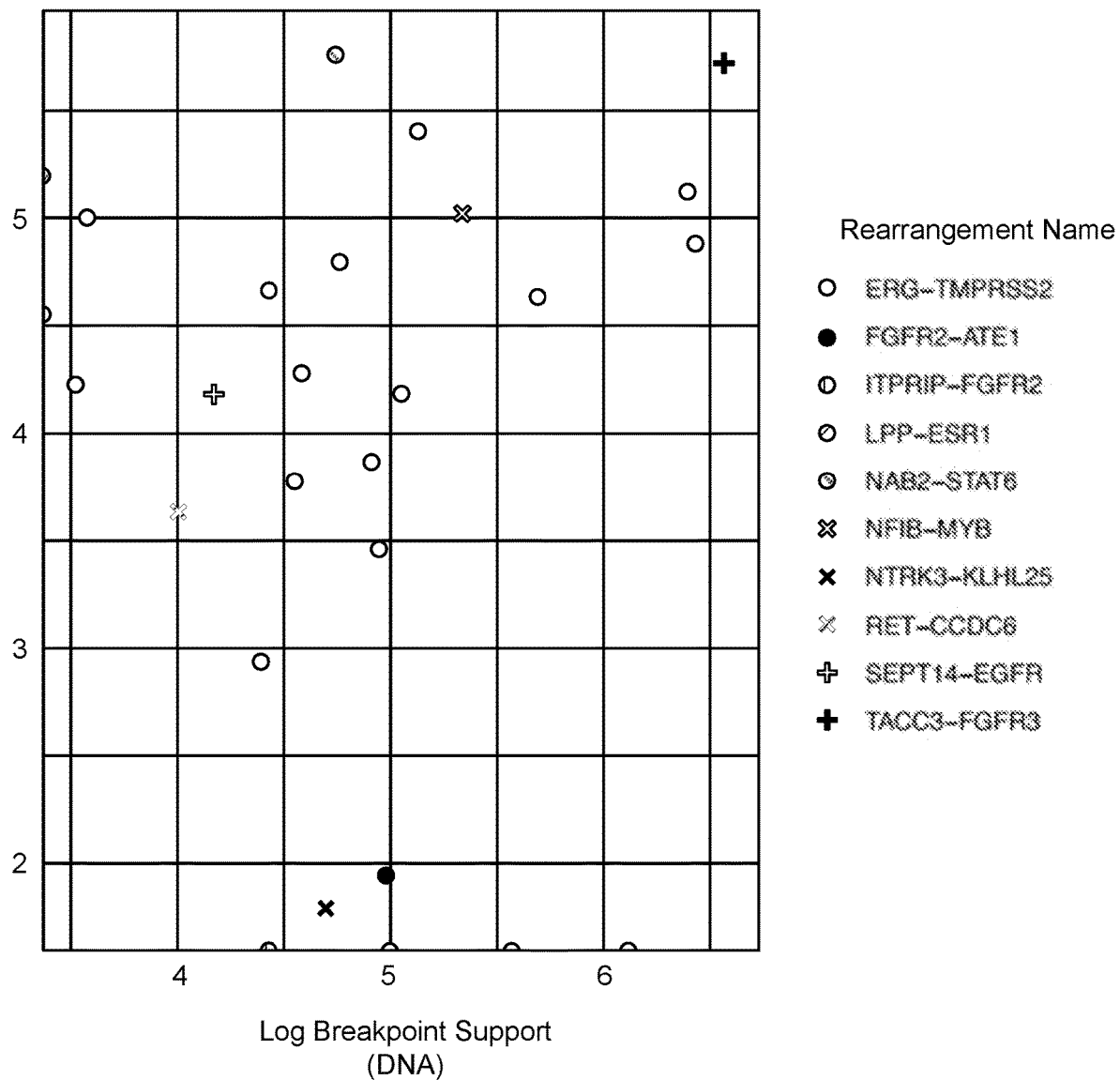
FIG. 33 is a plot of genomic rearrangements using DNA and RNA assays for the exemplary xT panel.
Figure 35:
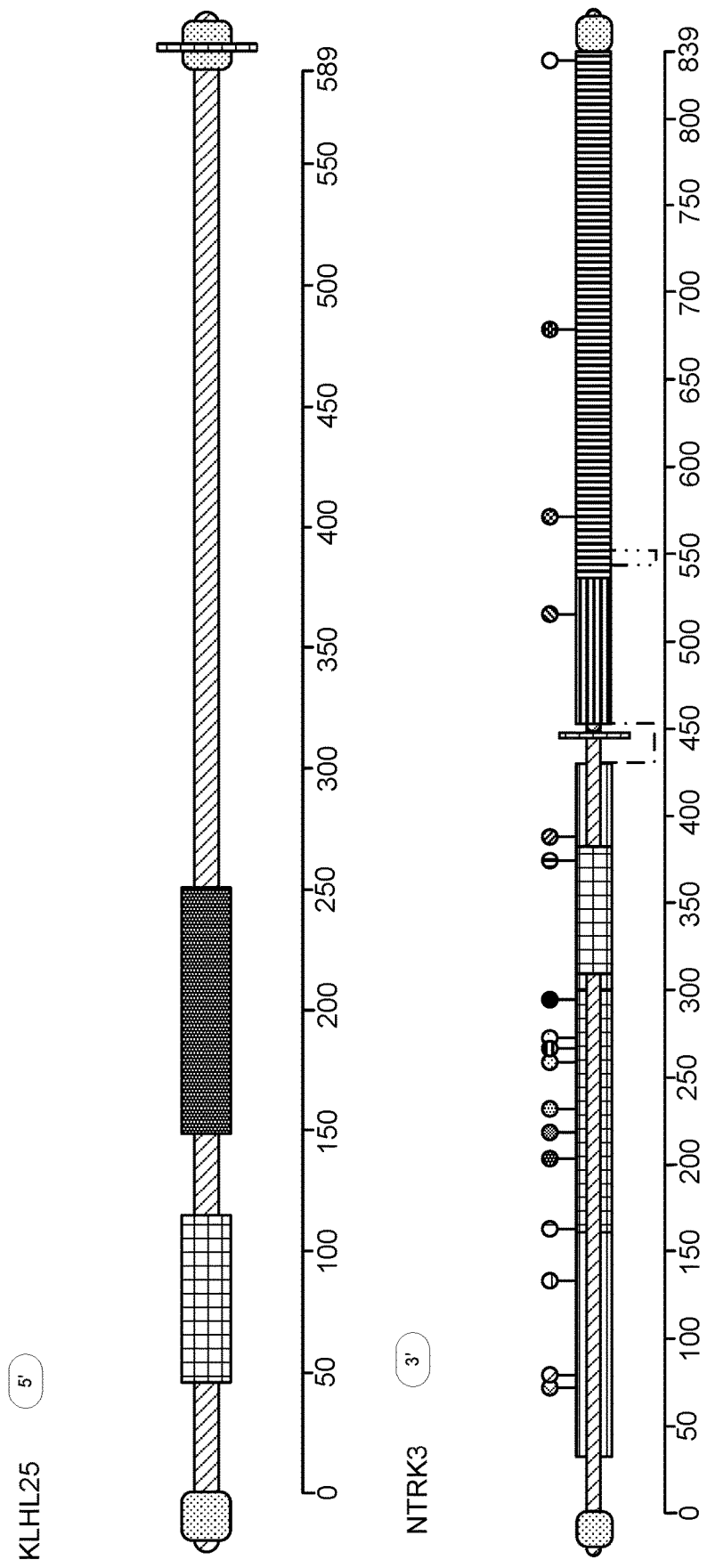
FIG. 35 is a schematic illustrating data related to a second rearrangement detected via RNA sequencing related to the exemplary xT panel.

In order to assess assay decision support for clinically relevant genomic rearrangements, alterations detected using DNA or RNA sequencing assays were compared across assay type and for evidence matching them to therapeutic interventions. Overall, 28 total genomic rearrangements resulting in chimeric protein products were detected in the study group. 22 rearrangements were concordantly detected between assay type, four were detected via DNA-only assay, and two were detected via RNA-only assay (FIG. 33). Of the three rearrangements detected via RNA sequencing, two of the three were not targets on the DNA sequencing assay and thus not expected to be detected via DNA sequencing. The functionality of these fusions were further analyzed via their predicted structures (FIGS. 34 and 35). In all cases, algorithms predicted fully intact tyrosine kinase domains for RET and NTRK3 exemplar rearrangements, which may be potential therapeutic targets for tyrosine kinase inhibitors. This analysis indicates the utility of genomic rearrangement analyses as a source of clinically relevant information for therapeutic interventions.

To characterize the mutational landscape in all patients, the distribution of the mutational load across cancer types was analyzed. The median TMB across the study group was 2.09 mutations per megabase (Mb) of DNA with a range of 0-54.2 mutations/Mb.

Figure 36:
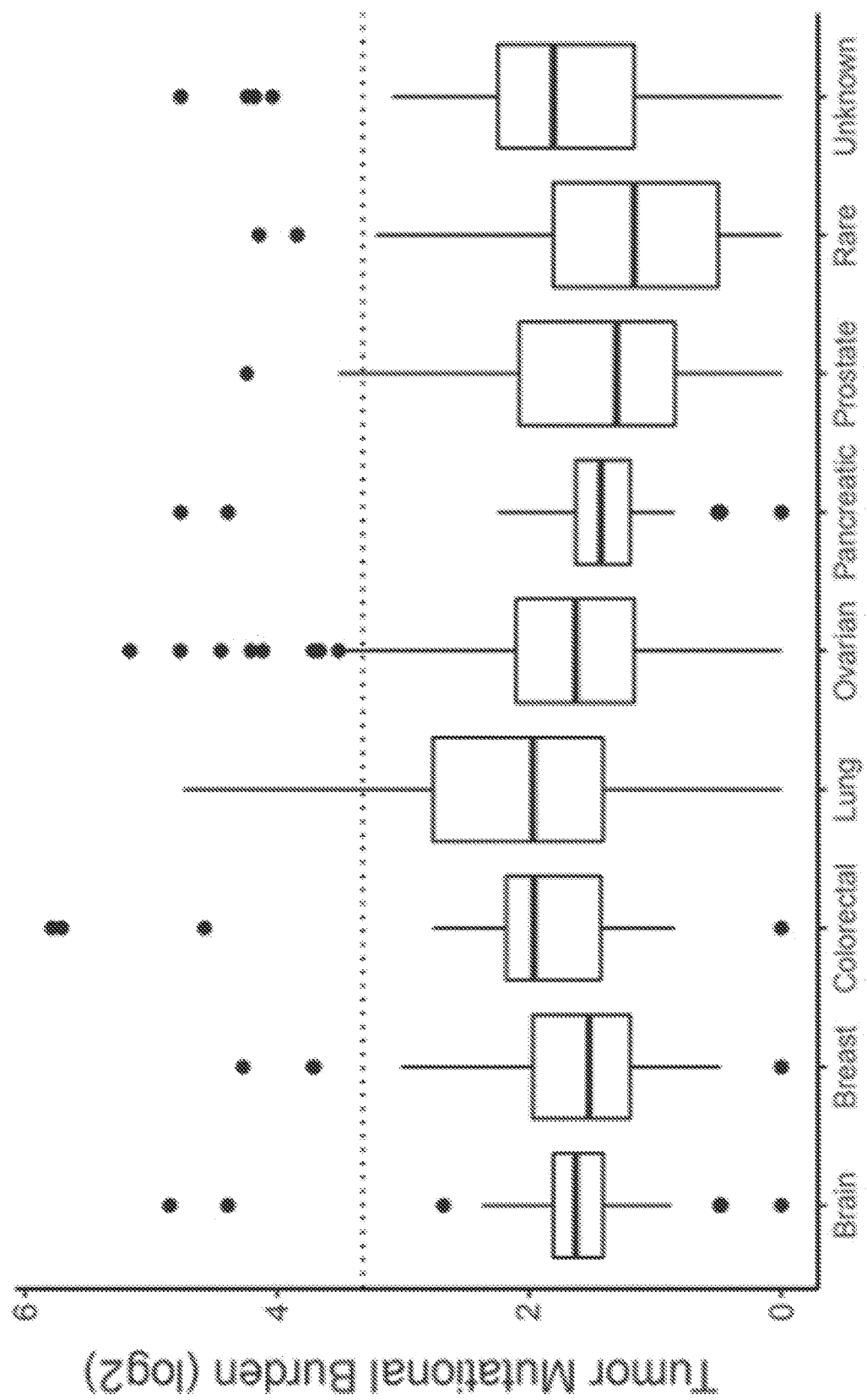
FIG. 36 includes a chart that illustrates the distribution of TMB varied by cancer type identified using techniques that are consistent with at least some aspects of the present disclosure related to the exemplary xT panel.
Figure 37:
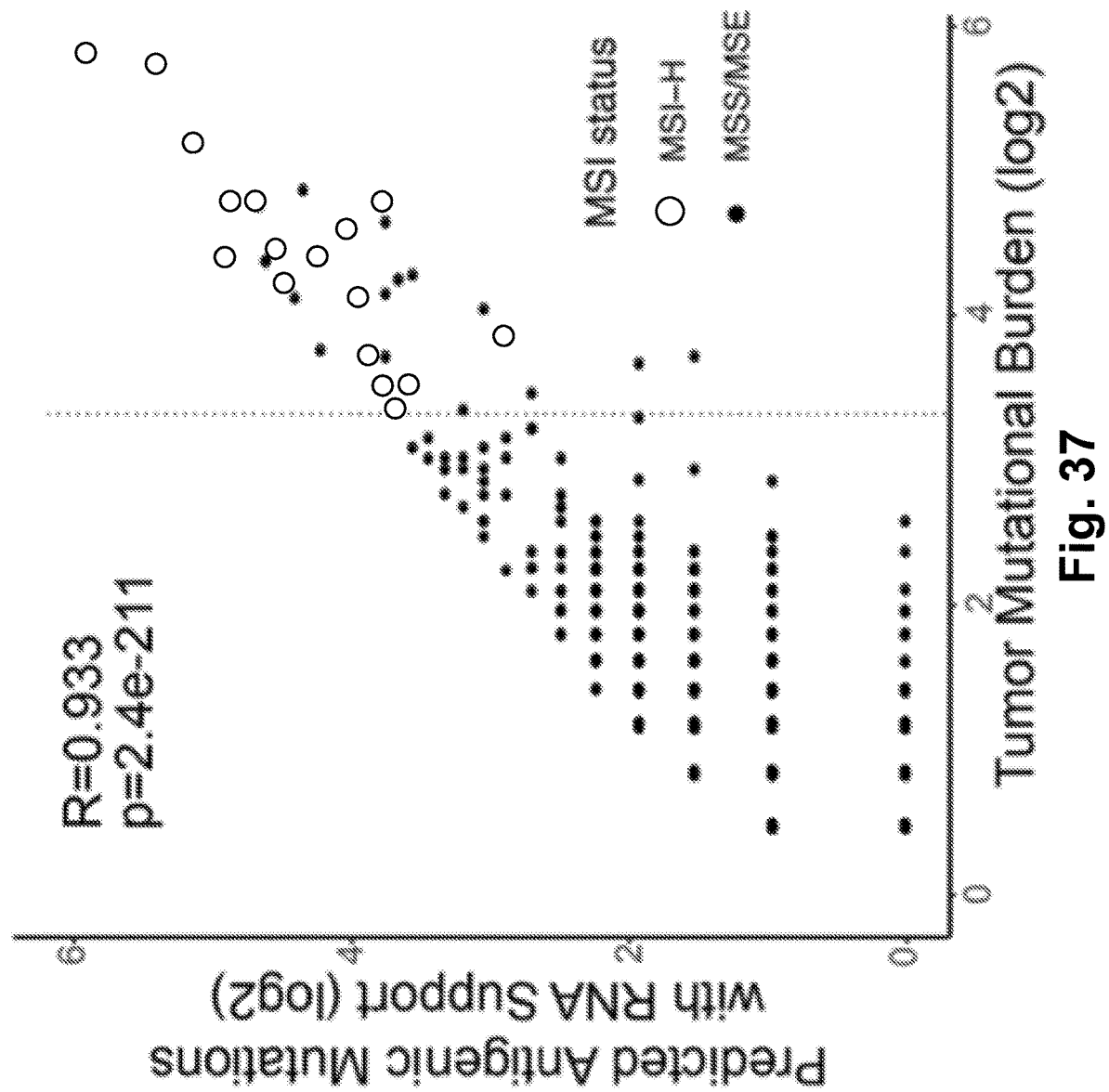
FIG. 37 includes data represented on a two dimensional plot showing TMB on one axis and predicted antigenic mutations with RNA support on the other axis that was generated using techniques that are consistent with at least some aspects of the present disclosure related to the exemplary xT panel.
Figure 38:
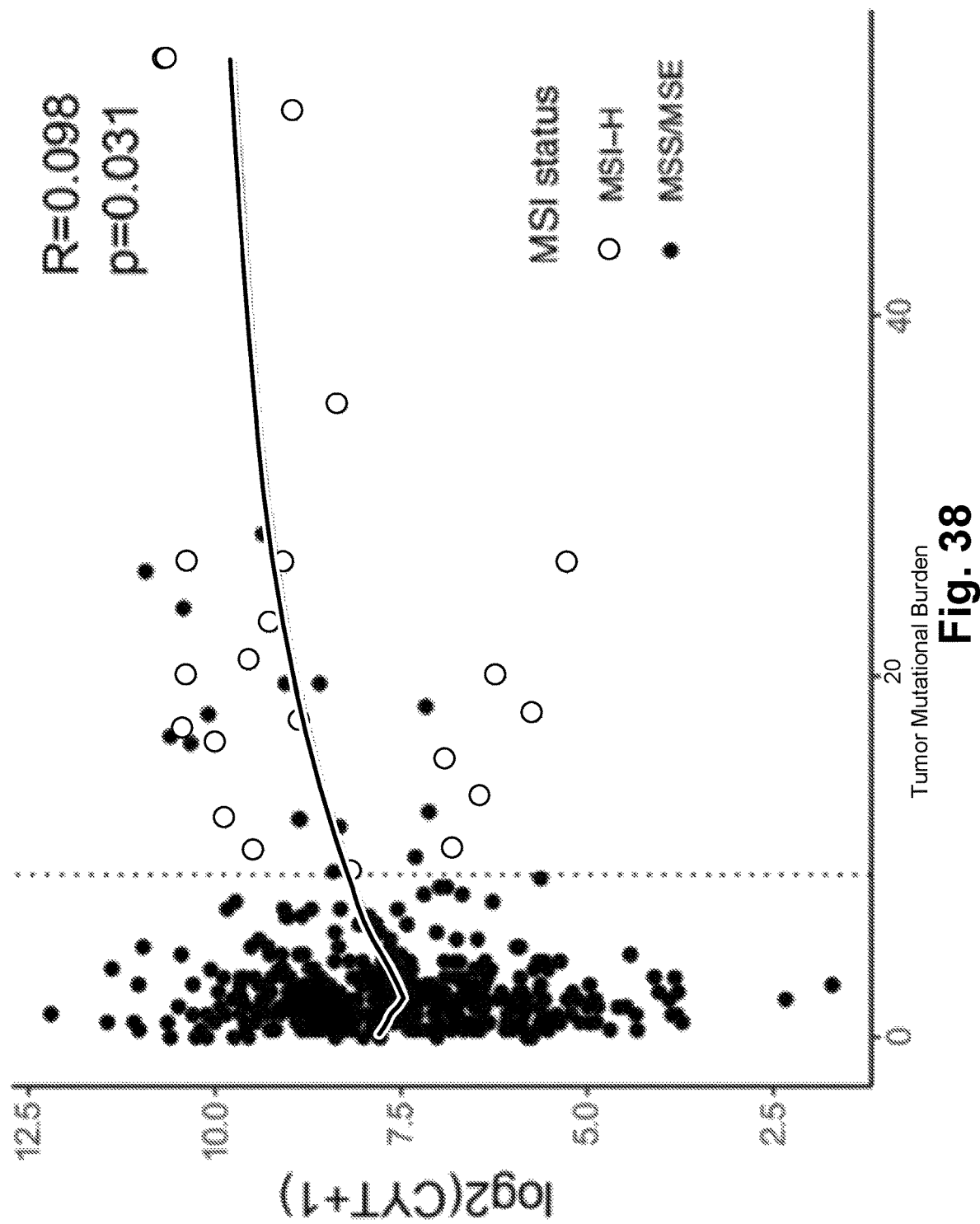
FIG. 38 includes additional data related to TMB generated using techniques that are consistent with at least some aspects of the present disclosure related to the exemplary xT panel.

The distribution of TMB varied by cancer type. For example, cancers that are associated with higher levels of mutagenesis, like lung cancer, had a higher median TMB (FIG. 36). We found that there is a population of hypermutated tumors with significantly higher TMB than the overall distribution of TMB for solid tumors. These hypermutators are found in all cancer types, including cancers typically associated with low TMB, like glioblastoma (FIG. 36). These hypermutated tumors are referred to as TMB-high, which are defined as tumors with a TMB greater than 9 mutations/Mb. This threshold was established by testing for the enrichment of tumors with orthogonally defined hypermutation (MSI-H) in a larger clinical database using the hypergeometric test. In this group, all MSI-H samples are in the TMB-high population (FIGS. 37 and 38). The high mutational burdens from the remaining TMB-high samples were primarily explained by mutational signatures associated with smoking, UV exposure, and APOBEC mediated mutagenesis.

While TMB is a measure of the number of mutations in a tumor, the neoantigen load is a more qualitative estimate of the number of somatic mutations that are actually presented to the immune system. We calculated neoantigen load as the number of mutations that have a predicted binding affinity of 500 nM or less to any of a patient's HLA class I alleles as well as at least one read supporting the variant allele in RNA sequencing data. TMB was found to be highly correlated with neoantigen load (R=0.933, p=$2.42\times10^{-211}$) (FIG. 37). This suggests that a higher tumor mutational burden likely results in a greater number of potential neoantigens.

The association of high TMB and MSI-H status with response to immunotherapy has been attributed to the greater immunogenicity of these highly mutated tumors. We used whole transcriptome sequencing to measure whether greater immunogenicity results in higher levels of immune infiltration and activation.

To test this, we assessed the relative levels of cytotoxic immune activity using a gene expression score, cytolytic index (CYT) (Rooney, M. S., Shukla, S. A., Wu, C. J., Getz, G. & Hacohen, N. Molecular and Genetic Properties of Tumors Associated with Local Immune Cytolytic Activity. Cell 160, 48-61 (2015)). We found that this two gene expression score is significantly higher in our TMB-high and MSI-high populations (p=$4.3\times10-5$ and p=0.015, respectively) (FIG. 39). This result demonstrates that even in patients with heavily pre-treated and advanced stage disease, a hypermutator status is strongly associated with greater cytotoxic immune activity.

Figure 40:
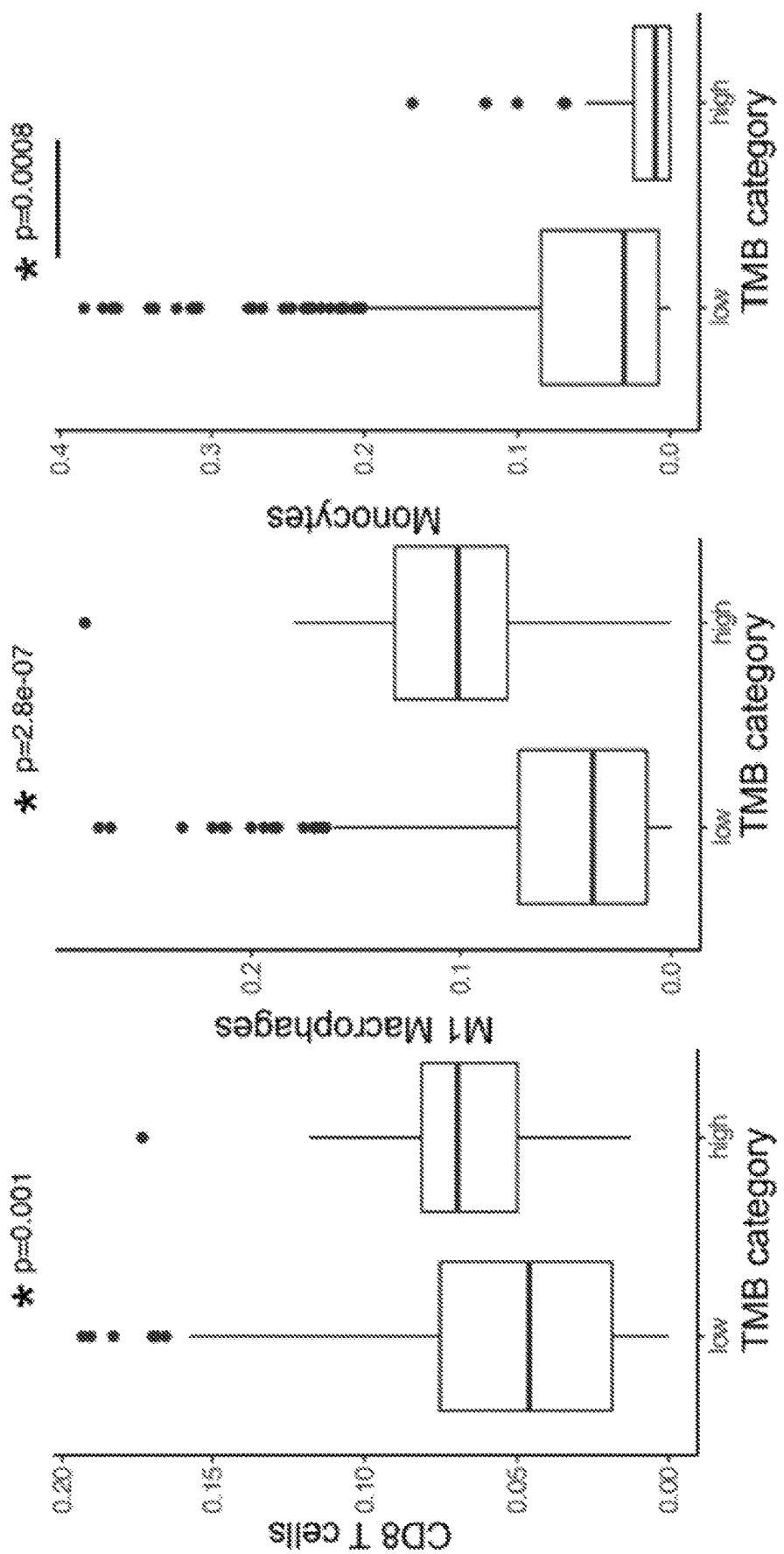
FIG. 40 includes three schematics illustrating data related to propensity of different types inflammatory immune and non-inflammatory immune cells in low and high TMB samples generated for the related xT panel.

Next, whether specific immune cell populations were differentially represented in the immune cell composition of TMB-high tumors compared to TMB-low was analyzed. We implemented a support vector regression-based deconvolution model to computationally estimate the relative proportion of 22 immune cell types in each tumor (Newman, A. M. et al. Robust enumeration of cell subsets from tissue expression profiles. Nat. Methods 12, 453-7 (2015)). In accordance to our cytolytic index analysis, we also found that inflammatory immune cells, like CD8 T cells and M1 polarized macrophages, were significantly higher in TMB-high samples, while non-inflammatory immune cells, like monocytes, were significantly lower in TMB-low samples (p=0.0001, p=$2.8\times10-7$, p=0.0008) (see FIG. 40).

Figure 41:
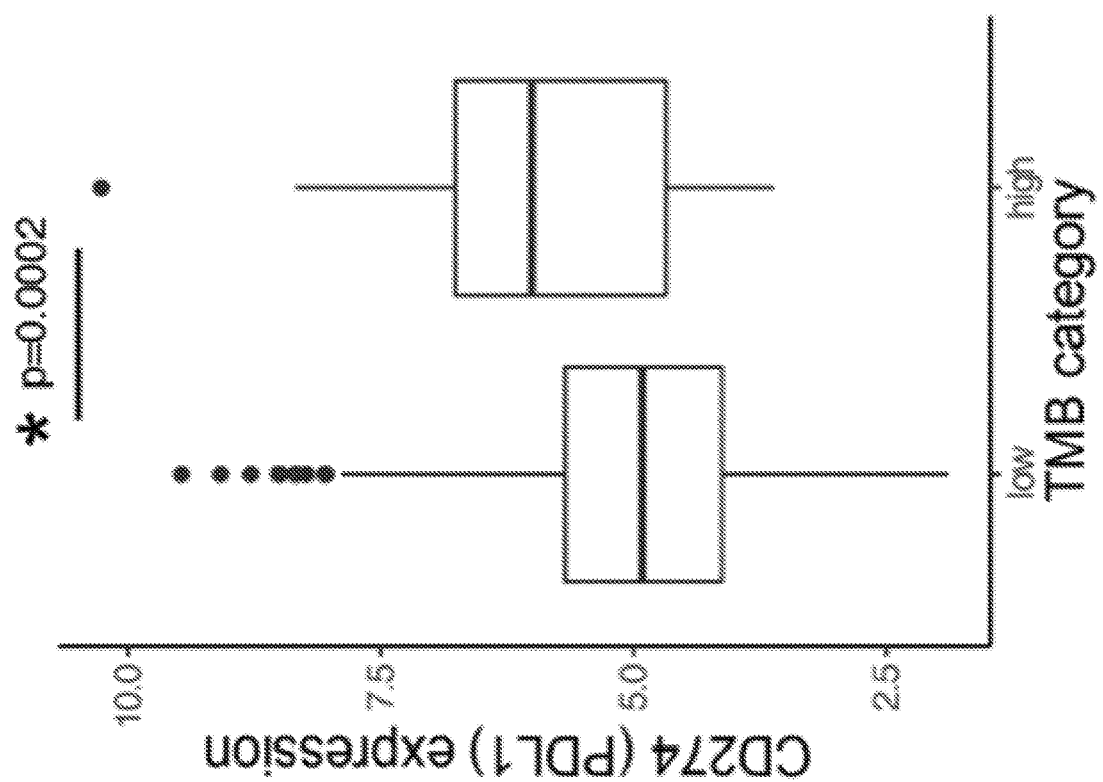
FIG. 41 includes a schematic illustrating data related to prevalence of CD274 expression in low and high TMB samples generated using techniques consistent with at least some aspects of the present disclosure generated for the related xT panel.
Figure 42:
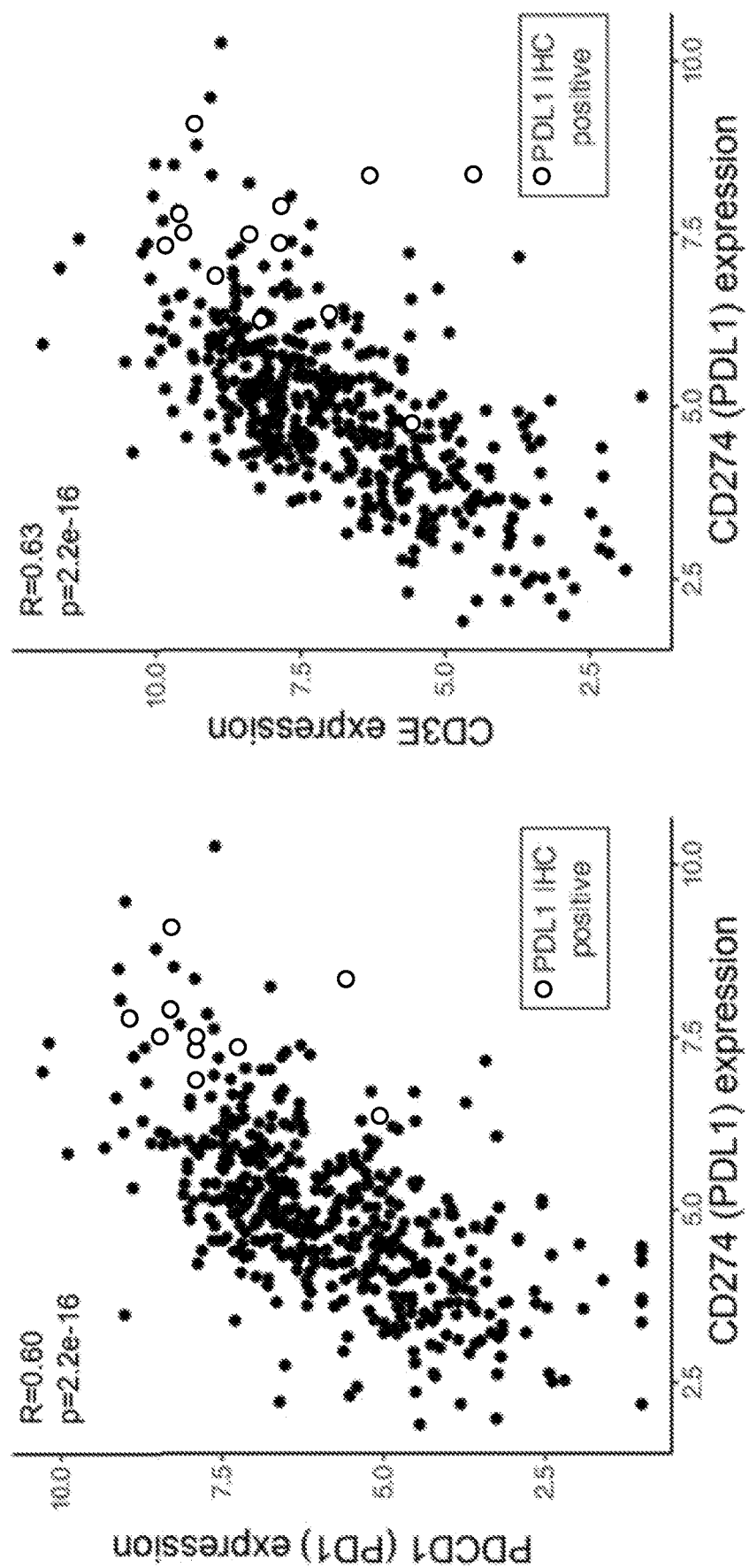
FIG. 42 includes two schematics illustrating correlations between CD274 expression and other cell types generated using techniques consistent with at least some aspects of the present disclosure generated for the related xT panel.

Increased immune pressure, like infiltration of more inflammatory immune cells, can lead tumors to express higher levels of immune checkpoint molecules like PD-L1 (CD274). These immune checkpoints function as a brake on the immune system, turning activated immune cells into quiescent ones. Accordingly, whole transcriptome analysis determined CD274 expression is significantly higher in the more immune-infiltrated TMB-high tumors (p=0.0002) (FIG. 41). CD274 expression is also highly correlated with the expression of its binding partner on immune cells, PDCD1 (PD-1), as well as other T cell lineage-specific markers like CD3E (FIG. 42). Furthermore, samples that stained positive for PD-L1 protein via clinically-validated IHC tests cluster with higher CD274 RNA expression levels (FIG. 42), suggesting the expression of CD274 may be used as a proxy for protein levels of PD-L1.

Figure 43:
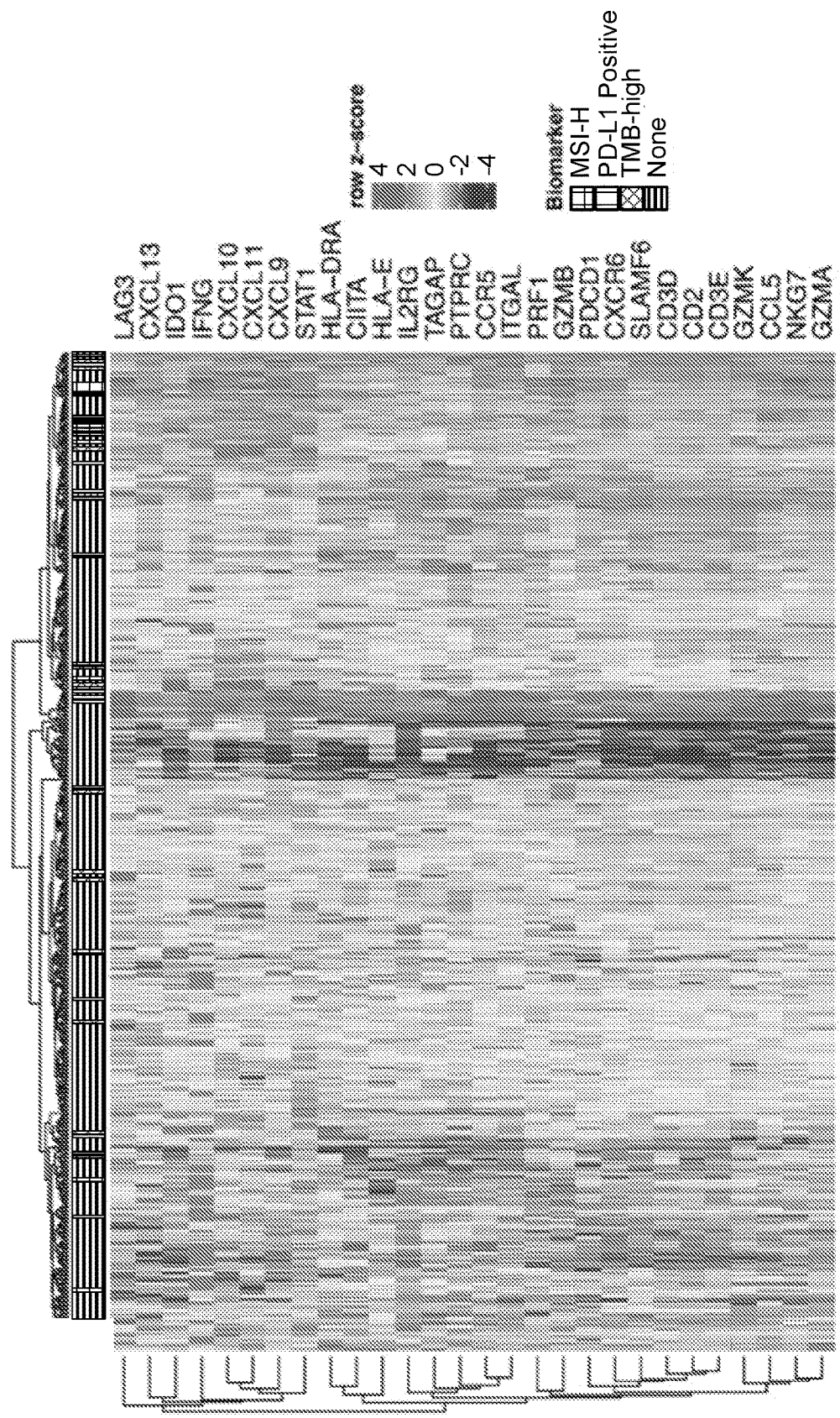
FIG. 43 is a schematic illustrating data generated via a 28 gene interferon gamma-related signature that is consistent with at least some aspects of the present disclosure.
Figure 44:
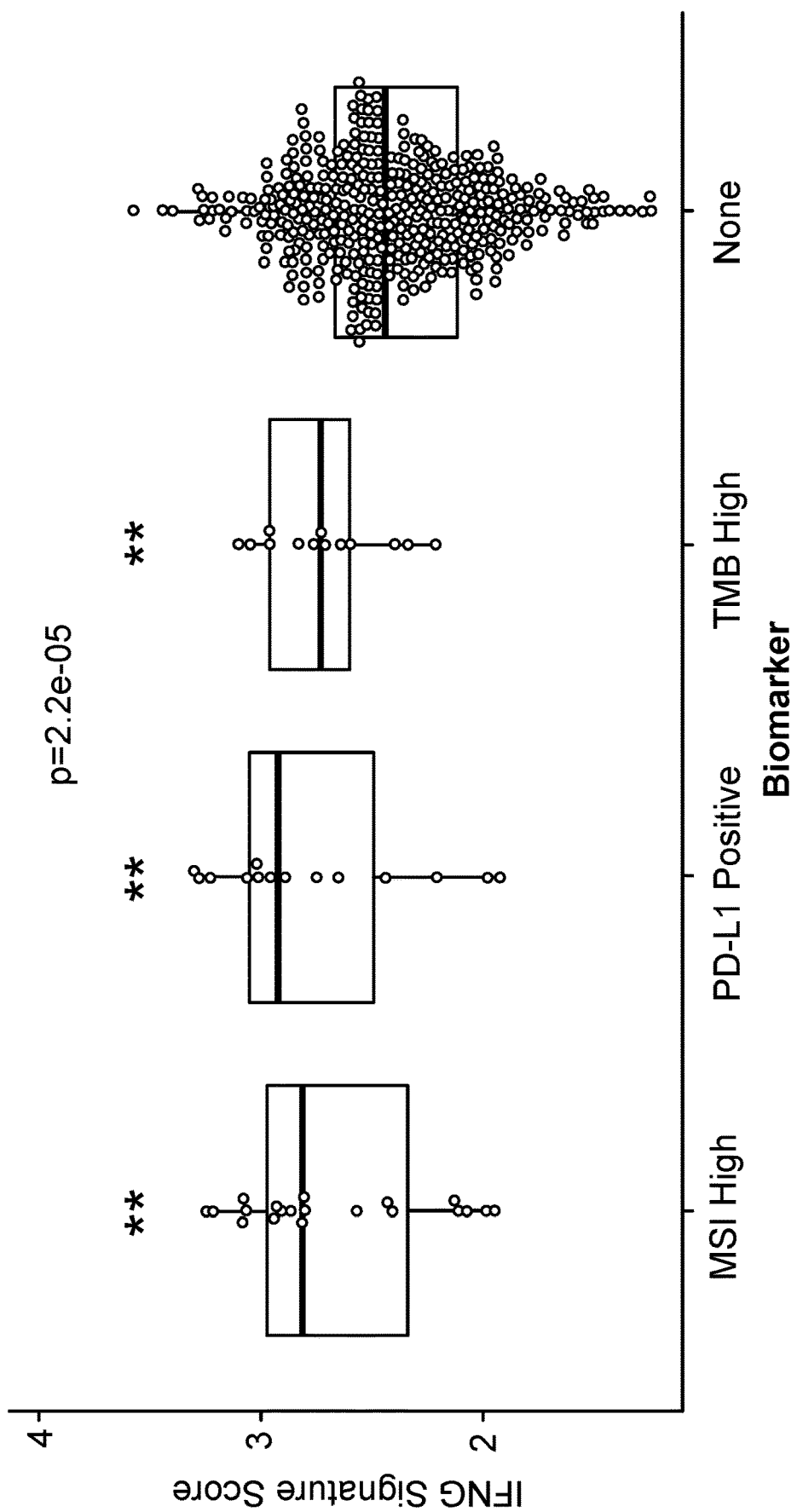
FIG. 44 includes data shown as a graph illustrating levels of interferon gamma-related genes versus TMB-high, MSI-high and PDL1 IHC positive tumors generated using techniques consistent with at least some aspects of the present disclosure.

Transcriptomic markers were utilized to further determine whether patients that lack classically defined immunotherapy biomarkers still exhibited immunologically similar tumors. Using a 28 gene interferon gamma-related signature, it was found that tumor samples could be broadly categorized as either immunologically active "hot" tumors or immunologically silent "cold" tumors based on gene expression (FIG. 43). The 28-gene set encompassed genes related to cytolytic activity (e.g., granzyme A/B/K, PRF1), cytokines/chemokines for initiation of inflammation (CXCR6, CXCL9, CCL5, and CCR5), T cell markers (CD3D, CD3E, CD2, IL2RG [encoding IL-2Rγ]), NK cell activity (NKG7, HLA-E), antigen presentation (CIITA, HLA-DRA), and additional immunomodulatory factors (LAG3, IDO1, SLAMF6). Results support this stratification, with the immunologically "hot" population enriched for samples that were TMB-high, MSI-high or PDL1 IHC positive. Furthermore, TMB-high, MSI-high, or PD-L1 IHC positive tumors expressed higher levels of interferon gamma-related genes versus tumors without any of those biomarkers (p=2.2×10-5) (FIG. 44). Hence, patients within this immunologically active cluster that lack traditional immunotherapy biomarkers represent an interesting patient population that may potentially benefit from immunotherapy.

Figure 56:
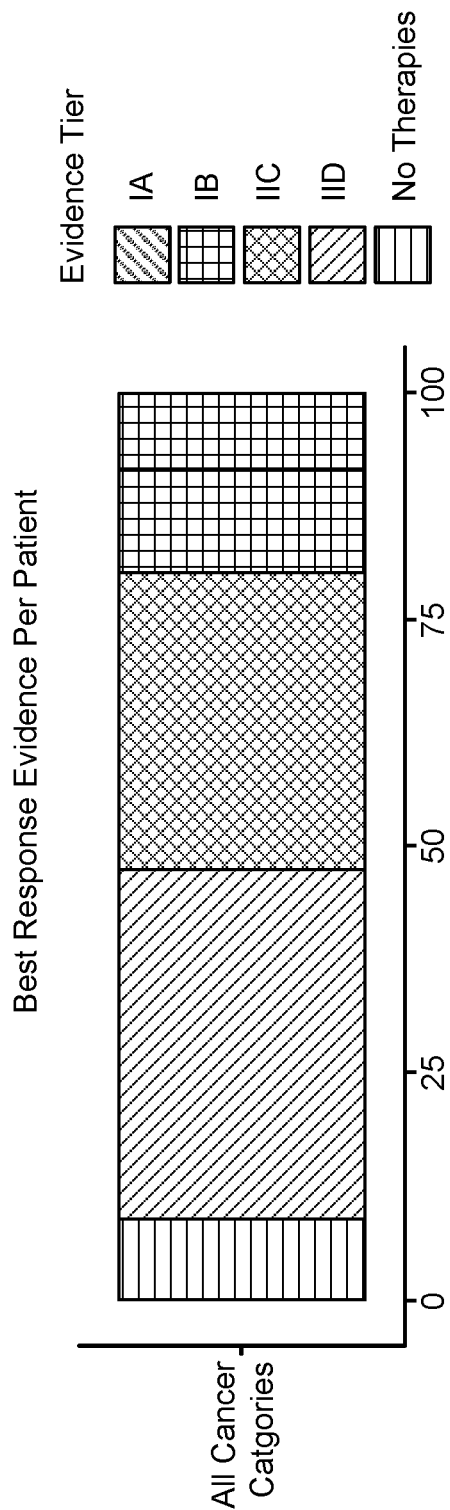
FIG. 56 includes a graph illustrating response evidence to therapies across all cancer types in an exemplary study using techniques consistent with at least some aspects of the present disclosure.
Figure 57:
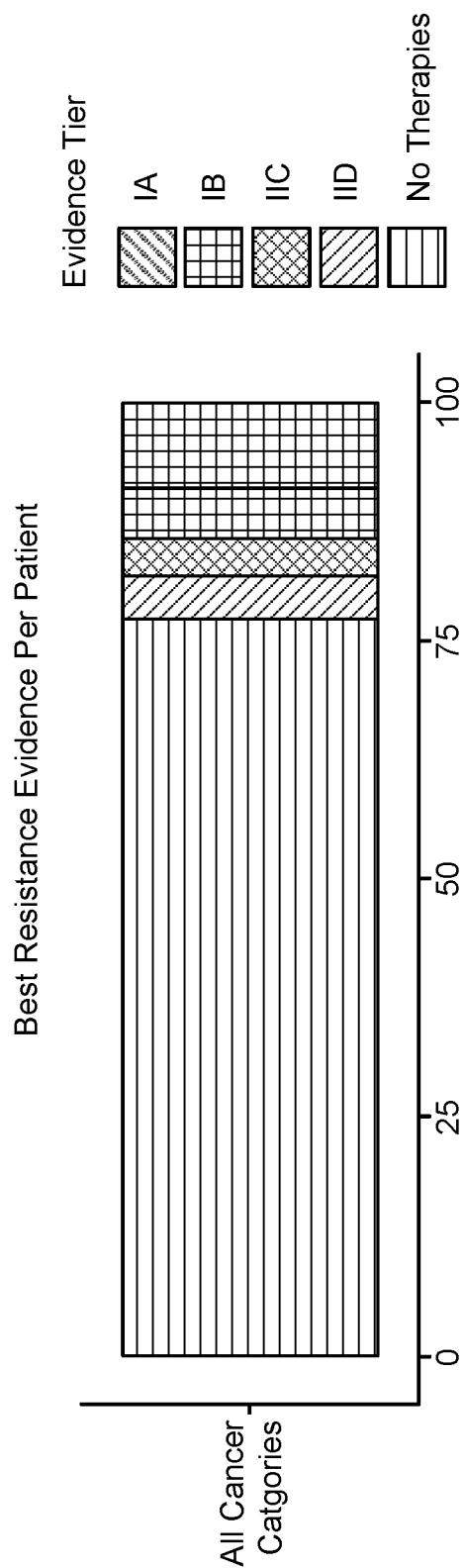
FIG. 57 includes a graph illustrating evidence of resistance to therapies across all cancer types in an exemplary study using techniques consistent with at least some aspects of the present disclosure.

The ultimate goal of the broad molecular profiling done in the xT assay is to match patients to therapies as effectively as possible, with targeted or immunotherapy options being the most desirable. We evaluated whether patients in the xT group matched to response and resistance therapeutic evidence based on consensus clinical guidelines by cancer type (see KDB in Methods). Across all cancer types, 90.6% matched to therapeutic evidence based on response to therapy (FIG. 56), and 22.6% matched to evidence based on resistance to therapy (FIG. 57).

Figure 45:
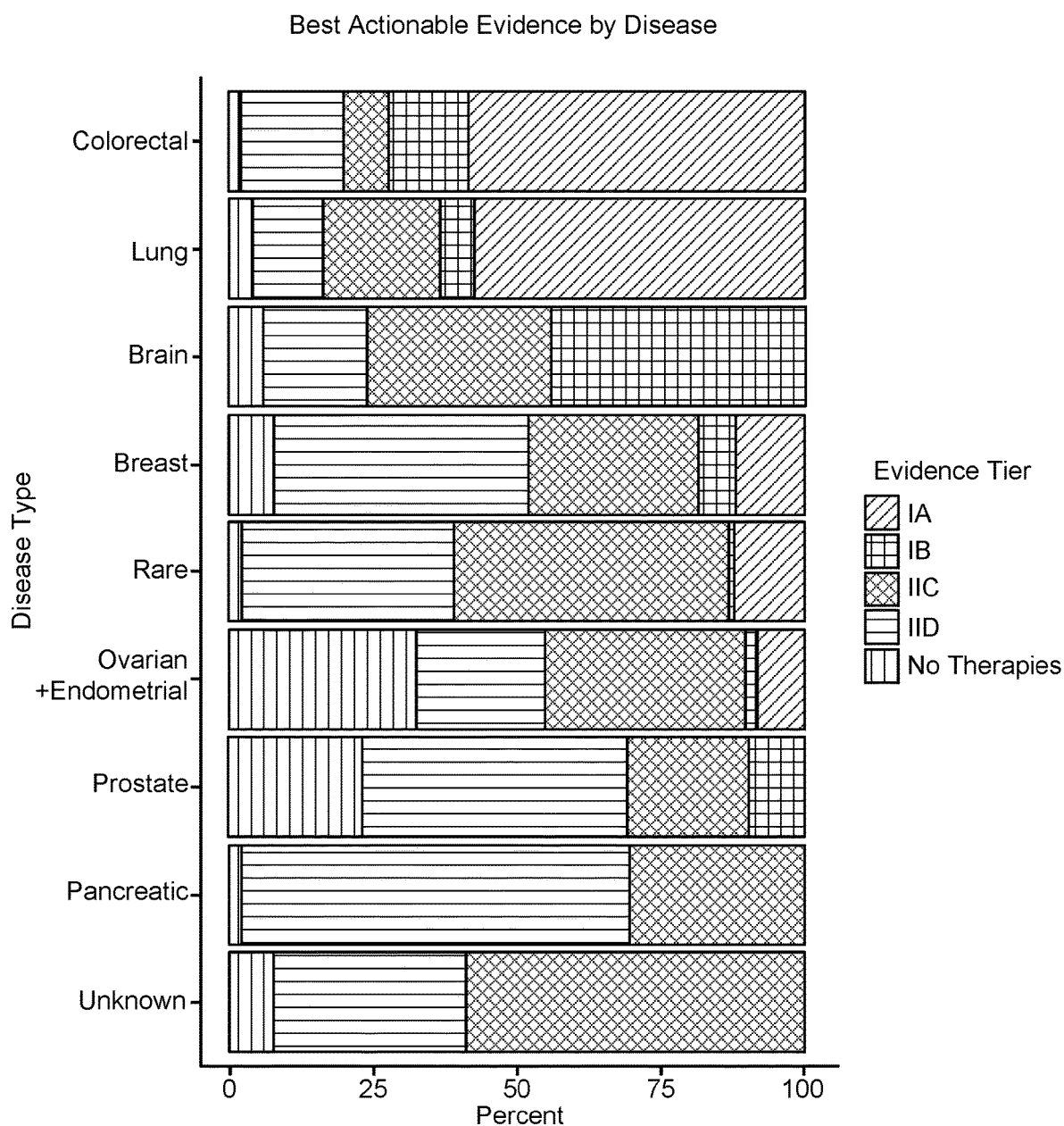
FIG. 45 includes a bar graph illustrating data related to therapeutic evidence as it varies among different cancer types generated using techniques consistent with at least some aspects of the present disclosure.
Figure 46:
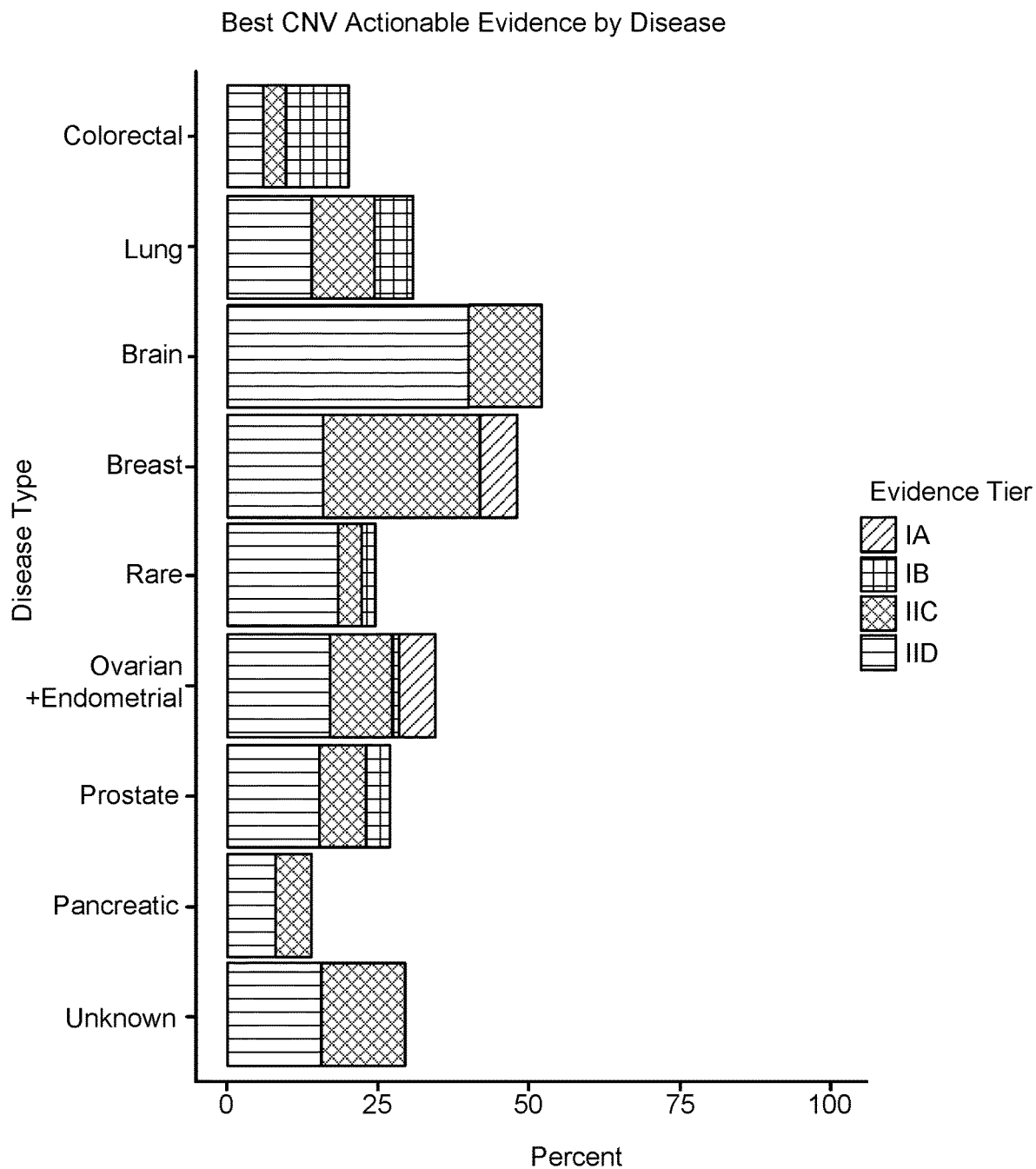
FIG. 46 includes a bar graph illustrating data related to specific therapeutic evidence matches based on copy number variants generating using techniques consistent with at least some aspects of the present disclosure.
Figure 47:
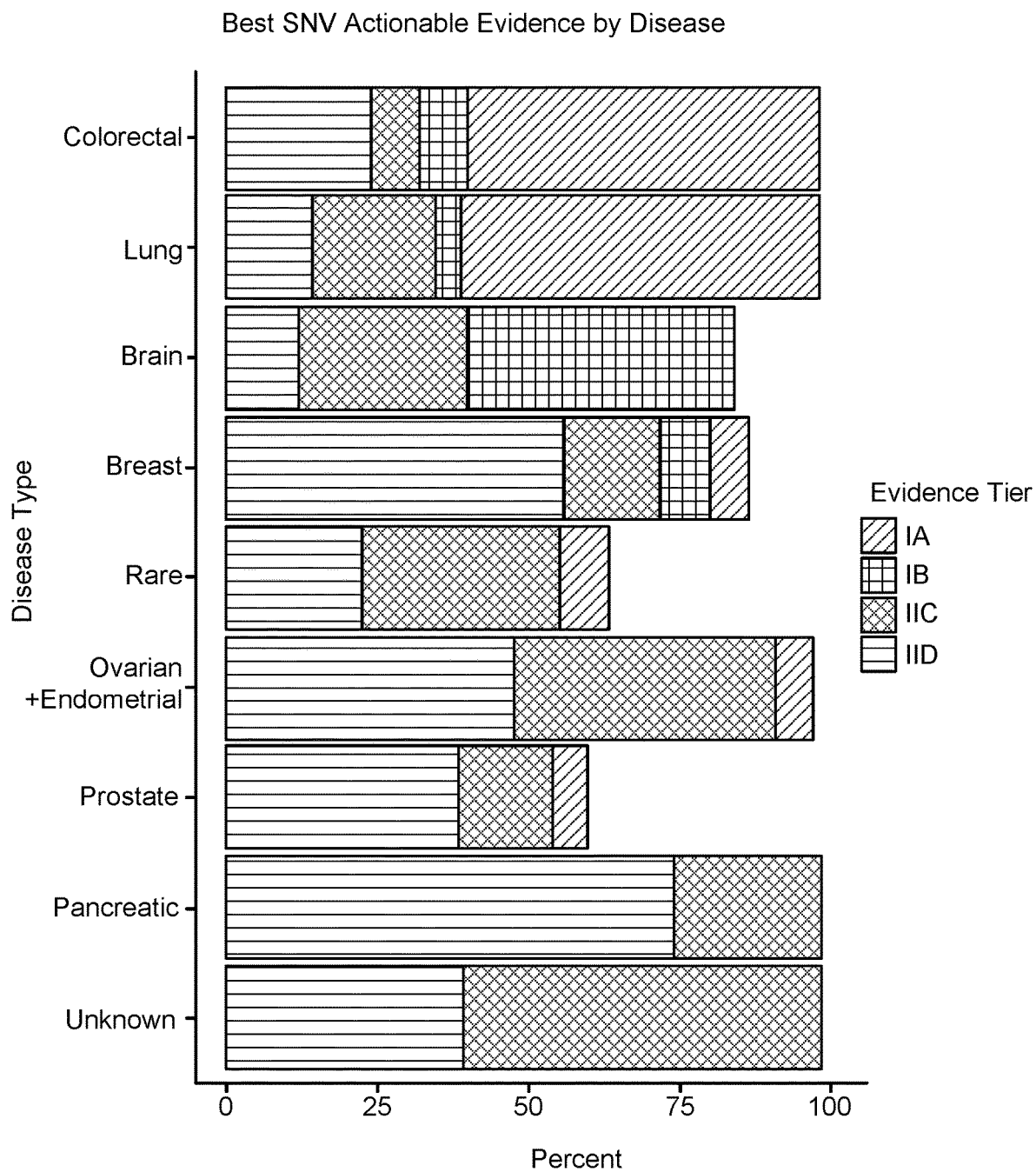
FIG. 47 includes a bar graph illustrating data related to specific therapeutic evidence matches based on single nucleotide variants and indels generating using techniques consistent with at least some aspects of the present disclosure.
Figure 58:
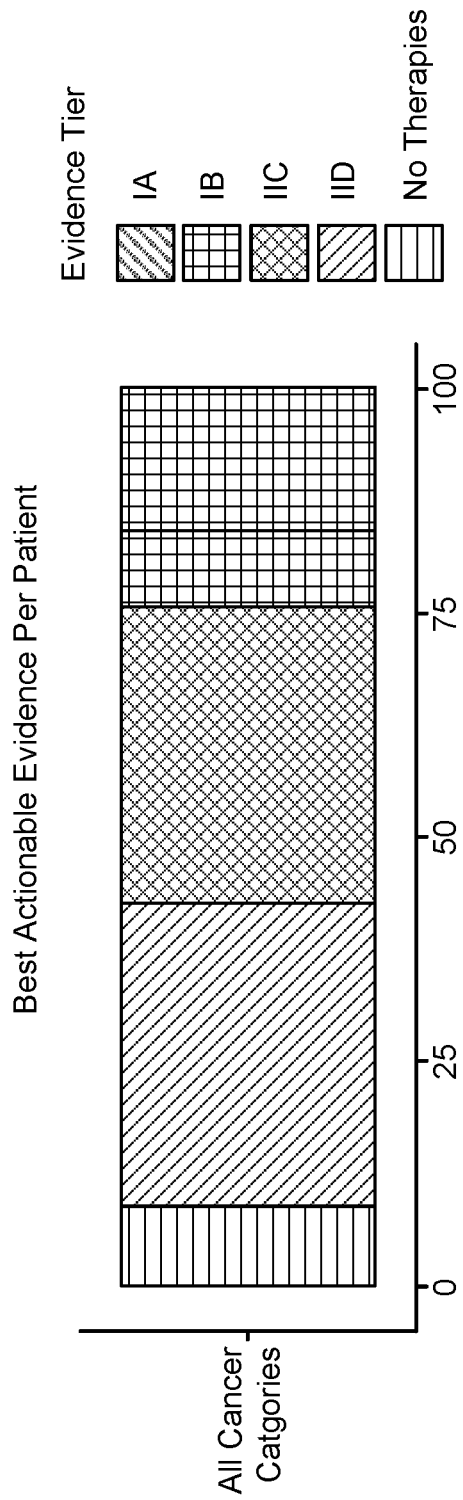
FIG. 58 includes a graph illustrating therapeutic evidence tiers for all cancer types in an exemplary study using techniques consistent with at least some aspects of the present disclosure.

For both response and resistance therapeutic evidence, approximately 24% of the group could be matched to a precision medicine option with at least a tier IB level. In particular, tier IA therapeutic evidence, as defined by joint AMP, ASCO, and CAP guidelines, was returned for 15.8% of patients (FIG. 58). The maximum tier of therapeutic evidence per patient varied significantly by cancer type (FIG. 45). For example, 58.0% of colorectal patients could be matched to tier IA evidence, the majority of which were for resistance to therapy based on detected KRAS mutations; while no pancreatic cancer patients could be matched to tier IA evidence. This is expected, as there are several molecularly based consensus guidelines in colorectal cancer, but fewer or none for other cancer types. Additionally, specific therapeutic evidence matches were made based on copy number variants (CNVs) (FIG. 46) and single nucleotide variants (SNVs) and indels (FIG. 47) for each cancer category.

Figure 48:
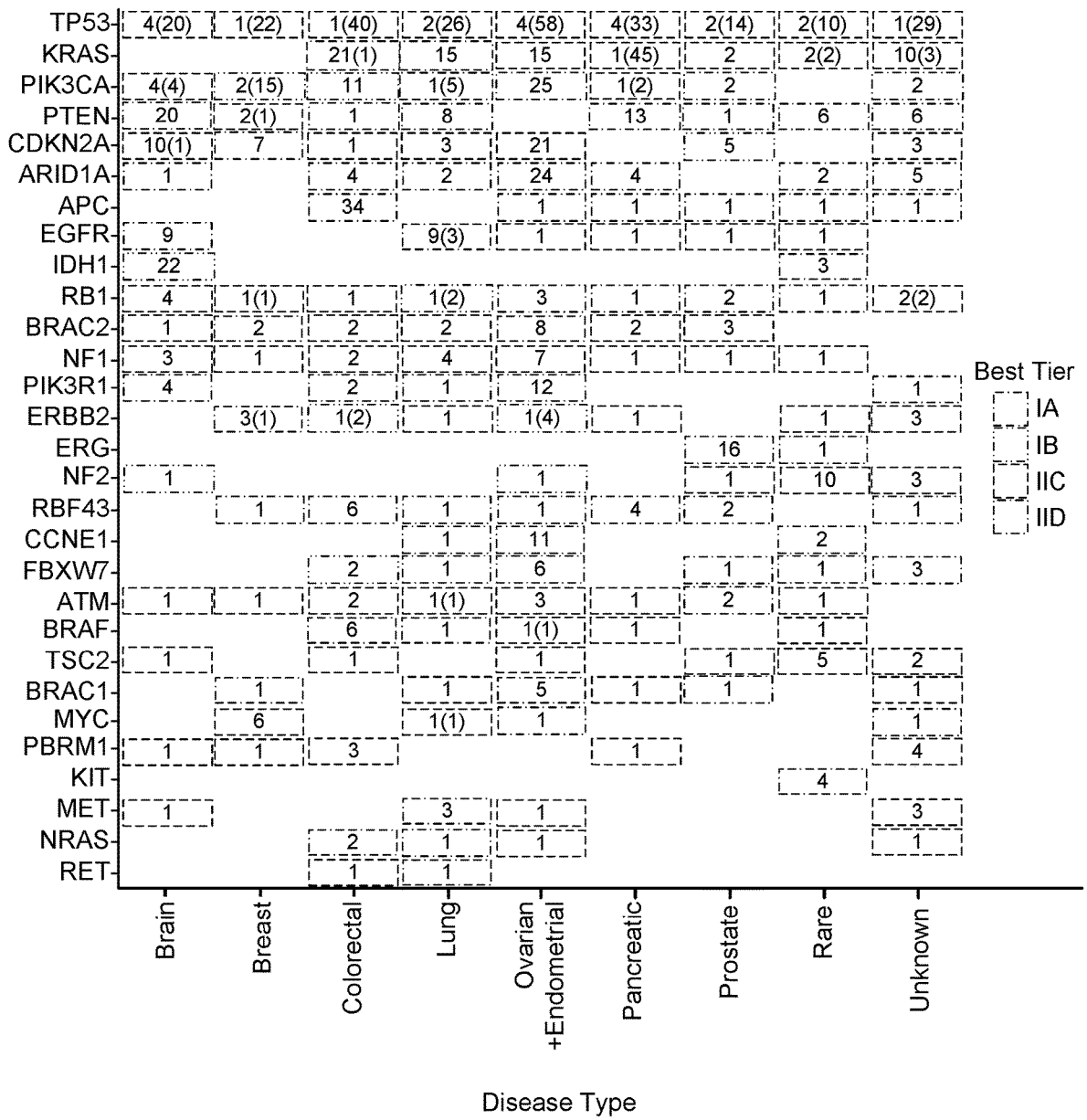
FIG. 48 includes a plot illustrating data related to single nucleotide variants and indels or CNVs by cancer type generating using techniques consistent with at least some aspects of the present disclosure.

Therapies were also matched to single gene alterations, either SNVs and indels or CNVs, and plotted by cancer type (FIG. 48). Unfortunately, the two most commonly mutated genes in cancer are TP53 and KRAS, with TP53 only having Tier IIC evidence and drugs in clinical trials, and KRAS having Tier 1A evidence, but as resistance to therapies targeting other proteins (36 patients). However, many less commonly mutated genes have Tier 1A evidence for targeted therapies across a variety of cancer types. Notable in this category are the PARP inhibitors for BRCA1 and BRCA2 mutated breast and ovarian cancer (16 patients), which are currently also in clinical trials or being used off-label in other disease types harboring BRCA mutations, such as prostate and pancreatic cancer. The majority of the remaining targetable mutations with Tier 1A evidence are from the druggable portions of the MAP kinase cascade (MAPK/ERK pathway), including EGFR, BRAF and NRAS across colorectal and lung cancer (18 patients).

Therapeutic options were further matched based on RNA sequencing data. We focused on the expression of 42 clinically relevant genes selected based on their relevance to disease diagnosis, prognosis, and/or possible therapeutic intervention. Over or underexpression of these genes may be reported to physicians.

Figure 49:
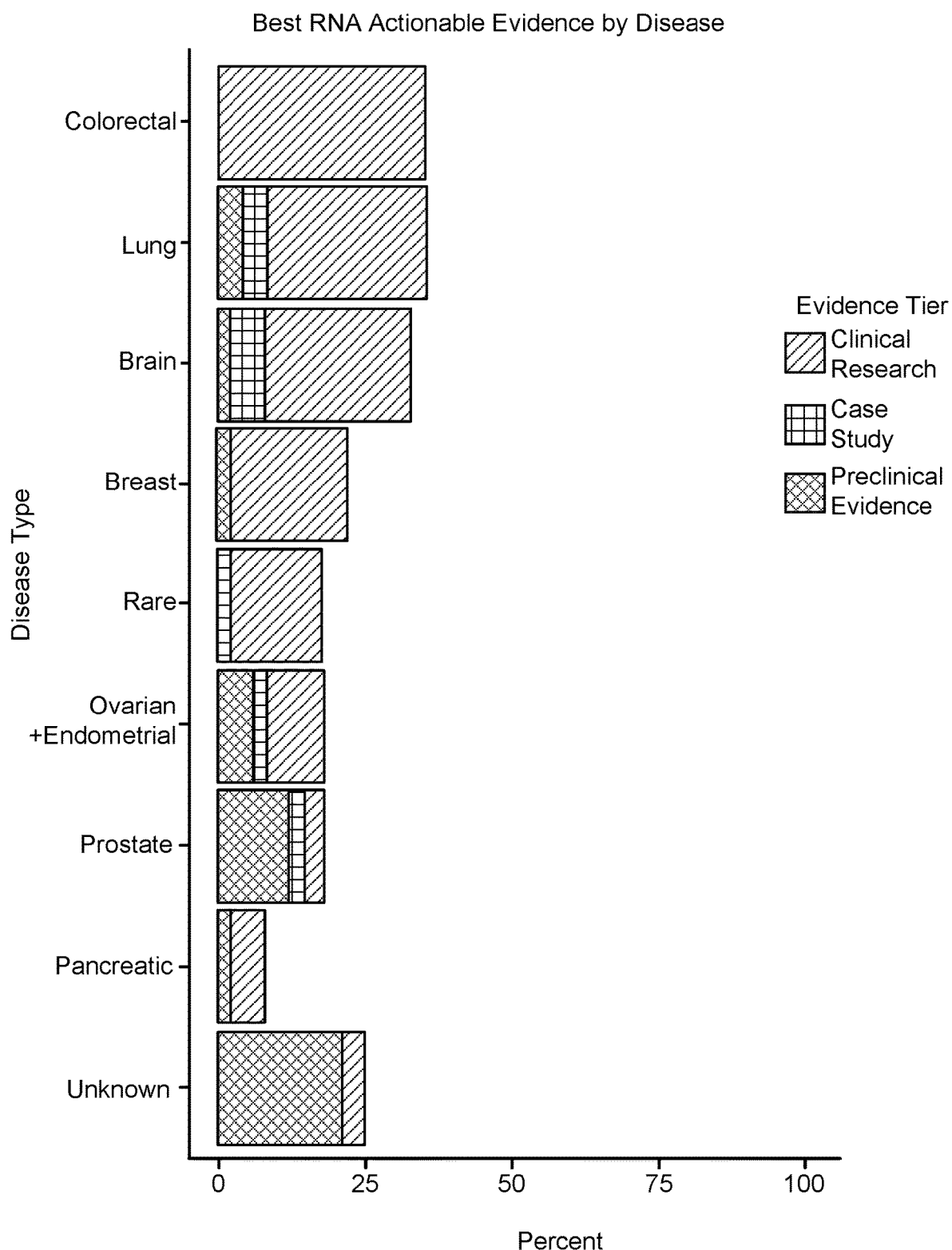
FIG. 49 includes a bar graph illustrating data that shows percent of patients with gene calls and evidence for association between gene expression and drug response where the data was generated using techniques consistent with at least some aspects of the present disclosure.
Figure 54:
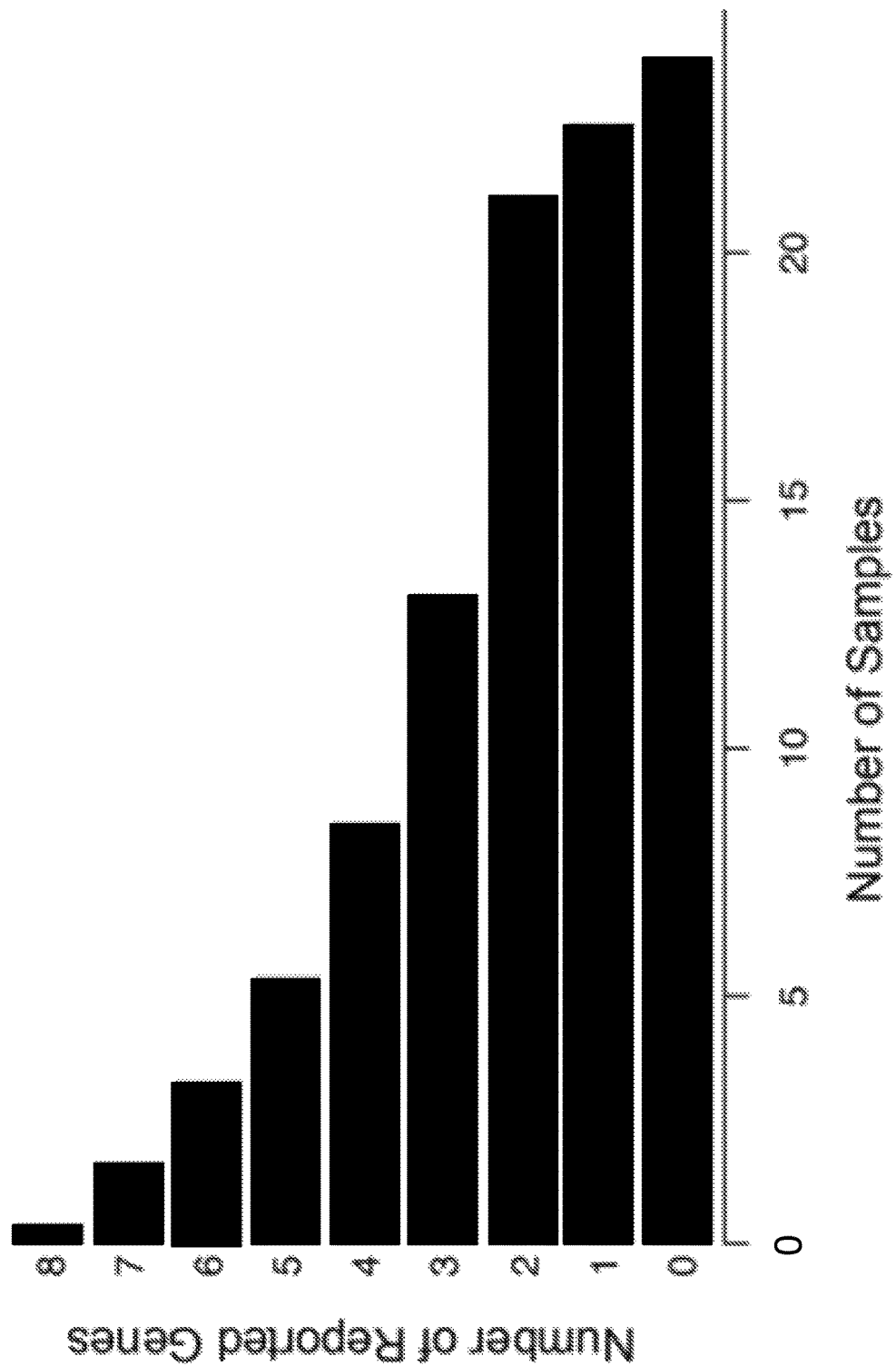
FIG. 54 includes a bar graph including data that shows exemplary distribution of expression calls by sample that was generated using techniques that are consistent with at least some aspects of the present disclosure.
Figure 55:
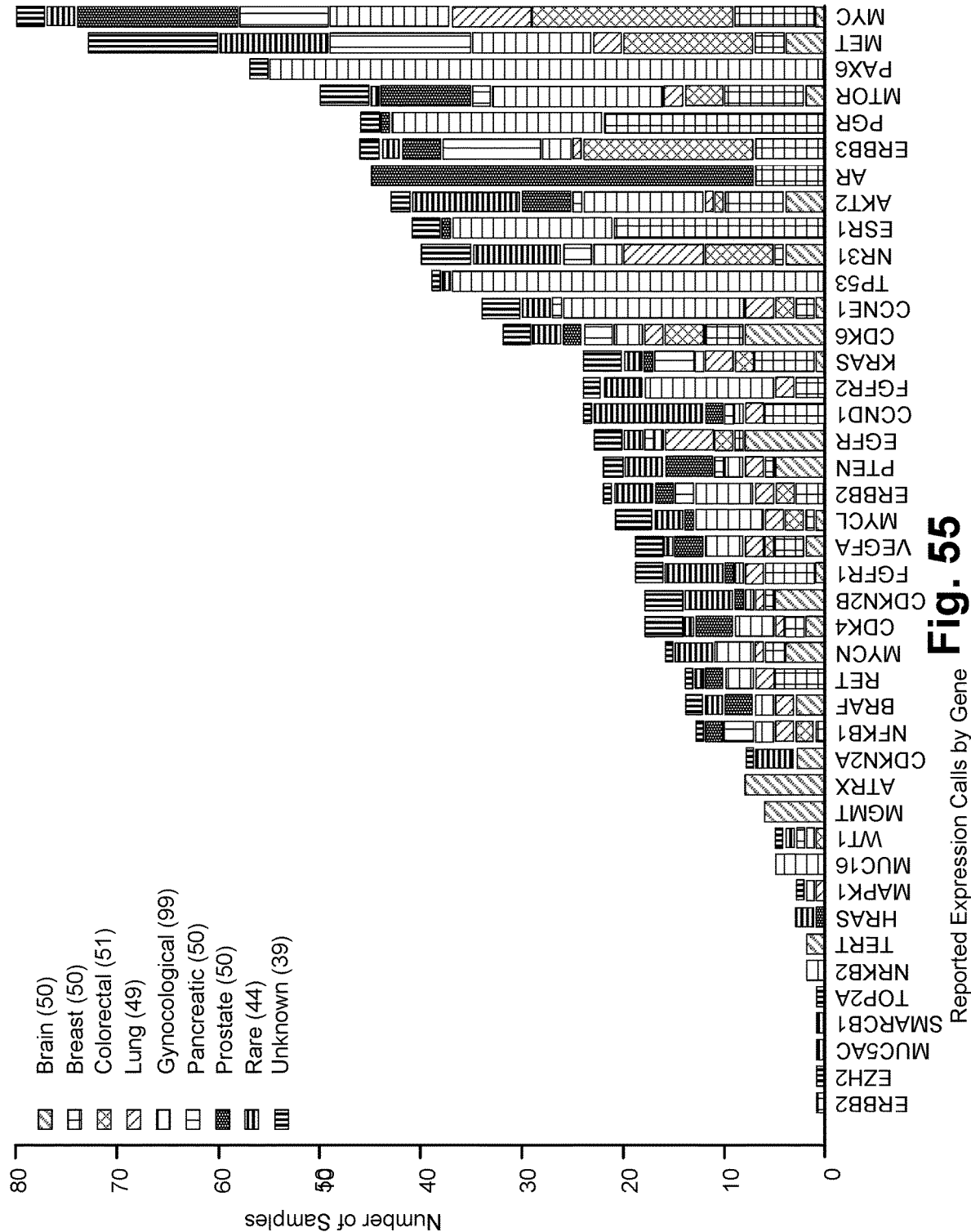
FIG. 55 includes a bar graph including data that shows exemplary distribution of expression calls by gene that was generated using techniques that are consistent with at least some aspects of the present disclosure.

Expression calls were made by comparison of the patient tumor expression to the tumor and normal tissue expression in the data vault database 180 based on overall comparisons as well as tissue-specific comparisons. For example, each breast cancer case was compared to all cancer samples, all normal samples, all breast cancer samples, and all normal breast samples. At least one gene in 76% of patients with gene expression data was reported. The distribution of expression calls is shown by sample (FIG. 54) and by gene (FIG. 55). It was found that metastatic cases are equally as likely to have at least one reportable expression call compared to non-metastatic tumors (79% vs 75%, p-value=0.288). The most commonly reported gene is overexpression of MYC, which was seen in 80 (17%) patient tumors across the group. Next, the percent of patients with gene expression calls was determined and evidence for the association between gene expression and drug response (FIG. 49) was identified. Among the cases with reported expression calls, 25% of cases across cancer types included evidence based on clinical studies, case studies, and preclinical studies reported in the literature.

Figure 50:
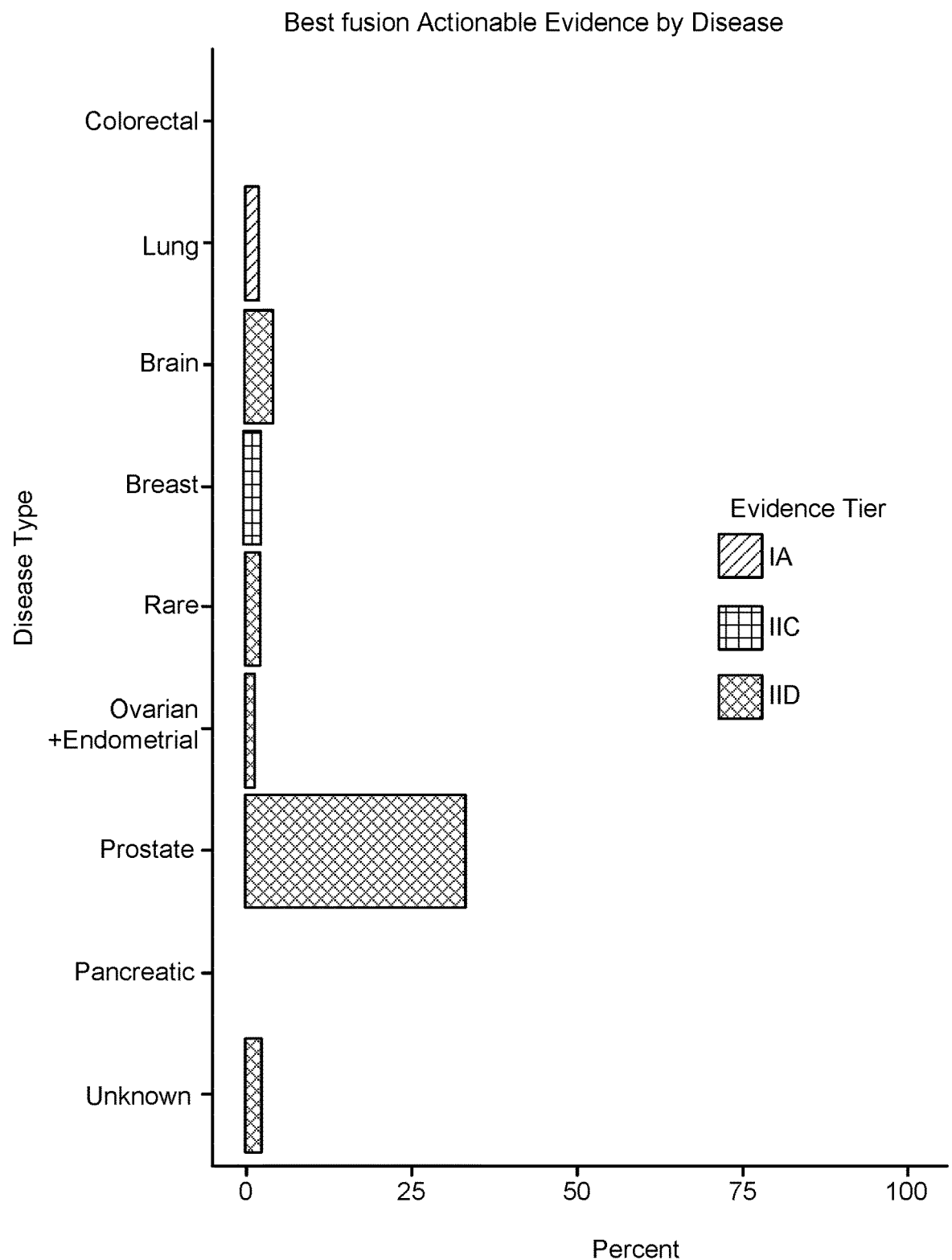
FIG. 50 includes a bar graph illustrating response to therapeutic options based on evidence tiers and broken down by cancer type.

Fusion proteins are proteins made from RNA that has been generated by a DNA chromosomal rearrangement, also known as a "fusion event." Fusion proteins can be oncogenic drivers that are among the most druggable targets in cancer. Of the 28 chromosomal rearrangements detected in the study group, 26 were associated with evidence of response to various therapeutic options based on evidence tiers and cancer type (FIG. 50). The majority of fusion events were TMPRSS-ERG fusions within prostate cancer patients in the group. TMPRSS-ERG fusions in prostate cancer were given a IID evidence level due to the early evidence around therapeutic response. Of the seven non-prostate cancer fusions, one was rated as evidence level IA, one was rated as IIC and five were rated evidence level IID. These detected fusions are clear drivers of cancer, part of consensus therapeutic guidelines and shown to be present with high sensitivity by the xT assay referred to herein.

Figure 51:
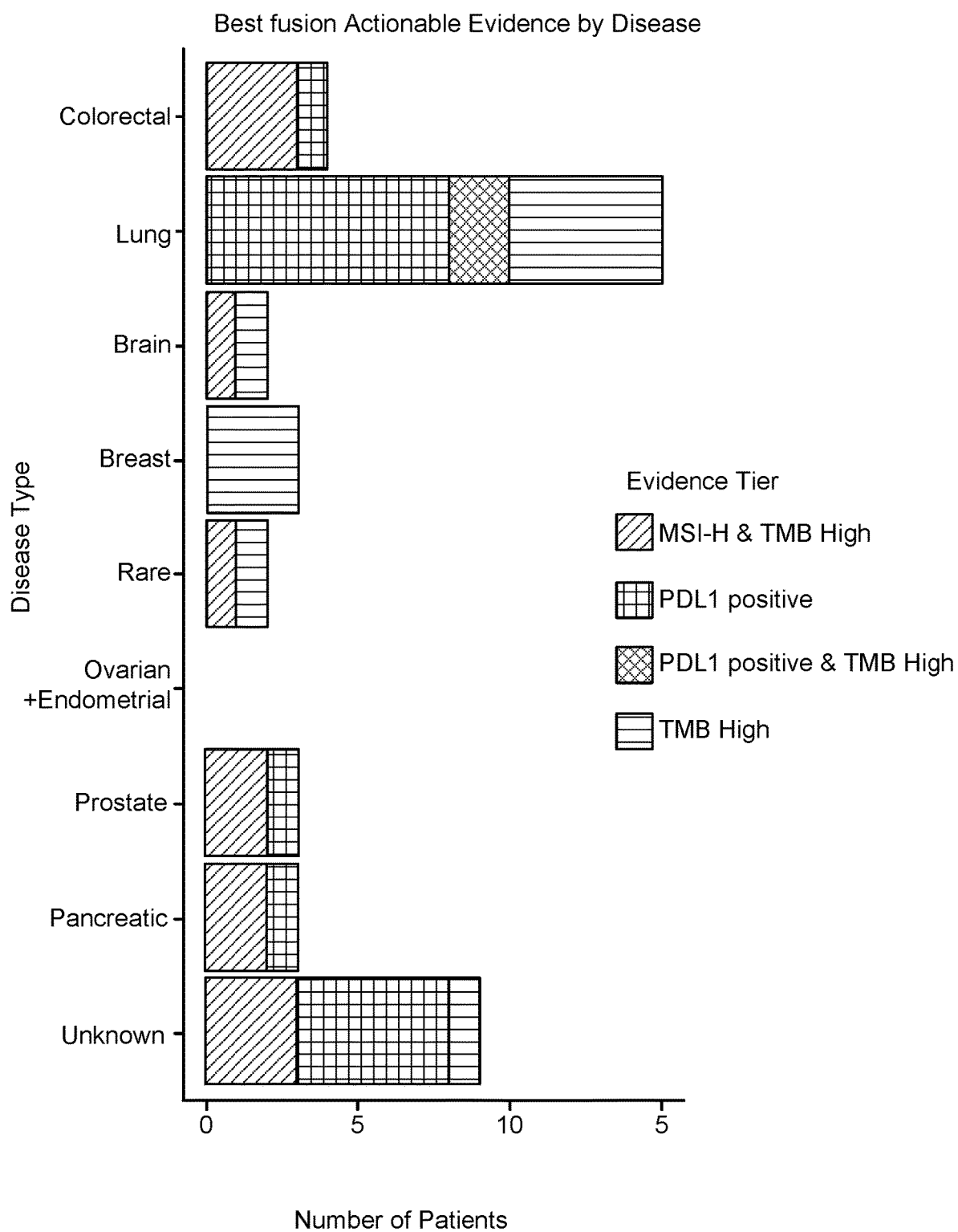
FIG. 51 includes a bar graph showing data related to patients that are potential candidates for immunotherapy broken down by cancer type where the data is based on techniques consistent with the present disclosure.

Based on the immunotherapy biomarkers identified by the xT assays, we investigated what percentage of the group would be eligible for immunotherapy. We discovered 10.1% of the xT group would be considered potential candidates for immunotherapy based on TMB, MSI status, and PD-L1 IHC results alone (FIG. 51). The number of MSI-high and TMB-high cases were distributed among cancer types. This represents the most common immunotherapy biomarkers measured in the group with 4% of patients positive for both TMB-high and MSI-high status. PD-L1 positive IHC alone were measured in 3% of the eligibility group, and was found to be the highest among lung cancer patients. TMB-high status alone was measured in 2.6% of the eligibility group, primarily in lung and breast cancer cases. PD-L1 positive IHC and TMB-high status was the minority of cases and measured in only 0.4% of the eligibility group.

Figure 52:
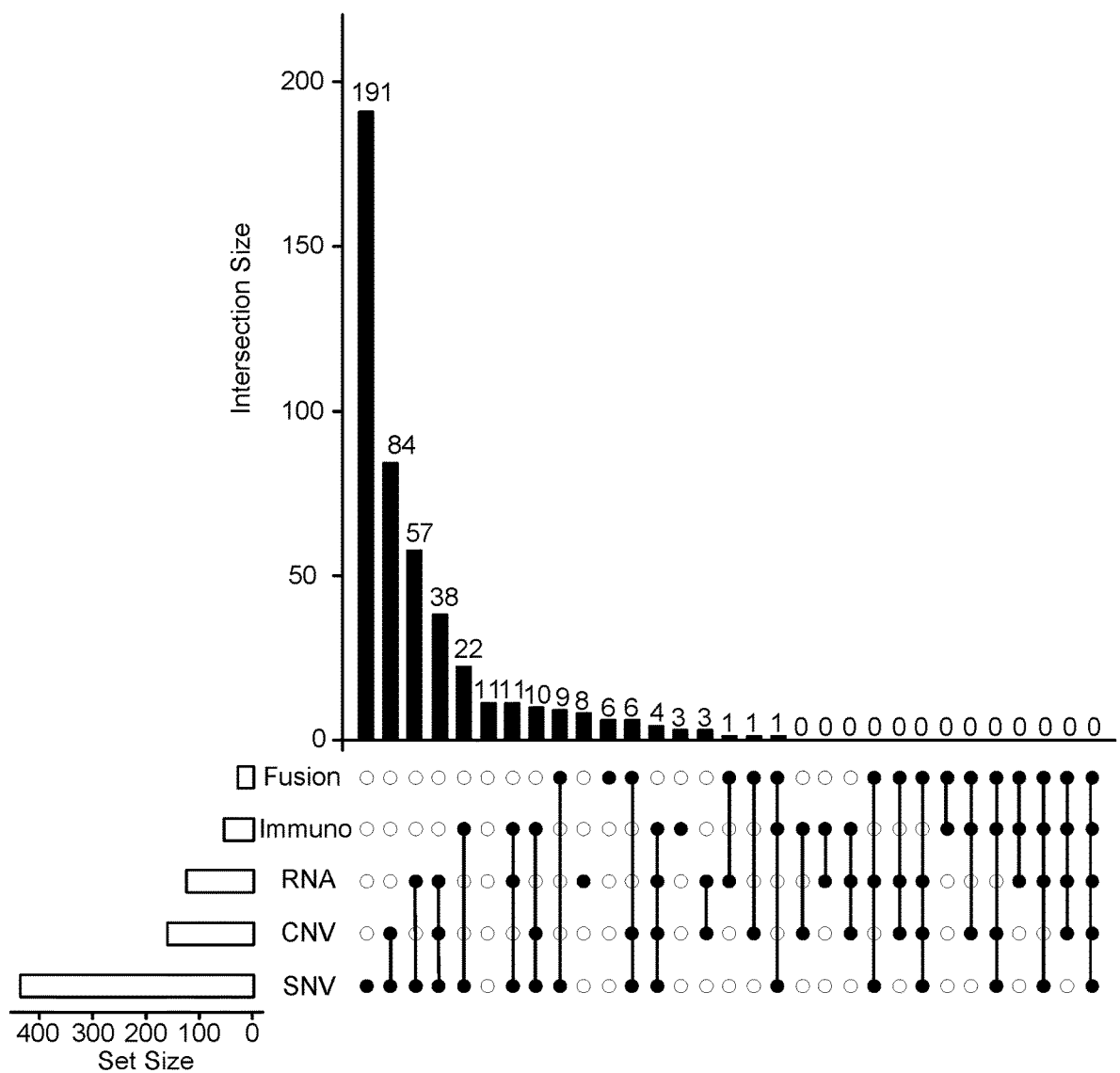
FIG. 52 is a bar graph presenting data related to relevant molecular insights for a patent group based on CNVs, indels, CNVs, gene expression calls and immunotherapy biomarker assays where the data was generated using techniques that are consistent with various aspects of the present disclosure.

Overall, clinically relevant molecular insights were uncovered for over 90% of the group based on SNVs, indels, CNVs, gene expression calls, and immunotherapy biomarker assays (FIG. 52). The majority of therapeutic matches to patients were based on clinically relevant xT findings reported on SNVs and indels. This was followed by matches based on CNVs, gene expression calls, fusion detection, and immunotherapy biomarkers. In addition to therapeutic matching, we determined clinical-trial matching for the group based on molecular insights from the xT assay.

Figure 53:
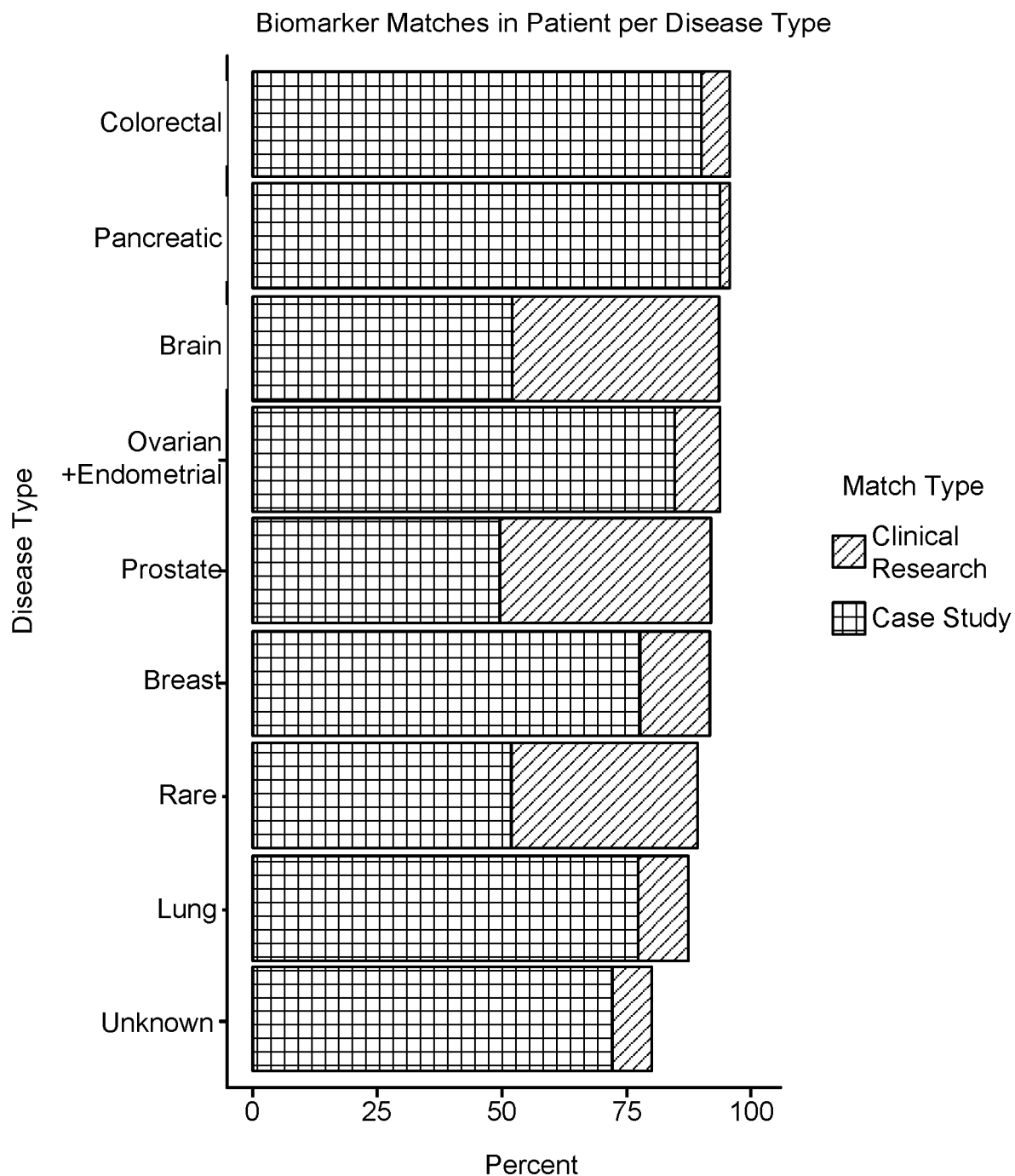
FIG. 53 includes a bar graph illustrating disease-based trial matches and biomarker based match percentages based that reflect results of techniques that are consistent with at least some aspects of the present disclosure.

In total, 1952 clinical trials were reported for the xT 500 patient group. The majority of patients, 91.6%, were matched to at least one clinical trial, with 73.6% matched with at least one biomarker-based clinical trial for a gene variant on their final report. The frequency of biomarker-based clinical trial matches varied by diagnosis and outnumbered disease-based clinical trial matches (FIG. 53). For example, gynecological and pancreatic cancers were typically matched to a biomarker-based clinical trial; while rare cancers had the least number of biomarker-based clinical trial matches and an almost equal ratio of biomarker-based to disease-based trial matching. The differences between biomarker versus disease-based trial matching appears to be due to the frequency of targetable alterations and heterogeneity of those cancer types.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

Thus, the invention is to cover all modifications, equivalents, and alternatives falling within the spirit and scope of the invention as defined by the following appended claims.

The invention claimed is:

1. A method for conducting genomic sequencing, the method comprising the steps of:
   storing a set of user application programs wherein each of the programs requires an application specific subset of data to perform application processes and generate user output;
   for each of a plurality of patients that have cancerous cells and that receive cancer treatment:
   (a) obtaining clinical records data in original forms where the clinical records data includes cancer state information, treatment types and treatment efficacy information;
   (b) storing the clinical records data in a semi-structured first database;
   (c) for each patient, using a next generation genomic sequencer to generate genomic sequencing data for the patient's cancerous cells and normal cells;
   (d) storing the sequencing data in the first database;
   (e) shaping at least a subset of the first database data to generate system structured data including clinical record data and sequencing data wherein the system structured data is optimized for searching;
   (f) storing the system structured data in a second database;
   (g) for each user application program:

(i) selecting the application specific subset of data from the second database; and (ii) storing the application specific subset of data in a structure optimized for application program interfacing in a third database.

2. The method of claim 1 further including the step of storing a plurality of micro-service programs where each micro-service program includes a data consume definition, a data product to generate definition and a data shaping process that converts consumed data to a data product, the step of shaping including running a sequence of micro-service programs on data in the first database to retrieve data, shape the retrieved data into data products and publish the data products back to the second database as structured data.

3. The method of claim 2 further including storing a new data alert in an alert list in response to a new clinical record or a new micro-service data product being stored in the second database.

4. The method of claim 3 further including each micro-service program monitoring the alert list and determining if stored data is to be consumed by that micro-service program independent of all other micro-service programs.

5. The method of claim 4 wherein at least a subset of the micro-service programs operate sequentially to condition data.

6. The method of claim 4 wherein at least a subset of the micro-service programs specify the same data to consume definition.

7. The method of claim 3 wherein the step of shaping includes at least one manual step to be performed by a system user and wherein the system adds a data shaping activity to a user's work queue in response to at least one of the alerts being added to the alert list.

8. The method of claim 2 wherein the first database includes both unstructured original clinical data records and semi-structured data generated by the micro-service programs.

9. The method of claim 2 wherein each micro-service program operates automatically and independently when data that meets the data to consume definition is stored to the first database.

10. The method of claim 2 wherein at least one of the micro-services is a variant annotation service.

11. The method of claim 1 wherein the application programs include operational programs and wherein at least a subset of the operational programs comprise a physician suite of programs useable to consider cancer state treatment options.

12. The method of claim 11 wherein at least a subset of the operational programs comprise a suite of data shaping programs usable by a system user to shape data stored in the first database.

13. The method of claim 12 wherein the data shaping programs are for use by a radiologist.

14. The method of claim 12 wherein the data shaping programs are for use by a pathologist.

15. The method of claim 11 further including a set of visualization tools and associated interfaces useable by a system user to analyze the second database data.

16. The method of claim 1 wherein the third database includes a subset of the second database data.

17. The method of claim 16 wherein the third database includes data derived from the second database data.

18. The method of claim 1 further including the steps of presenting a user interface to a system user that includes data that indicates how genomic sequencing data affects different treatment efficacies.

19. The method of claim 1 wherein each cancer state includes a plurality of factors, the method further including the steps of using a processor to automatically perform the steps of analyzing patient genomic sequencing data that is associated with patients having at least a common subset of cancer state factors to identify treatments of genomically similar patients that experience treatment efficacies above a threshold level.

20. The method of claim 1 wherein each cancer state includes a plurality of factors, the method further including the steps of using a processor to automatically identify, for specific cancer types, highly efficacious cancer treatments and, for each highly efficacious cancer treatment, identify at least one genomic sequencing data subset that is different for patients that experienced treatment efficacy above a first threshold level when compared to patients that experienced treatment efficacy below a second threshold level.

21. The method of claim 1 wherein the sequencing data includes DNA sequencing data.

22. The method of claim 1 wherein the sequencing data includes only DNA sequencing data.

23. The method of claim 1 wherein the sequencing data includes only RNA sequencing data.

24. The method of claim 1 wherein the sequencing is conducted using a tumor gene panel.

25. The method of claim 24, wherein the sequencing is conducted using a plurality of genes from the tumor gene panel.

26. The method of claim 24, wherein the sequencing is conducted using at least one gene from the cell-free gene panel.

27. The method of claim 24 further including detecting a fusion event.

28. The method of claim 27 wherein the fusion event is a TMPRSS-ERG fusion.

29. The method of claim 1 wherein the sequencing is conducted using a whole-exome gene panel.

30. The method of claim 29 wherein the sequencing is conducted using at least one gene from the whole-exome gene panel.

31. The method of claim 1 wherein sequencing is done on the KRAS gene of the patient's cancerous cells and normal cells.

32. The method of claim 1 wherein sequencing is done on the PIK3CA gene of the patient's cancerous cells and normal cells.

33. The method of claim 1 wherein sequencing is done on the CDKN2A gene of the patient's cancerous cells and normal cells.

34. The method of claim 1 wherein sequencing is done on the PTEN gene of the patient's cancerous cells and normal cells.

35. The method of claim 1 wherein sequencing is done on the ARID1A gene of the patient's cancerous cells and normal cells.

36. The method of claim 1 wherein sequencing is done on the APC gene of the patient's cancerous cells and normal cells.

37. The method of claim 1 wherein sequencing is done on the ERBB2 gene of the patient's cancerous cells and normal cells.

38. The method of claim 1 wherein sequencing is done on the EGFR gene of the patient's cancerous cells and normal cells.

39. The method of claim 1 wherein sequencing is done on the IDH1 gene of the patient's cancerous cells and normal cells.

40. The method of claim 1 wherein sequencing is done on the CDKN2B gene of the patient's cancerous cells and normal cells.

41. The method of claim 1 wherein the sequencing includes MAP kinase cascade.

42. The method of claim 41 wherein the sequencing includes EGFR.

43. The method of claim 41 wherein the sequencing includes BRA.

44. The method of claim 41 wherein the sequencing includes NRAS.

45. The method of claim 1 wherein the sequencing is performed on a particular cancer type.

46. The method of claim 1 wherein the application programs include operational programs and wherein at least one of the operational programs is a variant annotation program.

47. The method of claim 1 wherein the application programs include operational programs and wherein at least one of the operational programs is a clinical data structuring application for converting unstructured raw clinical medical records into structured records.

48. The method of claim 1 wherein the second database includes a database of molecular sequencing data.

49. The method of claim 48 wherein the molecular sequencing data includes DNA data.

50. The method of claim 48 wherein the molecular sequencing data includes RNA data.

51. The method of claim 48 wherein the molecular sequencing data includes normalized RNA data.

52. The method of claim 48 wherein the molecular sequencing data includes tumor-normal sequencing data.

53. The method of claim 48 wherein the molecular sequencing data includes variant calls.

54. The method of claim 48 wherein the molecular sequencing data includes variants of unknown significance.

55. The method of claim 48 wherein the molecular sequencing data includes germline variants.

56. The method of claim 48 wherein the molecular sequencing data includes MSI information.

57. The method of claim 48 wherein the molecular sequencing data includes TMB information.

58. The method of claim 1 further including the step of determining an MSI value for the cancerous cells.

59. The method of claim 1 further including determining a TMB value for the cancerous cells.

60. The method of claim 59 further including identifying a TMB value greater than 9 mutations/Mb.

61. The method of claim 1 further including detecting a genomic alteration that results in a chimeric protein product.

62. The method of claim 1 further including detecting a genomic alteration that drives EML4-ALK.

63. The method of claim 1 further including the step of determining neoantigen load.

64. The method of claim 1 further including the step of identifying a cytolytic index.

65. The method of claim 1 further including distinguishing a population of immune cells based on TMB value.

66. The method of claim 1 further including the step of determining CD274 expression.

67. The method of claim 1 further including reporting an overexpression of MYC.

68. The method of claim 1 further including the step of detecting a PD-L1 in a lung cancer patient.

69. The method of claim 1 further including indicating a PARP inhibitor.

70. The method of claim 69 wherein the PARP inhibitor is for BRCA1.

71. The method of claim 69 wherein the PARP inhibitor is for BRCA2.

72. The method of claim 1 further including the steps of recommending an immunotherapy.

73. The method of claim 72 wherein the recommended immunotherapy is one of CAR-T therapy, antibody therapy, cytokine therapy, adoptive t-cell therapy, anti-CD47 therapy, anti-GD2 therapy, immune checkpoint inhibitor and neoantigen therapy.

74. The method of claim 1 wherein the cancerous cells are from a tumor tissue and the normal cells are blood cells.

75. The method of claim 1 wherein the genomic sequence data for the patient's cancerous cells is derived from cell free DNA from blood.

76. The method of claim 1 wherein the cancerous cells are from fresh tissue.

77. The method of claim 1 wherein the cancerous cells are from a FFPE slide.

78. The method of claim 1 wherein the cancerous cells are from frozen tissue.

79. The method of claim 1 wherein the cancerous cells are from biopsied tissue.

80. The method of claim 1 wherein sequencing is done on the TP53 gene of the patient's cancerous cells and normal cells.

81. A method for conducting genomic sequencing, the method comprising the steps of:
   for each of a plurality of patients that have cancerous cells and that receive cancer treatment:
   (a) obtaining clinical records data in original forms where the clinical records data includes cancer state information, treatment types and treatment efficacy information;
   (b) storing the clinical records data in a semi-structured first database;
   (c) obtaining a tumor specimen from the patient;
   (d) growing the tumor specimen into a plurality of tissue organoids;
   (e) treating each tissue organoid with an organoid specific treatment;
   collecting and storing organoid treatment efficacy information in the first database;
   (g) using a processor to examine the first database data including organoid treatment efficacy and clinical record data to identify at least one optimal treatment for a specific cancer patient;
   (h) storing a set of user application programs wherein each of the programs requires an application specific subset of data to perform application processes and generate user output;
   (i) shaping at least a subset of the first database data to generate system structured data including clinical record data and organoid treatment efficacy data wherein the system structured data is optimized for searching;
   (j) storing the system structured data in a second database; and
   (k) for each user application program, selecting the application specific subset of data from at least one of the first and second databases and storing the application specific subset of data in a structure optimized for application program interfacing in a third database.

82. The method of claim 81 further including the steps of using a genomic sequencer to generate genomic sequencing data for each of the patients and the patient's cancerous cells and storing the sequencing data in the first database, the step of examining the first database data including examining each of the organoid treatment efficacy data, the genomic sequencing data and the clinical record data to identify at least one optimal treatment for a specific cancer patient.

83. The method of claim 82 wherein the sequencing data include RNA sequencing data.

* * * * *

UNITED STATES PATENT AND TRADEMARK OFFICE
CERTIFICATE OF CORRECTION

| | |
|---|---|
| PATENT NO. | : 11,640,859 B2 |
| APPLICATION NO. | : 16/771451 |
| DATED | : May 2, 2023 |
| INVENTOR(S) | : Shane Colley et al. |

It is certified that error appears in the above-identified patent and that said Letters Patent is hereby corrected as shown below:

In the Claims

Claim 81, Column 64, Line 49, "collecting and storing organoid treatment efficacy information" should be --(f) collecting and storing organoid treatment efficacy information--.

Signed and Sealed this
Sixth Day of February, 2024

Katherine Kelly Vidal
*Director of the United States Patent and Trademark Office*